United States Patent
Rassaf et al.

(10) Patent No.: US 12,344,644 B2
(45) Date of Patent: Jul. 1, 2025

(54) AMELIORATION AND TREATMENT OF INFARCTION DAMAGE WITH A POLYPEPTIDE SEGEMENT OF BNIP3

(71) Applicant: Bimyo GmbH, Monheim (DE)

(72) Inventors: Tienush Rassaf, Essen (DE); Ulrike Hendgen-Cotta, Dinslaken (DE)

( * ) Notice: Subject to any disclaimer, the term of this patent is extended or adjusted under 35 U.S.C. 154(b) by 0 days.

(21) Appl. No.: 18/413,753

(22) Filed: Jan. 16, 2024

(65) Prior Publication Data

US 2024/0228565 A1    Jul. 11, 2024

Related U.S. Application Data

(63) Continuation of application No. PCT/EP2022/080979, filed on Nov. 7, 2022.

(60) Provisional application No. 63/276,028, filed on Nov. 5, 2021.

(51) Int. Cl.
| | |
|---|---|
| A61K 38/17 | (2006.01) |
| A61P 9/10 | (2006.01) |
| C07K 14/47 | (2006.01) |
| C07K 19/00 | (2006.01) |

(52) U.S. Cl.
CPC ...... *C07K 14/4747* (2013.01); *A61K 38/1761* (2013.01); *A61P 9/10* (2018.01); *C07K 19/00* (2013.01)

(58) Field of Classification Search
CPC .... C07K 14/4747; A61K 38/1761; A61P 9/10
See application file for complete search history.

(56) References Cited

U.S. PATENT DOCUMENTS

| | | |
|---|---|---|
| 7,452,869 B2 | 11/2008 | Greenberg et al. |
| 2004/0152650 A1 | 8/2004 | Webster |
| 2017/0224654 A1* | 8/2017 | Armstrong ........... A61K 31/517 |

FOREIGN PATENT DOCUMENTS

| | | |
|---|---|---|
| WO | 200202743 A1 | 1/2002 |
| WO | 2004009780 | 1/2004 |
| WO | 2018165494 A1 | 9/2018 |
| WO | 2020229362 A1 | 11/2020 |
| WO | 2020240025 A1 | 12/2020 |

OTHER PUBLICATIONS

Product datasheet for "Human BNIP3 Antibody", Catalog No. AF4147, R&D Systems, Feb. 6, 2018 revision, p. 1 of 1.*
Sun et al (2016. Evid Based Complement Alternat Med, vol. 2016, Article ID 6093783, 16 pages).*
Gupta (2009) "The mitochondrial death pathway: a promising therapeutic target in diseases" J. Cell. Mol. Med. vol. 13, No. 6, pp. 1004-1033.
Hendgen-Cotta (2019) "Mitochondria at the Crossroads of Survival and Demise" Oxidative Medicine and CellularLongevity vol. 2019, Article ID 2608187, 2 pages.
Hendgen-Cotta et al. (2017) "Cytosolic BNIP3 Dimer Interacts with Mitochondrial BAX Forming Heterodimers in theMitochondrial Outer Membrane under Basal Conditions" Int. J. Mol. Sci. 18, 687.
International Application No. PCT/EP2022/080979, Search Report and Written Opinion mailed May 22, 2023, 16 pages.
Kothari et al.(2003) "BNIP3 plays a role in hypoxic cell death in human epithelial cells that is inhibited by growth factorsEGF and IGF" Oncogene 22, 4734-4744.
Kubasiak (2002) "Hypoxia and acidosis activate cardiac myocyte death through the Bcl-2 family protein BNIP3" PNASOct. 1, 2002 vol. 99 No. 20 12825-12830.
Kubli (2007) "Bnip3 mediates mitochondrial dysfunction and cell death through Bax and Bak" Biochem J (2007) 405 (3): 407-415.
Michel (2018) "Real-time Pressure-volume Analysis of Acute Myocardial Infarction in Mice" Journal of VisualizedExperiments Jul. 2018 | 137 | e57621.
Mizutani (2002) "A Zinc-finger Protein, PLAGL2, Induces the Expression of a Proapoptotic Protein Nip3, Leading toCellular Apoptosis" JBC vol. 277, No. 18, Issue of May 3, pp. 15851-15858, 2002.
Rassaf (2016) "Vasculoprotective Effects of Dietary Cocoa Flavanols in Patients on Hemodialysis: A Doble-Blind, Randomized, Placebo-Controlled Trial" Clin. J. Am. Soc. Nephrol. Jan. 7, 2016 11(1):108-118.
Schultz Moriera (2020) "9-PAHSA Prevents Mitochondrial Dysfunction and Increases the Viability of SteatoticHepatocytes" Int. J. Mol. Sci. 2020, 21, 8279.
Taylor (2020) "Review: Cell Penetrating Peptides, Novel Vectors for Gene Therapy" Pharmaceutics 2020, 12, 225.
Totzeck (2015) "Concepts of hypoxic No signaling in remote ischemic Preconditioning" World J Cardiol Oct. 26, 2015; 7(10): 645-651.

* cited by examiner

*Primary Examiner* — Zachary C Howard
(74) *Attorney, Agent, or Firm* — Garrett H. Anderson

(57) ABSTRACT

Infarction damage is ameliorated or treated through the administration of a mitochondrial degradation inhibitor, such as one that acts by inhibiting translocation of one or more molecules across a mitochondrial membrane, for example BAX/BNIP3 complexes involved in mitochondrial degradation. By preventing mitochondrial degradation, one allows more efficient oxygenation of an infarcted region, allowing for a greater degree of cell survival and a more successful recovery.

18 Claims, 73 Drawing Sheets

Specification includes a Sequence Listing.

Sham I/R   I/R $_{10}$ + Vehicl   I/R $_{10}$ + ΔTM

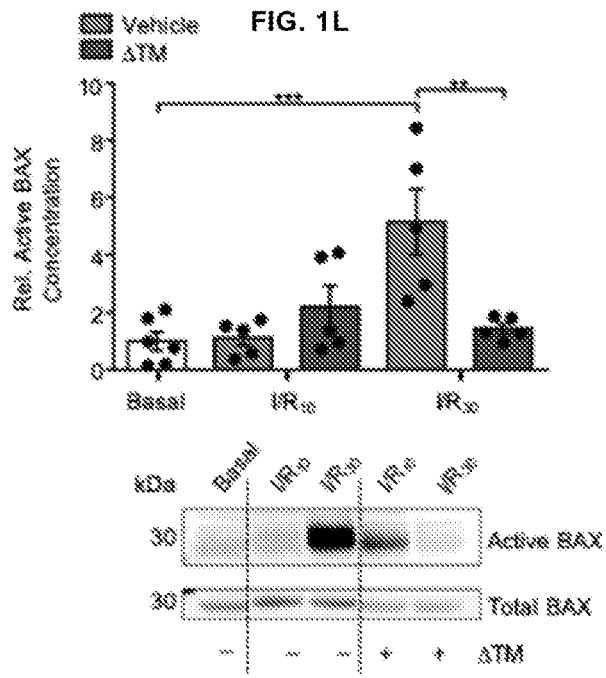
FIG. 1L
FIG. 1M
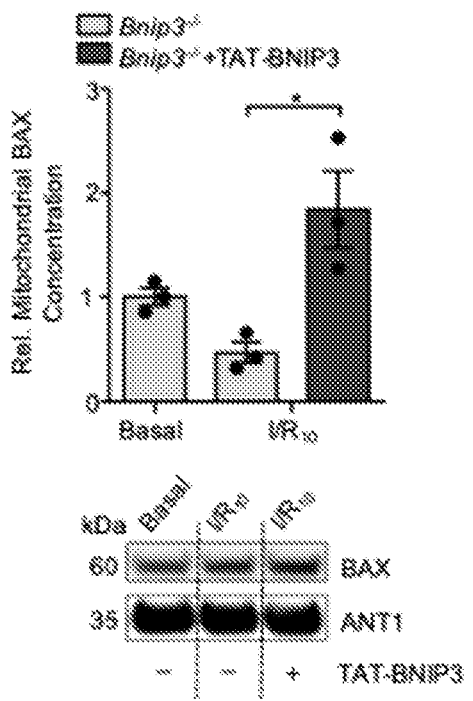

FIG. 1N
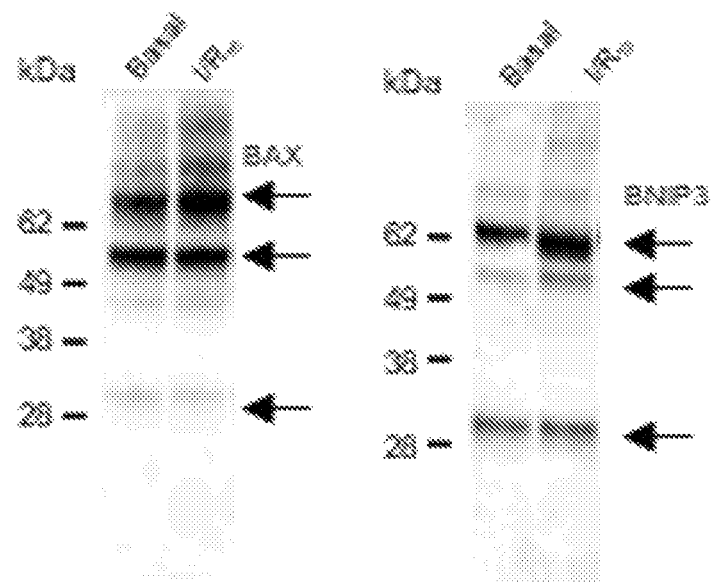
FIG. 1O
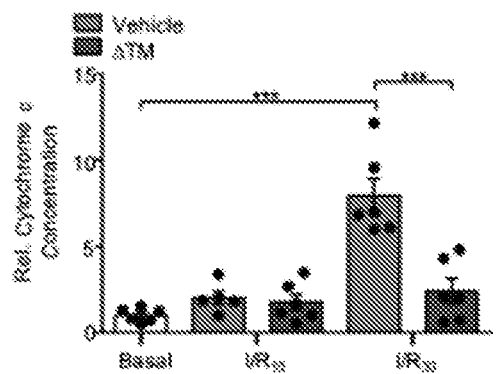

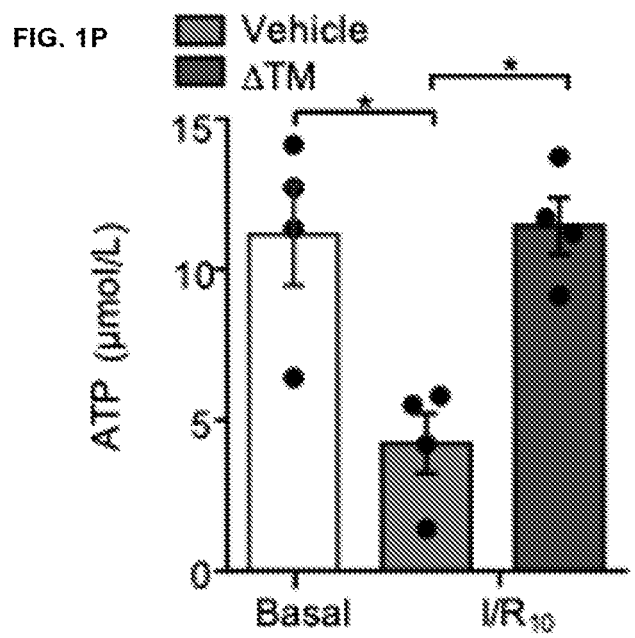
FIG. 1P
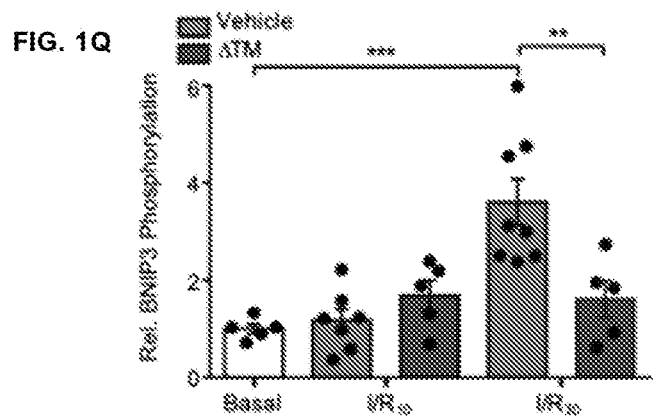
FIG. 1Q
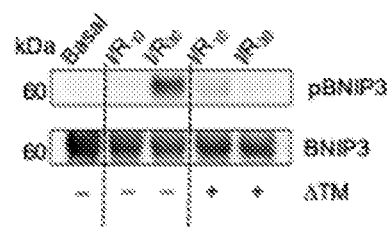

BNIP3

BNIP3  N- terminus (1-20):
MSQSGEENLQGSWVELHFSN

```
Mus musculus    1   MSQSG      -----EENLQGSWVELHFSN-GNGSSVPASVSIYNGDMEKILLDA    44
Homo sapiens   66   MSQNGAPGMQEESLQGSWVELHFSNNGNGGSSVPASVSIYNGDMEKILLDA  115

Mus musculus   45   QHESGRSSSKSSHCDSPPRSQTPQDTNRA--EIDSHSFGEKNSTLSEEDYI   93
Homo sapiens  116   QHESGRSSSKSSHCDSPPRSQTPQDTNRASETDTHSIGEKNSSQSEEDDI  165

Mus musculus   94   ERRREVESILKKNSDWIWDW SSRPENIPPKEFLFKHPKRTATLSMRNTSVM  143
Homo sapiens  166   ERRKEVESILKKNSDWIWDWSSRPENIPPKEFLFKHPKRTATLSMRNTSV  225

Mus musculus  144   KKGGIFSADFLKVFLPSLLLSHLLAIGLGIYIGRRLTTSTSTF         187
Homo sapiens  226   MKKGGIFSAEFLKVFLPSLLLSHLLAIGLGIYIGRRLTTSTSTF        259
```

FIG. 3G

WVELHFFN

Additional Preventative treatment data

Pre-treatment - D7
D5   -D3   -D1 D0
5' pre ischemia n=3

Pre-treatment
- D7   -D5   -D3   -D1 n=5

Effect size of 40% vs. untreated
control manifested
Recovery of LV function

Pre- and post-treatment: 5' before reperfusion and on d1, d3, d5, d7 of reperfusion Echocardiography:    pre and post infarction on d1, d3, d5, d7

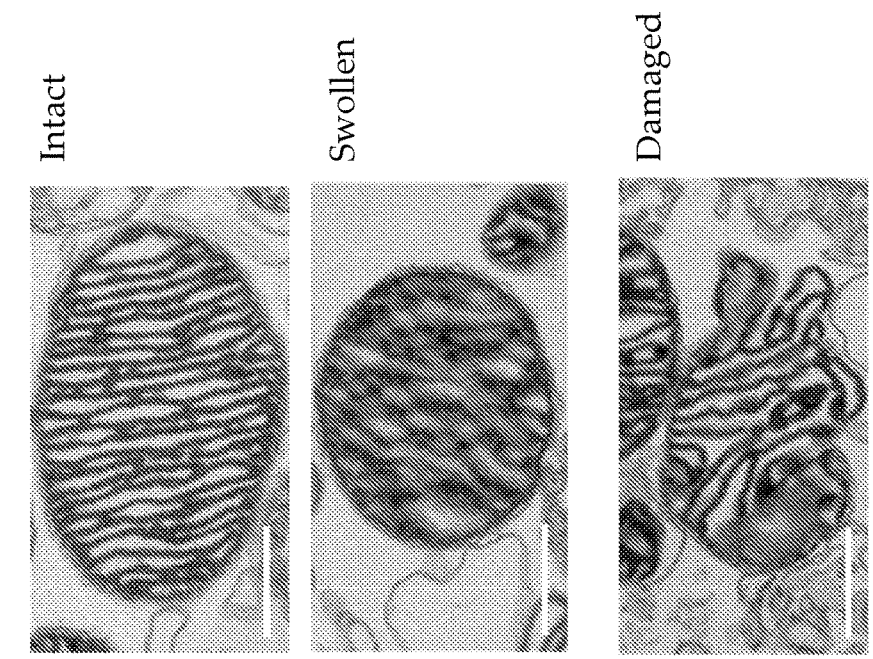
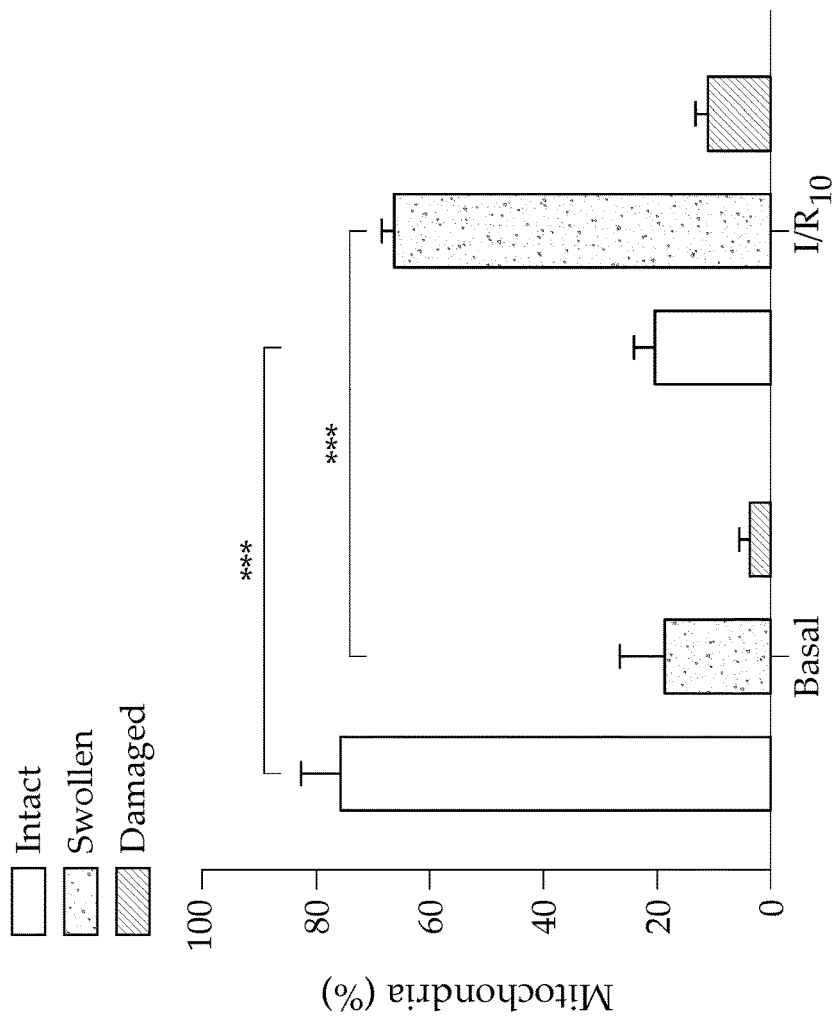
FIG. 8B

Mouse heart

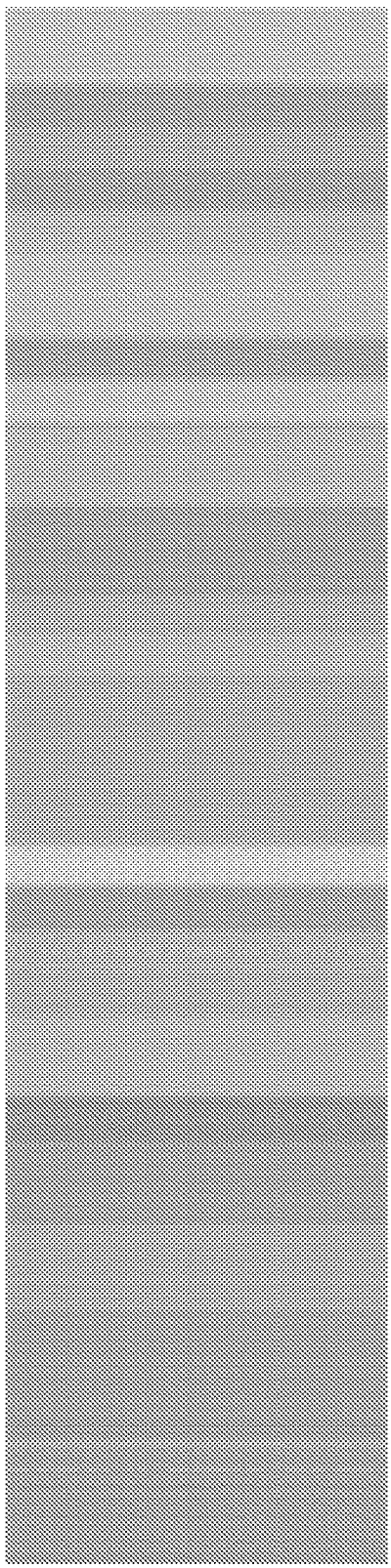

MSQSGEENLQGSWVELHAAA
MSQSGEENLQGSWVELAAAN
MSQSGEENLQGSWVEAAASN
MSQSGEENLQGSWVAAAFSN
MSQSGEENLQGSWAAAHFSN
MSQSGEENLQGSAAALHFSN
MSQSGEENLQGAAAELHFSN
MSQSGEENLQAAAVELHFSN
MSQSGEENLAAAWVELHFSN
MSQSGEENAAASWVELHFSN
MSQSGEEAAAGSWVELHFSN
MSQSGEAAAQGSWVELHFSN
MSQSGAAALQGSWVELHFSN
MSQSAAANLQGSWVELHFSN
MSQAAAENLQGSWVELHFSN
MSAAAEENLQGSWVELHFSN
MAAASEENLQGSWVELHFSN
AAASGEENLQGSWVELHFSN
MSQSGEENLQGSWVELHFAA
MSQSGEENLQGSWVELHAAN
MSQSGEENLQGSWVELAASN
MSQSGEENLQGSWVEAAFSN
MSQSGEENLQGSWVAAHFSN
MSQSGEENLQGSWAALHFSN
MSQSGEENLQGSAAELHFSN
MSQSGEENLQGAAVELHFSN
MSQSGEENLQAAWVELHFSN
MSQSGEENLAASWVELHFSN
MSQSGEENAAGSWVELHFSN
MSQSGEEAAQGSWVELHFSN
MSQSGEAALQGSWVELHFSN
MSQSGAANLQGSWVELHFSN
MSQSAAENLQGSWVELHFSN
MSQAAEENLQGSWVELHFSN
MSAAGEENLQGSWVELHFSN
MAASGEENLQGSWVELHFSN
AAQSGEENLQGSWVELHFSN

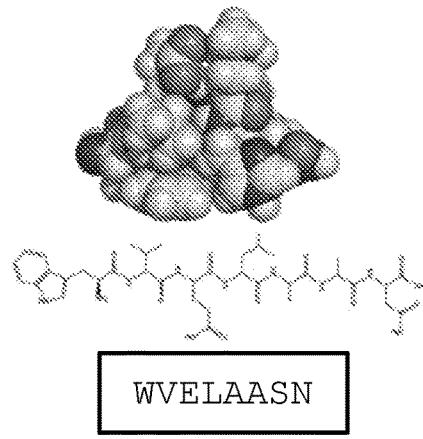

WVELAASN

| Peak # | RT [min] | Width [min] | Area | Area % |
|---|---|---|---|---|
| 1 | 1.541 | 0.0 | 65.8 | 0.5 |
| 2 | 1.613 | 0.1 | 13430.7 | 95.8 |
| 3 | 1.786 | 0.1 | 324.8 | 2.3 |
| 4 | 2.286 | 0.1 | 37.9 | 0.3 |
| 5 | 2.816 | 0.0 | 135.7 | 1.0 |
| 6 | 3.181 | 0.1 | 24.3 | 0.2 |

| Peak # | RT [min] | Width [min] | Area | Area % |
|---|---|---|---|---|
| 1 | 1.309 | 0.0 | 98.4 | 1.1 |
| 2 | 1.378 | 0.1 | 8180.7 | 92.9 |
| 3 | 1.497 | 0.1 | 371.2 | 4.2 |
| 4 | 2.454 | 0.1 | 32.3 | 0.4 |
| 5 | 2.879 | 0.0 | 103.1 | 1.2 |
| 6 | 3.219 | 0.1 | 19.7 | 0.2 |

Confocal microscopy. Magnification: 40x. Scale bar: 20μm. 10 μM DOX, 20 μM TAT-WVELHFFN, 22 h.

Data derives from 3-4 independent experiments. Data are mean ± SD, Shapiro-Wilk normality test passed, ordinary one-way ANOVA, p ≤ 0.01, *p ≤ 0.001.

Fig. 14A

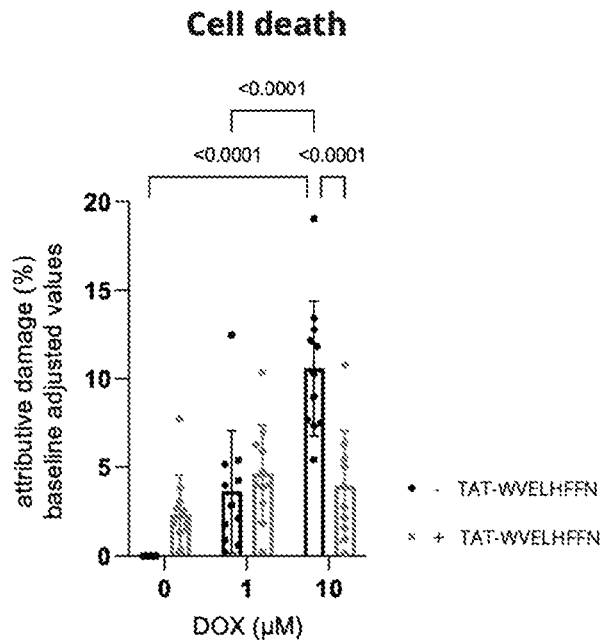

Incubation. 4h. TAT-WVELHFFN ~ 1.5 pM. Data derives from 11 independent experiments from 2 individual donors. Data are mean ± SD, Shapiro-Wilk normality test passed, two-way ANOVA.

Fig. 14B

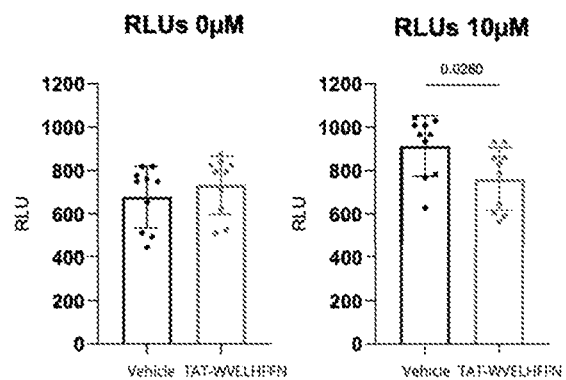

RLU for baseline-adjusted values.

Incubation: 4h. TAT-WVELHFFN ~ 1.5 pM. Data derives from 11 independent experiments from 2 individual donors. Data are mean ± SD, Shapiro-Wilk normality test passed, two-way ANOVA.

TAT-WVELHFFN prevents mPTP-opening

Representative images of donor-HCM. Incubation: 4h DOX 10µM. Magnification: 40x. Scale bar: 20µm.

n=6 independent experiments of two different human donors. Shapiro-Wilk normality test passed, two-way ANOVA.

Incubation: 22h DOX 10μM. n=5 independent experiments

TAT-WVELHFFN reduces formation of ROS

Representative images of donor-HCM. Incubation: 4h DOX 10μM. Magnification: 40x. Scale bar: 20μm n=12/8 independent experiments of two different donors.
Shapiro-Wilk normality test passed, ordinary one-way ANOVA,
*p ≤ 0.05.

Fig. 25 | BAX peptides

Peptide Sequences

```
MDGSGEQLGSGGPTSSEQIM
SEQIMKTGAFLLQGFIQDRA
AGRMAGETPELTLEQPPQDA
DASTKKLSECLRRIGDELDS
ELDSNMELQRMIADVDTDSP
TDSPREVFFRVAADMFADGN
WGRVVALFYFASKLVLKALC
VPELIRTIMGWTLDFLRERL
RLLVWIQDQGGWEGLLSYFG
TWQTVTIFVAGVLTASLTIW
MFADGNFNWGRVVALFYFAS
LVWIQDQGGWEGLLSYFGTP
ASTKKLSECLRRIGDELDSN
```

Fig. 26 | BNIP3 peptides truncated

Peptide sequences

| | | |
|---|---|---|
| MSQSGEENLQGSWVELHFSN | N | M |
| QG | SN | MS |
| LQGS | FSN | MSQ |
| NLQGSW | HFSN | MSQS |
| ENLQGSWV | LHFSN | MSQSG |
| EENLQGSWVE | ELHFSN | MSQSGE |
| GEENLQGSWVEL | VELHFSN | MSQSGEE |
| SGEENLQGSWVELH | WVELHFSN | MSQSGEEN |
| QSGEENLQGSWVELHF | SWVELHFSN | MSQSGEENL |
| SQSGEENLQGSWVELHFS | GSWVELHFSN | MSQSGEENLQ |
| | QGSWVELHFSN | MSQSGEENLQG |
| | LQGSWVELHFSN | MSQSGEENLQGS |
| | NLQGSWVELHFSN | MSQSGEENLQGSW |
| | ENLQGSWVELHFSN | MSQSGEENLQGSWV |
| | EENLQGSWVELHFSN | MSQSGEENLQGSWVE |
| | GEENLQGSWVELHFSN | MSQSGEENLQGSWVEL |
| | SGEENLQGSWVELHFSN | MSQSGEENLQGSWVELH |
| | QSGEENLQGSWVELHFSN | MSQSGEENLQGSWVELHF |
| | SQSGEENLQGSWVELHFSN | MSQSGEENLQGSWVELHFS |

Fig. 27A  BNIP3 peptides substituted

Peptide sequences

| | | | | |
|---|---|---|---|---|
| MSQSGEENLQG SWVALHFSN | MSQSGERNLQG SWVELHFSN | MSQSKEENLQG SWVELHFSN | MSQSGEENCQG SWVELHFSN | MSQSGEENLQG SWVELHFSS |
| MSQSGEENLQG SWVCLHFSN | MSQSGESNLQG SWVELHFSN | MSQSLEENLQG SWVELHFSN | MSQSGEENDQG SWVELHFSN | MSQSGEENLQG SWVELHFST |
| MSQSGEENLQG SWVDLHFSN | MSQSGETNLQG SWVELHFSN | MSQSMEENLQG SWVELHFSN | MSQSGEENEQG SWVELHFSN | MSQSGEENLQG SWVELHFSV |
| MSQSGEENLQG SWVFLHFSN | MSQSGEVNLQG SWVELHFSN | MSQSNEENLQG SWVELHFSN | MSQSGEENFQG SWVELHFSN | MSQSGEENLQG SWVELHFSW |
| MSQSGEENLQG SWVGLHFSN | MSQSGEWNLQG SWVELHFSN | MSQSPEENLQG SWVELHFSN | MSQSGEENGQG SWVELHFSN | MSQSGEENLQG SWVELHFSY |
| MSQSGEENLQG SWVHLHFSN | MSQSGEYNLQG SWVELHFSN | MSQSQEENLQG SWVELHFSN | MSQSGEENHQG SWVELHFSN | MSQSGEEALQG SWVELHFSN |
| MSQSGEENLQG SWVILHFSN | MSQSGEENLQG SWVELHASN | MSQSREENLQG SWVELHFSN | MSQSGEENIQG SWVELHFSN | MSQSGEECLQG SWVELHFSN |
| MSQSGEENLQG SWVKLHFSN | MSQSGEENLQG SWVELHCSN | MSQSSEENLQG SWVELHFSN | MSQSGEENKQG SWVELHFSN | MSQSGEEDLQG SWVELHFSN |
| MSQSGEENLQG SWVLLHFSN | MSQSGEENLQG SWVELHDSN | MSQSTEENLQG SWVELHFSN | MSQSGEENMQG SWVELHFSN | MSQSGEEELQG SWVELHFSN |
| MSQSGEENLQG SWVMLHFSN | MSQSGEENLQG SWVELHESN | MSQSVEENLQG SWVELHFSN | MSQSGEENNQG SWVELHFSN | MSQSGEEFLQG SWVELHFSN |
| MSQSGEENLQG SWVNLHFSN | MSQSGEENLQG SWVELHGSN | MSQSWEENLQG SWVELHFSN | MSQSGEENPQG SWVELHFSN | MSQSGEEGLQG SWVELHFSN |
| MSQSGEENLQG SWVPLHFSN | MSQSGEENLQG SWVELHHSN | MSQSYEENLQG SWVELHFSN | MSQSGEENQQG SWVELHFSN | MSQSGEEHLQG SWVELHFSN |
| MSQSGEENLQG SWVQLHFSN | MSQSGEENLQG SWVELHISN | MSQSGEENLQG SWVELAFSN | MSQSGEENRQG SWVELHFSN | MSQSGEEILQG SWVELHFSN |
| MSQSGEENLQG SWVRLHFSN | MSQSGEENLQG SWVELHKSN | MSQSGEENLQG SWVELCFSN | MSQSGEENSQG SWVELHFSN | MSQSGEEKLQG SWVELHFSN |

Fig. 27B

| | | | | |
|---|---|---|---|---|
| MSQSGEENLQG SWVSLHFSN | MSQSGEENLQG SWVELHLSN | MSQSGEENLQG SWVELDFSN | MSQSGEENTQG SWVELHFSN | MSQSGEELLQG SWVELHFSN |
| MSQSGEENLQG SWVTLHFSN | MSQSGEENLQG SWVELHMSN | MSQSGEENLQG SWVELEFSN | MSQSGEENVQG SWVELHFSN | MSQSGEEMLQG SWVELHFSN |
| MSQSGEENLQG SWVVLHFSN | MSQSGEENLQG SWVELHNSN | MSQSGEENLQG SWVELFFSN | MSQSGEENWQG SWVELHFSN | MSQSGEEPLQG SWVELHFSN |
| MSQSGEENLQG SWVWLHFSN | MSQSGEENLQG SWVELHPSN | MSQSGEENLQG SWVELGFSN | MSQSGEENYQG SWVELHFSN | MSQSGEEQLQG SWVELHFSN |
| MSQSGEENLQG SWVYLHFSN | MSQSGEENLQG SWVELHQSN | MSQSGEENLQG SWVELIFSN | ASQSGEENLQG SWVELHFSN | MSQSGEERLQG SWVELHFSN |
| MSQSGAENLQG SWVELHFSN | MSQSGEENLQG SWVELHRSN | MSQSGEENLQG SWVELKFSN | CSQSGEENLQG SWVELHFSN | MSQSGEESLQG SWVELHFSN |
| MSQSGCENLQG SWVELHFSN | MSQSGEENLQG SWVELHSSN | MSQSGEENLQG SWVELLFSN | DSQSGEENLQG SWVELHFSN | MSQSGEETLQG SWVELHFSN |
| MSQSGDENLQG SWVELHFSN | MSQSGEENLQG SWVELHTSN | MSQSGEENLQG SWVELMFSN | ESQSGEENLQG SWVELHFSN | MSQSGEEVLQG SWVELHFSN |
| MSQSGFENLQG SWVELHFSN | MSQSGEENLQG SWVELHVSN | MSQSGEENLQG SWVELNFSN | FSQSGEENLQG SWVELHFSN | MSQSGEEWLQG SWVELHFSN |
| MSQSGGENLQG SWVELHFSN | MSQSGEENLQG SWVELHWSN | MSQSGEENLQG SWVELPFSN | GSQSGEENLQG SWVELHFSN | MSQSGEEYLQG SWVELHFSN |
| MSQSGHENLQG SWVELHFSN | MSQSGEENLQG SWVELHYSN | MSQSGEENLQG SWVELQFSN | HSQSGEENLQG SWVELHFSN | MSQSGEENLAG SWVELHFSN |
| MSQSGIENLQG SWVELHFSN | MSQSGEENLQA SWVELHFSN | MSQSGEENLQG SWVELRFSN | ISQSGEENLQG SWVELHFSN | MSQSGEENLCG SWVELHFSN |
| MSQSGKENLQG SWVELHFSN | MSQSGEENLQC SWVELHFSN | MSQSGEENLQG SWVELSFSN | KSQSGEENLQG SWVELHFSN | MSQSGEENLDG SWVELHFSN |
| MSQSGLENLQG SWVELHFSN | MSQSGEENLQD SWVELHFSN | MSQSGEENLQG SWVELTFSN | LSQSGEENLQG SWVELHFSN | MSQSGEENLEG SWVELHFSN |
| MSQSGMENLQG SWVELHFSN | MSQSGEENLQE SWVELHFSN | MSQSGEENLQG SWVELVFSN | NSQSGEENLQG SWVELHFSN | MSQSGEENLFG SWVELHFSN |
| MSQSGNENLQG SWVELHFSN | MSQSGEENLQF SWVELHFSN | MSQSGEENLQG SWVELWFSN | PSQSGEENLQG SWVELHFSN | MSQSGEENLGG SWVELHFSN |
| MSQSGPENLQG SWVELHFSN | MSQSGEENLQH SWVELHFSN | MSQSGEENLQG SWVELYFSN | QSQSGEENLQG SWVELHFSN | MSQSGEENLHG SWVELHFSN |

Fig. 27C

| | | | | |
|---|---|---|---|---|
| MSQSGQENLQG SWVELHFSN | MSQSGEENLQI SWVELHFSN | MSQSGEENLQG SWVEAHFSN | RSQSGEENLQG SWVELHFSN | MSQSGEENLIG SWVELHFSN |
| MSQSGRENLQG SWVELHFSN | MSQSGEENLQK SWVELHFSN | MSQSGEENLQG SWVECHFSN | SSQSGEENLQG SWVELHFSN | MSQSGEENLKG SWVELHFSN |
| MSQSGSENLQG SWVELHFSN | MSQSGEENLQL SWVELHFSN | MSQSGEENLQG SWVEDHFSN | TSQSGEENLQG SWVELHFSN | MSQSGEENLLG SWVELHFSN |
| MSQSGTENLQG SWVELHFSN | MSQSGEENLQM SWVELHFSN | MSQSGEENLQG SWVEEHFSN | VSQSGEENLQG SWVELHFSN | MSQSGEENLMG SWVELHFSN |
| MSQSGVENLQG SWVELHFSN | MSQSGEENLQN SWVELHFSN | MSQSGEENLQG SWVEFHFSN | WSQSGEENLQG SWVELHFSN | MSQSGEENLNG SWVELHFSN |
| MSQSGWENLQG SWVELHFSN | MSQSGEENLQP SWVELHFSN | MSQSGEENLQG SWVEGHFSN | YSQSGEENLQG SWVELHFSN | MSQSGEENLPG SWVELHFSN |
| MSQSGYENLQG SWVELHFSN | MSQSGEENLQQ SWVELHFSN | MSQSGEENLQG SWVEHHFSN | MSQSGEENLQG SWVELHFSA | MSQSGEENLRG SWVELHFSN |
| MSQSGEANLQG SWVELHFSN | MSQSGEENLQR SWVELHFSN | MSQSGEENLQG SWVEIHFSN | MSQSGEENLQG SWVELHFSC | MSQSGEENLSG SWVELHFSN |
| MSQSGECNLQG SWVELHFSN | MSQSGEENLQS SWVELHFSN | MSQSGEENLQG SWVEKHFSN | MSQSGEENLQG SWVELHFSD | MSQSGEENLTG SWVELHFSN |
| MSQSGEDNLQG SWVELHFSN | MSQSGEENLQT SWVELHFSN | MSQSGEENLQG SWVEMHFSN | MSQSGEENLQG SWVELHFSE | MSQSGEENLVG SWVELHFSN |
| MSQSGEFNLQG SWVELHFSN | MSQSGEENLQV SWVELHFSN | MSQSGEENLQG SWVENHFSN | MSQSGEENLQG SWVELHFSF | MSQSGEENLWG SWVELHFSN |
| MSQSGEGNLQG SWVELHFSN | MSQSGEENLQW SWVELHFSN | MSQSGEENLQG SWVEPHFSN | MSQSGEENLQG SWVELHFSG | MSQSGEENLYG SWVELHFSN |
| MSQSGEHNLQG SWVELHFSN | MSQSGEENLQY SWVELHFSN | MSQSGEENLQG SWVEQHFSN | MSQSGEENLQG SWVELHFSH | MSASGEENLQG SWVELHFSN |
| MSQSGEINLQG SWVELHFSN | MSQSAEENLQG SWVELHFSN | MSQSGEENLQG SWVERHFSN | MSQSGEENLQG SWVELHFSI | MSCSGEENLQG SWVELHFSN |
| MSQSGEKNLQG SWVELHFSN | MSQSCEENLQG SWVELHFSN | MSQSGEENLQG SWVESHFSN | MSQSGEENLQG SWVELHFSK | MSDSGEENLQG SWVELHFSN |
| MSQSGELNLQG SWVELHFSN | MSQSDEENLQG SWVELHFSN | MSQSGEENLQG SWVETHFSN | MSQSGEENLQG SWVELHFSL | MSESGEENLQG SWVELHFSN |
| MSQSGEMNLQG SWVELHFSN | MSQSEEENLQG SWVELHFSN | MSQSGEENLQG SWVEVHFSN | MSQSGEENLQG SWVELHFSM | MSFSGEENLQG SWVELHFSN |

Fig. 27D

| | | | | |
|---|---|---|---|---|
| MSQSGENNLQG SWVELHFSN | MSQSFEENLQG SWVELHFSN | MSQSGEENLQG SWVEWHFSN | MSQSGEENLQG SWVELHFSP | MSGSGEENLQG SWVELHFSN |
| MSQSGEPNLQG SWVELHFSN | MSQSHEENLQG SWVELHFSN | MSQSGEENLQG SWVEYHFSN | MSQSGEENLQG SWVELHFSQ | MSHSGEENLQG SWVELHFSN |
| MSQSGEQNLQG SWVELHFSN | MSQSIEENLQG SWVELHFSN | MSQSGEENAQG SWVELHFSN | MSQSGEENLQG SWVELHFSR | MSISGEENLQG SWVELHFSN |

| | | | | |
|---|---|---|---|---|
| MSKSGEENLQG SWVELHFSN | MSQSGEENLQG TWVELHFSN | MDQSGEENLQG SWVELHFSN | MSQKGEENLQG SWVELHFSN | MSQSGEENLQG SWRELHFSN |
| MSLSGEENLQG SWVELHFSN | MSQSGEENLQG VWVELHFSN | MEQSGEENLQG SWVELHFSN | MSQLGEENLQG SWVELHFSN | MSQSGEENLQG SWSELHFSN |
| MSMSGEENLQG SWVELHFSN | MSQSGEENLQG WWVELHFSN | MFQSGEENLQG SWVELHFSN | MSQMGEENLQG SWVELHFSN | MSQSGEENLQG SWTELHFSN |
| MSNSGEENLQG SWVELHFSN | MSQSGEENLQG YWVELHFSN | MGQSGEENLQG SWVELHFSN | MSQNGEENLQG SWVELHFSN | MSQSGEENLQG SWWELHFSN |
| MSPSGEENLQG SWVELHFSN | MSQSGEENLQG SWVELHFCN | MHQSGEENLQG SWVELHFSN | MSQPGEENLQG SWVELHFSN | MSQSGEENLQG SWYELHFSN |
| MSRSGEENLQG SWVELHFSN | MSQSGEENLQG SWVELHFDN | MIQSGEENLQG SWVELHFSN | MSQQGEENLQG SWVELHFSN | MSQSGEENLQG SAVELHFSN |
| MSSSGEENLQG SWVELHFSN | MSQSGEENLQG SWVELHFEN | MKQSGEENLQG SWVELHFSN | MSQRGEENLQG SWVELHFSN | MSQSGEENLQG SCVELHFSN |
| MSVSGEENLQG SWVELHFSN | MSQSGEENLQG SWVELHFFN | MLQSGEENLQG SWVELHFSN | MSQTGEENLQG SWVELHFSN | MSQSGEENLQG SDVELHFSN |
| MSWSGEENLQG SWVELHFSN | MSQSGEENLQG SWVELHFGN | MMQSGEENLQG SWVELHFSN | MSQVGEENLQG SWVELHFSN | MSQSGEENLQG SEVELHFSN |
| MSYSGEENLQG SWVELHFSN | MSQSGEENLQG SWVELHFHN | MNQSGEENLQG SWVELHFSN | MSQWGEENLQG SWVELHFSN | MSQSGEENLQG SFVELHFSN |
| MSQSGEENLQG AWVELHFSN | MSQSGEENLQG SWVELHFIN | MPQSGEENLQG SWVELHFSN | MSQYGEENLQG SWVELHFSN | MSQSGEENLQG SGVELHFSN |
| MSQSGEENLQG CWVELHFSN | MSQSGEENLQG SWVELHFKN | MQQSGEENLQG SWVELHFSN | MSQSGEENLQG SWAELHFSN | MSQSGEENLQG SHVELHFSN |
| MSQSGEENLQG DWVELHFSN | MSQSGEENLQG SWVELHFLN | MRQSGEENLQG SWVELHFSN | MSQSGEENLQG SWCELHFSN | MSQSGEENLQG SIVELHFSN |

Fig. 27E

| | | | | |
|---|---|---|---|---|
| MSQSGEENLQG EWVELHFSN | MSQSGEENLQG SWVELHFMN | MTQSGEENLQG SWVELHFSN | MSQSGEENLQG SWDELHFSN | MSQSGEENLQG SKVELHFSN |
| MSQSGEENLQG FWVELHFSN | MSQSGEENLQG SWVELHFNN | MVQSGEENLQG SWVELHFSN | MSQSGEENLQG SWEELHFSN | MSQSGEENLQG SLVELHFSN |
| MSQSGEENLQG GWVELHFSN | MSQSGEENLQG SWVELHFPN | MWQSGEENLQG SWVELHFSN | MSQSGEENLQG SWFELHFSN | MSQSGEENLQG SMVELHFSN |
| MSQSGEENLQG HWVELHFSN | MSQSGEENLQG SWVELHFQN | MYQSGEENLQG SWVELHFSN | MSQSGEENLQG SWGELHFSN | MSQSGEENLQG SNVELHFSN |
| MSQSGEENLQG IWVELHFSN | MSQSGEENLQG SWVELHFRN | MSQAGEENLQG SWVELHFSN | MSQSGEENLQG SWHELHFSN | MSQSGEENLQG SPVELHFSN |
| MSQSGEENLQG KWVELHFSN | MSQSGEENLQG SWVELHFTN | MSQCGEENLQG SWVELHFSN | MSQSGEENLQG SWIELHFSN | MSQSGEENLQG SQVELHFSN |
| MSQSGEENLQG LWVELHFSN | MSQSGEENLQG SWVELHFVN | MSQDGEENLQG SWVELHFSN | MSQSGEENLQG SWKELHFSN | MSQSGEENLQG SRVELHFSN |
| MSQSGEENLQG MWVELHFSN | MSQSGEENLQG SWVELHFWN | MSQEGEENLQG SWVELHFSN | MSQSGEENLQG SWLELHFSN | MSQSGEENLQG SSVELHFSN |
| MSQSGEENLQG NWVELHFSN | MSQSGEENLQG SWVELHFYN | MSQFGEENLQG SWVELHFSN | MSQSGEENLQG SWMELHFSN | |
| MSQSGEENLQG PWVELHFSN | MSQSGEENLQG SWVELHFAN | MSQGGEENLQG SWVELHFSN | MSQSGEENLQG SWNELHFSN | |
| MSQSGEENLQG QWVELHFSN | MAQSGEENLQG SWVELHFSN | MSQHGEENLQG SWVELHFSN | MSQSGEENLQG SWPELHFSN | |
| MSQSGEENLQG RWVELHFSN | MCQSGEENLQG SWVELHFSN | MSQIGEENLQG SWVELHFSN | MSQSGEENLQG SWQELHFSN | | ic

AMELIORATION AND TREATMENT OF INFARCTION DAMAGE WITH A POLYPEPTIDE SEGEMENT OF BNIP3

CROSS-REFERENCE TO RELATED APPLICATIONS

This document claims the benefit of priority to U.S. Provisional Application Ser. No. 63/276,028, filed Nov. 5, 2021, the contents of which are hereby incorporated by reference in their entirety, and this document is a continuation of PCI Application Number PCT/EP2022/080979, filed Nov. 7, 2022, the contents of which are hereby incorporated by reference in their entirety.

SEQUENCE LISTING

The instant application contains a Sequence Listing which has been submitted electronically in XML file format and is hereby incorporated by reference in its entirety. Said XML copy, created on Jan. 12, 2024, is named HNM_001US2_SL.xml and is 435,340 bytes in size.

BACKGROUND

Side effects are an ongoing concern in the broad field of patient intervention. A recurrent concern is that an intervention may inadvertently or secondarily harm a patient by triggering secondary responses in a patient that are contradictory to the intended effect.

These secondary responses are particularly problematic if they result in cell signaling that may lead to initiation of cell death, A number of interventions independently pose this risk. These range from chemotherapy intended to target proliferating cancer cells, incidental trauma associated with surgery, peripheral nerve injury, compression of parts of the body that causes muscle breakdown, burn injury, and wasting illness such as or associated with, for example, cancer, pulmonary, neurological and hematological diseases or re-oxygenation of the heart muscle or brain tissue of an individual suffering from a circulatory disruption such as a heart attack or stroke, among others.

A common theme among these interventions is that they risk initiating any number of programmed cell death pathways in cells of the individual intended to be treated. These cell death pathways are often mitochondrially triggered or comprise a mitochondrial component, such as aberrations in calcium ion or reactive oxygen species accumulation, changes in inner membrane polarization, pore formation in the outer membrane, release of cytochrome c, mitochondrial swelling or even lysis.

Treating acute circulatory disruptions, for example, presents a number of challenges. During circulatory disruption, cells, cell populations, tissue or organs (collectively, impacted areas') are starved of oxygen. This has a great negative impact upon cellular respiration at the mitochondria. However, rapid reintroduction of oxygen into an impacted area triggers a number of responses in the mitochondria, such as disintegration of mitochondrial membranes, which counterintuitively leads to initiation of cell death pathway signaling that manifests cardiac dysfunction.

Similarly, chemotherapy targeted towards selective killing of malignancy-driving cells or of tumors generally is similarly problematic. Either the targeted cells themselves or other cells in the patient may respond to the treatment by initiating a cell death pathway that involves changes in mitochondrial status, such as mitochondrial disintegration. This may often signal a similar response in related cells, which may exacerbate the detrimental side effects of a chemotherapy or even limit its efficacy by preventing the use of chemotherapeutic at a level sufficient to target the malignancy or harmful cells.

Disintegration of mitochondrial membranes is implicated as a final cell death pathway (Karch and Molkentin, 2015; Murphy et al., 2016; Hendgen-Cotta et al. 2019). Loss of the impermeability of the mitochondrial inner membrane (MIM) to small solutes causes depolarization ($\Delta\psi m$) with cessation of ATP synthesis, mitochondrial swelling followed by membrane rupture and necrotic cell death (Bernardi et al., 2015; Kwong and Molkentin, 2015; Galluzzi et al., 2018). Pore formation in the outer mitochondrial membrane (MOMP) facilitates cytosolic release of apoptogens like cytochrome c, apoptosis inducing factor (AIF) and endonuclease G leading to apoptosis (Ong and Gustafsson, 2012). Accordingly, damaged mitochondria contribute to various pathologies including neurological and cardiovascular disorders (Hendgen-Cotta et al., 2008; Kloner et al., 2017; Nunnari and Suomalainen, 2012; Fuchs and Steller, 2011). Prior research on reducing mitochondrial-driven cell death in humans has largely focused on mitochondrial proteins or phospholipids, e.g., cyclophilin D and cardiolipin. However, this requires a direct interaction of therapeutic agents with mitochondria (Atar et al., 2015; Cung et al., 2015; Gibson et al., 2016; Schaller et al., 2010). Despite generally promising experimental evidence, such agents have failed to reduce cell death (Atar et al., 2015; Cung et al., 2015; Gibson et al., 2016; Hausenloy et al., 2017; Schaller et al., 2010). Deathly mitochondrial pathways are proposed to be, inter alia, regulated by BCL-2 family members (Galluzzi et al., 2018), with the functional importance of BAX being confirmed as the paramount effector (Garner et al., 2019; Kalkavan and Green, 2018; Karch and Molkentin, 2015; Wei et al., 2001; Whelan et al., 2012). The precise molecular activator and the mechanisms governing BAX translocation to mitochondria, its activation, mitochondrial interaction and pore formation in vivo are largely unknown (Luna-Vargas and Chipuk, 2016).

Evidence from in vitro and ex vivo experiments suggests a pathogenic role for the BH3-only protein BNIP3, being primarily localized to mitochondria, in mitochondrial perturbation by homodimerization (Diwan et al., 2007; Gustafsson, 2011; Hamacher-Brady et al., 2007; Karch and Molkentin, 2015; Kubasiak et al., 2002; Kubli et al., 2007, Regula et al., 2002; Vande Velde et al., 2000).

Recent findings that BNIP3 is able to interact with recombinant and mitochondrial BAX in vitro, whose binding seems to be important for their insertion into the MOM (Hendgen-Cotta et al., 2017), suggest the possibility of BNIP3 as a regulator of BAX. That may signify BNIP3/BAX an important potential cytosolic therapeutic target for mitochondria and cell protection. Elucidating the BNIP3 activity on cell death remains challenging because the structural basis of BNIP3 function is incomplete. Accordingly, the precise mechanisms of the detrimental functionality of BNIP3 on BAX and mitochondrial-driven cell death and to develop a therapy option was investigated, with the goal of understanding mitochondrial signaling as well as understanding approaches to modulating the impact of treatments on mitochondrial-induced cell death signaling to prevent mitochondrial damage with down-stream signaling that leads to both cell dysfunction and cell death and may manifest cardiac dysfunction, cardiotoxicity and cardiac wasting.

SUMMARY

Disclosed herein are methods, compositions, compositions for use and treatment regimens for ameliorating a side effect of an intervention. Some such are methods, compositions, compositions for use and treatment regimens comprise administering a mitochondrial protecting or stabilizing agent such as a mitochondrial interaction and import inhibitor. Without being bound by theory, such a treatment may decrease cell death signaling arising from destabilized mitochondria, thereby reducing cell death signaling that may otherwise accompany an intervention. Through practice of the disclosure herein, one is able to reduce the harm resulting from the methods, compositions, compositions for use and treatment regimens of an intervention.

A number of exemplary intervention events are consistent with the disclosure herein, Some intervention events comprise reoxygenation in response to a circulatory disruption so as to ameliorate infarction damage or risk of infarction damage, such as may occur pursuant to reoxygenation of oxygen starved tissue, such as may occur through application of a stent or other circulatory restorative procedure.

Additional intervention events comprise administration of a radiotherapeutic or a chemotherapeutic, such as a chemotherapeutic that targets a cancerous cell, cell population, or tumor Some such chemotherapeutics cause off-target or unintended cell death, such as cardiomyocyte death or dysfunction, which may lead to e.g. cardiac dysfunction or cardiac wasting (with or without chemotherapy or cancer therapy). Exemplary chemotherapeutics used to target cancer cells or tumors comprise, for example, a compound selected from the list consisting of an Alkylating agent, such as altretamine, busulfan carboplatin, carmustine, cisplatin, cyclophosphamide, dacarbazine, ifosfamide, lomustine, melphalan, temozolomide, trabectedin: Antimetabolite, such as 5-fluorouracil, 6-mercaptopurine, azacitidine, capecitabine, clofarabine, cytarabine, floxuridine, fludarabine, gemcitabine, methotrexate, pemetrexed, pentostatin, pralatrexate, trifluridine and tipiracil; a Plant alkyloid, such as, vincristine, vinblastine, vinorelbine, paclitaxel, docetaxel, etoposide, teniposide, irinotecan, topotecan; antibodies, such as HER2 inhibitors e.g. trastuzumab, pertuzumab, margetuximab, immune checkpoint inhibitors e.g. nivolumab (anti-PD-1), avelumab (anti-PD-L1), ipilimumab (anti-CTLA-4), relatlimab (anti-LAG-3); an anti-tumor agent, such as, daunorubicin, doxorubicin doxorubicin liposomal, epirubicin, idarubicin, and valrubicin. Exemplary chemotherapeutics include anthracyclines, such as daunorubicin, doxorubicin, doxorubicin liposomal, epirubicin, idarubicin, and valrubicin, for example doxorubicin.

Some mitochondrial stabilization factors, such as mitochondrial interaction and import inhibitors consistent with the disclosure herein inhibit or block BNIP3 activity. Mitochondrial indications beneficially impacted by inhibitors disclosed herein variously comprise at least one indication selected from the list comprising doxorubicin (DOX) cell death induction, mitochondrial membrane potential destabilization mitochondrial pore opening prevention, mitochondrial calcium ion overload prevention, mitochondrial ROS or accumulation prevention. Administration a mitochondrial stabilizer such as an interaction and import inhibitor may in various embodiments attenuate cardiomyocyte dysfunction, death or cardiotoxicity, inflammatory response, cardiac dysfunction or cardiac wasting, preserve cardiac function, increase mitochondrial fitness, preserve autophagic flux, or otherwise stabilize t mitochondrion so as to inhibit mitochondrion-mediated cell dysfunction and death signaling, and inflammatory response.

Compositions consistent with the disclosure herein may be contacted to an individual through a broad range of routes, such as ingestion, transdermal administration, or injection, among others.

Exemplary mitochondrial protection and/or stabilizing agents include mitochondrial interaction and import inhibitors such as BNIP3 fragments as disclosed herein or BAX fragments and other agents in the art.

Consistent with the above and elsewhere in the present disclosure, also disclosed herein are compositions for use in ameliorating a negative impact of a treatment. Some such compositions comprise oxygen or a chemotherapeutic, for example, and a mitochondrial protecting and/or stabilizing agent such as a mitochondrial import inhibitor.

Some such compositions and methods disclosed herein further comprise identifying a patient to which a mitochondrial protecting and/or stabilizing agent such as a mitochondrial interaction and import inhibitor is to be co-administered. A patient may be identified, most directly, as suffering from a circulatory disruption such as a heart attack or stroke. Such a patient may be subjected to a treatment to restore circulation and oxygen exposure to one or more tissues, and may be co-administered a mitochondrial protecting and/or stabilizing agent such as a mitochondrial interaction and import inhibitor pursuant to addressing the circulatory interruption, Such a treatment may comprise administration of a pharmaceutical, or subjecting the patient to a circulatory deblocking process such as application of a stent, or both.

A patient may further be identified by being a candidate for a cancer therapy such as chemotherapy or radiotherapy, for example, or may be an individual scheduled or expecting a surgical intervention, or a patient undergoing or having undergone such an intervention, such as an intervention that may result in patient bruising or blood clot formation. Additional patient identification criteria include status as a human patient having an elevated or substantial chronic infarction risk, such as a risk associated with a particular condition. Examples include, among others, Diabetes, Hypertension, Hyperlipidemia, Obesity, Genetic disorders, Stress, Smoking or smoking related lung or other tissue harm, heart disease, stroke, burn injury, crush injuries, peripheral nerve injuries, cardiac wasting, cachexia, sarcopenia and muscle wasting in e.g. cancer, pulmonary, neurological, viral, hematological, renal and hepatic disease or (auto)Inflammatory diseases. Additional patient identification criteria are contemplated and consistent with the disclosure herein.

Consistent with the above, disclosed herein are compositions and methods for the treatment and amelioration of intervention related cell death such as infarction damage, for example as occurs upon disruption of oxygenation of a cell population in a mammal. Through practice of the disclosure herein, one is able to reduce the harm resulting from infarction, through administration subsequent to, concurrent with, or prior to an infarction event or infarction intervention, of a medicament to regulate mitochondrial activity or viability, such as a composition comprising a mitochondrial interaction inhibitor or a mitochondrial translocation inhibitor, or other mitochondrial integrity-preserving agent.

A number of compositions are consistent with the disclosure herein. Exemplary compositions comprise a regulator of mitochondrial activity or viability. Some such regulators act by inhibiting mitochondrial membrane potential degradation, inhibiting cytochrome c release, or otherwise inhibiting mitochondrial degradation, such as mitochondrial degradation involved in or signaling cellular apoptosis, necrosis or other cell death signaling pathway. Some such regulators stabilize mitochondria, maintain mitochondria homeostasis, or inhibit mitochondrial interaction, or mitochondrial import or signaling.

Some such compositions effect this inhibition by blocking signaling to the mitochondria, for example, by inhibiting some or all interactions with or translocation across at least one mitochondrial membrane, or by inhibiting both interactions with and translocation actoss mitochondrial membranes. In some cases, the block is general, while in alternate cases a particular molecule, complex or signaling moiety is prevented from translocation across the membrane. For example, some compositions act by inhibiting protein complexes, such as BAX/BNIP3 complexes from protein-protein interactions, insertion into the membrane or translocation across the membrane.

Sone such compositions effect this inhibition by blocking signaling to the mitochondria, for example, by inhibiting formation or configurational changes in signaling or catalytic molecule complexes in the cytoplasm. In some cases, the block is general, while in alternate cases a particular molecule, complex or signaling moiety is prevented from forming or undergoing a conformational change. For example, some compositions act by inhibiting protein complexes, such as BAX/BNIP3 complexes from forming or from undergoing conformational changes, such as changes pursuant to or prerequisite for translocation across a membrane.

Exemplary compositions inhibit proteins or protein complexes through a number of mechanisms, for example by presenting a portion of one of the protein constituents, so as to interfere with a binding partner's ability to interact with a corresponding region of the native protein of which the inhibitor comprises a portion. The portion of the protein constituent may be wild-type or unaltered. Alternately, some compositions comprise a protein or polypeptide or peptide having a region that exhibits some identity to one of the protein constituents of a complex, but that has been modified at one or more regions, such as one or more amino acid residue positions, such as to improve stability, binding, complex inhibition, or other activity.

Some such compositions inhibit or influence BAX/BNIP3 complexes so as to impact mitochondrial interaction and translocation and comprise a segment of a complex constituent. Exemplary segments include BNIP3 segments, such as N-terminal segments of BNIP3, for example regions drawn from MSQSGEENLQGSWVELHFSN (SEQ ID NO: 1) of BNIP3, in particular WVELHFSN (SEQ ID NO: 2) of BNIP3. Some such composition present unmodified segments of BNIP3, while alternate compositions present modified BNIP3 segments, such as polypeptides or peptides comprising the sequence WVELHFFN (SEQ ID NO: 3), sometimes referred to as a PepB sequence herein.

Accordingly, disclosed herein are compositions and methods relating to reduction of infarction harm. Some such methods relate to ameliorating infarction or infarction damage to a subject at risk of infarction or an infarction damage risk event. Alternately or in combination, some such methods relate to ameliorating infarction damage to a subject suffering from or having experienced an infarction event such as an acute infarction event.

Similarly, disclosed herein are compositions and methods relating to reduction of harm arising from chemotherapy or radiotherapy. Some such methods relate to ameliorating secondary chemotherapy effects to a subject undergoing chemotherapy or radiotherapy, wherein the subject is at risk of infarction or an infarction damage risk event. Alternately or in combination, some such methods relate to ameliorating infarction damage to a subject suffering from or having experienced an infarction event such as an acute infarction event.

Said methods variously comprise administering a mitochondrial membrane interaction and translocation inhibitor, or other mitochondrial integrity-preserving agent. Some such mitochondrial membrane interaction and translocation inhibitors inhibit BAX translocation into or through a mitochondrial membrane. Some such mitochondrial membrane interaction and translocation inhibitors inhibit BNIP3 interaction with, translocation into or through a mitochondrial membrane, or both BAX and BNIP3 interaction with, translocation into or through a mitochondrial membrane.

The infarction damage risk event variously comprises a heart attack, stroke, kidney failure, hepatic failure, organ transplantation, chemotherapy or other cancer treatment, surgery, burn injury, crush injuries, peripheral nerve injury, cardiac wasting, cachexia, sarcopenia and wasting illness such as, for example, pulmonary, neurological viral, and hematological diseases or any disorder associated with or arising from a failure to oxygenate an organ, tissue or cell population, in particular an acute circulation failure, or any disorder associated with disruption on mitochondrial activity, stability or homeostasis, such as may result in cell dysfunction and death signaling.

Interaction and translocation inhibitors, or other mitochondrial integrity-preserving agents, are often administered intravenously or via catheter, such as at an injection or introduction site proximal to a site of likely infarction damage, either through continuous administration or as a single bolus or plurality of bolus dosages. Alternate routes of administration comprise injection, via catheter transdermal administration or ingestion.

The interaction inhibitor, translocation inhibitor, or other mitochondrial integrity-preserving agent, is administered prior to an infarction damage risk event, during or even subsequent to or over a certain period of time post an infarction damage risk event, such as surgery organ transplant, bruising or other harm.

In particular, in some cases the interaction and translocation inhibitor or other mitochondrial integrity-preserving agent is administered prior to or concurrent with an acute event such as a surgery, such as a surgery for which an infarction risk is associated. Similarly, the interaction and translocation inhibitor is in some cases administered to a patient having suffered an acute event such as a trauma which is associated with a higher subsequent risk of an infarction event. Alternately, as above, in some cases the interaction and translocation inhibitor is administered subsequent to an infarction event such as an acute infarction event. In some cases the interaction and translocation inhibitor or other mitochondrial integrity-preserving agent is administered prior to or concurrent with a cancer therapy intervention such as a chemotherapy treatment regimen. The interaction and translocation inhibitor administered subsequent to an infarction event such as an acute infarction event is optionally administered prior to, concurrent with or in addition over a certain period of time post reoxygenation of an infarcted tissue or cell population.

Interaction and translocation inhibitors are in these cases variously administered in carriers that lack available oxygen molecules, or possess oxygen molecules at a concentration insufficient to lead to reoxygenation. Alternatively, in some cases interaction and translocation inhibitors are administered concurrently with or in a carrier comprising oxygen molecules, such as at a concentration sufficient to effect reoxygenation of infarcted tissues or cell populations, or at a level consistent with preparing infarcted tissues or cell populations for subsequent oxygenation.

The interaction and translocation inhibitor or other mitochondrial integrity-preserving agent is variously administered continuously, through multiple regular or irregular doses or in a single dose.

Alternately, some methods herein relate to treatment of chronic infarction risk conditions. In these cases, the interaction and translocation inhibitor or other medicament is administered alone or as part of a treatment regimen administered to a mammal such as a human patient having an elevated or substantial chronic infarction risk, such as a risk associated with a particular condition. Examples include, among others, Diabetes, Hypertension, Hyperlipidemia, renal failure, hepatic failure, Obesity, Genetic disorders, Stress, Smoking or smoking related lung or other tissue harm, heart disease, stroke, burn injury, crush injuries, peripheral nerve injuries, cachexia, sarcopenia and muscle wasting, wasting illness such as pulmonary, neurological, viral, hematological disease, cardiac wasting or (auto)Inflammatory diseases. Often, these embodiments of the disclosure comprise repeated or regular administration of an inhibitor, such as through injection, in a manner somewhat analogous to regular insulin administration for blood sugar level management or via a port.

Some preferred interaction and translocation inhibitors or other mitochondrial integrity-preserving agents comprise a chimeric protein, polypeptide or peptide, such as segment having at least 75% identity to at least 8 consecutive residues of BNIP3, such as a segment wherein the at least 8 consecutive residues of BNIP3 comprise a phenylalanine residue at a $7^{th}$ of the at least 8 consecutive residues of BNIP3. In some cases, these 8 consecutive residues comprise residues having at least 75% identity to residues corresponding to residues 13-20 of BNIP3. The 8 consecutive residues in some cases comprise residues having at least 87.5% identity to residues corresponding to residues 13-20 of BNIP3.

Larger protein complex fragments are also contemplated as constituents of compositions to be used in the compositions and methods disclosed herein. For example, again looking to the BAX/BNIP3 complex targeting approach, compositions variously comprise BAX or a BNIP a segment having at least 87.5% identity or at least 75% identity to no more than 50 residues of a complex constituent such as BNIP3. In representative embodiments, the BNIP3 fragment does not comprise a BH3 motif, and or does not comprise a PESTQ motif (SEQ ID NO: 4), and or does not comprise a transmembrane domain or C-terminal BNIP3 domain. Often, the protein segment comprises a BAX binding motif, a BNIP3 binding motif or a segment that binds at least one of BAX and BNIP3.

Protein or peptide segments for use in methods herein often comprise constituent segments from multiple sources; that is, protein or peptide segments as contemplated for use herein are often part of chimeric proteins, for example in combination with a cellular import signal or cellular localization signal, such as the HIV TAT cellular import signal motif.

Methods contemplated herein in some cases comprise inhibiting mitochondrial interaction and translocation, for example using protein segments or peptide segments discussed above or other compositions consistent with the disclosure herein to inhibit mitochondrial translocation, exhibit efficacy in reducing damage from subsequent, concurrent or prior infarction events. In various cases, herein the translocation inhibitor or other mitochondrial integrity-preserving agent reduces damage from a subsequent infarction event by at least 10%, at least 20%, at least 30%, at least 40%, at least 50% or at least 75%. Similarly, in various cases herein the interaction and translocation inhibitor reduces recovery time from a subsequent infarction event by at least 10%, at least 20%, at least 30%, at least 40%, at least 50% or at least 75%. Various methods herein reduce BAX mitochondrial concentration by at least 30% or for example by at least 10%, at least 20%, at least 30%, at least 40%, at least 50% or at least 75% relative to an untreated reference relative to an untreated reference. Various methods herein reduce BNIP mitochondrial concentration by at least 30% or for example by at least 10%, at least 20%, at least 30%, at least 40%, at least 50% or at least 75% relative to an untreated reference relative to an untreated reference. Various methods herein reduce mitochondrial swelling by at least 30% or for example by at least 10%, at least 20%, at least 30%, at least 40%, at least 50% or at least 75% relative to an untreated reference relative to an untreated reference. Various methods herein reduce BAX active concentration by at least 30% or for example by at least 10%, at least 20%, at least 30%, at least 40%, at least 50% or at least 75% relative to an untreated reference relative to an untreated reference. Various methods herein reduce cytochrome c release by at least 30% or for example by at least 10%, at least 20%, at least 30%, at least 40%, at least 50% or at least 75% relative to an untreated reference relative to an untreated reference. Various methods herein improve Inf/AAR by at least 50% or for example by at least 10%, at least 20%, at least 30%, at least 40%, at least 50%, at least 60%, at least 70%, at least 80% or at least 90% relative to an untreated reference relative to an untreated reference. Various methods herein reduce caspase activity by at least 30% or for example by at least 10%, at least 20%, at least 30%, at least 40%, at least 50% or at least 75% relative to an untreated reference relative to an untreated reference. Various methods herein reduce membrane depolarization by at least 30% or for example by at least 10%, at least 20%, at least 30%, at least 40%, at least 50% or at least 75% relative to an untreated reference.

Some methods disclose herein further comprise monitoring infarction damage recovery, monitoring mitochondrial status, or monitoring both infarction damage recovery and monitoring mitochondrial status, such that often one is able to determine an impact of treatment upon a mammal such as a human patient's recovery.

Also disclosed herein are compositions and methods for the identification of a molecule suitable for amelioration, reduction or treatment of infarction or infarction associated cell or tissue damage. Some such methods relate to binding of BAX/BNIP3 oligomeric complexes as indicators of a role for the binding molecule in the inhibition of BAX/BNIP3 mediated necrosis and or apoptosis.

Some such methods for the identification of a molecule suitable for amelioration, reduction or treatment of infarction or infarction associated cell or tissue damage comprise assaying for binding of the molecule to BAX/BNIP3 oligomeric complexes, in particular, wherein binding of the molecule to the BAX/BNIP3 oligomeric complex indicates efficacy in infarction amelioration. Assaying for binding variously comprises assaying for colocalization of a molecule and BAX/BNIP3 oligomeric complexes, for example as determined by fluorescence microscopy. Alternately or in combination, said assaying comprises assaying for comigration of the molecule and BAX/BNIP3 oligomeric complexes, often wherein said comigration is performed under conditions to maintain oligomeric BAX/BNIP3 oligomeric complex integrity, such as nondenaturing conditions. Comigration is determined, for example using any of gel electrophoresis, SDS-PAGE or Western Blot analysis. Assaying for binding may additionally or alternately comprise assaying for coprecipitation of the molecule and BAX/BNIP3 oligomeric complexes, for example using co-immunoprecipitation. Any of the assays above are performed on cells or cell extracts, for example cells or cell extracts subjected to oxygen starvation, and are in some cases performed shortly after oxygen starvation, such as within 10 minutes of oxygen starvation, or alternately no more than any of 1, 2, 3, 4, 5, 6, 7, 8, 9, 10, 11, 12, 13, 14, 15, 20, 25, 30 or more than 30 minutes after oxygen starvation. Any of these assays may be performed at baseline, or after ischemia at 5 minutes, 10 minutes, 30 minutes, 1 hour, 2 hours, 4 hours, 8 hours 16 hours 24 hours or longer after reperfusion.

Some such methods for the identification of a molecule suitable for amelioration, reduction or treatment of infarction or infarction associated cell or tissue damage comprise assaying for BAX/BNIP3 complex localization upon contacting to the molecule. Said contacting may occur, for example, in a cell subjected to oxygen starvation or an extract of a cell subjected to oxygen starvation, in particular an extract that comprises functional mitochondrial membranes or functional mitochondria. In some such assays, retention of BAX/BNIP3 outside of a mitochondrion of the cell indicates efficacy in infarction amelioration. Similarly, inhibition of BAX/BNIP3 translocation into a mitochondrion of the cell in some cases indicates efficacy in infarction amelioration. Inhibition of BAX translocation into a mitochondrion of the cell in some cases indicates efficacy in infarction amelioration. In some cases inhibition of BNIP3 translocation into a mitochondrion of the cell indicates efficacy in infarction amelioration. Assaying for BAX, BNIP3 or BAX/BNIP3 localization may comprise fluorescence assays, such as may be effected using fluorescently labeled antibodies or fluorescent-protein or epitope labeled BAX, BNIP3 or BAX and BNIP3 proteins. Alternately, or in combination, molecule localization may be determined using immunofluorescence or detection or a radiolabel and overlaying such signal against an image of the cell or mitochondrion in question. Alternately or in combination, complex localization comprises one or more of assaying for mitochondrial integrity, assaying for mitochondrial swelling, assaying for cytochrome c release, or assaying for caspase-3 activity. Any of the assays above are performed on cells or cell extracts, for example cells or cell extracts subjected to oxygen starvation, and are in some cases performed shortly after oxygen starvation, such as within 10 minutes of oxygen starvation, or alternately no more than any of 1, 2, 3, 4, 5, 6, 7, 8, 9, 10, 11, 12, 13, 14, 15, 20, 25, 30 or more than 30 minutes after oxygen starvation. Any of these assays may be performed at baseline, or after ischemia at 5 minutes, 10 minutes, 30 minutes, 1 hour, 2 hours, 4 hours, 8 hours 16 hours 24 hours or longer after reperfusion.

INCORPORATION BY REFERENCE

All publications, patents, and patent applications mentioned in this specification are herein incorporated by reference to the same extent as if each individual publication, patent, or patent application was specifically and individually indicated to be incorporated by reference. In particular, WO 02/02743, published Jan. 10, 2002 is hereby incorporated by reference in its entirety. Similarly, WO 2020/229632, published Nov. 19, 2020 is hereby incorporated by reference in its entirety.

BRIEF DESCRIPTION OF THE DRAWINGS

FIG. 1L. delta-TM reduces relative active BAX concentration to near basal levels at I/R30.
FIG. 1M. TAT-BNIP3 induces mitochondrial BAX accumulation in a Bnip3$^{-/-}$ genetic background.
FIG. 1N. BAX and BNIP3 blots.
FIG. 1O. delta-TM maintains relative cytochrome c concentration at near basal levels at I/R30.
FIG. 1P. delta-TM restores ATP to basal levels.
FIG. 1Q. delta-TM maintains relative BNIP3 phosphorylation at near basal levels.
FIG. 3G. Mouse/human alignment. Figure discloses SEQ ID NOS 38-39, respectively, in order of appearance.

FIG. 8B. Mitochondrial swelling and damage assays related to FIG. 1H and FIG. 1I.

FIG. 10A. Mutation alanine scan heat map related to FIG. 3H. Figure discloses SEQ ID NOS 54-86, respectively, in order of appearance.

FIG. 10B. WVELAASN (SEQ ID NO: 7) folding prediction related to FIG. 3L.

FIG. 14A. TAT-WVELHFFN ("WVELHFFN" disclosed as SEQ ID NO: 3) counters DOX induced cell death at high DOX concentrations. Figure discloses "WVELHFFN" as SEQ ID NO: 3.

FIG. 14B. TAT-WVELHFFN ("WVELHFFN" disclosed as SEQ ID NO: 3) reduces RLU count at 10 uM DOX administration. Figure discloses "WVELHFFN" as SEQ ID NO: 3.

FIG. 25. BAX peptide sequences. Figure discloses SEQ ID NOS 87, 494, 88-91, 26, 33-34, 29, 92, 31, and 93, respectively in order of appearance.

FIG. 26. BNIP3 peptides truncated. Figure discloses SEQ ID NOS 1, 94-101, 53, 52, 51, 8, 2, 50, 49, 48, 47, 46, 45, 44, 43, 42, 41, 40, and 102-117, respectively, in order of columns.

FIG. 27A-FIG. 27E. BNIP3 peptides substituted. Figures disclose discloses SEQ ID NOS 118-493, respectively, in order of appearance.

DETAILED DESCRIPTION

Figure 1A:
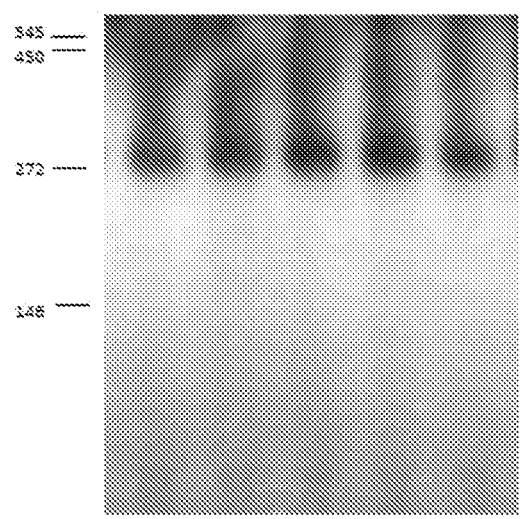
FIG. 1A. BNIP3 oligomeric expression.

To improve outcomes of individuals suffering from or at risk of infarction damage resulting from disruption in oxygenation at an affected area, we developed methods and compositions for the treatment of or amelioration of symptoms of disruption in oxygenation to an affected area. This work was then expanded to include a broad range of approaches for amelioration of secondary damage pursuant to an intervention, particularly by effecting mitochondrial stabilization, such as through the inhibition of mitochondrial interaction and import involved in mitochondrial destruction signaling.

Our research identified systems, methods and compositions for the amelioration, or treatment of ischemia/reperfusion (I/R) injury. In particular, we disclose herein compositions and methods for treatment of I/R injury conditions, for the prophylactic treatment of individuals at risk of I/R injury as well as for the additional post-treatment of individuals at risk of I/R injury consequences, so as to reduce the harm that may arise from a subsequent I/R event in an individual at risk thereof. We further disclose compositions and methods for the amelioration of a number of interventions associated with detrimental effects arising from mitochondrial destabilization.

We used unbiased biochemical approaches, computational modeling, and in vivo models of myocardial and brain I/R injury caused by a mixture of necrotic and apoptotic cell death as clinically relevant and elegant systems. Our results identify interaction and translocation across mitochondrial membranes as a mechanism to perturbate to reduce mitochondrial cell death signaling in response to reperfusion and to other sources of secondary deleterious effects. We further identify, as a particular example validating this mechanism, cytosolic BNIP3 as a key regulator of BAX in a heteromeric state for both mitochondrial necrotic and apoptotic signaling in mammalian cells including human cardiomyocytes.

As a specific example relating to the general idea of mitochondrial stabilization, we found that cytosolic oligomers comprising BNIP3/BAX heterodimers are critical mitochondrial membrane attack complexes with BNIP3-phosphorylation as the master switch for necrotic and apoptotic cell death-inducing activity. By combining in silico BNIP3 3D modelling with structural and binding behavioral interrogation of BNIP3 and BAX-derived peptides, we developed a BNIP3 octapeptide antagonist that prevents the identified mitochondrial membrane attack of oligomeric BNIP3/BAX heterodimers. This effectively reduces cell death in human cardiomyocytes, mouse and pig tissues in I/R injury by 40-60%. These results were found to generalizable to other sources of secondary deleterious effects, such those associated with chemotherapeutic intervention, where mitochondrial stabilization through import inhibition yielded similar improvements in outcomes in cell death in human cardiomyocytes, mouse and pig tissue Our results have implications for understanding the molecular mechanism of mitochondrial membrane disintegration leading to necrosis and apoptosis and pinpoint the therapeutic potential of a BNIP3 antagonist for I/R injury conditions such as myocardial infarction and stroke in humans. Our results further have implications for methods of treatment and compositions for use in treatment, in that incorporation of a mitochondrial protecting and/or stabilizing agent such as a mitochondrial interaction and import inhibitor as disclosed herein may have a substantial positive effect in the reduction of secondary cell death.

Mitochondria are essential end effectors in physiological and pathological cell death induction (Kwong and Molkentin, 2015). When damaged, they translate their injury into lethal signaling pathways (Nunnari and Suomalainen, 2012). Previous studies postulated BNIP3 as a potential upstream modulator of BAX disturbing MOM and MIM integrity and inducing necrotic and apoptotic cell death (Hamacher-Brady et al., 2007; Kubli et al., 2007, 2008). In particular, BNIP3 is suggested to exert its pro-death activity as stable homodimers localized to the MOM by orchestrating BAX activation (Kubli et al., 2007). However, fundamental issues regarding the underlying mechanisms remained unresolved, in part because the complete structure of BNIP3 is lacking. Since spin-labeling followed by pulsed electron paramagnetic resonance spectroscopy has identified that BNIP3 and BAX are able to heterodimerize (Hendgen-Cotta et al., 2017), we explored the activity of BNIP3/BAX in a potential heterodimeric state, which may cause mitochondrial disintegration. We developed a general strategy for preventing mitochondrial-induced necrosis and apoptosis based on further insights into underlying mechanisms. We have discovered that BNIP3 and BAX form inert heterodimers in the cytosol, which are assembled into higher molecular weight complexes under natural and IR conditions. Thereby, the first 20 amino acids including a conserved region represent the functional domain in binding to BAX. These oligomeric BNIP/BAX heterodimers are mandatory for the interaction with mitochondria inducing subsequently the depolarization of the MIM. Unexpectedly, BAX activation and pore formation did not occur contemporaneously. This is important as BAX activation is required for the apoptotic signaling cascade (Tang et al., 2019). These observations therefore render a post-translational modification of BNIP3 the potential stimulus to excite activation of BAX by conformational changes. Phosphorylation modifies proteins from hydrophobic apolar to hydrophilic polar, allowing the protein to change conformation when interacting with other molecules (Ardito et al., 2017). Our data represent the first report of phosphorylation of BNIP3 in regulating BAX activation and pore formation. During ischemia and the early phase of reperfusion ATP synthesis is highly limited (Chen and Zweier, 2014), which explains the chronological sequence of BNIP3/BAX interaction-induced necrosis and apoptosis in I/R. Taken together, our findings suggest that phosphorylation of BNIP3 may transduce BAX conformation to form MOMP. Protection of mitochondria to avoid mitochondrial-driven cell death limiting tissue injury is currently an unmet therapeutic goal (Nunnari and Suomalainen, 2012). The striking influence of BNIP3/BAX heterodimeric activity under the control of BNIP3 on cell death in response to e.g., reperfusion therapy, which is indispensable to rescue patients during ischemic events (Heusch and Rassaf, 2016; Kloner et al., 2017), signify BNIP3/BAX heterodimers an outstanding novel target for the development of a small peptide antagonist. Guided by the newly modelled 3D structural information of BNIP3 and the specific N-terminal sequence behavioral interrogations, we discovered the crucial amino acids and engineered the cell-permeant octapeptide TAT-WVELHFFN ("WVELHFFN" disclosed as SEQ ID NO: 3) that inhibits oligomeric mitochondrial membrane attack complexes containing BNIP3/BAX heterodimers in the cytosol as defense against mitochondrial damage and cell death. Treatment with the BNIP3 octapeptide antagonist TAT-WVELHFFN ("WVELHFFN" disclosed as SEQ ID NO: 3) shows superior tissue protection in myocardial infarction and in stroke. Highlighting the translational potential of this approach, the octapeptide TAT-WVELHFFN ("WVELHFFN" disclosed as SEQ ID NO: 3) prevents cell death in mice, pigs and human cardiomyocytes.

Accordingly, disclosed herein are compositions, compositions for use and methods relating to amelioration of I/R damage, for example through administration of a compositions comprising a mitochondrial membrane interaction and translocation inhibitor or other mitochondrial integrity-preserving agent. More generally, disclosed herein are compositions, compositions for use and methods for amelioration of secondary damage caused by an intervention regimen, such as a chemotherapeutic, radiotherapeutic, a surgical intervention, or chronic condition, among others.

A number of mitochondrial membrane interaction and translocation inhibitor or other mitochondrial integrity-preserving agents are consistent with the disclosure herein. Some mitochondrial membrane interaction and translocation inhibitors or other mitochondrial integrity-preserving agents disclosed or contemplated herein share an effect of protecting mitochondria from degradation upon reintroduction of oxygen following an ischemic event.

Others share a property of ameliorating a measurement of mitochondrial status change as presented in FIG. 13A through FIG. 25H, such as ROS accumulation, calcium ion accumulation, mitochondrial mPTP opening, mitochondrial membrane integrity preservation, caspase-3 activation or cytochrome c release. Protection from degradation variously comprises at least one of maintaining mitochondrial membrane potential, preventing cytochrome c release into the cytoplasm, reducing mitochondrial swelling, preventing protein translocation such as BAX protein or BNIP3 interaction with and translocation into the outer membrane, or other mitochondrial degradation. An effect of this protection is that there is no subsequent initiation of a cell death pathway in the affected cell, such that reperfusion of oxygen or therapeutic compound or regimen application can be accomplished without concurrent mitochondrial degradation and induction of cell death.

Attention is paid to particular protein, polypeptide or peptide mitochondrial membrane interaction and translocation inhibitors or other mitochondrial integrity-preserving agents. However, a number of protein, hormonal and small molecule effectors are consistent with the methods of the disclosure herein.

Representative mitochondrial integrity-preserving agent are seen in the substantial number of mitochondrial membrane translocation inhibitors derived from the BNIP3 near N-terminal fragments disclosed herein and previously in PCT Publication No. WO2020/229362, published Nov. 19, 2020, and incorporated by reference herein in its entirety.

Exemplary segments described herein include BNIP3 segments, such as N-terminal segments of BNIP3, for example regions drawn from MSQSGEEN-LQGSWVELHFSN (SEQ ID NO: 1) of BNIP3, in particular WVELHFSN (SEQ ID NO: 2) of BNIP3. Some such composition present unmodified segments of BNIP3, while alternate compositions present modified BNIP3 segments, such as polypeptides or peptides comprising the sequence WVELHFFN (SEQ ID NO: 3). These proteins, polypeptides or peptides optionally comprise a cellular localization signal such as an HIV TAT localization signal at their N- or C-terminus.

A number of routes of administration are consistent with the methods and compositions herein. Exemplary routes of administration comprise direct administration of a mitochondrial interaction and translocation inhibitor or other mitochondrial integrity-preserving agent in a biocompatible solution to a mammalian subject such as a human patient. Methods often comprise intravenous administration via a peripheral or central vein, intra-arterial administration via a peripheral artery, intra-arterial administration via catheter directly into an impacted area such as an impacted ventricle, or intra-arterial administration via catheter into a corresponding coronary artery or arteries as well as intra-peritoneal. Routes of administration often correlate to the impacted region for which I/R damage is to be ameliorated, and may vary for target areas such as heart, brain, kidney, or other impacted area.

Consistent with these routes of administration, a number of carriers are contemplated as part of the disclosure herein. NaCl solutions, Ringer solution and most solutions consistent with human administration are compatible with the compositions and methods herein. Solutions are in some cases selected or engineered to have a desired molecular oxygen concentration. In some cases, solutions are selected to be administered prior to reperfusion or reoxygenation and are formulated to have an oxygen concentration that is at least as low as the local impacted area concentration. Alternately, some solutions are formulated to accomplish a 'pre-oxygenation' by harboring an oxygen concentration that is elevated but below that of a subsequently applied high oxygen reperfusion composition. Alternately, some compositions are delivered in solutions having a high, or reperfusion level of dissolved oxygen, so as in some cases to effect concurrent mitochondrial translocation inhibition and oxygenation.

In addition to a carrier, a interaction and mitochondrial translocation inhibitor or other mitochondrial integrity-preserving agent is optionally administered concurrently with or in a composition comprising one or more additional factors, such as anesthetics, sedatives, anticoagulants, antibiotics, or other factors conducive to amelioration of an infarction event, prevention of a further infarction event, patient recovery or toleration of a procedure or any other reason conducive to a beneficial outcome. Exemplary anticoagulant cofactors include heparins, GPIIb/IIIa antagonists, any kind of platelet inhibitors, among others. Pain relief factors consistent with coadministration include morphine and/or morphine derivates or any other drugs which inhibit/relief pain, for example, fentanyl, hydromorphone, morphine, oxycodone, oxymorphone, dilaudid, tramado, as well as butorphanol, an NSAID (nonsteroidal anti-inflammatory drug, such as ibuprofen acetaminophen, Ketorolac or other pain medications consistent with liquid formulation. Compositions may alternately or additionally comprise a sedative, such as. Propofol or benzodiazepines. Similarly, compositions may alternately or additionally comprise an antibiotic.

Methods of administration optionally comprise concurrent administration through alternate routes of complementary medicaments, such as oral administration or inhalation. Examples include orally administered anticoagulants such as warfarin, orally administered painkillers such as opiates or NSAIS, among others, or inhaled or orally administered anesthetics, or antibiotics.

As disclosed herein, mitochondrial interaction and translocation inhibition has a beneficial effect in individuals suffering from an infarction event or undergoing a therapeutic intervention, and may be administered prior to, concurrent with or even subsequent to initiation of reoxygenation or application of the therapeutic. Compositions are variously administered no more than 48 hours, no more than 24 hours, no more than 12 hours, no more than 6 hours, no more than 5 hours, no more than 4 hours, no more than 3 hours, no more than 3 hours, no more than 1 hour, no more than 30 minutes, no more than 15 minutes, no more than 10 minutes, or no more than 5 minutes prior to reoxygenation. Administration is of a single dose, or alternately comprises an administration regimen of at least 2, 3, 4, 5, 6, 7, 8, 9, 10 or more than 10 doses. Doses comprise consecutive administration of comparable medicament amounts, or alternately comprise changes in dose volume or medicament concentration, such that in some cases effective composition may 'ramp up' from an initial low level prior to oxygenation.

Administration is often performed in a hospital setting, such as an operating room. Alternately, in some cases administration occurs before the patient enters the hospital or prior to surgery. For example, paramedics are in some cases able to administer the compositions herein as soon as they see a patient or as soon as an acute myocardial infarction is diagnosed or suspected. Early administration has the benefit of reducing time to infarction surgery, and extending the time that the mitochondrial interaction and translocation inhibitor or other mitochondrial integrity-preserving agent has to act prior to reoxygenation.

Administration is similarly performed prior to or concurrent with reperfusion of the ischemic myocardium. For example, using interventional catheter systems, a percutaneous coronary intervention is performed and the occluded coronary artery is recanalized using a wire, a balloon and/or a stent system. This procedure is often performed using anticoagulants like heparin to inhibit blood clotting, using platelets inhibitors like e.g. aspirin, clopidogrel, cangrelor, ticagrelor, prasugrel, GPIIB/IIIa antagonists, using drugs to inhibit/relief pain (like e.g. morphine or its derivates), using drugs to sedate and relax patients (like e.g. propofol, benzodiazepines etc.), oxygen in different concentration before, during and/or after the procedure. A mitochondrial interaction and translocation inhibitor is administered concurrently with, prior to subsequent to, or even additional over a certain period of time post such a procedure.

In some cases, myocardial infarction is treated using fibrinolysis. Fibrinolytic therapy is an important reperfusion strategy in settings where primary PCI cannot be offered in a timely manner, and prevents 30 early deaths per 1000 patients treated within 6 h after symptom onset. The largest absolute benefit is seen among patients at highest risk, including the elderly, and when treatment is offered is <2 h after symptom onset. A mitochondrial interaction and translocation inhibitor is administered concurrently with, prior to, subsequent to or even additional over a certain period of time post such a procedure.

In some cases, myocardial infarction is treated via CABG (coronary artery bypass graft) surgery in the operation room. Emergent CABG is considered for patients with a patent infarct related artery but with unsuitable anatomy for PCI, and either a large myocardial area at jeopardy or with cardiogenic shock. In patients with MI-related mechanical complications who require coronary revascularization, CABG is recommended at the time of repair. In STEMI patients with failed PCI or coronary occlusion not amenable to PCI, emergent CABG is infrequently performed because the benefits of surgical revascularization in this setting are uncertain. Again, a mitochondrial interaction and translocation inhibitor is administered concurrently with, prior to, subsequent to or even additional over a certain period of time post such a procedure.

Alternately, some methods disclosed herein comprise administration to a patient at risk of an infarction event. Infarction event such as strokes, for example, are a substantial risk to individuals undergoing surgery or suffering from a trauma such as a bruising trauma that may arise from a fall or accident. A number of surgeries carry higher infarction risk, such as cardiac surgery (valve surgery, heart failure surgery, coronary surgery or other cardiac or aortic surgery, as well as long lasting operations generally might affect the heart and lead to damage of the organ.

Individuals suffering from an acute infarction event such as a heart attack are in some cases at heightened risk of a second such event, such as a stroke, often due to disruption of blood clotting factors pursuant to treatment.

Additional acute events harboring an increased infarction event risk include, for example, myocarditis, SARS-Cov2 or other viral infection, such as infection leading to myocardial damage, particularly in ICU-patients. Similarly, trauma of the heart (e.g., accident with compression of the thorax), Hypoxia (e.g. as may be suffered by a mountaineer at high altitude, suffocation, ICU-treatment, for example), Anemia due to e.g. bleeding or hematologic diseases or cancer, or Hypertensive crisis. It is understood that additional acute conditions may lead to infarction or cardiac damage requiring reperfusion, each of which may be ameliorated by treatment with a composition or practice of a method herein.

Tissue or organ transplant often carries a heightened risk of infarction or myocardial damage. Explanting a heart and transporting this organ to a heart transplant recipient will often lead to damage and cell death, which may be ameliorated through practice of the disclosure herein. Compositions may be added to the preservation solution during transport or when given the patient before explanation of the heart or subsequent to the procedure. Aside from heart, the compositions disclosed herein in some cases protect cell and thus organ death in kidney, liver, lung or other transplants.

Similarly, some individuals exhibit higher infarction risk due to a chronic condition such as high blood pressure, high cholesterol, diabetes, malignant or benign cancer, obesity or even being moderate or mildly overweight, among other conditions raising infarction risk. In addition, prolonged treatment regimens such as cancer-therapy (radiation, chemotherapy, anti-cancer immunotherapies or other cancer therapy) or other treatment regimen comprising a course of repeated treatments may carry increased infarction risk and accordingly are suitable for concurrent practice of the methods or administration of compositions as disclosed or contemplated herein. A partial list of chemotherapeutics consistent with the mediation of mitochondrial degradation risk, or benefiting from mitochondrial stabilization as a concurrent step in therapy, include the radiotherapeutic or a chemotherapeutic, such as a chemotherapeutic that targets a cancerous cell, cell population, or tumor. Some such chemotherapeutics cause off-target or unintended cell death, such as cardiomyocyte death. Exemplary chemotherapeutics used to target cancer cells or tumors comprise, for example, a compound selected from the list consisting of an Alkylating agent, such as altretamine, busulfan, carboplatin, carmustine, cisplatin, cyclophosphamide, dacarbazine, ifosfamide, lomustine, melphalan, temozolomide, trabectedin: Antimetabolite, such as 5-fluorouracil, 6-mercaptopurine, azacitidine, capecitabine, clofarabine, cytarabine, floxuridine, fludarabine, gemcitabine, methotrexate, pemetrexed, penostatin, pralatrexate, trifluridine and tipiracil; antibodies, such as HER2 inhibitors e.g. trastuzumab, pertuzumab, margetuximab, immune checkpoint inhibitors e.g. nivolumab (anti-PD-1), avelumab (anti-PD-L1), ipilimumab (anti-CTLA-4), relatlimab (anti-LAG-3); a Plant alkyloid, such as, vincristine, vinblastine, vinorelbine, paclitaxel, docetaxel, etoposide, teniposide, irinotecan, topotecan; an antitumor agent, such as, daunorubicin, doxorubicin, doxorubicin liposomal, epirubicin, idarubicin, and valrubicin. Exemplary chemotherapeutics include anthracyclines, such as daunorubicin, doxorubicin, doxorubicin liposomal, epirubicin, idarubicin, and valrubicin, for example doxorubicin.

Accordingly, some methods comprise prophylactic or concurrent administration of a mitochondrial translocation inhibitor or other mitochondrial integrity-preserving agent to a subject at risk of an infarction event or otherwise at risk of secondary effects due to mitochondrial destabilization. Such administration may serve to ameliorate the harm directly, or to facilitate reperfusion in response to an event by preparing the impacted tissue, or the subject as a whole, for reperfusion at the impacted area.

Administration is in some cases acute, such as prior to surgery or in response to a trauma or other isolated infarction risk event.

Compositions are variously administered no more than 48 hours, no more than 24 hours, no more than 12 hours, no more than 6 hours, no more than 5 hours, no more than 4 hours, no more than 3 hours, no more than 2 hours, no more than 1 hour, no more than 30 minutes, no more than 15 minutes, no more than 10 minutes, or no more than 5 minutes prior to an upcoming infarction risk event. Alternately, compositions are variously administered at least or no more than 96 hours, no more than 72 hours, no more than 48 hours, no more than 24 hours, no more than 12 hours, no more than 6 hours, no more than 5 hours, no more than 4 hours, no more than 3 hours, no more than 2 hours, no more than 1 hour, no more than 30 minutes, no more than 15 minutes, no more than 10 minutes, or no more than 5 minutes subsequent to an infarction risk event. Administration is of a single dose, or alternately comprises an administration regimen of at least 2, 3, 4, 5, 6, 7, 8, 9, 10 or more than 10 doses. Doses comprise consecutive administration of comparable medicament amounts, or alternately comprise changes in dose volume or medicament concentration, such that in some cases effective composition may 'ramp up' from an initial low level prior to a risk event such as a surgery.

Alternately, administration is regular or sporadic in response to a chronic condition carrying an elevated risk of an infarction event. Administration is variously monthly, weekly, daily, or at other regular or irregular interval. Administration is often of a steady dose, although irregular dosages or time intervals are also contemplated herein. Irregular administration, such as in response to a biometric output such as insulin level, blood sugar level, cholesterol level or other biometric readout is also contemplated herein. Administration may be alone or in combination with, for example a cholesterol lowering or regulating medicament.

Compositions and methods herein improve outcomes for mammals such as human patients who suffer an infarction event or who are subject to a treatment regime comprising a risk of secondary mitochondrial destabilization. Improvement is measured any number of ways, starting with increased survival and extending to more specific measurements of increased performance among surviving individuals. Amelioration is measured in some cases through MRI visualization or measurement of infarcted area or measurement of the salvaged myocardium using the area at risk and the infarcted area. Measurement is also readily accomplished through SPECT, PET, CT or other scanning technology. Measurements may also be accomplished though echocardiography: measuring infarcted area using contrast agent, function of left ventricle (regional and global), or relying upon strain analyses.

For assessments specific to heart infarction recovery, one may rely upon EKG: ST-segment resolution. Assays may also be accomplished using Ventriculography in the cath lab using contrast agent and determining function of the left ventricle Lab analysis or blood-draw based assays include measurements of troponin, high sensitive troponin, creatine kinase, creatine kinase Mb.

Method or composition performance is often assessed as cell survival rate or infarction area. A higher cell survival rate correlates to lower size of infarction. Infarct size is of prognostic relevance and correlates with mortality. A higher cell survival rate is expected to correlate with smaller infarct size in MRI, higher myocardial salvage in MRI, lower infarct size in CT, PET, SPECT, with better and faster ST-segment resolution, with lower release of troponin, high sensitive troponin, creatine kinase, creatine kinase Mb, with lower infarct size in echocardiography, with better left ventricular function in echo, with normal strain/strain rate in echo, with better left ventricular function in ventriculography. Cell survival rate is improved relative to a control by in some cases at least 10%, at least 20%, at least 30%, at least 40%, at least 50%, at least 60%, at least 70% at least 80%, at least 90% or greater than 90%.

Method or composition performance may also be measured at the cellular level, by impact on mitochondrial membrane translocation, for example of BNIP3 or BAX, mitochondrial swelling, BAX mitochondrial active concentration, cytochrome c release, Inf/AAR proportion, or caspase activity. Reduction of any of these parameters is in some cases at least 10%, at least 20%, at least 30%, at least 40%, at least 50%, at least 60%, at least 70% at least 80%, at least 90% or greater than 90%.

Controls for these rates are variously selected from measurements of previous untreated individual or mammal outcomes, measurements of experimental controls, fixed values known in the field, values measured from control or untreated populations, or other reference parameters.

Also disclosed herein are methods and compositions for the identification of further candidate molecules for the prevention, amelioration or treatment of infarction or damage associated with infarction, or for the prevention, amelioration or treatment of secondary effects related to mitochondrial destabilization or degradation, such as mitochondrial import related degradation, and concomitant signaling. Without being bound to theory, some such methods relate to the discovery that BAX/BNIP3 complexes are oligomeric in the cytoplasm, and that binding to such oligomeric complexes or inhibition of BAX, BNIP3 or both BAX and BNIP3 translocation into the mitochondrion is indicative of candidate molecules for the prevention, amelioration or treatment of infarction or damage associated with infarction.

Methods are performed by contacting a composition comprising a candidate molecule to at least one cell, cell extract or tissue and assaying the interaction of the molecule or localization of the molecule, or impact of the molecule on localization of BAX, BNIP3, or BAX/BNIP3 heterodimers or oligomers.

Cells, cell extracts or tissue are subjected to oxygen starvation pursuant to induction of an infarction event or in simulation of the effect of an infarction event. A number of oxygen starvation regimes are consistent with the disclosure herein, such performing assays within 10 minutes of oxygen starvation, or alternately no more than any of 1, 2, 3, 4, 5, 6, 7, 8, 9, 10, 11, 12, 13, 14, 15, 20, 25, 30 or more than 30 minutes after oxygen starvation, or longer periods after oxygen starvation. Any of these assays may be performed at baseline, or after ischemia at 5 minutes, 10 minutes, 30 minutes, 1 hour, 2 hours, 4 hours, 8 hours 16 hours 24 hours or longer after reperfusion. In some cases oxygen starvation is absolute, while in alternatives oxygen levels are reduced relative to healthy conditions, or are in some cases unchanged relative to healthy conditions or even elevated. Exemplary extents of oxygen reduction include as much as 100%, 95%, 90%, 80%, 70%, 60%, 50%, 40%, 30%, 20%, 10%, 5%, or less than 5% reduction relative to healthy or pre-assay conditions.

Alternately, Cells, cell extracts or tissue are subjected to radiotherapeutic, chemotherapeutic or other treatment pursuant to induction of secondary mitochondrial destabilization. A number of treatment regimes are consistent with the disclosure herein, such performing assays within 10 minutes of treatment, or alternately no more than any of 1, 2, 3, 4, 5, 6, 7, 8, 9, 10, 11, 12, 13, 14, 15, 20, 25, 30 or more than 30 minutes after treatment, or longer periods after treatment. Any of these assays may be performed at baseline, or after treatment at 5 minutes, 10 minutes, 30 minutes, 1 hour, 2 hours, 4 hours, 8 hours 16 hours 24 hours or longer after treatment. A wide range of mitochondrial status outputs are available for assay, such as those used in FIG. 1A through FIG. 25H.

Intact cells are preferred in some embodiments, though in alternate cases cell extracts are used, such as cell extracts having intact mitochondria or mitochondrial membranes, or cell extracts that are generated without substantial disruption of oligomeric complexes such as BAX/BNIP3 complexes.

Molecules are assayed for capacity to bind to BAX, BNIP3, BAX/BNIP3 dimers or, in exemplary cases, BAX/BNIP3 oligomers. Without being bound by theory, binding to BAX, BNIP3, BAX/BNIP3 dimers or, in exemplary cases, BAX/BNIP3 oligomers is indicative of efficacy or potential for efficacy of a candidate molecule for the prevention, amelioration or treatment of infarction or damage associated with infarction.

A number of binding assays are consistent with the disclosure herein. Assaying for binding variously comprises assaying for colocalization of a molecule and BAX/BNIP3 oligomeric complexes, for example as determined by fluorescence microscopy. Alternately or in combination, said assaying comprises assaying for comigration of the molecule and BAX/BNIP3 oligomeric complexes, often wherein said comigration is performed under conditions to maintain oligomeric BAX/BNIP3 oligomeric complex integrity, such as nondenaturing conditions. Comigration is determined, for example using any of gel electrophoresis, SDS-PAGE or Western Blot analysis. Assaying for binding may additionally or alternatively comprise assaying for coprecipitation of the molecule and BAX/BNIP3 oligomeric complexes, for example using co-immunoprecipitation.

Alternately or in combination, molecules are assayed for an effect upon BAX/BNIP3 complex localization upon contacting to the molecule. Said contacting may occur, for example, in a cell subjected to oxygen starvation or an extract of a cell subjected to oxygen starvation, in particular an extract that comprises functional mitochondrial membranes or functional mitochondria. In some such assays, retention of BAX/BNIP3 outside of a mitochondrion of the cell indicates efficacy in infarction amelioration. Similarly, inhibition of BAX/BNIP3 translocation into a mitochondrion of the cell in some cases indicates efficacy in infarction amelioration. Inhibition of BAX translocation into a mitochondrion of the cell in some cases indicates efficacy in infarction amelioration. In some cases inhibition of BNIP3 translocation into a mitochondrion of the cell indicates efficacy in infarction amelioration. Assaying for BAX, BNIP3 or BAX/BNIP3 localization may comprise fluorescence assays, such as may be effected using fluorescently labeled antibodies or fluorescent-protein or epitope labeled BAX, BNIP3 or BAX and BNIP3 proteins. Alternately, or in combination, molecule localization may be determined using immunofluorescence or detection or a radiolabel and overlaying such signal against an image of the cell or mitochondrion in question. Assay for BAX, BNIP3 or BAX and BNIP3 in a mitochondrial fraction is an alternative approach toward determining localization.

Alternately or in combination, complex localization assays may be supported by or replaced by assaying for mitochondrial integrity, assaying for mitochondrial swelling, assaying for cytochrome c release, assaying for caspase-3 activity, or other assay for mitochondrial activity or necrosis or apoptosis related mitochondrial degradation.

Alternately or in combination, efficacy may be measured by an ability to ameliorate an impact of a treatment on mitochondrial integrity, stability, or cell death signaling.

Numbered Embodiments. The disclosure is further elucidated with reference to the following partial list of numbered embodiments. 1. A method of ameliorating infarction damage to a subject at risk of an infarction damage risk event comprising administering a mitochondrial membrane translocation inhibitor. 2. The method of any previous embodiment, wherein the mitochondrial membrane translocation inhibitor inhibits BAX translocation into a mitochondrial membrane. 3. The method of any previous embodiment, wherein the mitochondrial membrane translocation inhibitor inhibits BNIP3 translocation into a mitochondrial membrane. 4. The method of any previous embodiment, wherein the infarction damage risk event comprises a heart attack. 5. The method of any previous embodiment, wherein the infarction damage risk event comprises a stroke. 6. The method of any previous embodiment, wherein the infarction damage risk event comprises kidney failure. 7. The method of any previous embodiment, wherein the infarction damage risk event comprises an acute circulation failure. 8. The method of any previous embodiment, wherein the infarction damage risk event comprises an organ transplantation. 9. The method of any previous embodiment, wherein the infarction damage risk event comprises surgery. 10. The method of any previous embodiment, wherein the translocation inhibitor is administered intravenously. 11. The method of any previous embodiment, wherein the translocation inhibitor is administered prior to an infarction damage risk event. 12. The method of any previous embodiment, wherein the translocation inhibitor is administered prior to an infarction damage risk event. 13. The method of any previous embodiment, wherein the infarction damage risk event comprises surgery. 14. The method of any previous embodiment, wherein the translocation inhibitor is administered subsequent to an infarction damage risk event. 15. The method of any previous embodiment, wherein the translocation inhibitor is administered prior to reperfusion. 16. The method of any previous embodiment, wherein the infarction damage risk event comprises bruising. 17. The method of any previous embodiment, wherein the infarction damage risk event comprises heart failure. 18. The method of any previous embodiment, wherein the infarction damage risk event comprises a physiological response to stress. 19. The method of any previous embodiment, wherein the infarction damage risk event comprises a physiological response to diabetes. 20. The method of any previous embodiment, wherein the infarction damage risk event comprises a physiological response to hypertension. 21. The method of any previous embodiment, wherein the infarction damage risk event comprises a physiological response to hyperlipidemia. 22. The method of any previous embodiment, wherein the infarction damage risk event comprises a physiological response to obesity. 23. The method of any previous embodiment, wherein the infarction damage risk event comprises a physiological response to a genetic disorder. 24. The method of any previous embodiment, wherein the infarction damage risk event comprises a physiological response to a lung disorder. 25. The method of any previous embodiment, wherein the infarction damage risk event comprises an inflammatory response. 26. The method of any previous embodiment, wherein the infarction damage risk event comprises an autoinflammatory response. 27. The method of any previous embodiment, wherein the BAX translocation inhibitor is administered in multiple doses. 28. The method of any previous embodiment, wherein the multiple doses are administered at regular intervals. 29. The method of any previous embodiment, wherein the BAX translocation inhibitor comprises a chimeric peptide. 30. The method of any previous embodiment, wherein the chimeric peptide comprises a segment having at least 75% identity to at least 8 consecutive residues of BNIP3. 31. The method of any previous embodiment, wherein the at least 8 consecutive residues of BNIP3 comprise a phenylalanine residue at a 7th of the at least 8 consecutive residues of BNIP3. 32. The method of any previous embodiment, wherein the 8 consecutive residues comprise residues having at least 75% identity to residues corresponding to residues 13-20 of BNIP3. 33. The method of any previous embodiment, wherein the 8 consecutive residues comprise residues having at least 87.5% identity to residues corresponding to residues 13-20 of BNIP3. 34. The method of any previous embodiment, wherein the chimeric protein comprises a segment having 75% identity to no more than 50 residues of BNIP3. 35. The method of any previous embodiment, wherein the chimeric protein comprises a segment having 87.5% identity to no more than 50 residues of BNIP3. 36. The method of any previous embodiment, wherein the chimeric protein does not comprise a BH3 motif. 37. The method of any previous embodiment, wherein the chimeric protein does not comprise a PESTQ motif (SEQ ID NO: 4). 38. The method of any previous embodiment, wherein the chimeric protein comprises a BAX binding motif. 39. The method of any previous embodiment, wherein the translocation inhibitor reduces damage from a subsequent infarction event by at least 10%, 40. The method of any previous embodiment, wherein the translocation inhibitor reduces damage from a subsequent infarction event by at least 20%, 41. The method of any previous embodiment, wherein the translocation inhibitor reduces damage from a subsequent infarction event by at least 30%. 42. The method of any previous embodiment, wherein the translocation inhibitor reduces damage from a subsequent infarction event by at least 40%. 43. The method of any previous embodiment, wherein the translocation inhibitor reduces damage from a subsequent infarction event by at least 50%. 44. The method of any previous embodiment, wherein monitoring infarction damage recovery. 45. A method of reducing damage of an infarction event to a subject suffering from an infarction event, comprising administering a mitochondrial membrane translocation inhibitor. 46. The method of any previous embodiment, wherein the translocation inhibitor is administered prior to reoxygenation pursuant to treatment of the infarction event. 47. The method of any previous embodiment, wherein the peptide is administered at least 5 minutes prior to reperfusion. 48. The method of any previous embodiment, wherein the peptide is administered no more than 5 minutes prior to reperfusion. 49. The method of any previous embodiment, wherein the peptide is administered at least one day prior to an infarction risk event. 50. The method of any previous embodiment, wherein the peptide is administered at least two days prior to an infarction risk event. 51. The method of any previous embodiment, wherein the peptide is administered at least three days prior to an infarction risk event. 52. The method of any previous embodiment, wherein the peptide is administered at least seven days prior to an infarction risk event. 53. The method of any previous embodiment, wherein the translocation inhibitor is administered concurrent with reoxygenation pursuant to treatment of the infarction event. 54. The method of any previous embodiment, wherein the treatment reduces BAX mitochondrial concentration by at least 30% relative to an untreated reference. 55. The method of any previous embodiment, wherein the treatment reduces BNIP3 mitochondrial concentration by at least 30% relative to an untreated reference. 56. The method of any previous embodiment, wherein the treatment reduces mitochondrial swelling by at least 30% relative to an untreated reference. 57. The method of any previous embodiment, wherein the treatment reduces BAX active concentration by at least 75% relative to an untreated reference. 58. The method of any previous embodiment, wherein the treatment reduces cytochrome c release by at least 75% relative to an untreated reference. 59. The method of any previous embodiment, wherein the treatment improves Inf/AAR proportion by at least 50% relative to an untreated reference. 60. The method of any previous embodiment, wherein the treatment reduces caspase activity relative to an untreated reference. 61. The method of any previous embodiment, wherein the treatment reduces membrane depolarization relative to an untreated reference. 62. The method of any previous embodiment, wherein the infarction damage risk event comprises a heart attack. 63. The method of any previous embodiment, wherein the infarction damage risk event comprises a stroke. 64. The method of any previous embodiment, wherein the translocation inhibitor is administered intravenously. 65. The method of any previous embodiment, wherein the translocation inhibitor is administered via catheter. 66. The method of any previous embodiment, wherein the translocation inhibitor comprises a chimeric peptide. 67. The method of any previous embodiment, wherein the chimeric protein comprises a segment having at least 75% identity to at least 8 consecutive residues of BNIP3. 68. The method of any previous embodiment, wherein the at least 8 consecutive residues of BNIP3 comprise a phenylalanine residue at a 7th of the at least 8 consecutive residues of BNIP3. 69. The method of any previous embodiment, wherein the 8 consecutive residues comprise residues corresponding to residues 13-20 of BNIP3. 70. The method of any previous embodiment, wherein the chimeric protein comprises a segment having 75% identity to no more than 50 residues of BNIP3. 71. The method of any previous embodiment, wherein the chimeric protein does not comprise a BH3 motif 72. The method of any previous embodiment, wherein the chimeric protein does not comprise a PESTQ motif (SEQ ID NO: 4). 73. The method of any previous embodiment, wherein the chimeric protein comprises a BAX binding motif 74. The method of any previous embodiment, comprising monitoring infarction damage recovery. 75. A method of assessing a molecule for infarction amelioration, said method comprising assaying for binding of the molecule to BAX/BNIP3 oligomeric complexes. 76. The method of any previous embodiment, wherein binding of the molecule to the BAX/BNIP3 oligomeric complex indicates efficacy in infarction amelioration. 77. The method of any previous embodiment, wherein said assaying comprises assaying for colocalization of a molecule and BAX/BNIP3 oligomeric complexes. 78. The method of any previous embodiment, wherein said colocalization is assayed by fluorescence microscopy. 79. The method of any previous embodiment, wherein said assaying comprises assaying for comigration of the molecule and BAX/BNIP3 oligomeric complexes. 80. The method of any previous embodiment, wherein said comigration is performed under conditions to maintain oligomeric BAX/BNIP3 oligomeric complex integrity. 81. The method of any previous embodiment, wherein said comigration is assayed using gel electrophoresis. 82. The method of any previous embodiment, wherein said gel electrophoresis comprises SDS-PAGE. 83. The method of any previous embodiment, wherein said gel electrophoresis comprises western blot analysis. 84. The method of any previous embodiment, wherein said comigration is performed under nondenaturing conditions. 85. The method of any previous embodiment, wherein said assaying comprises assaying for coprecipitation of the molecule and BAX/BNIP3 oligomeric complexes. 86. The method of any previous embodiment, wherein said coprecipitation comprises immunoprecipitation. 87. The method of any previous embodiment, wherein said assay comprises contacting said molecule to a cell subjected to oxygen starvation. 88. The method of any previous embodiment, wherein said assay comprises contacting said molecule to a cell within 10 minutes of subjecting the cell to oxygen starvation. 89. A method of assessing a molecule for infarction amelioration, said method comprising contacting the molecule to a cell subjected to oxygen starvation and assaying for BAX/BNIP3 complex localization. 90. The method of any previous embodiment, wherein retention of BAX/BNIP3 outside of a mitochondrion of the cell indicates efficacy in infarction amelioration. 91. The method of any previous embodiment, wherein inhibition of BAX/BNIP3 translocation into a mitochondrion of the cell indicates efficacy in infarction amelioration. 92. The method of any previous embodiment, wherein inhibition of BAX translocation into a mitochondrion of the cell indicates efficacy in infarction amelioration. 93. The method of any previous embodiment, wherein inhibition of BNIP3 translocation into a mitochondrion of the cell indicates efficacy in infarction amelioration. 94. The method of any previous embodiment, wherein assaying for BAX/BNIP3 complex localization comprises immunofluorescence. 95. The method of any previous embodiment, wherein assaying for BAX/BNIP3 complex localization comprises assaying for mitochondrial integrity. 96. The method of any previous embodiment, wherein assaying for BAX/BNIP3 complex localization comprises assaying for mitochondrial swelling. 97. The method of any previous embodiment, wherein assaying for BAX/BNIP3 complex localization comprises assaying for cytochrome c release. 98. The method of any previous embodiment, wherein assaying for BAX/BNIP3 complex localization comprises assaying for caspase-3 activity. 99. The method of any previous embodiment, wherein said assay comprises contacting said molecule to a cell within 10 minutes of subjecting the cell to oxygen starvation. 100. A method of ameliorating a side effect of a treatment, comprising administering a mitochondrial Protecting and/or stabilizing agent. 101. The method of any previous embodiment, wherein the treatment comprises administering a chemotherapeutic. 102. The method of any previous embodiment, wherein the mitochondrial protecting and/or stabilizing agent comprises a mitochondrial interaction and import inhibitor. 103. The method of any previous embodiment, wherein the chemotherapeutic targets a cancerous cell. 104. The method of any previous embodiment, wherein the chemotherapeutic targets a tumor. 105. The method of any previous embodiment, wherein the chemotherapeutic causes cardiomyocyte cell death. 106. The method of any previous embodiment, wherein the chemotherapeutic comprises a compound selected from the list consisting of an Alkylating agent, such as altretamine, busulfan, carboplatin, carmustine, cisplatin, cyclophosphamide, dacarbazine, ifosfamide, lomustine, melphalan, temozolomide, trabectedin; Antimetabolite, such as 5-fluorouracil, 6-mercaptopurine, azacitidine, capecitabine, clofarabine, cytarabine, floxuridine, fludarabine, gemcitabine, methotrexate, pemetrexed, pentostatin, pralatrexate, trifluridine and tipiracil; antibodies, such as HER2 inhibitors e.g. trastuzumab, pertuzumab, margetuximab, immune checkpoint inhibitors e.g. nivolumab (anti-PD-1) avelumab (anti-PD-L1), ipilimumab (anti-CTLA-4), relatlimab (anti-LAG-3); a Plant alkyloid, such as, vincristine, vinblastine, vinorelbine, paclitaxel, docetaxel, etoposide, teniposide, irinotecan, topotecan; an antitumor agent, such as, daunorubicin, doxorubicin, doxorubicin liposomal, epirubicin, idarubicin, and valrubicin. 107. The method of any previous embodiment, wherein the chemotherapeutic comprises a compound selected from the list consisting of daunorubicin, doxorubicin, doxorubicin liposomal, epirubicin, idarubicin, and valrubicin. 108. The method of any previous embodiment, wherein the chemotherapeutic comprises an anthracycline. 109. The method of any previous embodiment, wherein the anthracycline comprises doxorubicin. 110. The method of any previous embodiment, wherein the inhibitor impacts BNIP3 activity. 111. The method of any previous embodiment, wherein the inhibitor impacts at least one indication selected from the list comprising DOX cell death induction, mitochondrial membrane potential stabilization, mitochondrial pore opening prevention, mitochondrial Calcium ion overload prevention, mitochondrial ROS or accumulation prevention. 112. The method of any previous embodiment, wherein the inhibitor attenuates cardiotoxicity. 113. The method of any previous embodiment, wherein the inhibitor attenuates cardiomyocyte death. 114. The method of any previous embodiment, wherein the inhibitor preserves cardiac function. 115. The method of any previous embodiment, wherein the inhibitor increases mitochondrial fitness. 116. The method of any previous embodiment, wherein the inhibitor preserves autophagic flux. 117. The method of any previous embodiment, wherein the inhibitor comprises a polypeptide. 118. The method of any previous embodiment, wherein the inhibitor comprises a BNIP3 fragment. 119. The method of any previous embodiment, wherein the inhibitor comprises a BAX fragment. 120. The method of any previous embodiment, wherein administering comprises injecting. 121. A composition for use in ameliorating a negative impact of a treatment, the composition comprising a chemotherapeutic and a mitochondrial interaction and import inhibitor. 122. The composition for use of any previous embodiment, wherein the chemotherapeutic targets a cancerous cell. 123. The composition for use of any previous embodiment, wherein the chemotherapeutic targets a tumor. 124. The composition for use of any previous embodiment, wherein the chemotherapeutic causes cardiomyocyte cell death. 125. The composition for use of any previous embodiment, wherein the chemotherapeutic comprises a compound selected from the list consisting of an Alkylating agent, such as altretamine, busulfan, carboplatin, carmustine, cisplatin, cyclophosphamide, dacarbazine, ifosfamide, lomustine, melphalan, temozolomide, trabectedin; Antimetabolite, such as 5-fluorouracil, 6-mercaptopurine, azacitidine, capecitabine, clofarabine, cytarabine, floxuridine, fludarabine, gemcitabine, methotrexate, pemetrexed, pentostatin, pralatrexate, trifluridine and tipiracil; antibodies, such as HER2 inhibitors e.g. trastuzumab, pertuzumab, margetuximab, immune checkpoint inhibitors e.g. nivolumab (anti-PD-1), avelumab (anti-PD-L1), ipilimumab (anti-CTLA-4), relatlimab (anti-LAG-3); a Plant alkyloid, such as, vincristine, vinblastine, vinorelbine, paclitaxel, docetaxel, etoposide, teniposide, irinotecan, topotecan; an anti-tumor agent, such as, daunorubicin, doxorubicin, doxorubicin liposomal, epirubicin, idarubicin, and valrubicin. 126. The composition for use of any previous embodiment, wherein the chemotherapeutic comprises a compound selected from the list consisting of daunorubicin, doxorubicin, doxorubicin liposomal, epirubicin, idarubicin, and valrubicin. 127. The composition for use of any previous embodiment, wherein the chemotherapeutic comprises an anthracycline. 128. The composition for use of any previous embodiment, wherein the anthracycline comprises doxorubicin. 129. The composition for use of any previous embodiment, wherein the inhibitor impacts BNIP3 activity. 130. The composition for use of any previous embodiment, wherein the inhibitor impacts at least one indication selected from the list comprising DOX cell death induction, mitochondrial membrane potential stabilization, mitochondrial pore opening prevention, mitochondrial Calcium ion overload prevention, mitochondrial ROS or accumulation prevention. 131. The composition for use of any previous embodiment, wherein the inhibitor attenuates cardiotoxicity. 132. The composition for use of any previous embodiment, wherein the inhibitor attenuates cardiomyocyte death. 133. The composition for use of any previous embodiment, wherein the inhibitor preserves cardiac function. 134. The composition for use of any previous embodiment, wherein the inhibitor increases mitochondrial fitness. 135. The composition for use of any previous embodiment, wherein the inhibitor preserves autophagic flux. 136. The composition for use of any previous embodiment, wherein the inhibitor comprises a polypeptide. 137. The composition for use of any previous embodiment, wherein the inhibitor comprises a BNIP3 fragment. 138. The composition for use of any previous embodiment, wherein the inhibitor comprises a BAX fragment. 139. The composition for use of any previous embodiment, wherein administering comprises injecting. 140. A method of ameliorating harm to cardiac function, comprising identifying a patient at risk of harm related to mitochondrial disruption, and administering a mitochondrial import inhibitor to the patient. 141. The method of any previous embodiment, wherein the harm related to mitochondrial disruption is a risk of harm to cardiac function. 142. The method of any previous embodiment, wherein a patient at risk of harm to cardiac function comprises a patient suffering from a cardiac infarction. 143. The method of any previous embodiment, wherein a patient at risk of harm to cardiac function comprises a patient suffering from cardiac arrest. 144. The method of any previous embodiment, wherein a patient at risk of harm to cardiac function comprises a patient expected to undergo surgery. 145. The method of any previous embodiment, wherein a patient at risk of harm to cardiac function comprises a patient undergoing surgery. 146. The method of any previous embodiment, wherein a patient at risk of harm to cardiac function comprises a patient having undergone surgery. 147. The method of any previous embodiment, wherein a patient at risk of harm to cardiac function comprises a patient receiving a chemotherapeutic. 148. The method of any previous embodiment, wherein the chemotherapeutic targets a cancer. 149. The method of any previous embodiment, wherein the chemotherapeutic targets a tumor. 150. The method of any previous embodiment, wherein the chemotherapeutic and the mitochondrial import inhibitor are administered concurrently. 151. The method of any previous embodiment, wherein the chemotherapeutic and the mitochondrial import inhibitor are administered in a common composition. 152. The method of any previous embodiment, wherein the chemotherapeutic and the mitochondrial import inhibitor are not administered concurrently. 153. The method of any previous embodiment, wherein the chemotherapeutic targets a cancerous cell. 154. The method of any previous embodiment, wherein the chemotherapeutic targets a tumor. 155. The method of any previous embodiment, wherein the chemotherapeutic causes cardiomyocyte cell death. 156. The method of any previous embodiment, wherein the chemotherapeutic comprises a compound selected from the list consisting of an Alkylating agent, such as altretamine, busulfan, carboplatin, carmustine, cisplatin, cyclophosphamide, dacarbazine, ifosfamide, lomustine, melphalan, temozolomide, trabectedin; Antimetabolite, such as 5-fluorouracil, 6-mercaptopurine, azacitidine, capecitabine, clofarabine, cytarabine, floxuridine, fludarabine, gemcitabine, methotrexate, pemetrexed, pentostatin, pralatrexate, trifluridine and tipiracil; antibodies, such as HER2 inhibitors e.g. trastuzumab, pertuzumab, margetuximab, immune checkpoint inhibitors e.g. nivolumab (anti-PD-1), avelumab (anti-PD-L1), ipilimumab (anti-CTLA-4), relatlimab (anti-LAG-3); a Plant alkyloid, such as, vincristine, vinblastine, vinorelbine, paclitaxel, docetaxel, etoposide, teniposide, irinotecan, topotecan; an anti-tumor agent, such as, daunorubicin, doxorubicin, doxorubicin liposomal, epirubicin, idarubicin, and valrubicin. 157. The method of any previous embodiment, wherein the chemotherapeutic comprises a compound selected from the list consisting of daunorubicin, doxorubicin, doxorubicin liposomal, epirubicin, idarubicin, and valrubicin. 158. The method of any previous embodiment, wherein the chemotherapeutic comprises an anthracycline. 159. The method of any previous embodiment, wherein the anthracycline comprises doxorubicin. 160. The method of any previous embodiment, wherein the inhibitor impacts BNIP3 activity. 161. The method of any previous embodiment, wherein the inhibitor impacts at least one indication selected from the list comprising DOX cell death induction, mitochondrial membrane potential stabilization, mitochondrial pore opening prevention, mitochondrial Calcium ion overload prevention, mitochondrial ROS or accumulation prevention. 162. The method of any previous embodiment, wherein the inhibitor attenuates cardiotoxicity. 163. The method of any previous embodiment, wherein the inhibitor attenuates cardiomyocyte death. 164. The method of any previous embodiment, wherein the inhibitor preserves cardiac function. 165. The method of any previous embodiment, wherein the inhibitor increases mitochondrial fitness. 166. The method of any previous embodiment, wherein the inhibitor preserves autophagic flux. 167. The method of any previous embodiment, wherein the inhibitor comprises a polypeptide. 168. The method of any previous embodiment, wherein the inhibitor comprises a BNIP3 fragment. 169. The method of any previous embodiment, wherein the inhibitor comprises a BAX fragment. 170. The method of any previous embodiment, wherein administering comprises injecting.

Turning to the Figures, one sees the following.

Figure 7A:
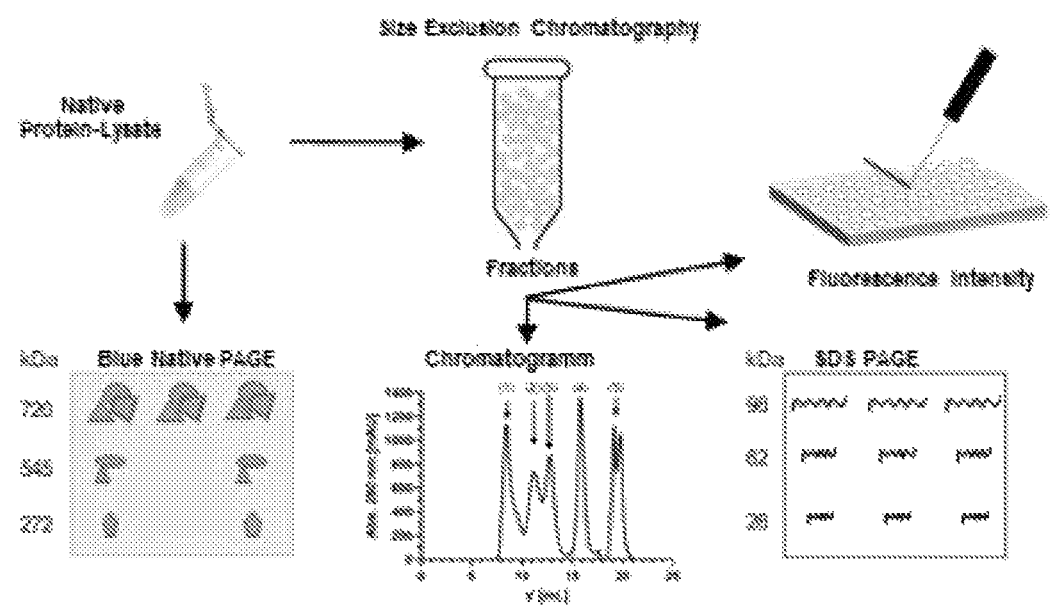
FIG. 7A. Assay flow diagram related to FIG. 1B.

FIG. 1A-Q. Cytosolic BNIP3 determines necrotic and apoptotic cell death successively by regulating BAX in a heterodimeric state (A) Immunoblot for cytosolic BNIP3 following blue native-PAGE at baseline (n=5). (B) Immunoblot for cytosolic BNIP3 following size exclusion chromatography (n=3) (FIG. 7A). (C) In vivo I/R model timeline and schematic of a heart section depicting the non-ischemic area (remote; blue), ischemic area (area at risk, AAR; red), and infarct area (white, embedded in the AAR). (D) Infarct sizes per area at risk (Inf/AAR) in wild-type and Bnip3$^{-/-}$ mice treated with TATBNIP3 as indicated (n=3-6). This indicates that increasing TAT-Bnip3 administration returns Inf/AAR percent ratios to wild-type levels. (See FIGS. 7B) (E-L and N-Q) Wild-type mice were treated with vehicle or TAT-BNIP3-ATM. (E) Representative images of the necrotic area (blue), troponin I (red) and nuclei (blue) at 24 hours reperfusion. Scale bars, 1 mm and plasma troponin I after 24 hours of reperfusion (n=4-12). Sham operated mice served as controls. Delta-TM administered mice show a substantiual return to sham treated Troponin I levels (See FIG. 7C. (F) Representative images of apoptotic cells (red) and nuclei (blue) in the AAR 4 hours after I/R. Scale bars, 2,000 m (left), 200 m (right) and apoptotic events in the whole heart and plane sections from apical to basal after 4 hours of reperfusion (n=3-5). (G) Depolarized mitochondria at baseline and for the indicated reperfusion times (n=3-5) assessed by flow cytometry (see FIG. 8A). At I/R$_{10}$, delta-TM mice showed a return to basal levels of depolarized mitochondria. For 2D scatter plots, see FIG. 8C. (H) Swollen mitochondria in the AAR after 10 minutes of reperfusion (OD, optical density; n=3-4). Sham operated mice served as controls. At I/R$_{10}$, delta-TM mice showed a return to basal levels of swollen mitochondria (I) Representative electron micrographs depicting swollen mitochondria in the AAR at 10 minutes reperfusion. Scale bars, 2 m (left in each pair), 1 μm (right) (n=3). For fragmented mitochondria, see FIGS. 8B and D. At I/R$_{10}$, delta-TM mice showed a return to basal levels of mitochondrial swelling (J and K) Quantification and representative immunoblots of the mitochondrial BAX concentration (J) and mitochondrial BNIP3 level (*p=0.0148 and *p=0.0185) (K) in the area at risk (AAR) at baseline and 10 minutes reperfusion (AAR) (n=5-7) (see FIG. 8E-I). Delta-TM mice showed a return to basal levels for both assays. (L) Quantification and representative immunoblot of active BAX at baseline and the indicated reperfusion time point (n=5). At I/R$_{30}$, delta-TM mice showed a return to basal levels of active BAX concentration (see FIG. 9A-C). (M) Quantification and representative immunoblot of mitochondrial BAX levels in the AAR of Bnip3−/− mice untreated and treated with TAT-BNIP3 (n=3; *p=0.0152). At I/R$_{10}$, delta-TM mice showed shift opposite that of untreated Bnip3−/− mice alone. (N) Western blot monitoring of cytosolic BAX co-immunoprecipitated with BNIP3 (left) and cytosolic BNIP3 co-immunoprecipitated with BAX (right) at baseline and after 10 and 30 minutes of reperfusion (n=3) (O) Cytoplasmic cytochrome c in the AAR at baseline and for the indicated reperfusion time points (n=5-6). At I/R$_{30}$, delta-TM mice maintained basal levels of cytochrome c. (P) ATP in the AAR at baseline and 10 minutes reperfusion (n=4; *p=0.0153 and *p=0.011). At I/R$_{10}$, delta-TM mice maintained basal levels of ATP. (Q) Serine-phosphorylated BNIP3 levels at baseline and the indicated reperfusion time points (n=5-8) (see FIG. 9D). Data represent the means±SEM; p values were determined by two-way ANOVA with Bonferroni's correction. At I/R$_{30}$, delta-TM mice maintained basal levels of BNIP3 phosphorylation.

FIG. 2A-G. N-terminus is the interacting domain of BNIP3 (A) Images of membranes spotted with BAX and BNIP3 and incubated with fluorescently labelled (Dy650) BNIP3 (left) and BAX (right). (B) Schematic of the protocol designed by JPT (Germany, Berlin). (C) Heat map depiction of BNIP3 incubation with the BAX peptide library displaying the helices α5, α6 and α7+α8 as interaction sites. Color coding ranges from white (low or no intensity) to yellow (middle intensity) and red (high intensity) and structure of mouse BAX (PDB 4S0OZit) in ribbon representation with BNIP3 interaction sites colored blue (α5), green (α6), yellow (α7) and orange (α8). (D and E) 3D structural model of BNIP3 predicted by Modeller 9.15 with marked helices. (F) Circular dichroism (CD) spectroscopic analysis of BNIP3. (G) Cartoon representations of BAX/BNIP3 interactions with the indicated binding sites resulting from in silico docking experiments using HADDOCK. BNIP3 is colored turquoise, and BAX is colored green. Interaction sites are in purple (BAX) and orange (BNIP3).

Figure 3A:
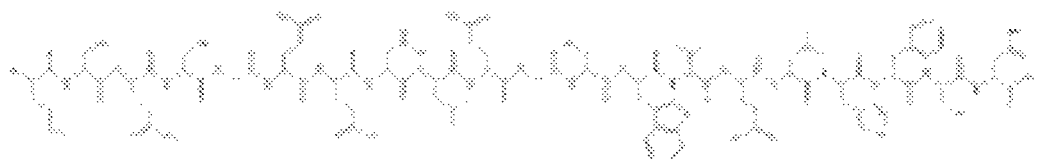
FIG. 3A. TAT-20A MSQGEENLQGSWVELHFSN (SEQ ID NO: 5). Figure discloses "MSQSGEENLQGSWVELHFSN" as SEQ ID NO: 1.
Figure 3B:
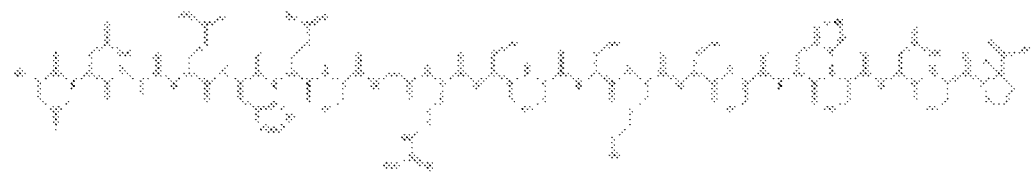
FIG. 3B. TAT-20C LDAQHESGRSSSKSSHCDSP (SEQ ID NO: 6). Figure discloses "LDAQHESGRSSSKSSHCDSP" as SEQ ID NO: 6.
Figure 3C:
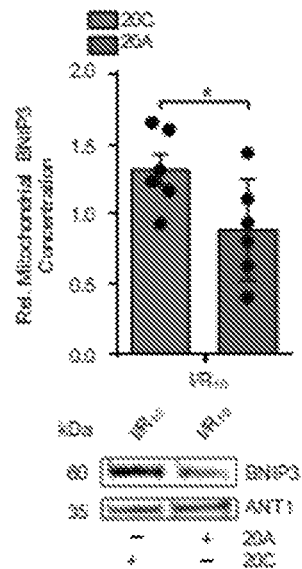
FIG. 3C. 20A shows reduced relative BNIP3 mitochondrial concentration.
Figure 3D:
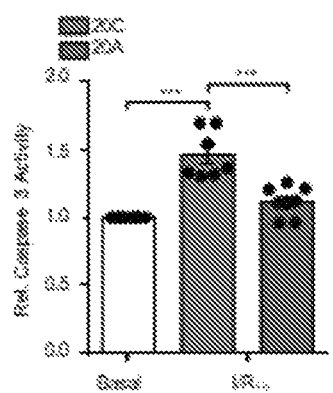
FIG. 3D. 20A restores basal relative caspase 3 activity.
Figure 3E:
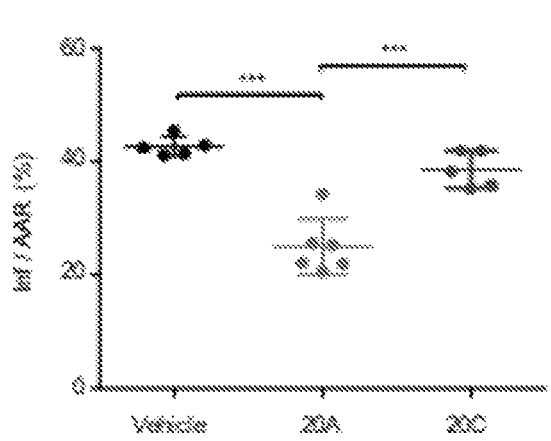
FIG. 3E. 20A improves Inf/AAR percent relative to vehicle or 20C.
Figure 3F:
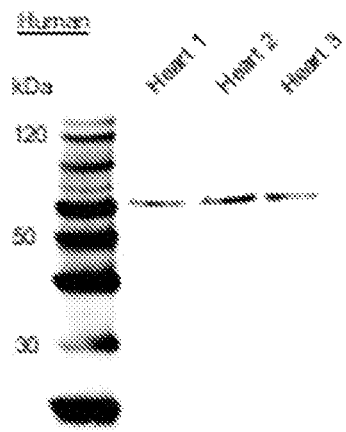
FIG. 3F. Human protein blot.
Figure 3H:
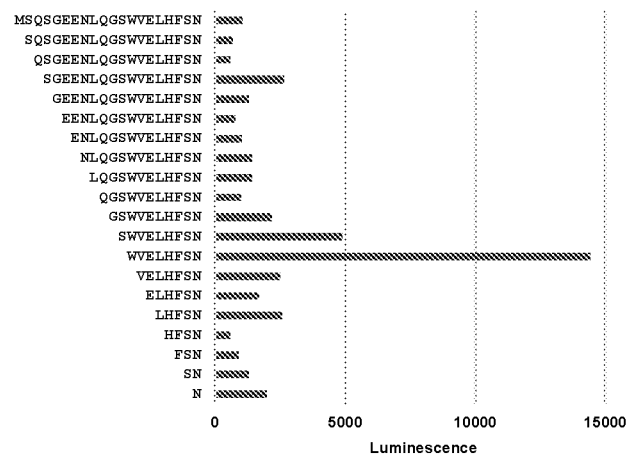
FIG. 3H. Truncation fluorescence assay for 20A N-terminal truncations. WVELHFSN (SEQ ID NO: 2) shows elevated levels. Figure discloses SEQ ID NOS 1, 40-50, 2, 8, and 51-53, respectively, in order of appearance.
Figure 3I:
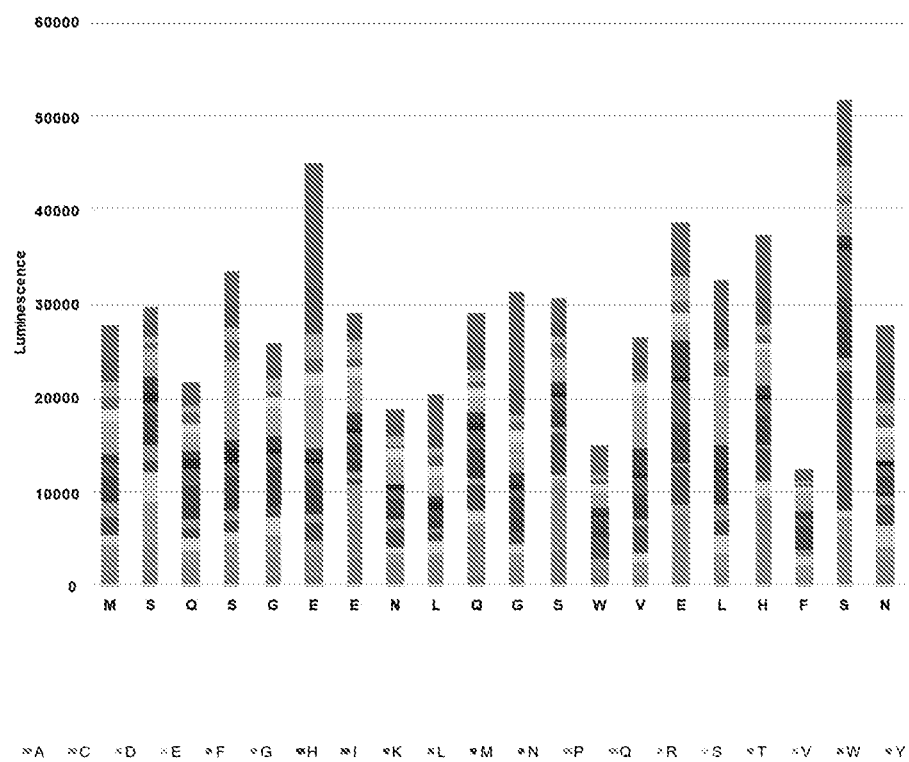
FIG. 3I. Substitution fluorescence assay.
Figure 3J:
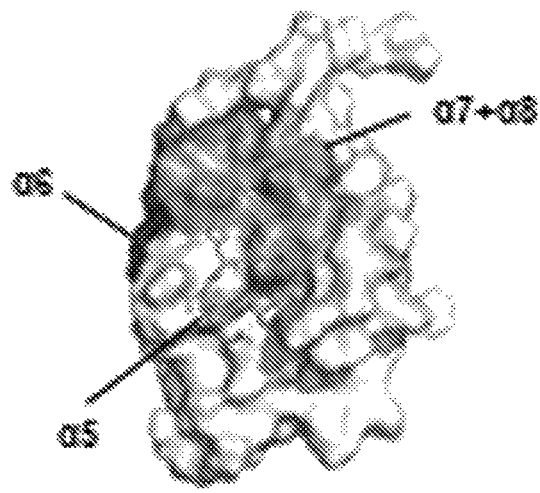
FIG. 3J. Binding pocket prediction.
Figure 3K:
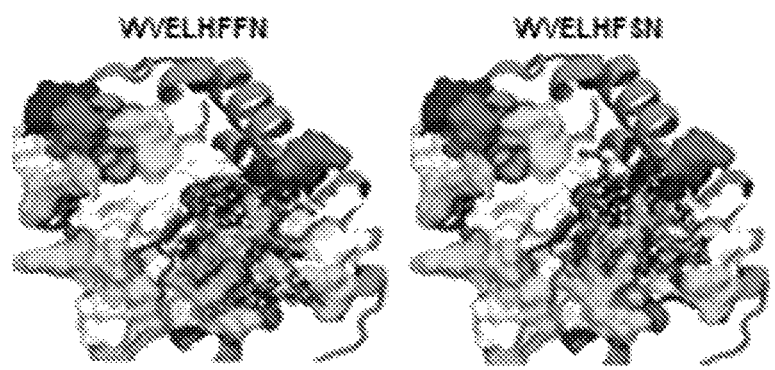
FIG. 3K. Interaction heat map. Figure discloses SEQ ID NOS 3, 2, 1, 2, 3, and 7, respectively, in order of appearance.
Figure 3L:
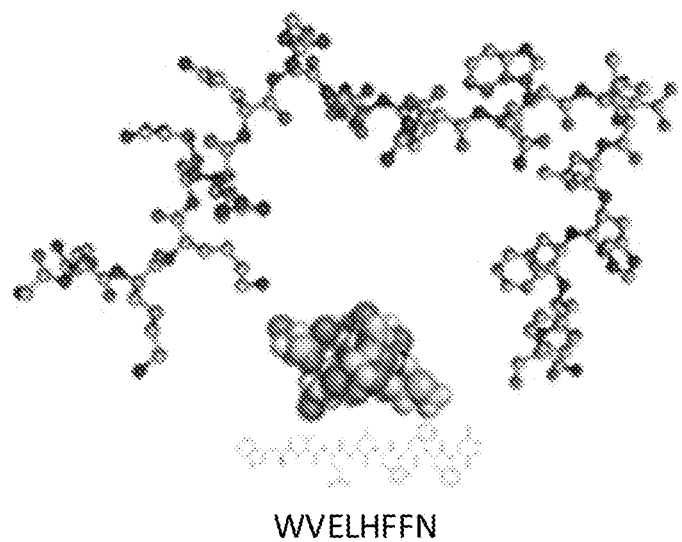
FIG. 3L. Interaction model. Figure discloses "WVELHFFN" as SEQ ID NO: 3.
Figure 3M:
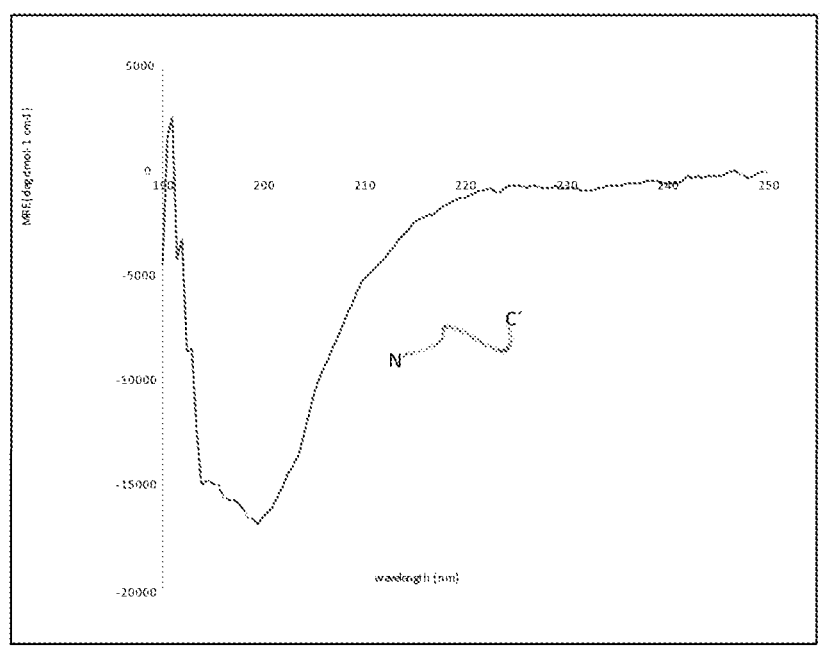
FIG. 3M. Folding prediction.
Figure 3N:
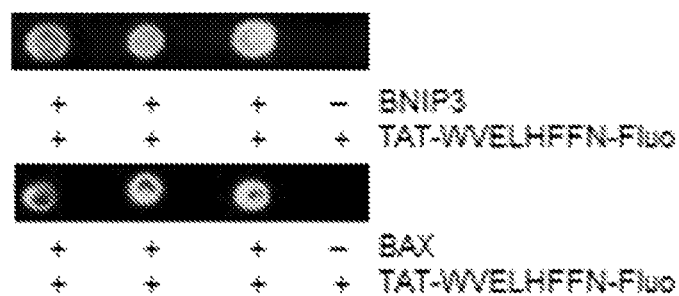
FIG. 3N. TAT-WVELHFFN ("WVELHFFN" disclosed as SEQ ID NO: 3) binds BNIP3 and BAX. Figure discloses "WVELHFFN-Fluo" as SEQ ID NO: 9.
Figure 3O:
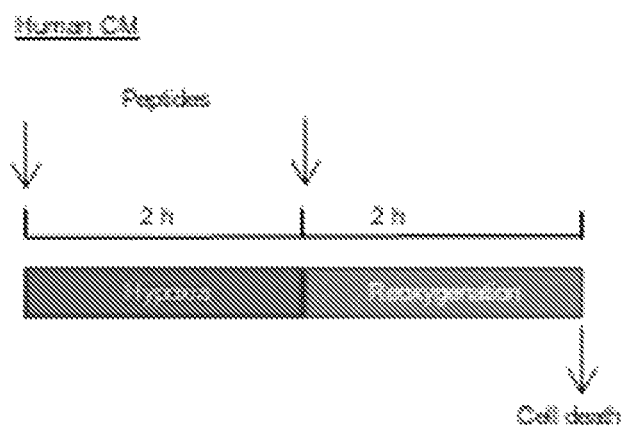
FIG. 3O. Time course model.
Figure 3P:
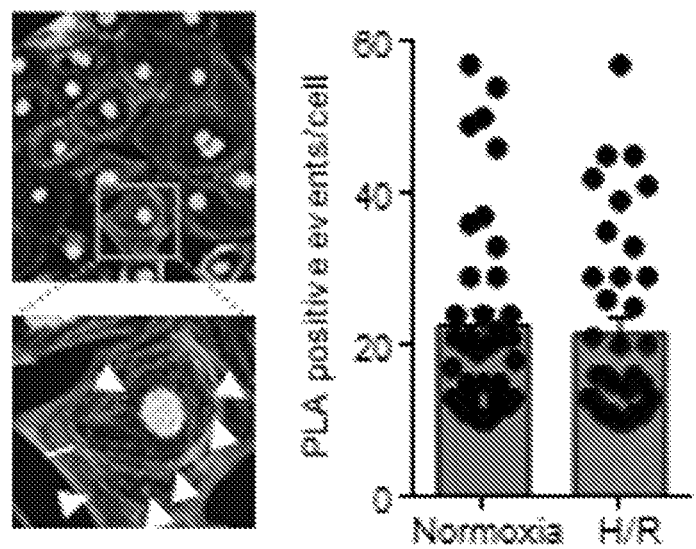
FIG. 3P. PLA positive events per cell.
Figure 3Q:
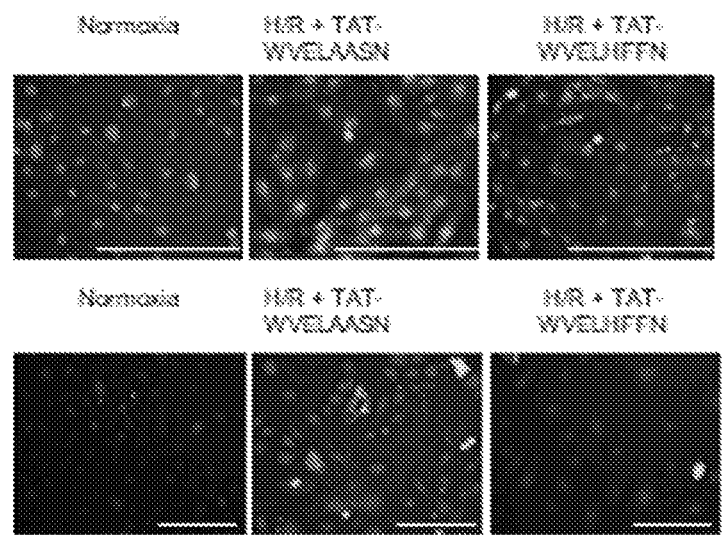
FIG. 3Q. Comparison of TAT-peptide variants. Figure discloses "WVELHFFN" as SEQ ID NO: 3 and "WVELAASN" as SEQ ID NO: 7.

FIG. 3A-Q. N-terminus of BNIP3 is a critical functional domain in human cardiomyocytes protection (A) Structural formula of TAT-BNIP3-20A. (B) Structural formula of TAT-BNIP3-20C. (C-E) Mice were treated with TAT-BNIP3-20A (20A) or TAT-BNIP3-20C (20C). (C) Quantification and representative immunoblot of mitochondrial BNIP3 levels in the area at risk (AAR) at 10 minutes reperfusion (n=6). 20A mice showed a lower relative mitochondrial BNIP3 concentration. (D) Quantification of caspase-3 activity in the AAR at 1 hour reperfusion (n=7). 20A mice showed a lower relative Capsase 3 activity, closer to basal levels. (E) Infarct sizes per AAR (Inf/AAR) in wild-type mice treated with vehicle (NaCl), 20A or 20C at 24 hours reperfusion (n=5-6). 20A mice showed a lower INF/AAR percent than either vehicle or 20C (F) Immunoblot of BNIP3 in three human heart samples. (G) Alignment of the human and mouse BNIP3 sequences. The red box indicates the amino acids WVELHFSN (SEQ ID NO: 2), with the highest binding intensity representing a conserved region. (H and I) Peptide microarrays of BNIP3 with the N-terminal sequence of BNIP3 (1-20 aa). (H) N-terminal sequence truncation analysis elucidating BNIP3/peptide interactions. VELHFSN (SEQ ID NO: 8) showed a substantially higher luminescence (see FIG. 10A). (I) Single amino acid substitutions characterizing their binding capacities. (J) Docking experiments on BAX (PDB code 4S0O) with TAT-WVELHFFN ("WVELHFFN" disclosed as SEQ ID NO: 3) showing the interaction sites in BAX. (K) Docking experiments on BAX (PDB code 4S0O) with TAT-WVELHFFN ("WVELHFFN" disclosed as SEQ ID NO: 3) and TAT-WVELHFSN ("WVELHFSN" disclosed as SEQ ID NO: 2) and peptide microarrays of BAX with indicated peptide sequences. Addition of a third aromatic residue results in improved intrapeptide aromatic interactions, in particular for WVELHFFN (SEQ ID NO: 3). (L) Space-filling models and structure formula of TAT-WVELHFFN ("WVELHFFN" disclosed as SEQ ID NO: 3) (see FIG. 10B). (M) Circular dichroism (CD) spectroscopic analysis of TAT-WVELHFFN ("WVELHFFN" disclosed as SEQ ID NO: 3). (N) Images of membranes spotted with BNIP3 (upper) and BAX (bottom) and incubated with fluorescently labelled TAT-WVELHFFN ("WVELHFFN" disclosed as SEQ ID NO: 3) (TAT-WVELHFFN-fluo ("WVELHFFN-fluo" disclosed as SEQ ID NO: 9)). (O) Timeline of the in vitro hypoxia/reoxygenation (H/R) study design in human ventricular cardiomyocytes derived from human induced pluripotent stem cells (human CMs). (P) BNIP3/BAX interactions in human CMs after 1 h hypoxia/1 h of reperfusion (PLA, proximity ligation assay) (n=5) and representative staining confocal images. Cell structure (green), nucleus (blue), PLA spots (red; marked by white arrows), 40×. (Q) Depolarized mitochondria (green), healthy mitochondria (red), nucleus (blue) after 1 h hypoxia/1 h reoxygenation (upper panel). Apoptotic (green), necrotic (red) and healthy (blue) human CMs after 2 h hypoxia/2 h reoxygenation, treated with TAT-WVE-LAASN ("WVELAASN" disclosed as SEQ ID NO: 7) and TAT-WVELHFFN ("WVELHFFN" disclosed as SEQ ID NO: 3) (bottom panel). Scale bars, 200 m. Data represent the means±SEM; p values were determined by two-way ANOVA with Bonferroni's correction or two-tailed Student's t-test.

FIG. 4A-H. WVELHFFN peptide functions in necrotic and apoptotic signaling prevention in vivo (A) Timeline of the in vivo ischemia/reperfusion model. (B) Uptake of labelled TAT-WVELHFFN ("WVELHFFN" disclosed as SEQ ID NO: 3) in different organs at 10 minutes reperfusion. TAT-WVELHFFN ("WVELHFFN" disclosed as SEQ ID NO: 3) was administered 5 minutes before reperfusion (see FIG. 1I A-C). (C) Representative 3D visualization of TAT-WVELHFFN-Cy5.5 ("WVELHFFN-Cy5.5" disclosed as SEQ ID NO: 10) (red) distribution across a whole murine heart after I/R (blue knot) with endogenous autofluorescence (green). (D-I) Mice were treated with TAT-WELVHFFN ("WELVHFFN" disclosed as SEQ ID NO: 11) or TAT-WELAASN ("WELAASN" disclosed as SEQ ID NO: 12). Sham operated mice served as controls. (D) Mitochondrial BNIP3 (*p=0.0161) and (E) mitochondrial BAX levels in the area at risk (AAR) at 10 minutes reperfusion. (n=5). (F) Swollen mitochondria from the AAR at 10 minutes reperfusion (OD, optical density; n=5). (G) Active BAX and (H) cytoplasmic cytochrome c levels in the AAR at 30 minutes reperfusion (n=5; *p=0.032). (I) Caspase-3 activity in the AAR at 1 hour reperfusion (n=8-12; *p=0.0164). Data represent the means±SEM; p values were determined by two-way ANOVA with Bonferroni's correction. In each of these assays, TAT-WELVHFFN ("WELVHFFN" disclosed as SEQ ID NO: 11) administration returned measurement outputs to near sham levels.

FIG. 5A-I. WVELHFFN functions in inhibition of BNIP3/BAX heterodimers as components of the mitochondrial membrane attack oligomers (A and B) Representative immunoblot for BNIP3 (A) and BAX (B) following SDS-PAGE at baseline and 10 minutes reperfusion. Mice were treated with TAT-WELVHFFN ("WELVHFFN" disclosed as SEQ ID NO: 11) and TAT-WVELAASN ("WVELAASN" disclosed as SEQ ID NO: 7). Sham operated mice served as controls (n=3). (C) Representative BAX immunoblot following co-immunoprecipitation of BNIP3 as in (A) (n=3) (D) Fluorescent immunoblot at 5 minutes of reperfusion. Mice were treated with vehicle (NaCl) and fluorescence-labelled TAT-WELVHFFN ("WELVHFFN" disclosed as SEQ ID NO: 11). (E) BAX and BNIP3 immunoblot following co-immunoprecipitation of cytosolic BNIP3 and BAX and photometric fluorescence measurement of cytosolic fraction (n=3). (F) Immunoblot for cytosolic BNIP3 and BAX in the area at risk (AAR) following blue native-PAGE at baseline and 10 minutes reperfusion (n=3). (G) Immunoblot for cytosolic BNIP3 following size exclusion chromatography at 10 minutes reperfusion with and without TAT-WVELHFFN ("WVELHFFN" disclosed as SEQ ID NO: 3) treatment (n=3). (H) Immunoblot for cytosolic BAX following size exclusion chromatography at baseline and 10 minutes reperfusion with and without TAT-WVELHFFN ("WVELHFFN" disclosed as SEQ ID NO: 3) treatment (n=3). (I) Fluorescence measurement of TAT-WVELHFFN-fluo ("WVELHFFN-fluo" disclosed as SEQ ID NO: 9) following size exclusion chromatography at 5 min reperfusion (n=3).

Figure 6A:
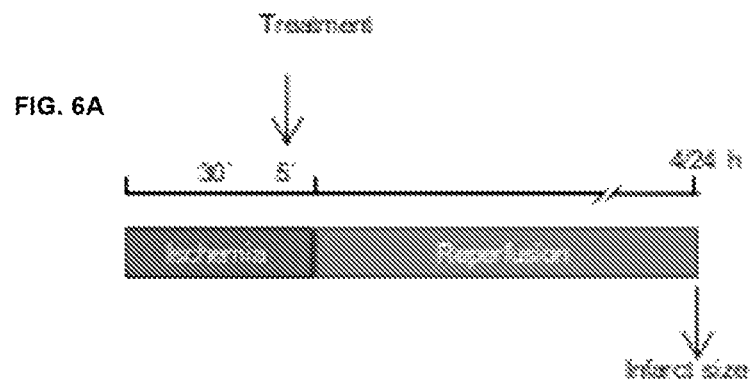
FIG. 6A. Assay time course schematic.
Figure 6B:
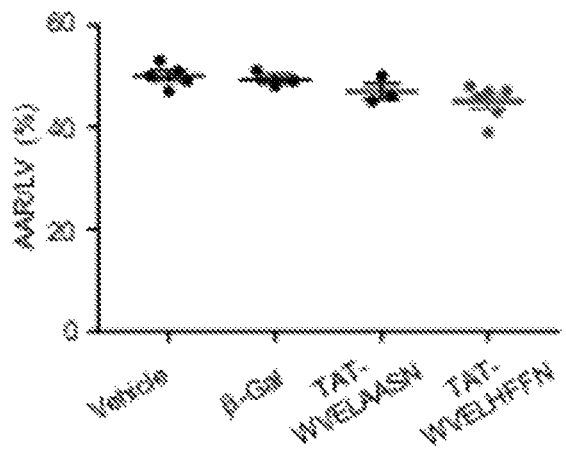
FIG. 6B. AAR/LV % for various treatments. Figure discloses SEQ ID NOS 7 and 3, respectively, in order of appearance.
Figure 6C:
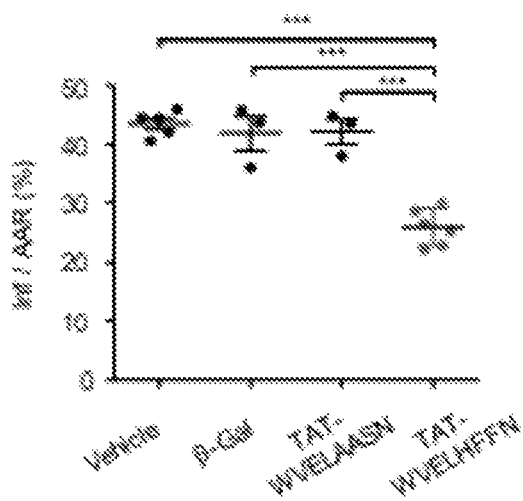
FIG. 6C. TAT-WVELHFFN ("WVELHFFN" disclosed as SEQ ID NO: 3) improves Inf/AAR %. Figure discloses SEQ ID NOS 7 and 3, respectively, in order of appearance.
Figure 6D:
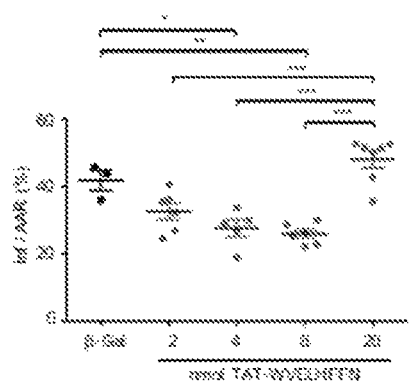
FIG. 6D. TAT-WVELHFFN ("WVELHFFN" disclosed as SEQ ID NO: 3) improves Inf/AAR % at concentrations below 20 nmol. Figure discloses SEQ ID NO: 3.
Figure 6E:
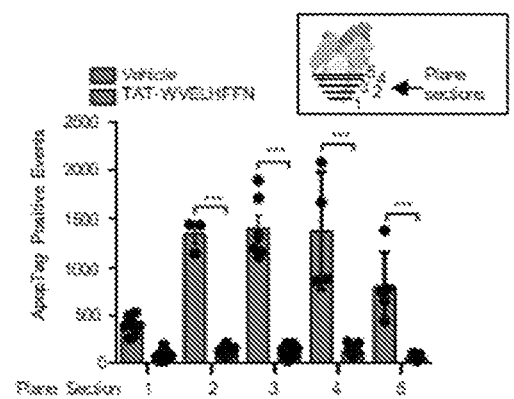
FIG. 6E. TAT-WVELHFFN ("WVELHFFN" disclosed as SEQ ID NO: 3) reduces ApopTag events. Figure discloses SEQ ID NO: 3.
Figure 6F:
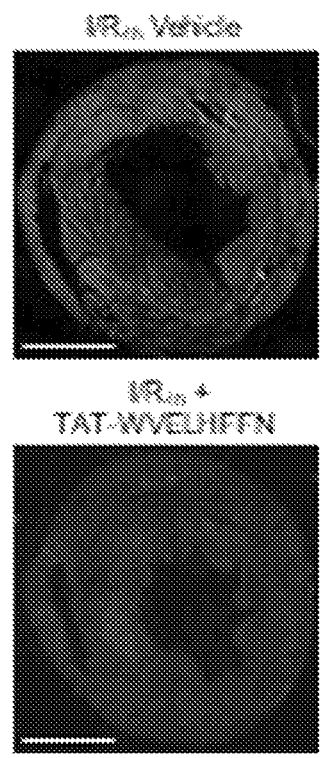
FIG. 6F. Treatment image. Figure discloses SEQ ID NO: 3.
Figure 6G:
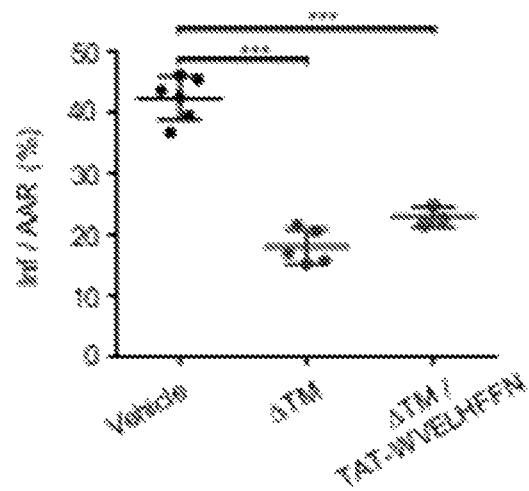
FIG. 6G. deltaTM and deltaTM/TAT-WVELHFFN ("WVELHFFN" disclosed as SEQ ID NO: 3) reduce Inf/AAR %. Figure discloses SEQ ID NO: 3.
Figure 6H:
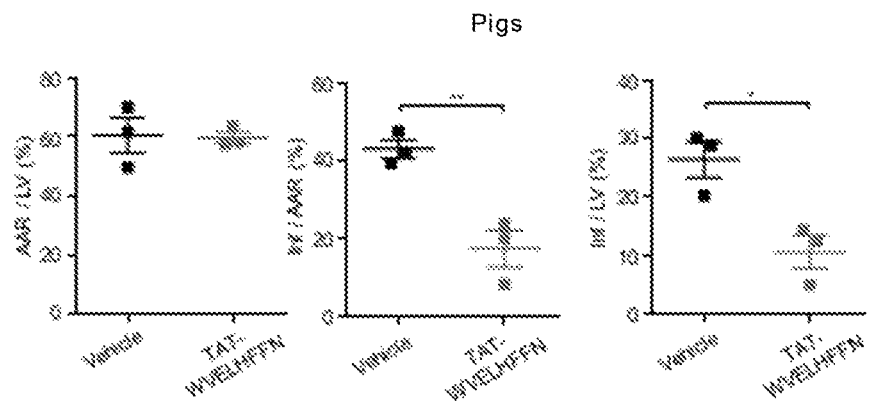
FIG. 6H. TAT-WVELHFFN ("WVELHFFN" disclosed as SEQ ID NO: 3) reduces Inf/AAR and Inf/LV in pig infarction events. Figure discloses "WVELHFFN" as SEQ ID NO: 3.
Figure 6I:
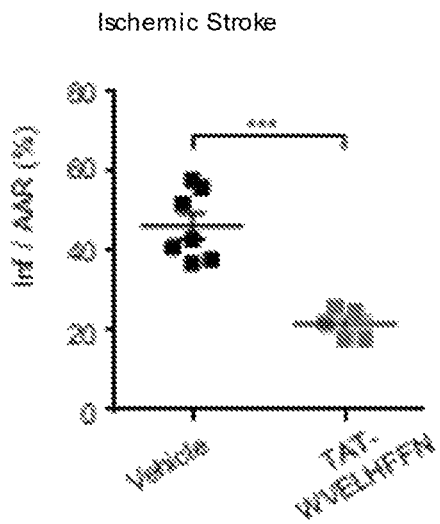
FIG. 6I. TAT-WVELHFFN ("WVELHFFN" disclosed as SEQ ID NO: 3) reduces Inf/AAR in pig ischemic stroke events. Figure discloses SEQ ID NO: 3.
Figure 6J:
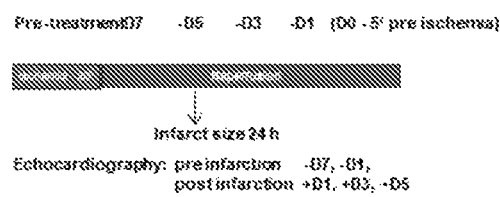
FIG. 6J. Treatment course.
Figure 6K:
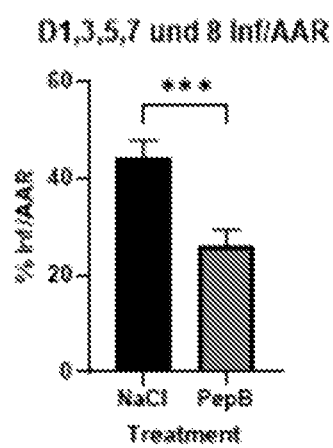
FIG. 6K PepB treatment reduces Inf/AAR.
Figure 6L:
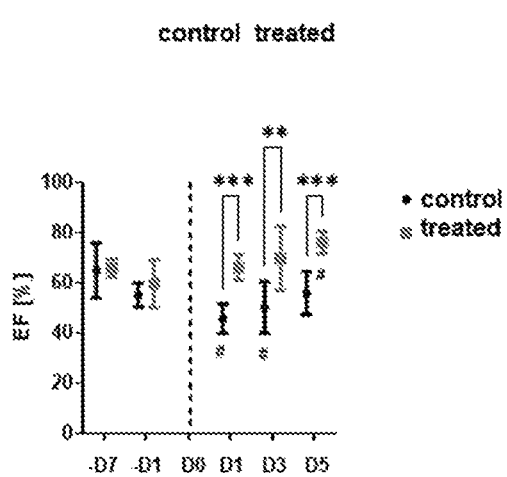
FIG. 6L. Pre-treatment preserves cardiac function over control.
Figures 6M, 6N:
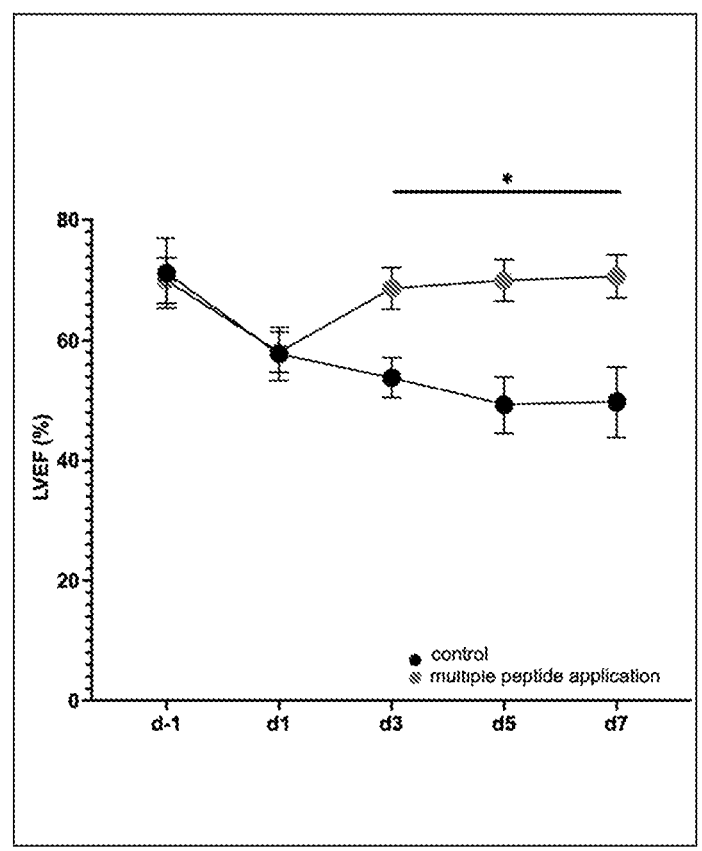
FIG. 6M. Treatment course.
FIG. 6N. Additional post-treatment improves cardiac function over control.

FIG. 6A-N. TAT-WVELHFFN ("WVELHFFN" disclosed as SEQ ID NO: 3) improves clinical outcomes (A) Timeline of the in vivo ischemia/reperfusion (I/R) model. Animals were injected with vehicle (sodium chloride), β-Gal, TAT-WVELAASN ("WVELAASN" disclosed as SEQ ID NO: 7) or TAT-WVELHFFN ("WVELHFFN" disclosed as SEQ ID NO: 3). (B) Area at risk (AAR) per left ventricle (LV) and (C) infarct sizes per AAR (Inf/AAR) at 24 hours myocardial reperfusion in wild-type mice treated as indicated (n=6). TAT-WELVHFFN ("WELVHFFN" disclosed as SEQ ID NO: 11) administration substantially reduced infarct size. (D) Infarct sizes at 24 hours myocardial reperfusion in wild-type mice treated with the indicated TAT-WVELHFFN ("WVELHFFN" disclosed as SEQ ID NO: 3) doses (n=3-7; *p=0.0172). TAT-WELVHFFN ("WELVHFFN" disclosed as SEQ ID NO: 11) substantially reduced infarct size at suitable doses of administration. (E) Apoptotic events in heart plane sections at 4 hours reperfusion. At all plane sections tested, TAT-WELVHFFN ("WELVHFFN" disclosed as SEQ ID NO: 11) administration reduced the number of apoptosis events. (F) Representative images of apoptotic cells (red) and nuclei (blue) in the AAR at 4 hours reperfusion. (G) Inf/AAR at 24 hours myocardial reperfusion in wild-type mice treated with TAT-BNIP3-ΔTM (ATM) 5 minutes before ischemia and additional with TAT-WVELHFFN ("WVELHFFN" disclosed as SEQ ID NO: 3) 5 minutes before reperfusion (n=3-6 mice). (H) in vivo myocardial I/R in pigs subjected to 60 minutes of ischemia and 4 hours of reperfusion and treated with vehicle or TAT-WVELHFFN ("WVELHFFN" disclosed as SEQ ID NO: 3) (n=3). AAR/LV (H), Inf/AAR (I) and Inf/LV (*p=0.02) (J). Inf/AAR and Inf/LV ratios were significantly reduced upon administration of TAT-WELVHFFN ("WELVHFFN" disclosed as SEQ ID NO: 11). (I) Brain Inf/AAR at 24 hours reperfusion in wild-type mice treated with vehicle or TAT-WVELHFFN ("WVELHFFN" disclosed as SEQ ID NO: 3) (n=5-7). Inf/AAR ratios were significantly reduced upon administration of TAT-WELVHFFN ("WELVHFFN" disclosed as SEQ ID NO: 11). (J) Pre-treatment timeline. (K) Inf/AAR for treated vs control subjects. Inf/AAR ratios were significantly reduced upon administration of TAT-WVELHFFN ("WVELHFFN" disclosed as SEQ ID NO: 3) (PepB). (L) Ejection fraction (EF) % for control vs treated individuals, assayed at D-7, D-1, D0, D1, D3, and D5. Treated individuals exhibited significantly higher EF %, as indicated by the asterisks. (M) Post-treatment timeline. (N) Left ventricular ejection fraction (LVEF) % for control vs multiple treated individuals, assayed at d-1, d1, d3, d5, and d7. Treated individuals exhibited recovery of LV function at day 3, as indicated by the asterisk.

Figure 7B:
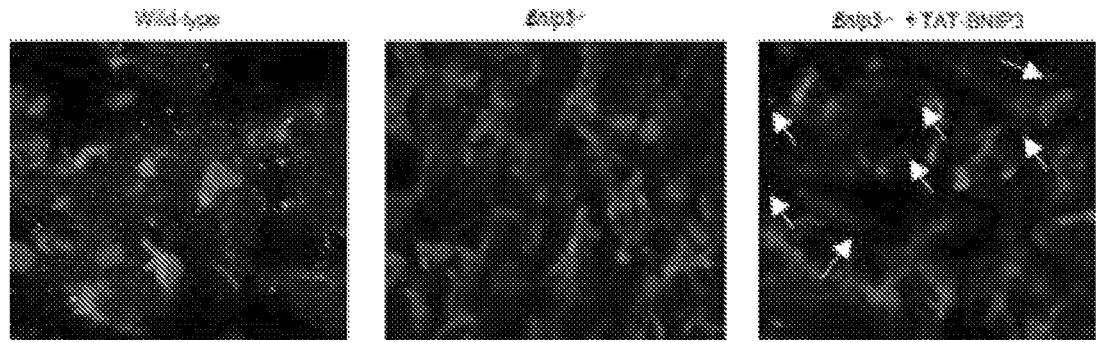
FIG. 7B. TAT-BNIP3 reduces signal in Bnip3$^{-/-}$ background related to FIG. 1D.
Figure 7C:
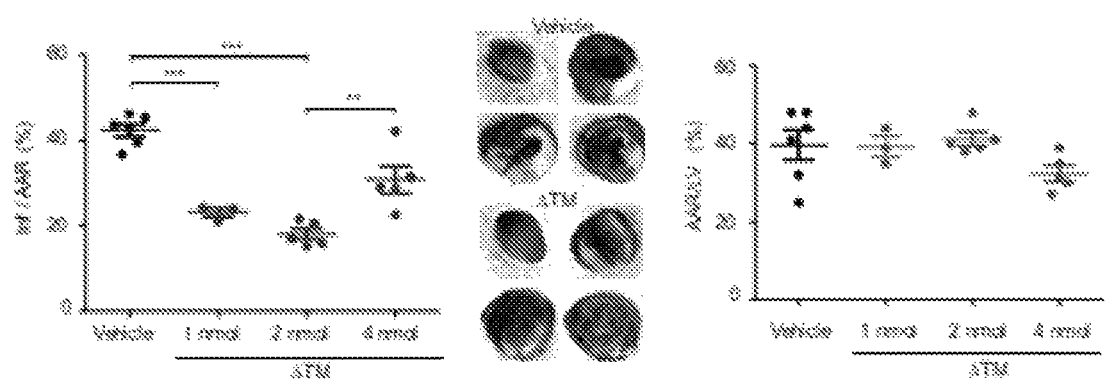
FIG. 7C. deltaTM reduces Inf/AAR relative to vehicle related to FIG. 1E.

FIG. 7A-C. Apoptosis and necrosis analyses in vivo, Related to FIG. 1(A) Workflow size exclusion chromatography. (B) Confocal microscopy images showing murine heart tissue from wild-type, Bnip3$^{-/-}$ and Bnip3$^{-/-}$ mice after injection of the TAT-BNIP3 fusion protein. Mitochondria were stained in red, nuclei in blue and BNIP3 in green. (C) Infarct sizes per area at risk (Inf/AAR) in wild-type mice treated as indicated (n=3-6; vehicle (NaCl), TAT-BNIP3 ATM, ATM (left). Representative images of TTC-stained heart sections from mice treated with vehicle (NaCl) or ATM at 24 hours reperfusion (middle). AAR/left ventricle (LV) at 24 hours reperfusion in wild-type mice (n=3-6 mice). Data represent the means±SEM; p values were determined by one-way ANOVA with Bonferroni's correction.

FIG. 8A-8I. Characterization of mouse cardiac mitochondria and BNIP3, Related to FIG. 1(A) Quantification of depolarized mitochondria at baseline and for the indicated reperfusion times in mouse myocardial I/R injury by flow cytometry (n=5). (B) Quantification of intact, swollen and damaged mouse heart mitochondria at baseline and at 10 minutes reperfusion (n=3-5) and representative electron micrographs. Scale bars, 1 μm. (C) Representative flow cytometry 2D dot plots of mitochondrial membrane potential using JC-1 dye. (D) Representative electron micrographs depicting fragmented mitochondria. Scale bar, 5 m (left), scale bars, 1 μm (right). (E) Immunoblot of BNIP3 in a whole murine heart and isolated cardiomyocytes. (F and G) Time course of ischemia/reperfusion injury: BNIP3 mRNA transcript levels (n=4) (F) and protein concentrations (n=9) (G) at baseline and for the indicated reperfusion times. Representative immunoblot of BNIP3. (H) Western blot monitoring of the subcellular localization of BNIP3. (I) Representative images of mitochondria (red), cytosolic BNIP3 (green; denoted by yellow arrows), mitochondrial BNIP3 (yellow; denoted by white arrows) and nuclei (blue) in mouse heart slices. 64× magnification.

FIG. 9A-9D. Mouse mitochondria in cardiac health and disease, Related to FIG. 1(A) Mitochondrial pore formation experiments in which isolated mitochondria were treated with cytoplasm and indicated inhibitors, demonstrating the need for BNIP3 in BAX pore formation, as shown by quantification of cytochrome c, AIF, and active BAX concentrations (n=3). (B and C) Schematics and representative traces of mitochondrial swelling experiments. assessed by measuring optical density (OD) in which mitochondria were treated with ΔTM and with either buffer inducing mitochondrial swelling (mPTP buffer) (B) or mitochondrial outer membrane rupture (non-mPTP inducing buffer) (C). (D) Quantification of BNIP3 serine phosphorylation and active BAX concentrations in HL-1 cells exposed to hypoxia (24 hours) and reoxygenation (1 hour) (H/R), treated or not with an AKT inhibitor (n=5 independent experiments). Data represent the means±SEM; p values were determined by two-way ANOVA with Bonferroni's correction.

FIG. 10A-10B. Alanine scan, Related to FIG. 3(A) Heat map depiction of the alanine scan with the N-terminal sequence of BNIP3 (1-20 aa) incubated with recombinant BNIP3. Color coding ranges from white (low or no intensity) to yellow (middle intensity) and red (high intensity). (B) Space filling model and structural formula of WVE-LAASN (SEQ ID NO: 7).

Figure 11A:
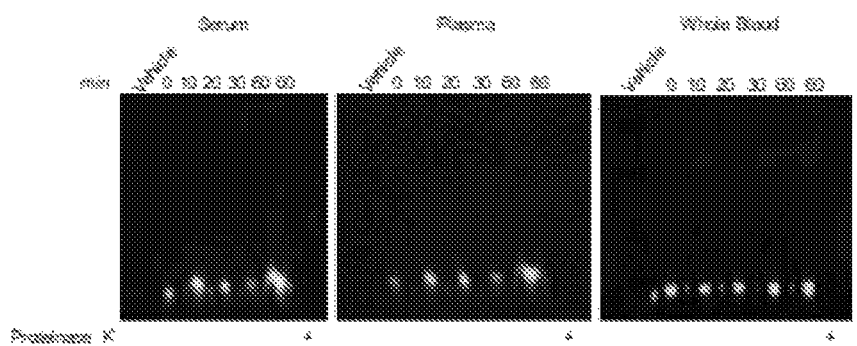
FIG. 11A. Proteinase K accumulation related to FIG. 4B. Figure discloses "WVELAASN" as SEQ ID NO: 7.
Figure 11B:
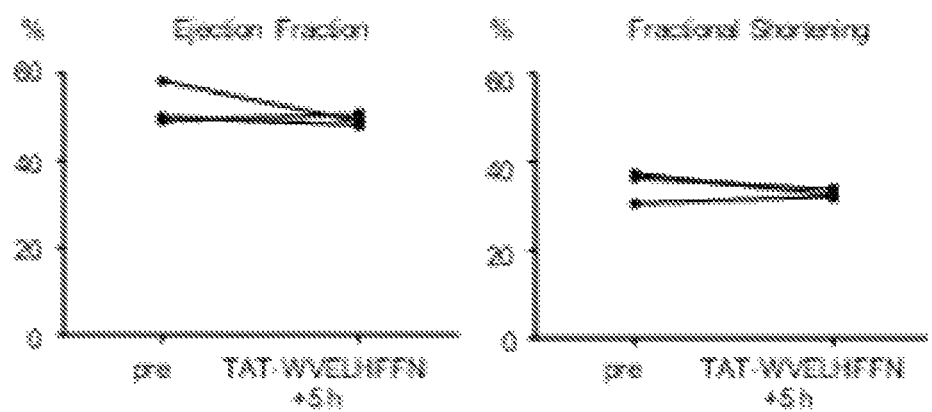
FIG. 11B WVELHFFN (SEQ ID NO: 3) impact on ejection fraction and fractional shortening related to FIG. 4B. Figure discloses "WVELHFFN" as SEQ ID NO: 3.
Figure 11C:
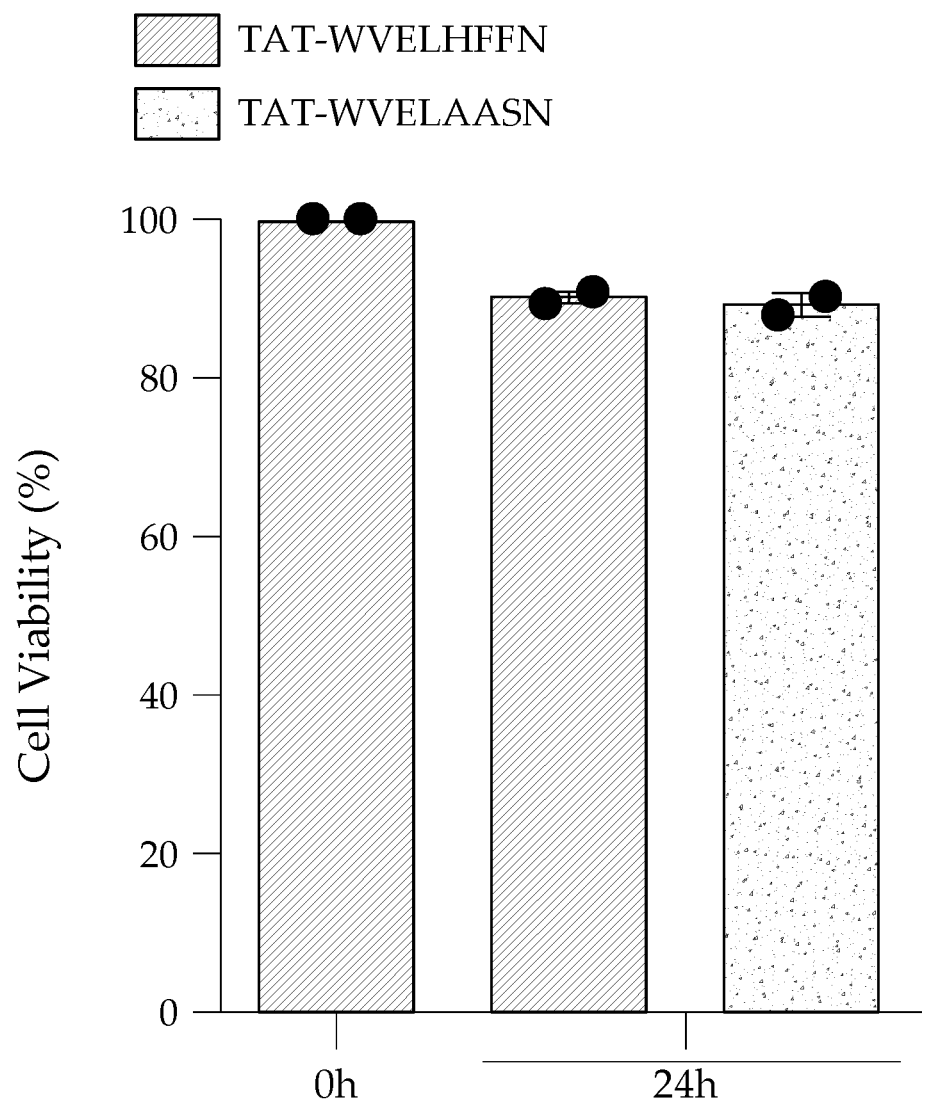
FIG. 11C. TAT-WVELAASN ("WVELAASN" disclosed as SEQ ID NO: 7) and TAT-WVELHFFN ("WVELHFFN" disclosed as SEQ ID NO: 3) have comparable effects on cell viability related to FIG. 4B. Figure discloses SEQ ID NOS 3 and 7, respectively, in order of appearance.
Figure 12A:
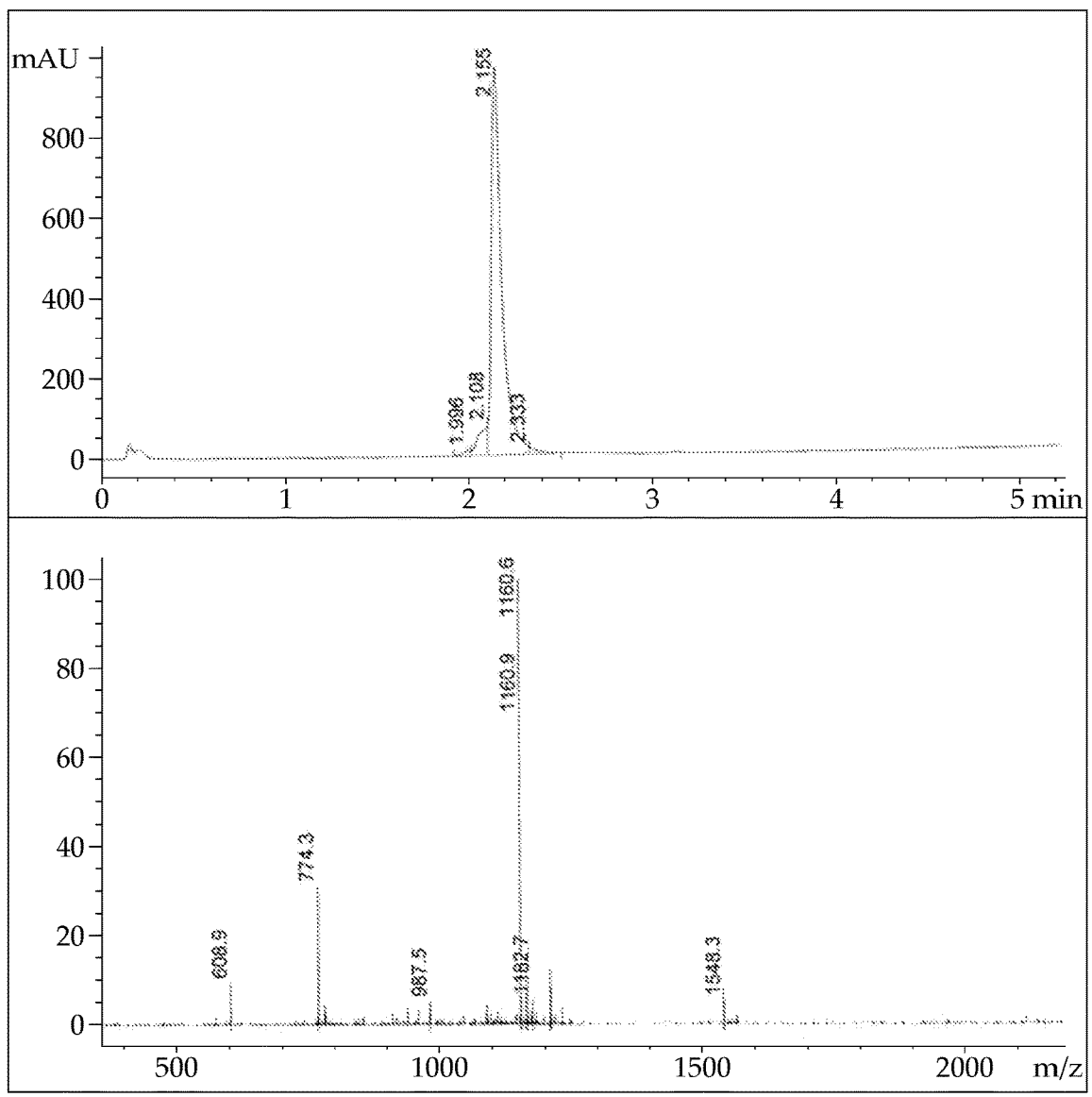
FIG. 12A. Confirmatory synthesis assay.
Figure 12B:
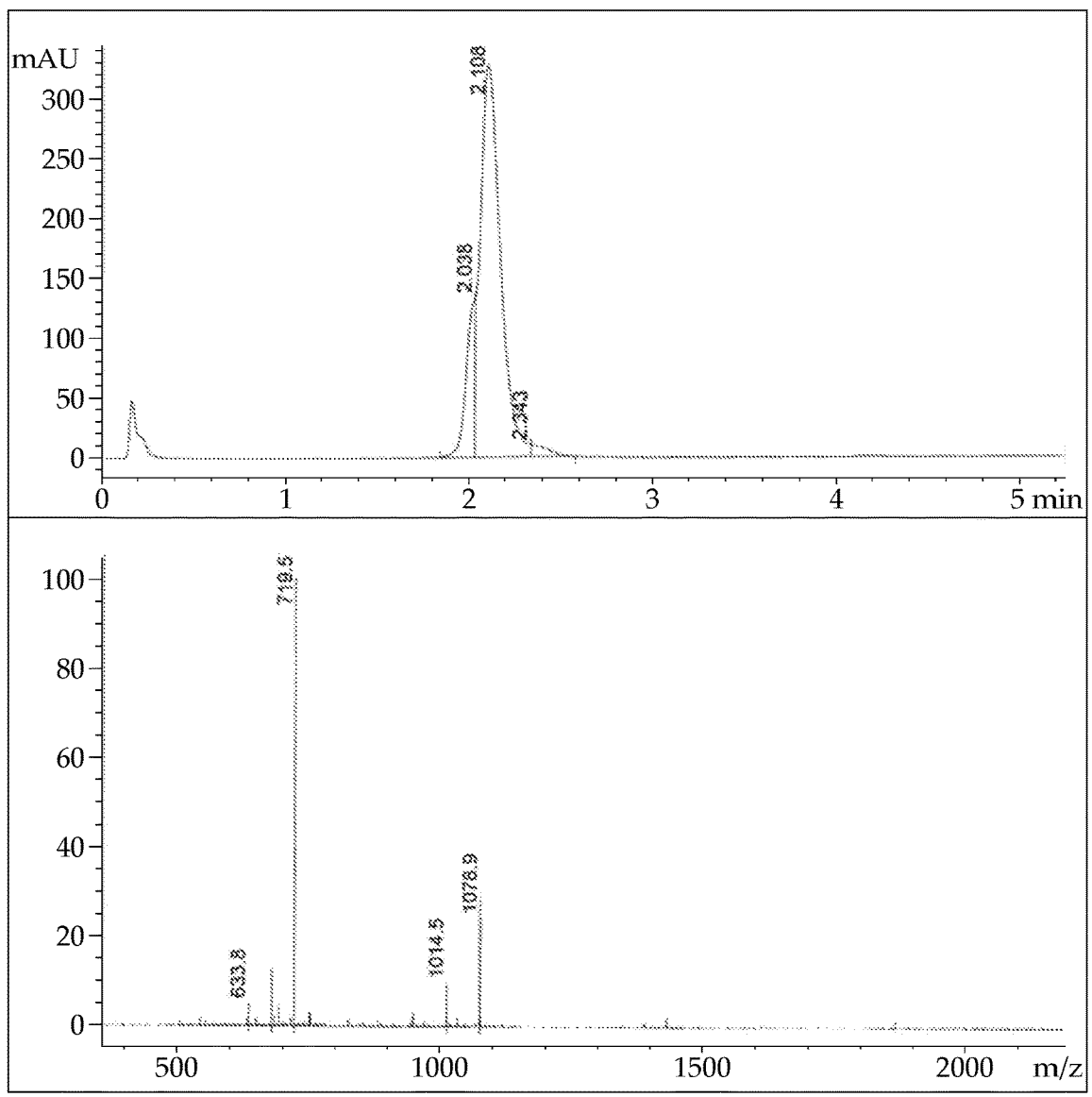
FIG. 12B. Confirmatory synthesis assay.
Figure 12C:
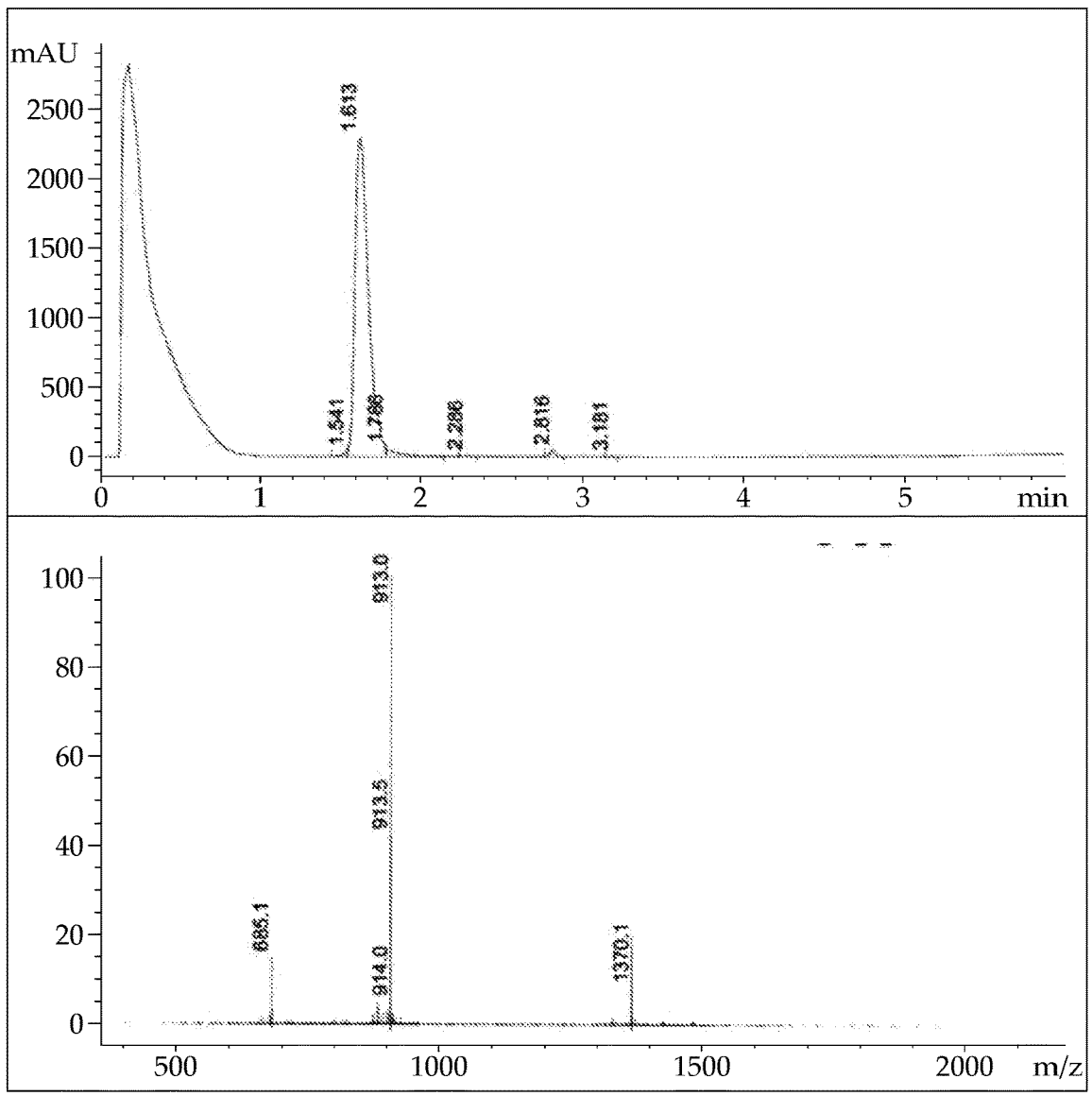
FIG. 12C. Confirmatory synthesis assay.
Figure 12D:
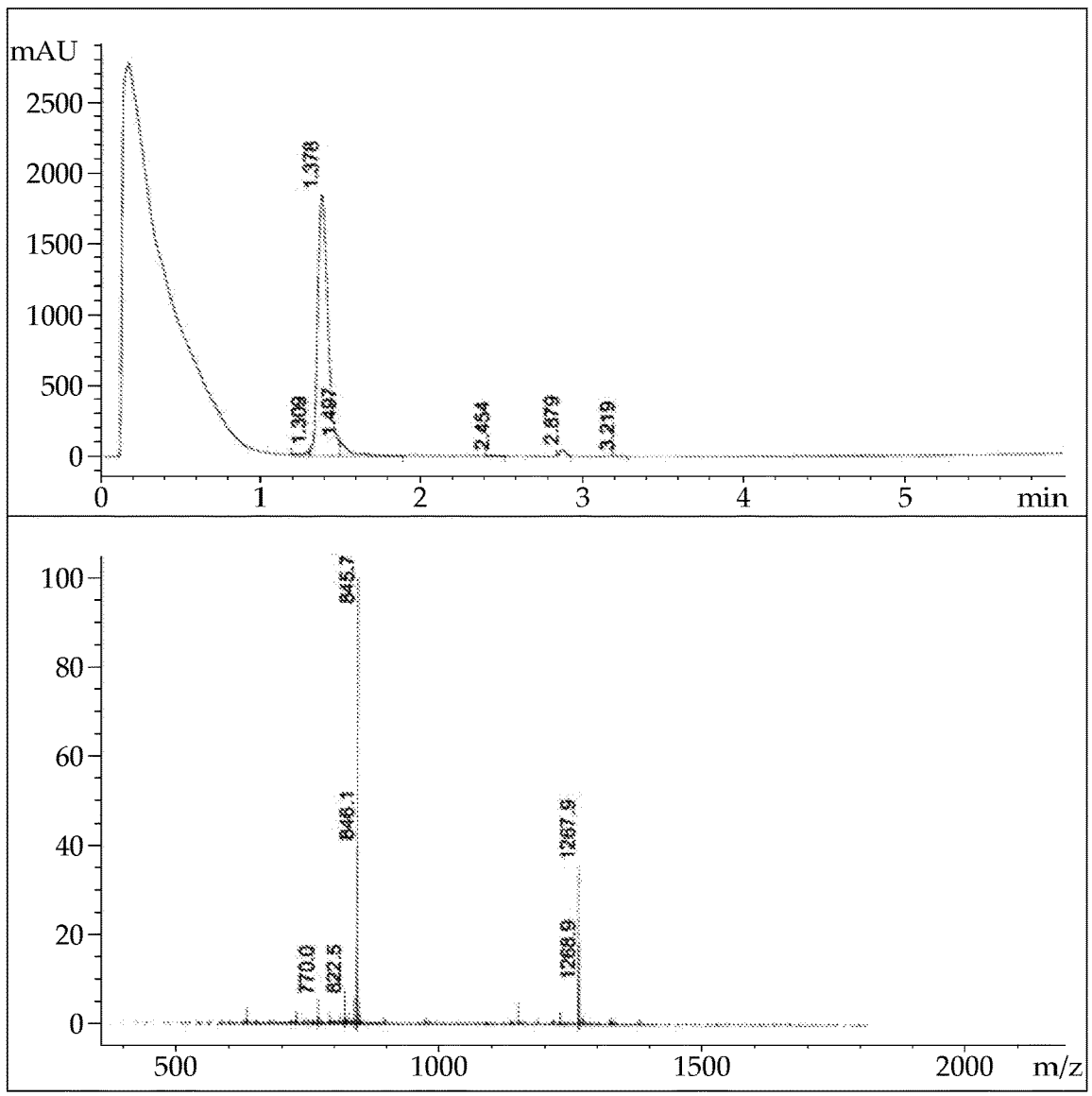
FIG. 12D. Confirmatory synthesis assay.

FIG. 11A-C. Identification and in vitro/in vivo effects of the advanced TAT-WVELHFFN peptide ("WVELHFFN" disclosed as SEQ ID NO: 3), Related to FIG. 4(A) Western blots of fluorescence-labelled TAT-WVELHFFN ("WVELHFFN" disclosed as SEQ ID NO: 3) level profiles in human serum, plasma, and whole blood after incubation at 37° C. for indicated times. Proteinase K treatment served as a control at 60 minutes. (B) Survival of isolated adult cardiomyocytes treated with TAT-WVELHFFN ("WVELHFFN" disclosed as SEQ ID NO: 3) and TAT-WVELAASN ("WVELAASN" disclosed as SEQ ID NO: 7) after 24 hours (n=2). (C) Echocardiographs, measured at baseline (pre) and 5 hours after injection of 8 nmol TAT-WVELHFFN ("WVELHFFN" disclosed as SEQ ID NO: 3) (n=3).

FIG. 12A-12D. TAT-peptides. HPLC (220 nm, C18, linear gradient) of newly synthesized chimera (A) MSQSGEEN-LQGSWVELHFSN (SEQ ID NO: 1); (B) LDAQHES-GRSSSKSSHCDSP (SEQ ID NO: 6); (C) WVELHFFN (SEQ ID NO: 3) and (D) WVELAASN (SEQ ID NO: 7).

Figure 13A:
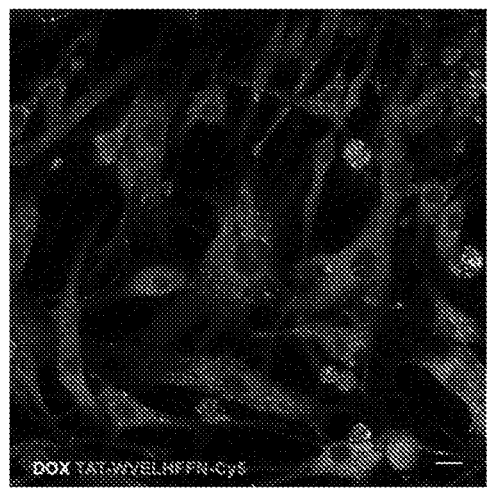
FIG. 13A. DOX and TAT-WVELHFFN ("WVELHFFN" disclosed as SEQ ID NO: 3) uptake. Figure discloses SEQ ID NOS 3, 10 and 3, respectively in order of appearance.
Figure 13B:
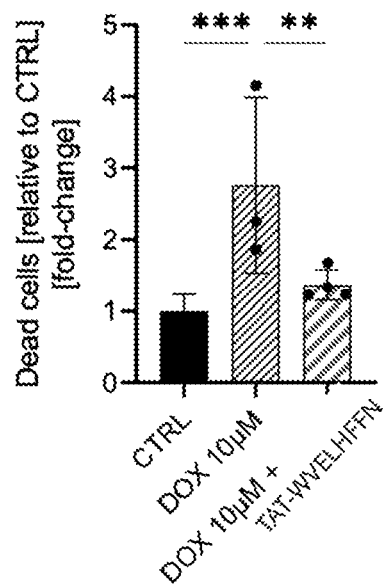
FIG. 13B. TAT-WVELHFFN ("WVELHFFN" disclosed as SEQ ID NO: 3) counters DOX induced cell death. Figure discloses SEQ ID NO: 3.

FIG. 13A-B. TAT-WVELHFFN ("WVELHFFN" disclosed as SEQ ID NO: 3) ameliorates DOX induced cell death in human cardiomyocytes. At FIG. 13(A), one sees an image indicating DOX and TAT-WVELHFFN ("WVELHFFN" disclosed as SEQ ID NO: 3) uptake. The image is generated using confocal microscopy. Magnification: 40×. Scale bar: 20 μm. 10 μM DOX, and 20 μM TAT-WVELHFFN ("WVELHFFN" disclosed as SEQ ID NO: 3) are administered, and the cells are visualized at 22 h. Dox is indicated in yellow, while TAT-WVELHFFN ("WVELHFFN" disclosed as SEQ ID NO: 3) is stained using Cy5. At FIG. 13(B) one sees that TAT-WVELHFFN ("WVELHFFN" disclosed as SEQ ID NO: 3) ameliorates DOX induced cell death in human cardiomyocytes. Dead cells are measured relative to the control, left, as compared to administration of DOX at 10 μM, center, and DOX at 10 μM plus TAT-WVELHFFN ("WVELHFFN" disclosed as SEQ ID NO: 3), right. Administration of the mitochondrial interaction and import inhibitor TAT-WVELHFFN ("WVELHFFN" disclosed as SEQ ID NO: 3) ameliorates the increased cell death induced by administration of the chemotherapeutic DOX, returning cell death to near control levels.

FIG. 14A-B. TAT-WVELHFFN ("WVELHFFN" disclosed as SEQ ID NO: 3) ameliorates DOX induced cell death in human cardiomyocytes. At FIG. 14(A) one sees that TAT-WVELHFFN ("WVELHFFN" disclosed as SEQ ID NO: 3) ameliorates DOX induced cell death in human cardiomyocytes. Attributive percent damage baseline adjusted values were measured for DOX concentrations of, from left to right, 0, 1, and 10 μM. For each concentration, results are shown without (left) and with (right) TAT-WVELHFFN ("WVELHFFN" disclosed as SEQ ID NO: 3). Cells were incubated for four hours, and TAT-WVELHFFN ("WVELHFFN" disclosed as SEQ ID NO: 3) was administered at 0 or 1.5 μM. The results show that the attributive damage caused by a 10 μM dose of the chemotherapeutic DOX is ameliorated by the mitochondrial interaction and import inhibitor TAT-WVELHFFN ("WVELHFFN" disclosed as SEQ ID NO: 3). At FIG. 14(B) one sees that TAT-WVELHFFN ("WVELHFFN" disclosed as SEQ ID NO: 3) ameliorates DOX induced cell death in human cardiomyocytes. RLUs, indicative of cell death, were measured for DOX concentrations of, from left to right, 1 and 10 μM. For each concentration, results are shown without (left) and with (right) TAT-WVELHFFN ("WVELHFFN" disclosed as SEQ ID NO: 3). Cells were incubated for four hours, and TAT-WVELHFFN ("WVELHFFN" disclosed as SEQ ID NO: 3) was administered at 0 or 1.5 μM. The results show that the attributive damage, indicated by an increase in RLU, caused by a 10 μM dose of the chemotherapeutic DOX is ameliorated by the mitochondrial interaction and import inhibitor TAT-WVELHFFN ("WVELHFFN" disclosed as SEQ ID NO: 3).

Figure 15A:
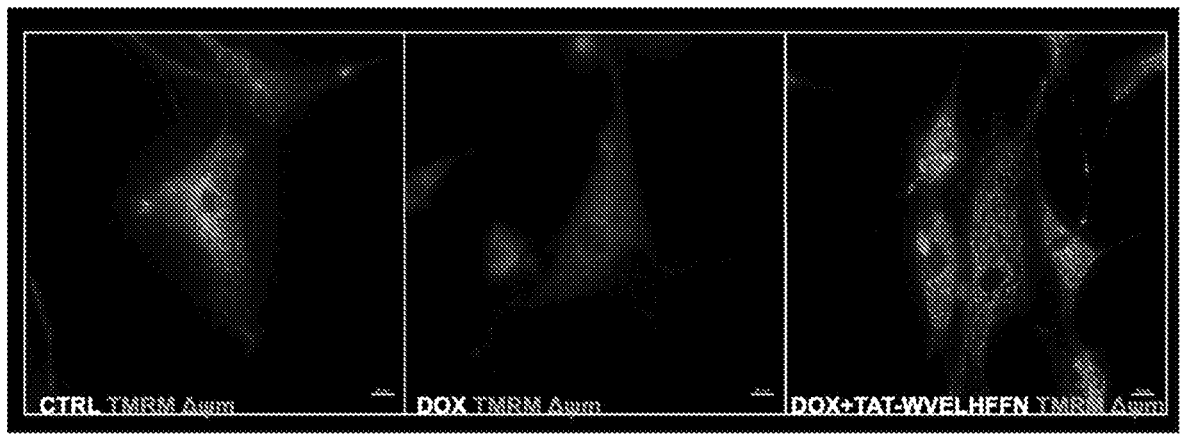
FIG. 15A. TAT-WVELHFFN ("WVELHFFN" disclosed as SEQ ID NO: 3) counters DOX induced mitochondrial membrane potential loss. Figure discloses SEQ ID NO: 3.
Figure 15B:
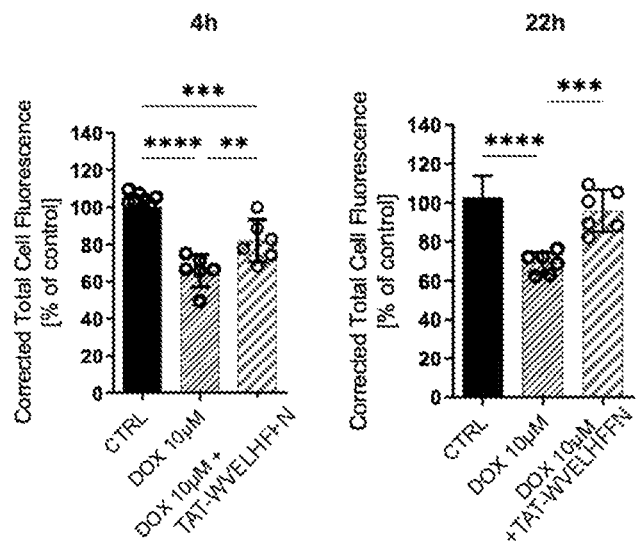
FIG. 15B. TAT-WVELHFFN ("WVELHFFN" disclosed as SEQ ID NO: 3) counters DOX induced mitochondrial membrane potential loss. Figure discloses "WVELHFFN" as SEQ ID NO: 3.

FIG. 15A-B. TAT-WVELHFFN ("WVELHFFN" disclosed as SEQ ID NO: 3) ameliorates mitochondrial membrane potential destabilization by DOX in human cardiomyocytes. At FIG. 15(A) one sees that WVELHFFN (SEQ ID NO: 3) ameliorates mitochondrial membrane potential destabilization by DOX. Representative images are of donor-human cardiomyocytes (HCM). Incubation is 4 h 10 μM DOX Magnification: 40×. Scale bar: 20 μM. Fluorescence at left indicates that membrane potential is preserved in the control. At center, lack of fluorescence indicates that membrane potential is disrupted by administration of 10 μM DOX, while at right, one sees that co-administration of TAT-WVELHFFN ("WVELHFFN" disclosed as SEQ ID NO: 3) ameliorates the negative effect of DOX on mitochondrial membrane potential. At FIG. 15(B), one sees a quantification of the results of FIG. 15(A). Results are shown for corrected total cell fluorescence relative to control, for four- and 22 hour-incubation times. For each chart, control is shown at left, followed by DOX at 10 μM, center, and DOX plus TAT-WVELHFFN ("WVELHFFN" disclosed as SEQ ID NO: 3). In both time incubations, one sees a decrease relative to the control for the DOX administration, and an amelioration of that decrease upon co-administration of TAT-WVELHFFN ("WVELHFFN" disclosed as SEQ ID NO: 3). This indicates that the negative effect of the chemotherapeutic on mitochondrial membrane potential is ameliorated by co-administration of TAT-WVELHFFN ("WVELHFFN" disclosed as SEQ ID NO: 3).

Figure 16A:
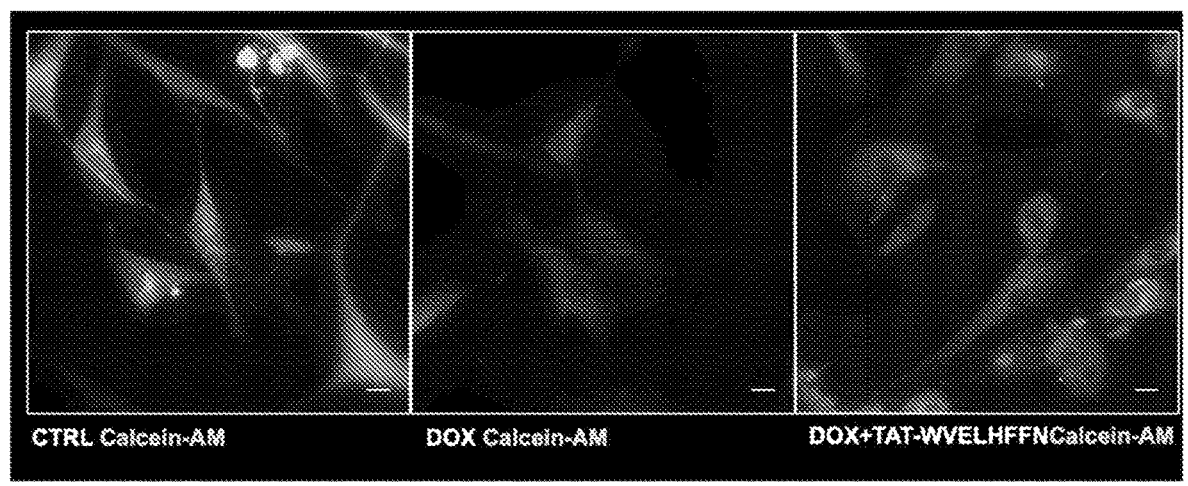
FIG. 16A. TAT-WVELHFFN ("WVELHFFN" disclosed as SEQ ID NO: 3) counters DOX induced mPTP-opening. Figure discloses "WVELHFFN" as SEQ ID NO: 3.
Figure 16B:
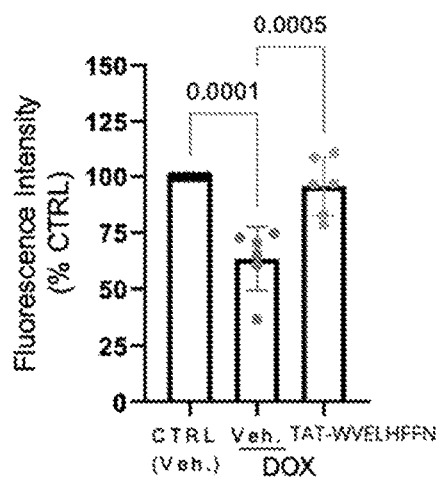
FIG. 16B. TAT-WVELHFFN ("WVELHFFN" disclosed as SEQ ID NO: 3) counters DOX induced mPTP-opening. Figure discloses SEQ ID NO: 3.

FIG. 16A-B. TAT-WVELHFFN ("WVELHFFN" disclosed as SEQ ID NO: 3) prevents mPTP opening by DOX in human cardiomyocytes. At FIG. 16(A) one sees that TAT-WVELHFFN ("WVELHFFN" disclosed as SEQ ID NO: 3) prevents mPTP opening by DOX.

Representative images are of donor-human cardiomyocytes (HCM). Incubation is 4 h 10 µM DOX Magnification: 40×. Scale bar: 20 µM. Calcein-AM fluorescence at left indicates that mPTP opening is prevented in the control. At center, lack of fluorescence indicates that mPTP opening is activated by administration of 10 µM DOX, while at right, one sees that co-administration of TAT-WVELHFFN ("WVELHFFN" disclosed as SEQ ID NO: 3) prevents the negative effect of DOX on mPTP opening. At FIG. 16(B), one sees a quantification of the results of FIG. 16(A). Results are shown for corrected total cell fluorescence relative to control, for 22 hour-incubation time. For each chart, the effect of DOX at 0 and 10 µM is shown without (left) and with (right) TAT-WVELHFFN ("WVELHFFN" disclosed as SEQ ID NO: 3). One sees a decrease relative to the control for 10 µM DOX administration, and an prevention of that decrease to near control levels upon co-administration of TAT-WVELHFFN ("WVELHFFN" disclosed as SEQ ID NO: 3). This indicates that the negative effect of the chemotherapeutic on mPTP opening is prevented by co-administration of TAT-WVELHFFN ("WVELHFFN" disclosed as SEQ ID NO: 3).

Figure 17A:
FIG. 17A. TAT-WVELHFFN ("WVELHFFN" disclosed as SEQ ID NO: 3) counters DOX induced calcium ion accumulation. Figure discloses "WVELHFFN" as SEQ ID NO: 3.
Figure 17B:
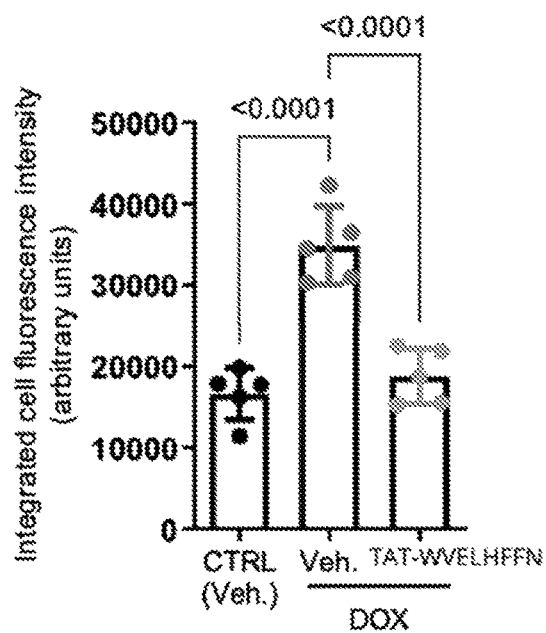
FIG. 17B. TAT-WVELHFFN ("WVELHFFN" disclosed as SEQ ID NO: 3) counters DOX induced calcium ion accumulation. Figure discloses SEQ ID NO: 3.

FIG. 17. TAT-WVELHFFN ("WVELHFFN" disclosed as SEQ ID NO: 3) prevents mitochondrial calcium ion overload triggered by DOX in human cardiomyocytes. At Figure E one sees that TAT-WVELHFFN ("WVELHFFN" disclosed as SEQ ID NO: 3) prevents mitochondrial calcium ion overload triggered by DOX. Representative images are of donor-human cardiomyocytes (HCM). Incubation is 4 h 10 µM DOX Magnification: 40×. Scale bar: 20 µM. Calcium-Rhodamin fluorescence at low levels, at left indicates that calcium overload does not occur in the control. At center, increase in fluorescence indicates that mitochondrial calcium ion overload is induced by administration of 10 uM DOX, while at right, one sees that co-administration of TAT-WVELHFFN ("WVELHFFN" disclosed as SEQ ID NO: 3) prevents the negative effect of DOX on calcium ion overload.

Figure 18A:
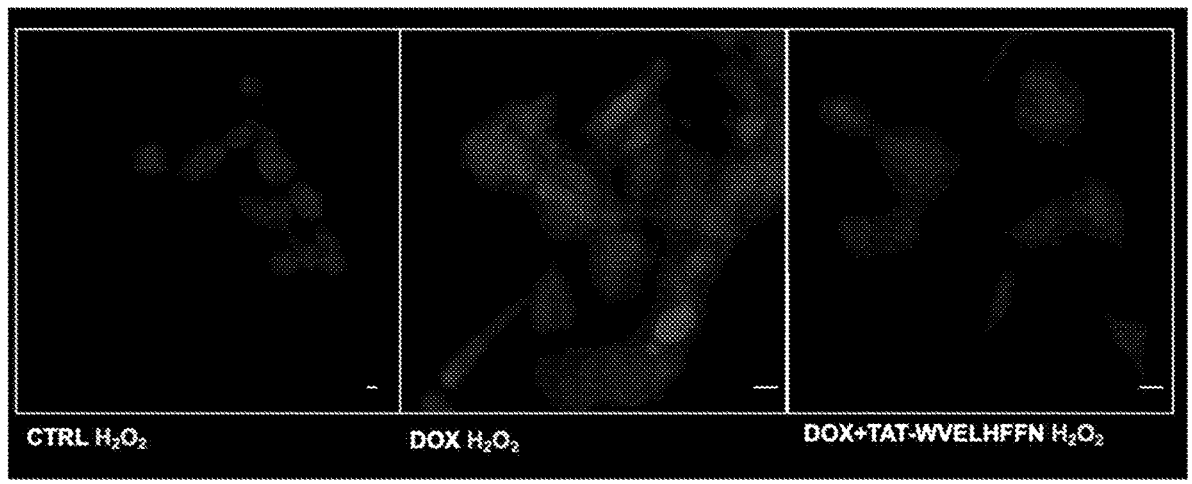
FIG. 18A. TAT-WVELHFFN ("WVELHFFN" disclosed as SEQ ID NO: 3) counters DOX induced reactive oxygen species (ROS) accumulation. Figure discloses "WVELHFFN" as SEQ ID NO: 3.
Figure 18B:
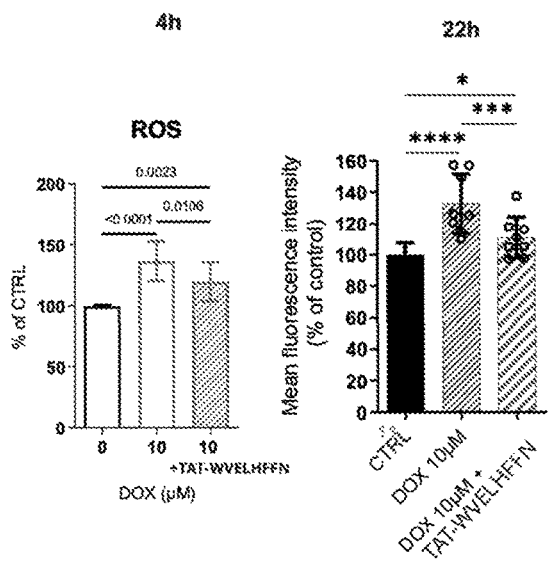
FIG. 18B. TAT-WVELHFFN ("WVELHFFN" disclosed as SEQ ID NO: 3) counters DOX induced reactive oxygen species (ROS) accumulation. Figure discloses "WVELHFFN" as SEQ ID NO: 3.

FIG. 18A-B. TAT-WVELHFFN ("WVELHFFN" disclosed as SEQ ID NO: 3) ameliorates mitochondrial reactive oxygen species (ROS) generation triggered by DOX in human cardiomyocytes. At FIG. 18(A) one sees that TAT-WVELHFFN ("WVELHFFN" disclosed as SEQ ID NO: 3) ameliorates mitochondrial ROS generation triggered by DOX. Representative images are of donor-human cardiomyocytes (HCM). Incubation is 4 h 10 µM DOX Magnification: 40×. Scale bar: 20 µM. ROS fluorescence at low levels, at left indicates that ROS do not accumulate in the control. At center, increase in fluorescence indicates that ROS generation is induced by administration of 10 µM DOX, while at right, one sees that co-administration of TAT-WVELHFFN ("WVELHFFN" disclosed as SEQ ID NO: 3) ameliorates the negative effect of DOX on ROS generation. At FIG. 18(B), one sees a quantification of the results of FIG. 18(A). Results are shown for corrected ROS generation relative to control, for four- and 22 hour-incubation times. For each chart, control is shown at left, followed by DOX at 10 µM, center, and DOX plus TAT-WVELHFFN ("WVELHFFN" disclosed as SEQ ID NO: 3). In both time incubations, one sees an increase relative to the control for the DOX administration, and an amelioration of that increase upon co-administration of TAT-WVELHFFN ("WVELHFFN" disclosed as SEQ ID NO: 3). This indicates that the negative effect of the chemotherapeutic on ROS generation is ameliorated by co-administration of TAT-WVELHFFN ("WVELHFFN" disclosed as SEQ ID NO: 3).

FIGS. 15-18: Collectively, these results indicate that the conclusions made previously also generally apply to treatment of human cells.

Figure 19:
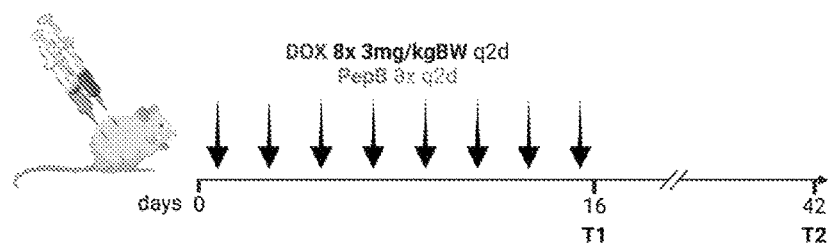
FIG. 19. Treatment regimen schematic.

FIG. 19. Administration time course of a chemotherapeutic and a mitochondrial import inhibitor.

Figure 20:
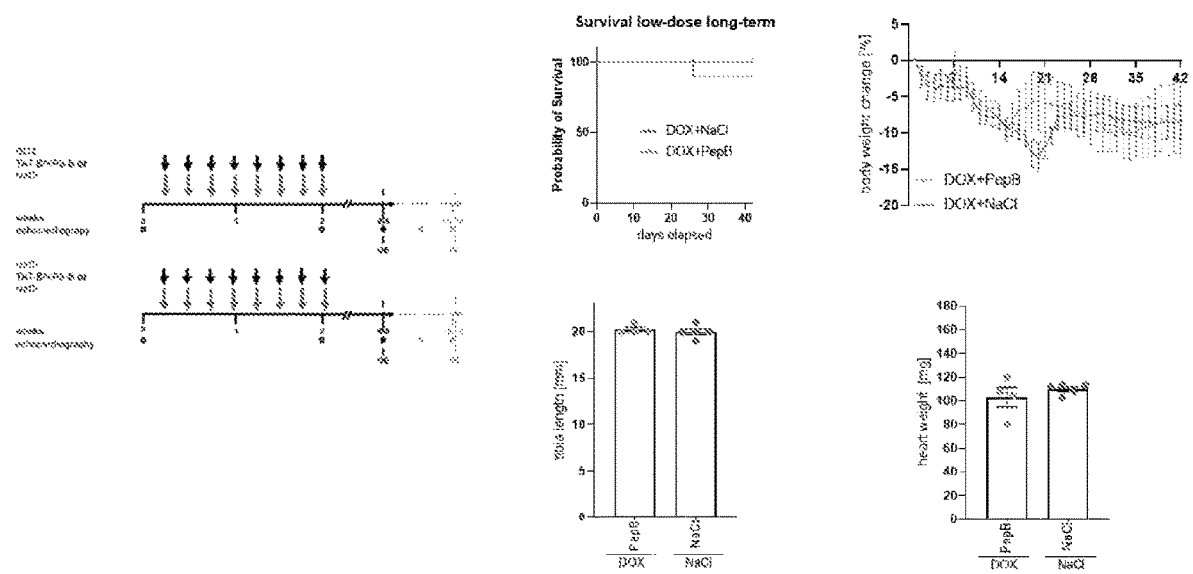
FIG. 20. Survival curves, body weight change measurements, tibial total length and heart weight measurements indicate that TAT-WVELHFFN ("WVELHFFN" disclosed as SEQ ID NO: 3) does not impact long term survival of healthy mice.

FIG. 20. PepB (TAT-WVELHFFN ("WVELHFFN" disclosed as SEQ ID NO: 3)) does not have long term detrimental effects on mammalian recipients. Probability of survival, body weight change over time, tibia length, and heart weight were measured and in each case no significant difference was observed upon pepB administration relative to an NaCL carrier control.

Figure 21:
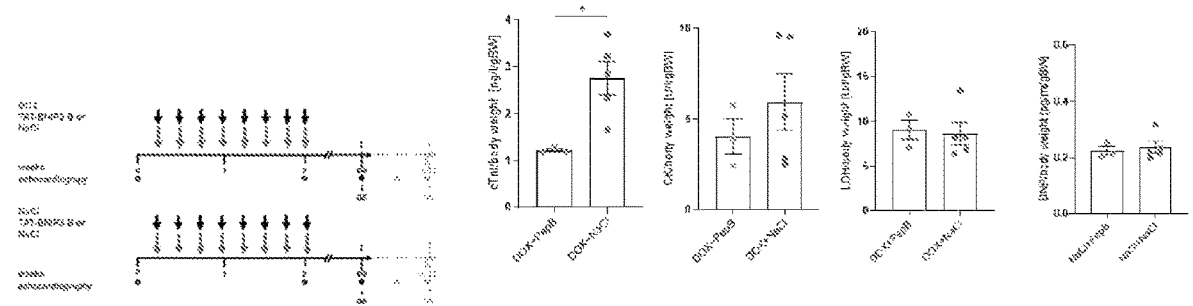
FIG. 21. TAT-WVELHFFN ("WVELHFFN" disclosed as SEQ ID NO: 3) influences cardiac troponin I/body weight and creatine kinase/body weight but not LDH/body weight or BNP/body weight for the indicated treatment regimen.
Figure 22A:
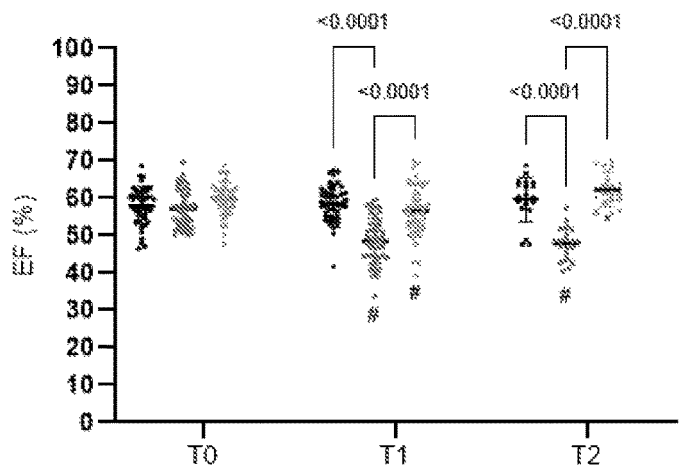
FIG. 22A. For non-zero time points, TAT-WVELHFFN ("WVELHFFN" disclosed as SEQ ID NO: 3) (right data points) counteracts the negative effect of DOX (center data points) to restores cardiac function to vehicle levels (left data points).
Figure 22B:
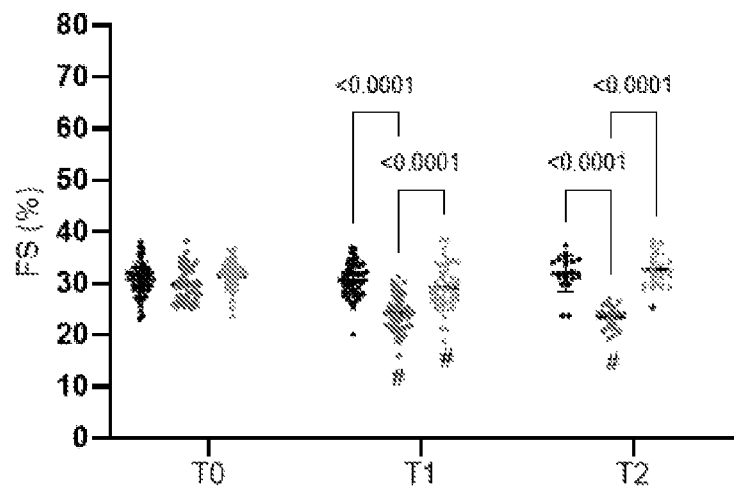
FIG. 22B. For non-zero time points, TAT-WVELHFFN ("WVELHFFN" disclosed as SEQ ID NO: 3) (right data points) counteracts the negative effect of DOX (center data points) to restores cardiac function to vehicle levels (left data points).
Figure 22C:
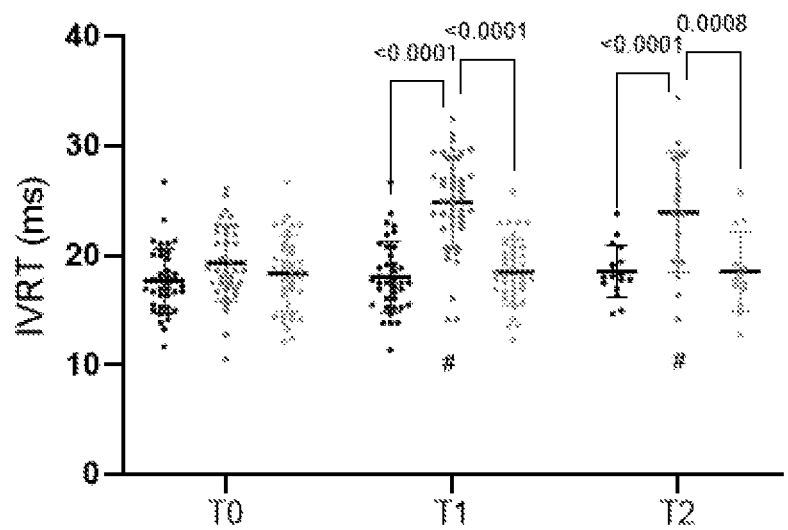
FIG. 22C. For non-zero time points, TAT-WVELHFFN ("WVELHFFN" disclosed as SEQ ID NO: 3) (right data points) counteracts the effect of DOX (center data points) to restores cardiac function to vehicle levels (left data points).
Figure 22D:
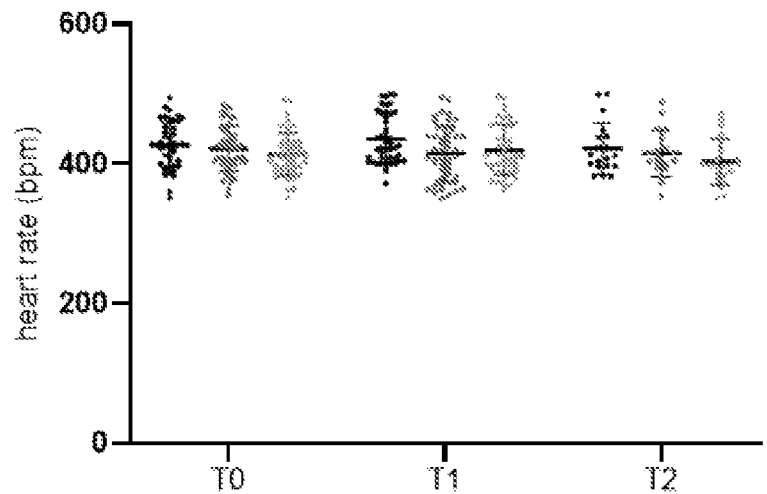
FIG. 22D. TAT-WVELHFFN ("WVELHFFN" disclosed as SEQ ID NO: 3) and DOX do not affect heart rate.
Figure 22E:
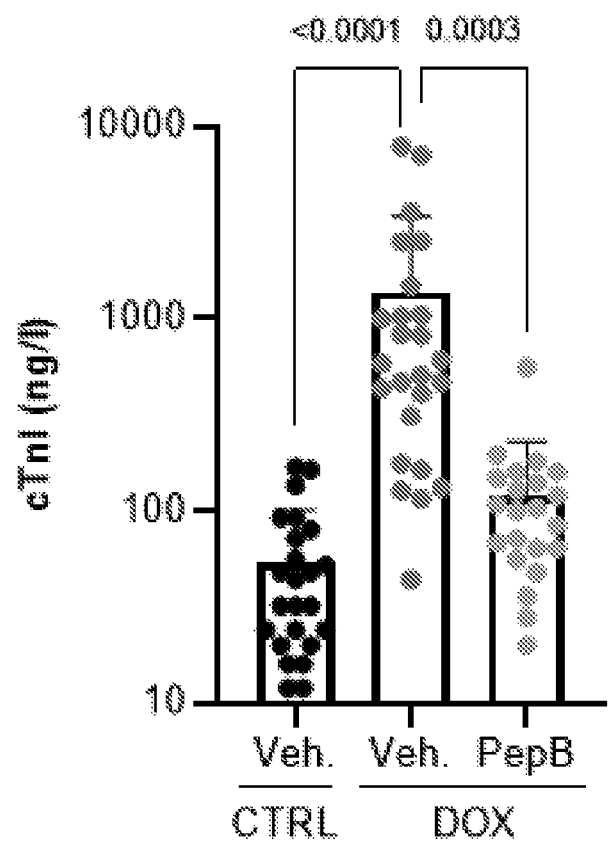
FIG. 22E. TAT-WVELHFFN ("WVELHFFN" disclosed as SEQ ID NO: 3) counteracts the effect of DOX to prevent cardiomyocyte death to vehicle levels.
Figure 23A:
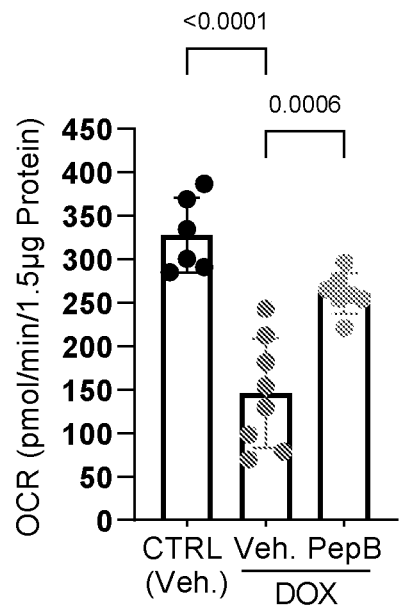
FIG. 23A. TAT-WVELHFFN ("WVELHFFN" disclosed as SEQ ID NO: 3) counteracts the effect of DOX to maintain respiratory reserve capacity.
Figure 23B:
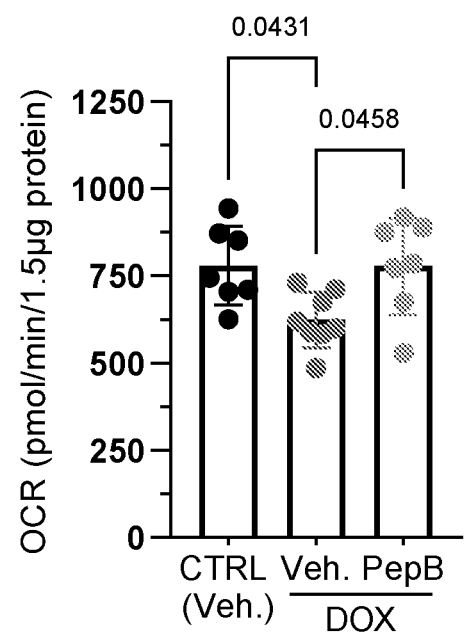
FIG. 23B. TAT-WVELHFFN ("WVELHFFN" disclosed as SEQ ID NO: 3) counteracts the effect of DOX to maintain maximal respiration capacity.
Figure 23C:
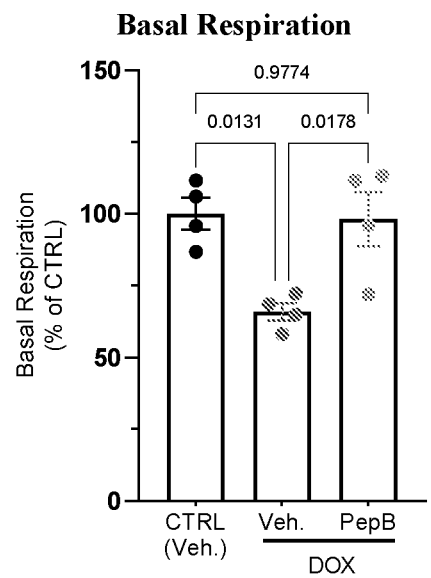
FIG. 23C. TAT-WVELHFFN ("WVELHFFN" disclosed as SEQ ID NO: 3) counteracts the effect of DOX to maintain basal respiration to vehicle levels.
Figure 23D:
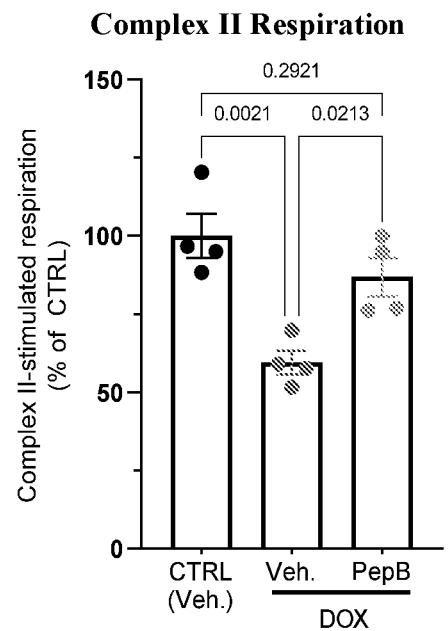
FIG. 23D. TAT-WVELHFFN ("WVELHFFN" disclosed as SEQ ID NO: 3) counteracts the effect of DOX to maintain Complex II stimulated respiration to vehicle levels as a measure of Reserve Capacity.
Figure 24A:
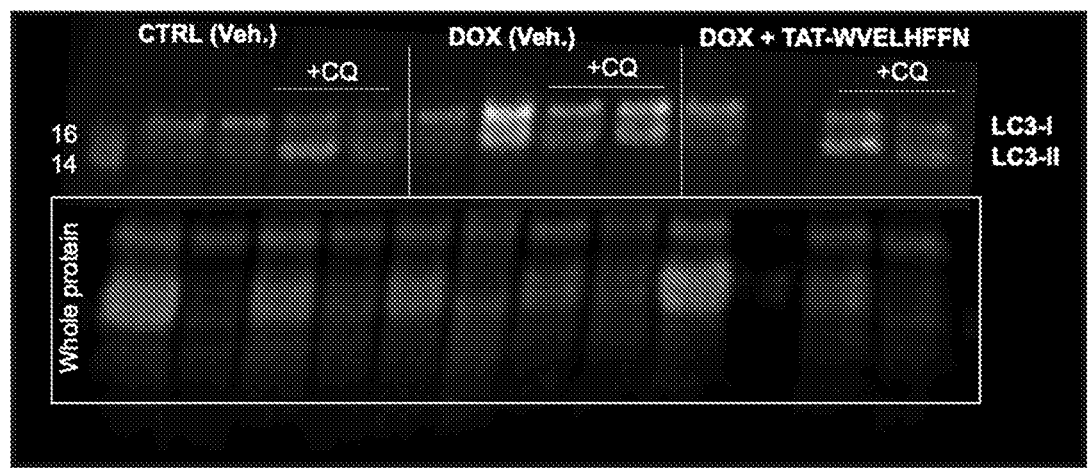
FIG. 24A. Protein blots. Figure discloses SEQ ID NO: 3.
Figure 24B:
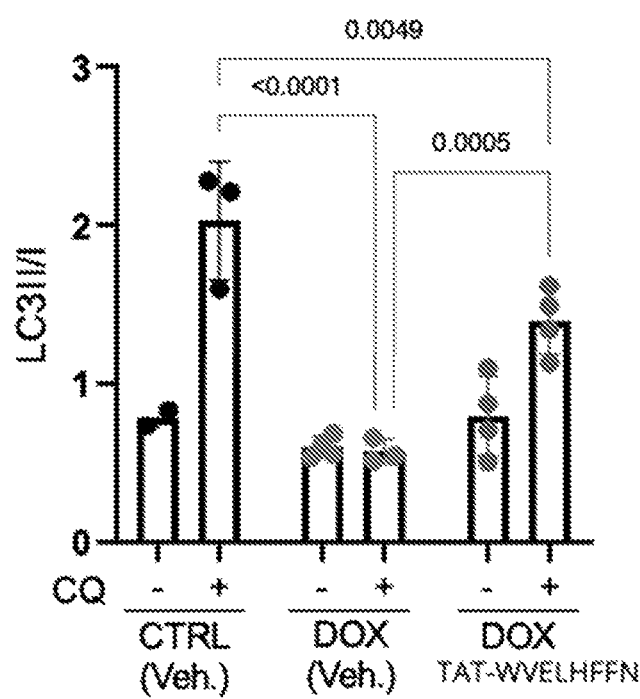
FIG. 24B. TAT-WVELHFFN ("WVELHFFN" disclosed as SEQ ID NO: 3) partially restores LC3II/I levels in response to cloroquine addition to DOX samples. Figure discloses SEQ ID NO: 3.
Figure 24C:
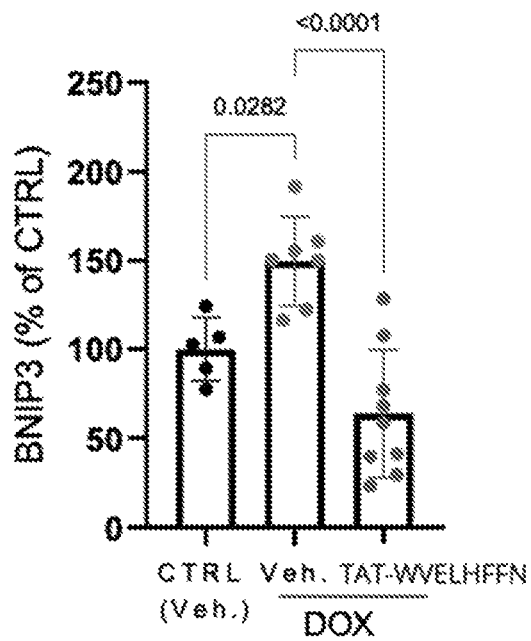
FIG. 24C. TAT-WVELHFFN ("WVELHFFN" disclosed as SEQ ID NO: 3) counteracts DOX induced BNIP3 accumulation. Figure discloses SEQ ID NO: 3.
Figure 24D:
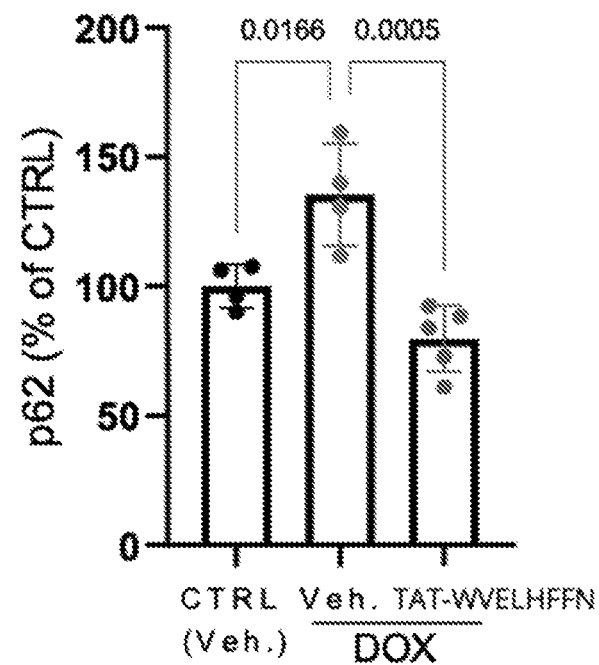
FIG. 24D. TAT-WVELHFFN ("WVELHFFN" disclosed as SEQ ID NO: 3) counteracts DOX induced p62 accumulation.

FIG. 21. PepB (TAT-WVELHFFN ("WVELHFFN" disclosed as SEQ ID NO: 3)) prevents cardiomyocyte death. At FIG. 21, one sees that for the administration regimen at left, PepB prevents cardiomyocyte death. From center to right, one sees that cardiac troponin I (cTNI)/body weight is significantly lower for DOX coadministration with PepB relative to DOX administration with an NaCl control. Similarly, creantine kinase (CK)/body weight is significantly lower for DOX coadministration with PepB relative to DOX administration with an NaCl control. Further to the right, one sees that LDH/body weight center right, and BNP/body weight, right were unchanged by administration of PepB.

FIG. 22A-E. Inhibition of BNIP3 preserves cardiac function. At FIG. 22(A) one sees the effects on ejection fraction (EF) % at each of three time points T0, T1, and T2, of from left, control, DOX, and DOX plus PepB (TAT-WVELHFFN ("WVELHFFN" disclosed as SEQ ID NO: 3)) administration. At both T1 (16 days) and T2 (42 days), DOX negatively impacts EF %, and this impact is ameliorated by concurrent PepB administration. At FIG. 22(B) one sees the effects on fractional shortening (FS) % at each of three time points T0, T1, and T2, of from left, control, DOX, and DOX plus PepB administration. At both T1 and T2, DOX negatively impacts FS %, and this impact is ameliorated by concurrent PepB administration. At FIG. 22(C) one sees the effects on isovolumetric relaxation time (IVRT) (ms) at each of three time points T0, T1, and T2, of from left, control, DOX, and DOX plus PepB administration. At both T1 and T2, DOX slowed IVRT, and this impact is ameliorated by concurrent PepB administration. At FIG. 22(D) one sees the effects on heart rate at each of three time points T0, T1, and T2, of from left, control, DOX, and DOX plus PepB administration. Heart rate was unaffected by DOX administration, alone or in combination with PepB. At FIG. 22(E), one sees the effect of a control, DOX, and DOX plus PepB on cardiac troponin I (cTnI) (ng/l), presented on a logarithmic scale. One sees that DOX has a dramatic positive effect on cTnI, and that this effect is ameliorated by coadministration of PepB.

FIG. 23A-D. Inhibition of BNIP3 upon DOX administration increases mitochondrial fitness. At FIG. 23(A), one sees that DOX inhibits oxygen consumption rate (OCR) at reserve capacity (pmol/min/1.5 ug protein), and that PepB (TAT-WVELHFFN ("WVELHFFN" disclosed as SEQ ID NO: 3)) ameliorates this inhibition. From left, control DOX and DOX plus PepB. At FIG. 23(B), one sees that DOX inhibits OCR at maximal respiration (pmol/min/1.5 ug protein), and that PepB ameliorates this inhibition. From left, control DOX and DOX plus PepB. At FIG. 23(C), one sees that DOX inhibits basal respiration (as a percent of control), and that PepB ameliorates this inhibition. From left, control DOX and DOX plus PepB. At FIG. 23(D), one sees that DOX inhibits Complex II-stimulated respiration (as a percent of control), and that PepB ameliorates this inhibition. From left, control DOX and DOX plus PepB.

FIG. 24A-D. Inhibition of BNIP3 upon DOX administration restores autophagic flux. At FIG. 24(A), one sees a western blot of proteins extracted from, from left, Control, DOX treated and DOX plus PepB (TAT-WVELHFFN ("WVELHFFN" disclosed as SEQ ID NO: 3)) treated tissues. For each protein source, the left two lanes are untreated while the sample source of the right two lanes is additionally treated with cloroquine (CQ). Electrophoresed proteins were probed with LC3-I and LC3-II. At FIG. 24(B), one sees that DOX inhibits CQ mediated LC3II/I increase. From left, control DOX and DOX plus PepB, each presented without, left, or with, right CQ treatment. DOX abolishes the CQ-induced increase, while addition of PepB partially restores this increase. At FIG. 24(C), one sees that DOX triggers p62 accumulation, and that addition of PepB counteracts this increase. P62 levels are shown as a percent of control for control, DOX treated and DOX plus PepB treated samples. At FIG. 24(D), one sees that DOX triggers BNIP3 accumulation, and that addition of PepB counteracts this increase. BNIP3 levels are shown as a percent of control for control, DOX treated and DOX plus PepB treated samples.

FIG. 25A-H. Results presented herein are applicable to human cardiocyes as well as mouse tissues as presented previously. At FIG. 25(A), one sees that PepB reduces DOX mediated mitochondrial membrane depolarization. Left, control, center DOX, and right, DOX plus PepB treatment of human cardiocytes. DOX triggers membrane depolarization, indicated by a lack of fluorescence, while DOX plus PepB treated human cells retain control-level fluorescence. At FIG. 25(B) one sees a quantification of the results in Figure M(A).

Fluorescence Intensity is presented as % of control for, from left, control, DOX treated, and DOX plus PepB treated human cardiocytes. The restoration of fluorescence upon PepB treatment indicates that PepB counteracts the negative effect of DOX on mitochondrial membrane depolarization. At FIG. 25(C), one sees that PepB reduces DOX mediated mPTP opening. Left, control, center DOX, and right, DOX plus PepB treatment of human cardiocytes. DOX triggers mPTP, indicated by a lack of fluorescence, while DOX plus PepB treated human cells retain control-level fluorescence. At FIG. 25(D) one sees a quantification of the results in Figure M(C). Fluorescence Intensity is presented as % of control for, from left, control, DOX treated, and DOX plus PepB treated human cardiocytes. The restoration of fluorescence upon PepB treatment indicates that PepB counteracts the negative effect of DOX on mPTP opening.

At FIG. 25(E), one sees that PepB reduces DOX mediated ROS production. Left, control, center DOX, and right, DOX plus PepB treatment of human cardiocytes. DOX triggers ROS production, indicated by an increase of fluorescence, while DOX plus PepB treated human cells retain control-level fluorescence. At FIG. 25(F) one sees a quantification of the results in FIG. 25(E). Fluorescence Intensity is presented as % of control for, from left, control, DOX treated, and DOX plus PepB treated human cardiocytes. The restoration of control levels of fluorescence upon PepB treatment indicates that PepB counteracts the inductive effect of DOX on ROS generation. At FIG. 25(G), one sees that PepB reduces DOX mediated Calcium ion overload. Left, control, center DOX, and right, DOX plus PepB treatment of human cardiocytes. DOX triggers ROS production, indicated by an increase of fluorescence, while DOX plus PepB treated human cells retain control-level fluorescence. At FIG. 25(H) one sees a quantification of the results in FIG. 25(G). Fluorescence Intensity is presented as % of control for, from left, control, DOX treated, and DOX plus PepB treated human cardiocytes. The restoration of control levels of fluorescence upon PepB treatment indicates that PepB counteracts the inductive effect of DOX on calcium ion accumulation.

Definitions

A partial list of definitions is as follows.

As used herein, "about" a number refers to a range spanning from 10% below to 10% above that number. "About" a range refers to an extended range spanning 10% below the listed lower limit of the range to 10% above the upper listed limit of the range.

As used herein the phrase "at least one of A, B, and C" refers to a set that may include only A, A and additional unlisted elements, A and B, A and B and additional unlisted elements, B, B and unlisted elements, A B and C, A B C and unlisted elements, B and C, B and C and unlisted elements, C alone, or C and unlisted elements.

As used herein, the terms peptide, polypeptide and protein are in some cases used interchangeably in reference to a molecule comprising a plurality of peptide bonds.

EXAMPLES

Figure 1B:
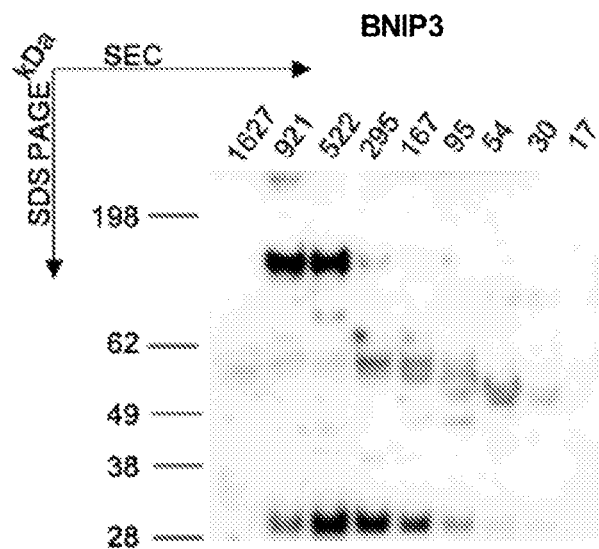
FIG. 1B. BNIP3 oligomeric expression.

Example 1. Cytosolic BNIP3 Determines Necrotic and Apoptotic Cell Death Successively by Regulating BAX in a Heterodimeric State We hypothesized that cytosolic BNIP3 directly acts on BAX in mitochondrial-driven cell death. To investigate this, we employed first blue native-PAGE (BN-PAGE) on cytosolic fractions of the myocardium followed by Western blotting. We detected BNIP3 in large-scale formation of oligomers with an apparent molecular mass between 272 kDa and 450 kDa by anti-BNIP3 antibody (FIG. 1A). Size exclusion chromatography followed by SDSPAGE/Western blotting (FIG. 7A) verified the apparent presence of BNIP3 in oligomers up to a molecular mass between 522 kDa and 921 kDa, but also showed oligomers down to a molecular mass of 54 kDa possessing BNIP3 (FIG. 1B).

Figure 1C:
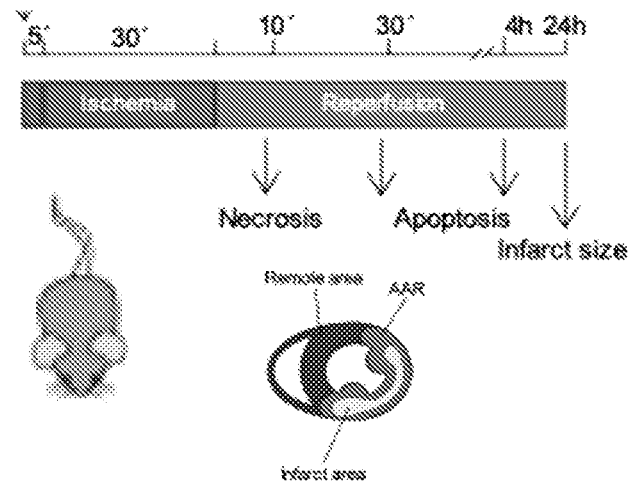
FIG. 1C. Schematic of assay progression.
Figure 1D:
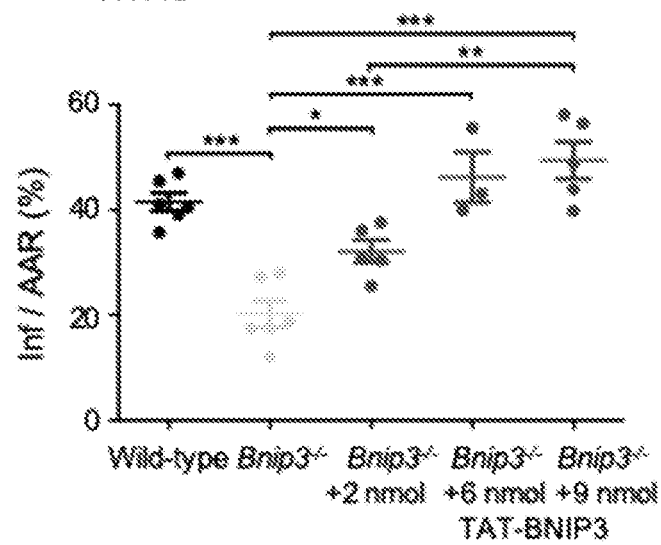
FIG. 1D. TAT-BNIP3 restores wild-type infarction ratios.
Figure 1E:
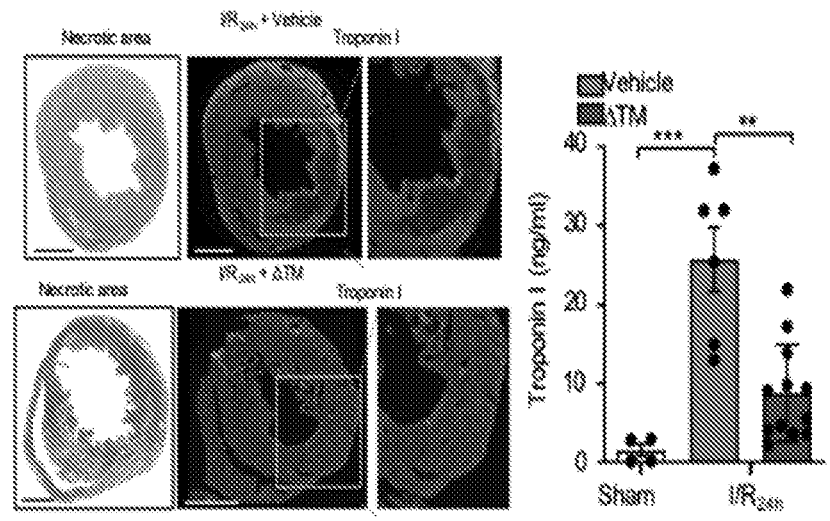
FIG. 1E. delta-TM administration returns Troponin I toward sham treatment levels.
Figure 1F:
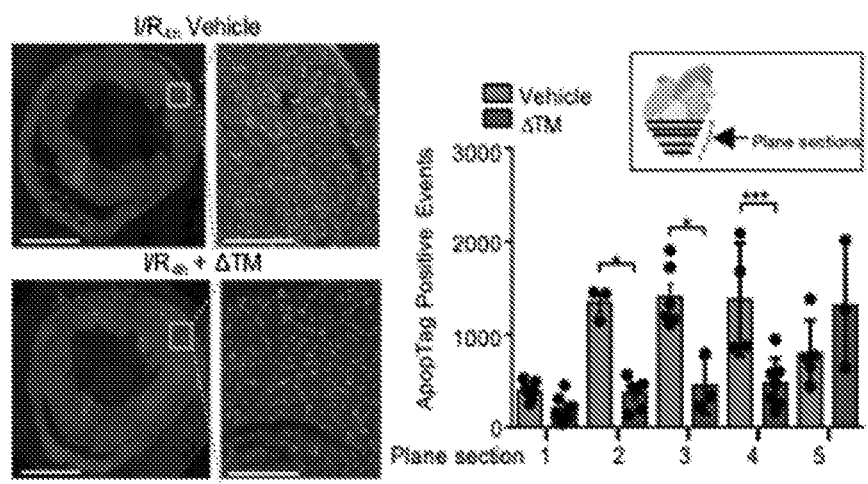
FIG. 1F. delta-TM reduces or delays ApopTag positive events relative to vehicle treated infarction tissue.
Figure 1G:
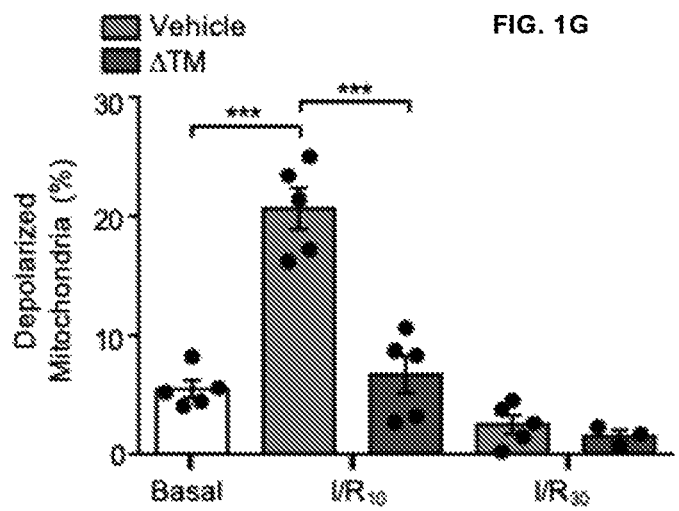
FIG. 1G. delta-TM reduces mitochondrial depolarization proportion.
Figure 1H:
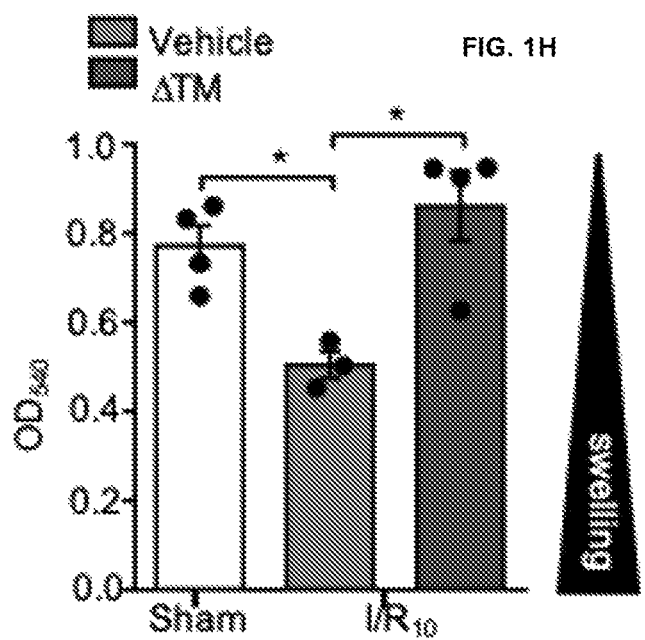
FIG. 1H. delta-TM reduces mitochondrial swelling to sham treatment levels, as indicated by increased OD540 values.
Figure 1I:
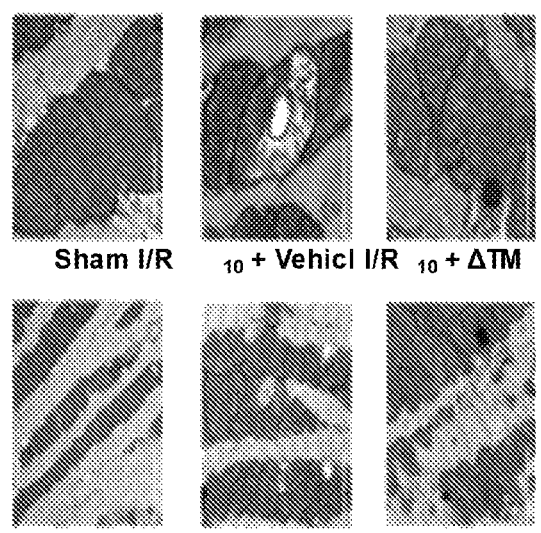
FIG. 1I. Images indicating that delta-TM reduces mitochondrial swelling to sham treatment levels.

We next evaluated the behavior of BNIP3 in necrosis and apoptosis using the well-established mouse myocardial in vivo I/R model as a clinically relevant system (Hendgen-Cotta et al. 2008; Luedike et al., 2012, Rassaf et al. 2014, Merz et al., 2019). Ischemia was induced by occlusion of the left coronary artery for 30 minutes, followed by 24 hours of reperfusion (FIG. 1C; see STAR Methods). By using Bnip3 deficient (Bnip3$^{-/-}$) mice, we found that Bnip3 deletion generally protected cardiac tissue from I/R injury, as evidenced by a reduction in infarct size by 51% compared to wild-type mice (FIG. 1D). BNIP3 restitution in Bnip3$^{-/-}$ mice by injection with a TAT-BNIP3 fusion protein (FIG. 7B) restored infarct sizes up to levels comparable to those of wild-type mice dose-dependently (FIG. 1D). Even in mice with acutely affected BNIP3 activity by administration of the dominant-negative form of BNIP3, TAT-BNIP3 ΔTM (Diwan et al., 2007; Hamacher-Brady et al., 2007), infarct sizes decreased dose-dependently up to a similar level (~55%) as in Bnip3$^{-/-}$ mice (FIG. 7C). This cell death attenuation was accompanied by a decreased cardiac troponin I release, an indicator of cardiomyocyte necrosis (FIG. 1E). We also found a general decrease in apoptotic cells at 4 hours reperfusion (FIG. 1F). In addition, the spatial distribution of apoptotic cells was minimized throughout the LV in mice with affected BNIP3 activity compared to control mice (FIG. 1F).

Figure 8A:
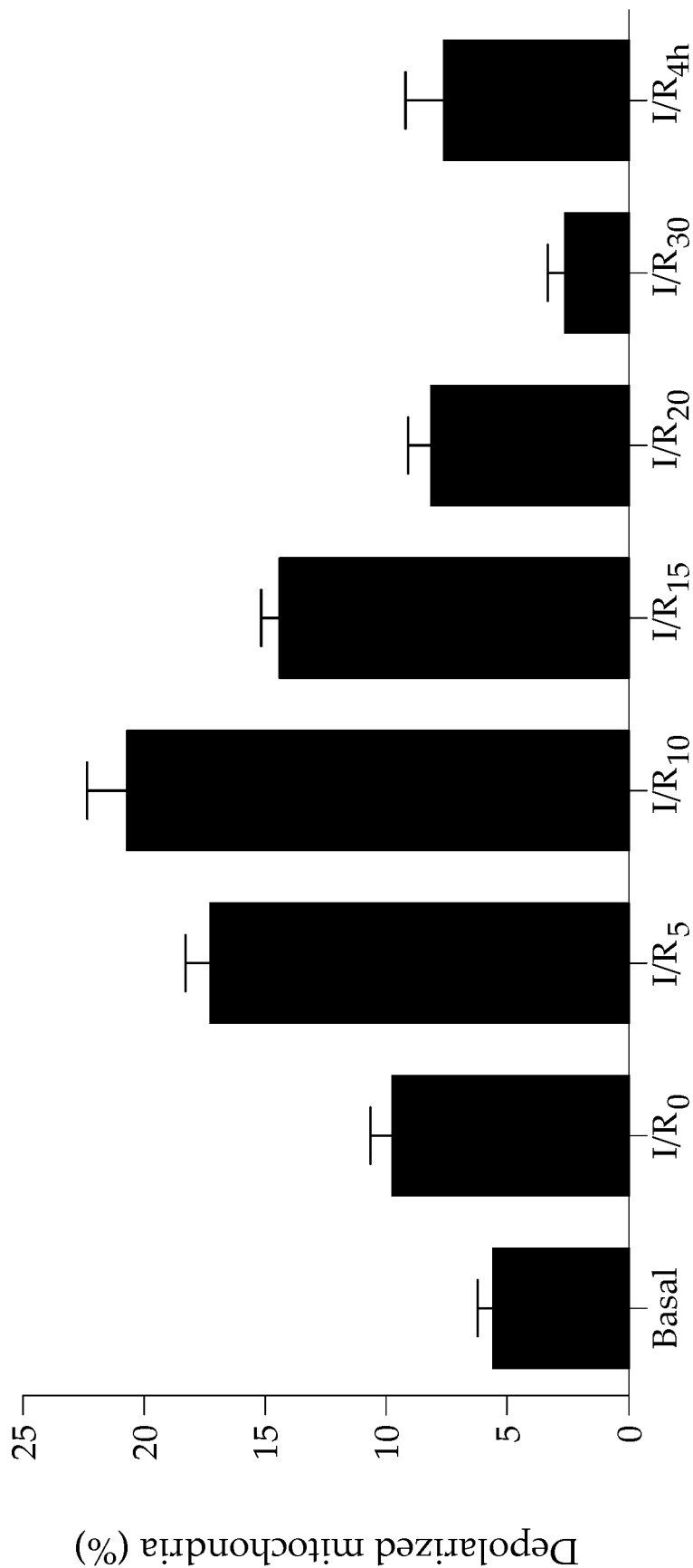
FIG. 8A. Mitochondrial depolarization assays related to FIG. 1G.
Figure 8C:
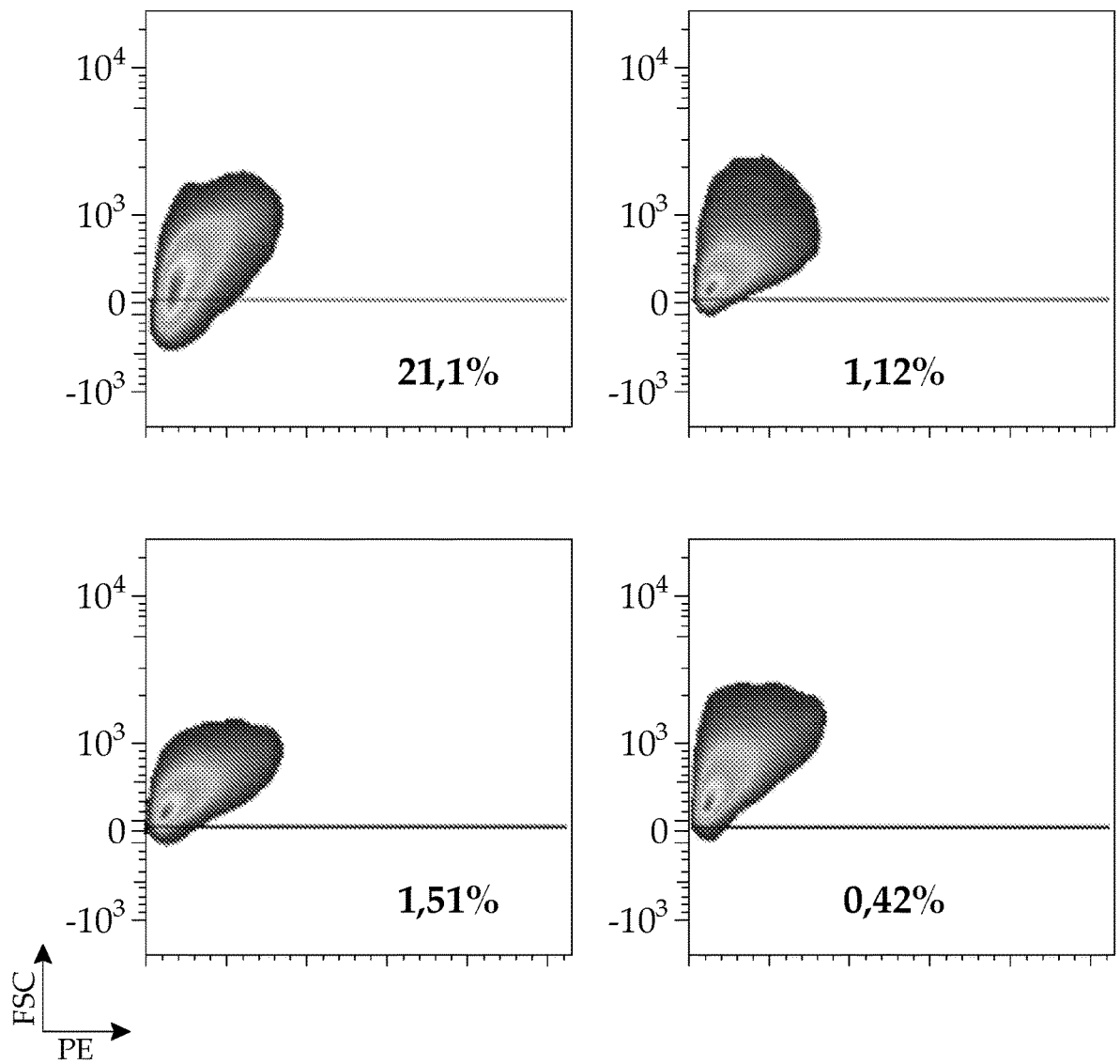
FIG. 8C. Flow cytometry results related to FIG. 1G.
Figure 8D:
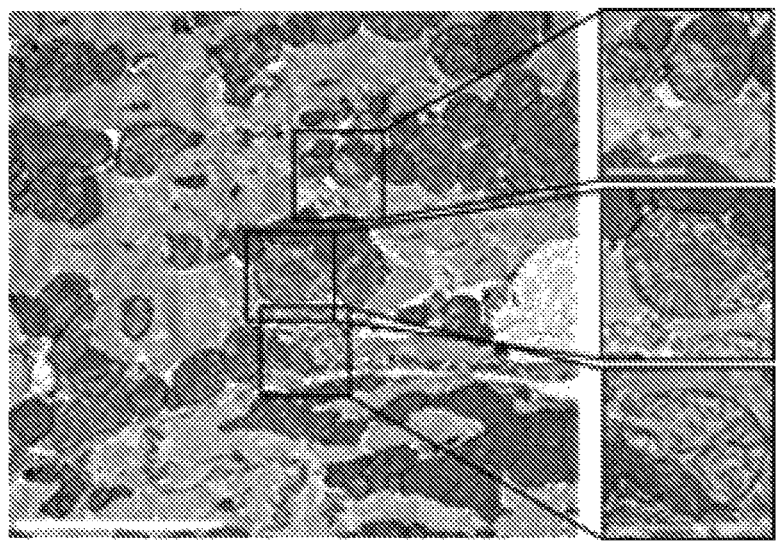
FIG. 8D. Mitochondrial images related to FIG. 1H and FIG. 1I.
Figure 8E:
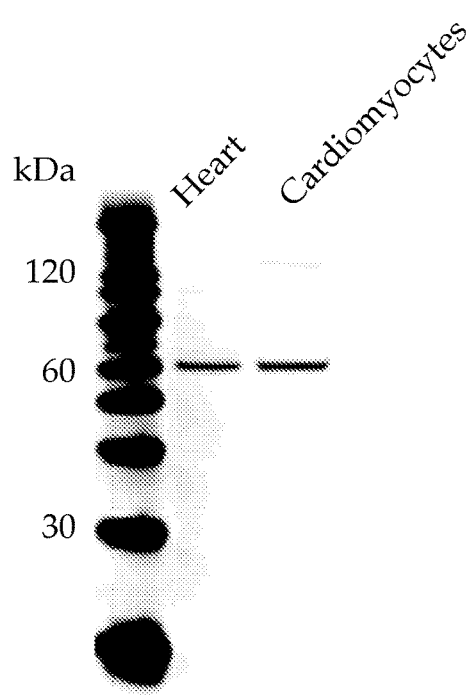
FIG. 8E. Heart and cardiomyocyte protein blot related to FIG. 1J and FIG. 1K.
Figure 8F:
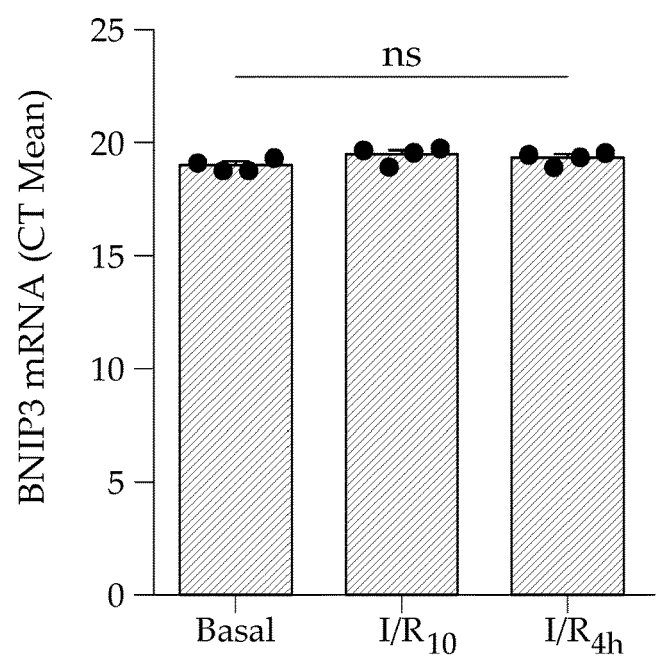
FIG. 8F. BNIP3 mRNA accumulation levels related to FIG. 1J and FIG. 1K.
Figure 8G:
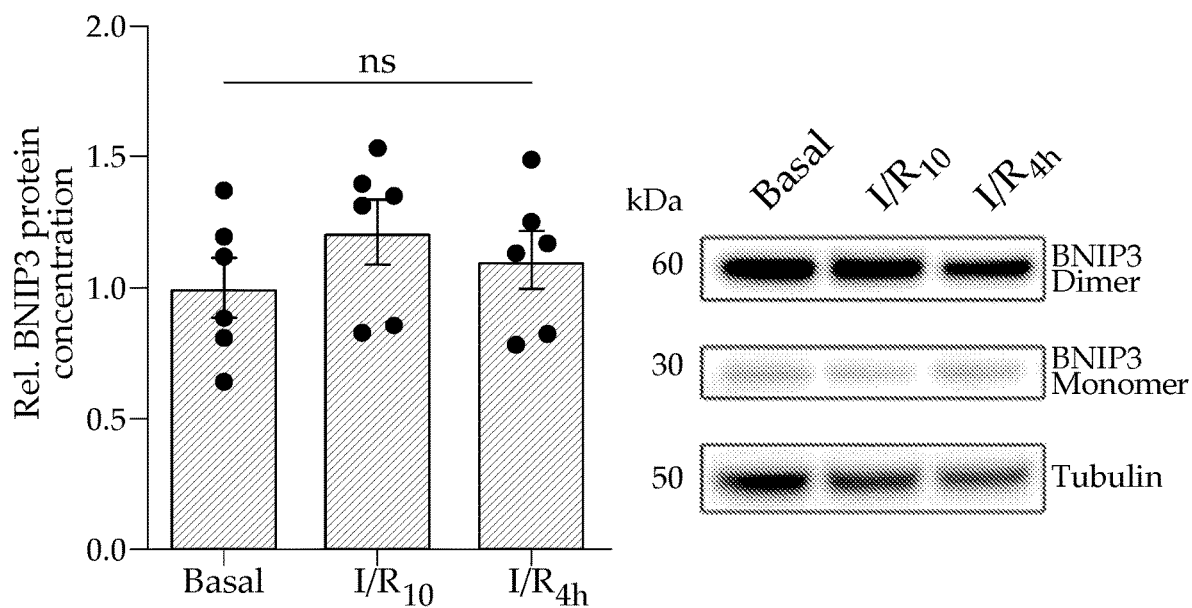
FIG. 8G. Relative BNIP3 protein concentrations related to FIG. 1J and FIG. 1K.
Figure 8H:
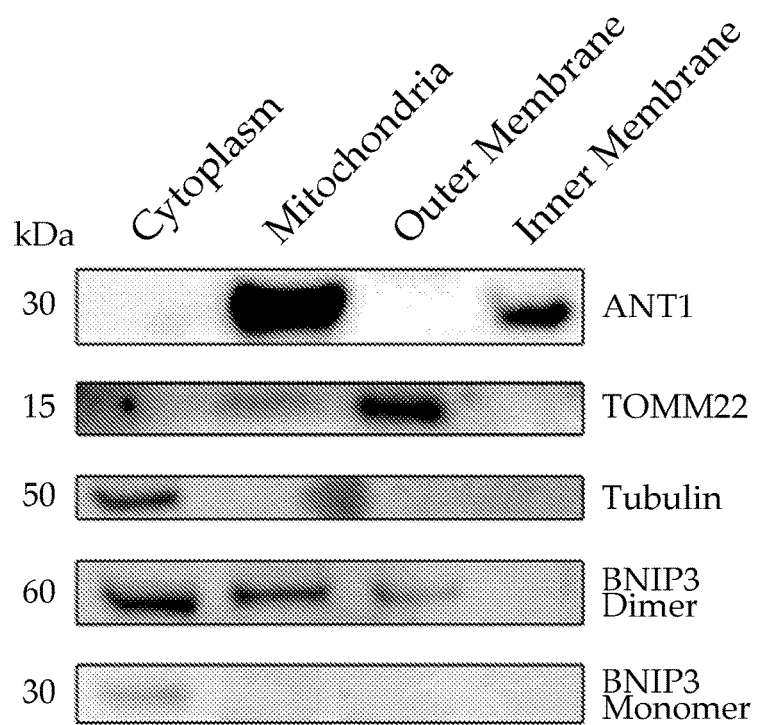
FIG. 8H. Subcellular fractionation studies for BNIP3 monomer and dimer. Dimers indicate increased mitochondrial localization related to FIG. 1J and FIG. 1K.
Figure 8I:
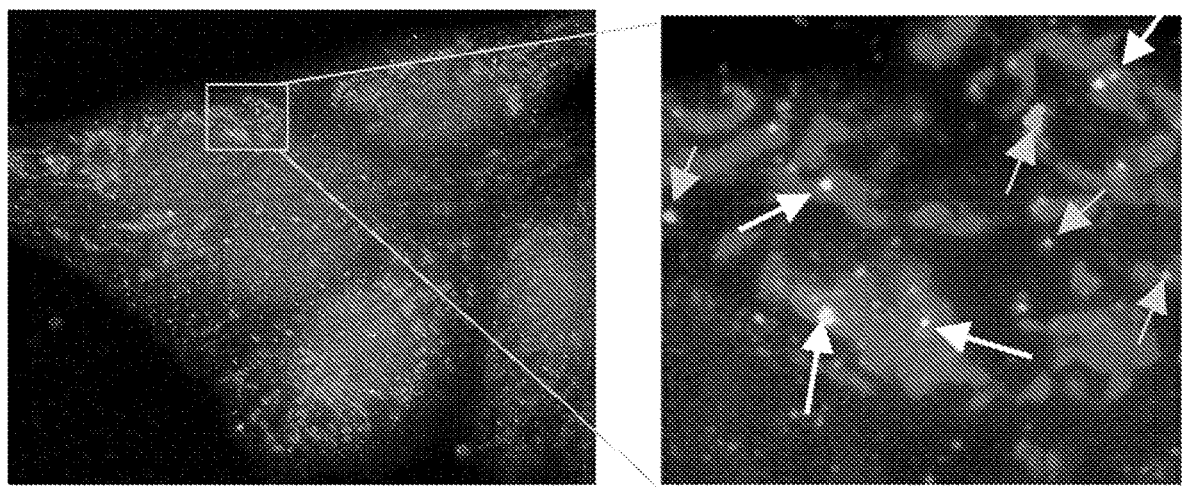
FIG. 8I. Mouse heart localization images related to FIG. 1J and FIG. 1K.

On the subcellular level, we identified a time dependent dissipation of the electrical potential difference across the MIM during reperfusion, which culminated in mitochondrial depolarization and swelling at 10 minutes reperfusion (FIGS. 8A and 8B). When we affected BNIP3 activity by TAT-BNIP3 ΔTM administration, only marginal MIM depolarization and minor mitochondrial swelling and fragmentation occurred (FIGS. 1G-1I, FIGS. 8C and 8D).

Figure 1J:
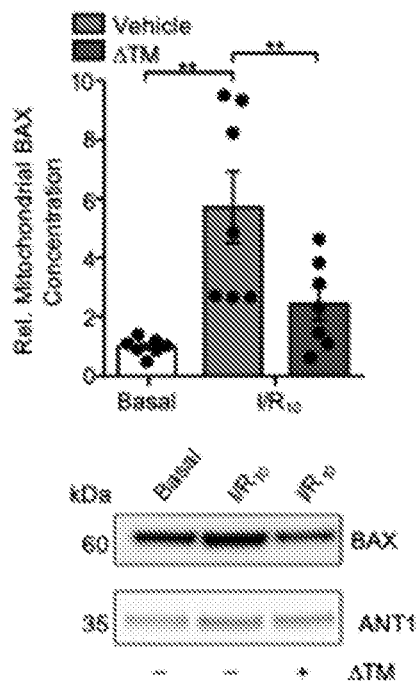
FIG. 1J. delta-TM reduces relative mitochondrial BAX levels to near sham levels.
Figure 1K:
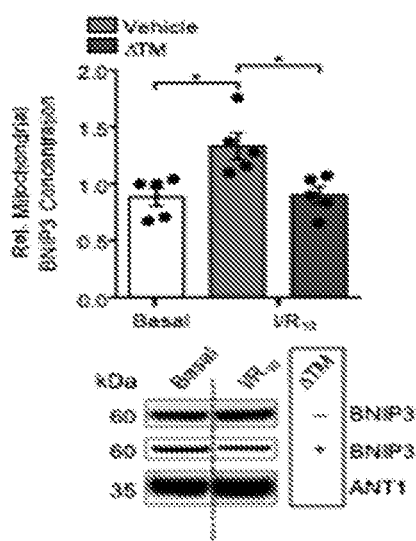
FIG. 1K. delta-TM reduces relative mitochondrial BNIP3 levels to sham levels.

Thus, our results raise the tantalizing idea that BNIP3 regulates necrotic signaling within the first 10 minutes of reperfusion. Transient opening of a pore in the MIM (mPTP) as crucial event for mitochondrial depolarization requires translocation of BAX at the MOM, but not its activation (Whelan et al., 2012, Karch et al. 2013). We first observed that BAX, but also BNIP3 translocated from the cytosol into the MOM (FIGS. 1J and 1K). Already at 10 minutes reperfusion, the time-point of loss of Δψm, significant elevated mitochondrial levels of BNIP3 and BAX dimers were present (FIGS. 1J and 1K), but no activated BAX was detectable (FIG. 1L). We observed the presence of activated BAX at 30 minutes of reperfusion. Notably, using TAT-BNIP3 ΔTM we found that the large-scale BAX translocation was strongly diminished and, hence, dependent on BNIP3 (FIG. 1J). This impact also applied to BNIP3 (FIG. 1K). Its cytosolic presence and constitutive expression of BNIP3 at transcript and protein level in cardiomyocytes during I/R substantiated a translocation from cytosol to mitochondria (FIGS. 8E-8I).

To further strengthen the notion for BAX dependency on cytosolic BNIP3, we performed I/R surgery in Bnip3-/- mice and obtained similar findings at 10 minutes reperfusion (FIG. 1M). BNIP3 restitution by injection with a TAT-BNIP3 fusion protein was indispensable to achieve BAX translocation at the MOM in BNIP3 deficient mice (FIG. 1M), making it highly likely that in native cardiomyocytes cytosolic BNIP3 dictates BAX translocation.

Co-immunoprecipitation experiments revealed that BAX and BNIP3 were physically associated in the cytosol at baseline and 10 minutes reperfusion, and this association was DTT-resistant corroborating their non-covalent heterodimeric structure (FIG. 1N). Regarding the apoptotic signaling, we found no cytochrome c release within the first 10 minutes of reperfusion, but a significant increase in cytosolic cytochrome c content at 30 minutes reperfusion (FIG. 1O). The release of this apoptogenic factor was prevented in mice with affected BNIP3 activity as demonstrated by attenuated cytosolic cytochrome c levels at 30 minutes reperfusion, which were similar to those at baseline and 10 min of reperfusion (FIG. 1O). However, MOMP induction requires the activation of BAX (Kalkavan and Green, 2018; Dewson and Kluck, 2009; Edlich et al., 2011). In accordance with this, the peak BAX activation occurred at 30 minutes reperfusion, and this activation was strongly inhibited by abrogation of BNIP3 activity (FIG. 1L).

Figure 9A:
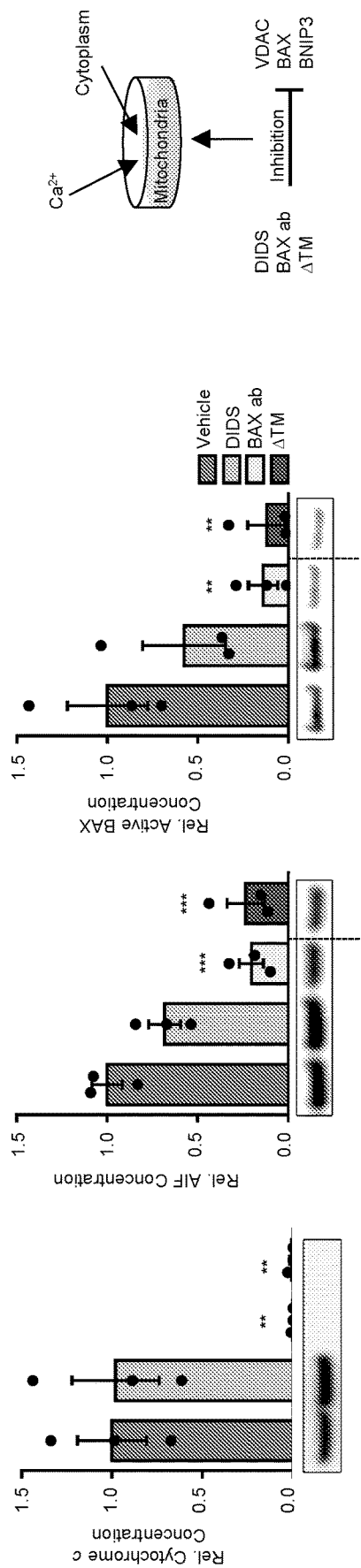
FIG. 9A. Accumulation levels for relative cytochrome c, AF, Active BAX, for Vehicle, DIDS, BAX and deltaTM, and assay schematic related to FIG. 1L.
Figure 9B:
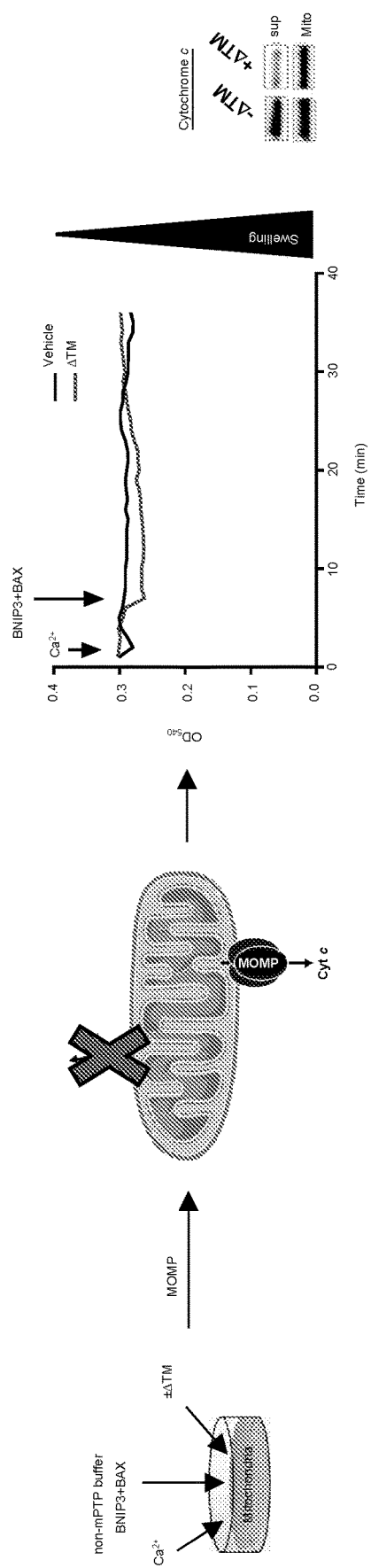
FIG. 9B. Assay schematic related to FIG. 1L.
Figure 9C:
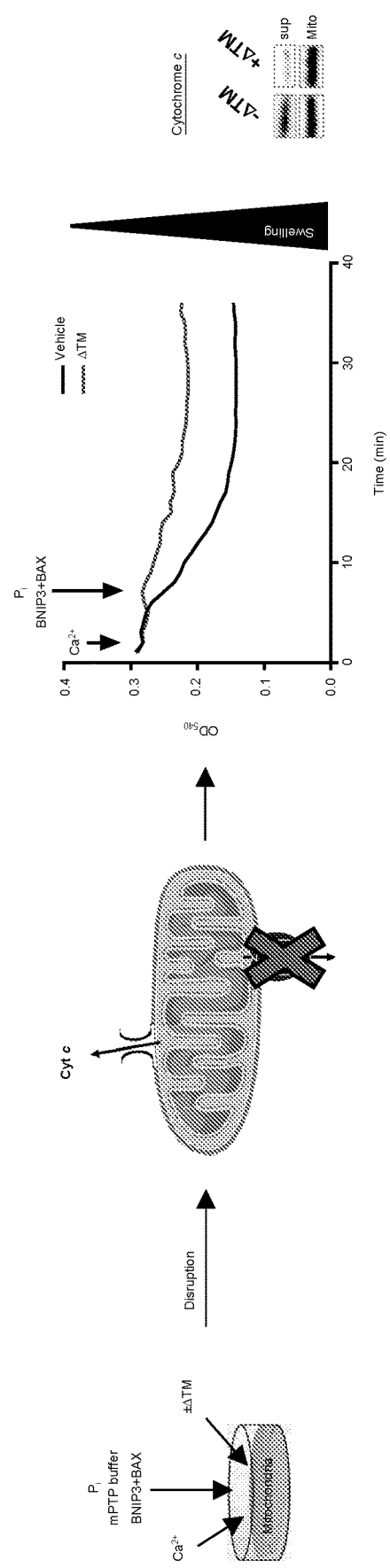
FIG. 9C. Assay schematic related to FIG. 1L.
Figure 9D:
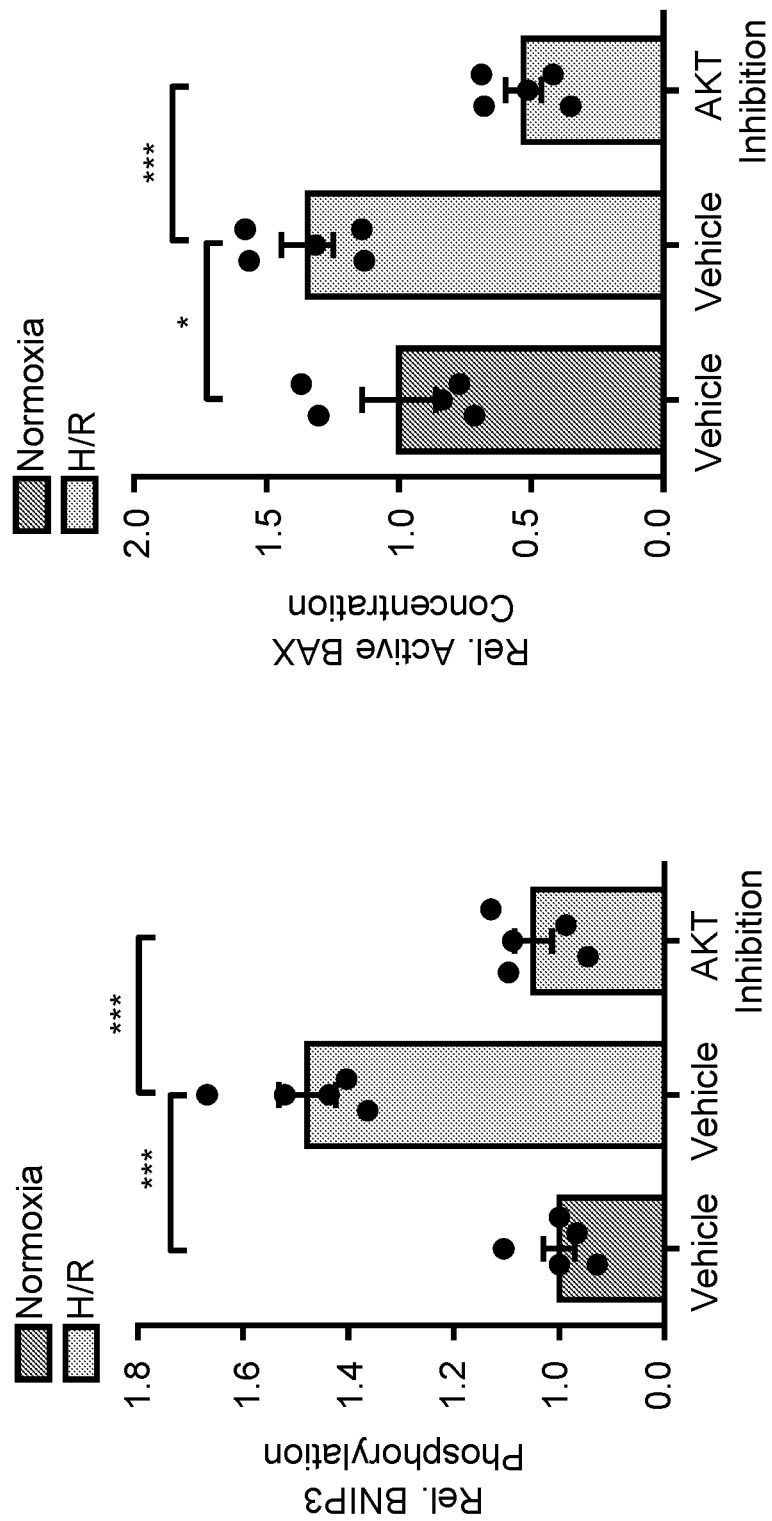
FIG. 9D. Relative BNIP3 phosphorylation and Active BAX concentration are impacted by AKT inhibition related to FIG. 1Q.

We confirmed the dependency of MOMP formation on cytosolic BNIP3 using isolated mouse cardiac mitochondria incubated with cytoplasm by inhibiting BNIP3, BAX and the voltage dependent anion channel (Westphal et al., 2011) (FIG. 9A). BAX activation with release of cytochrome c and AIF was decreased by its inhibition, but also when BNIP3 activity was affected (FIG. 9A). BNIP3-associated MIM and MOM damage was further validated in isolated mouse mitochondria challenged with recombinant BNIP3 and BAX to simulate cytosolic proteins and TAT-BNIP3 ΔTM. Both MIM perturbation and MOMP formation was diminished, as evidenced by limited cytochrome c release (FIGS. 9B and 9C). The data tempted us to speculate that a posttranslational modification of BNIP3 provokes BAX activation. To test this, we investigated the temporal phosphorylation of BNIP3 and a potential impact on BAX activation. In accordance with a demonstrated diminished cardiac capability of ATP synthesis within the first 10 minutes of reperfusion (FIG. 1P), the phosphorylation level of BNIP3 was similar to that at baseline, whereas BNIP3 was highly phosphorylated at 30 minutes reperfusion (FIG. 1Q), when BNIP3 drives BAX activation (FIG. 1N). We further confirmed BNIP3 phosphorylation and limited BAX activation by exposing HL-1 cells to hypoxia/reoxygenation and AKT inhibition (FIG. 9D).

Collectively, our findings identify that cytosolic BNIP3 activity governs necrotic and apoptotic cell death in a time-dependent manner by regulating BAX in a heterodimeric state. Thereby, phosphorylation of BNIP3 may activate BAX and MOMP formation constituting the master switch of BNIP3/BAX cell death activity from necrosis into apoptosis.

Example 2. N-Terminus is the Interacting Domain of BNIP3

Figure 2A:
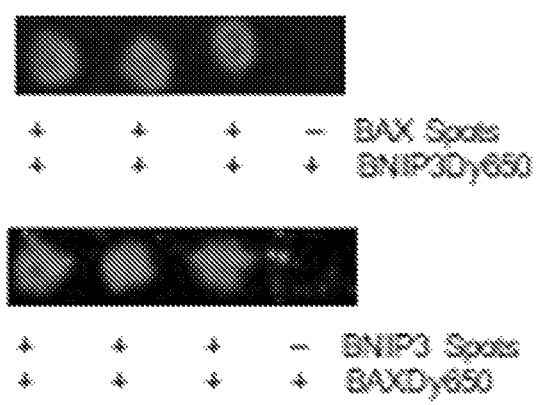
FIG. 2A. BAX and BNIP3 bind in a spot assay.
Figure 2B:
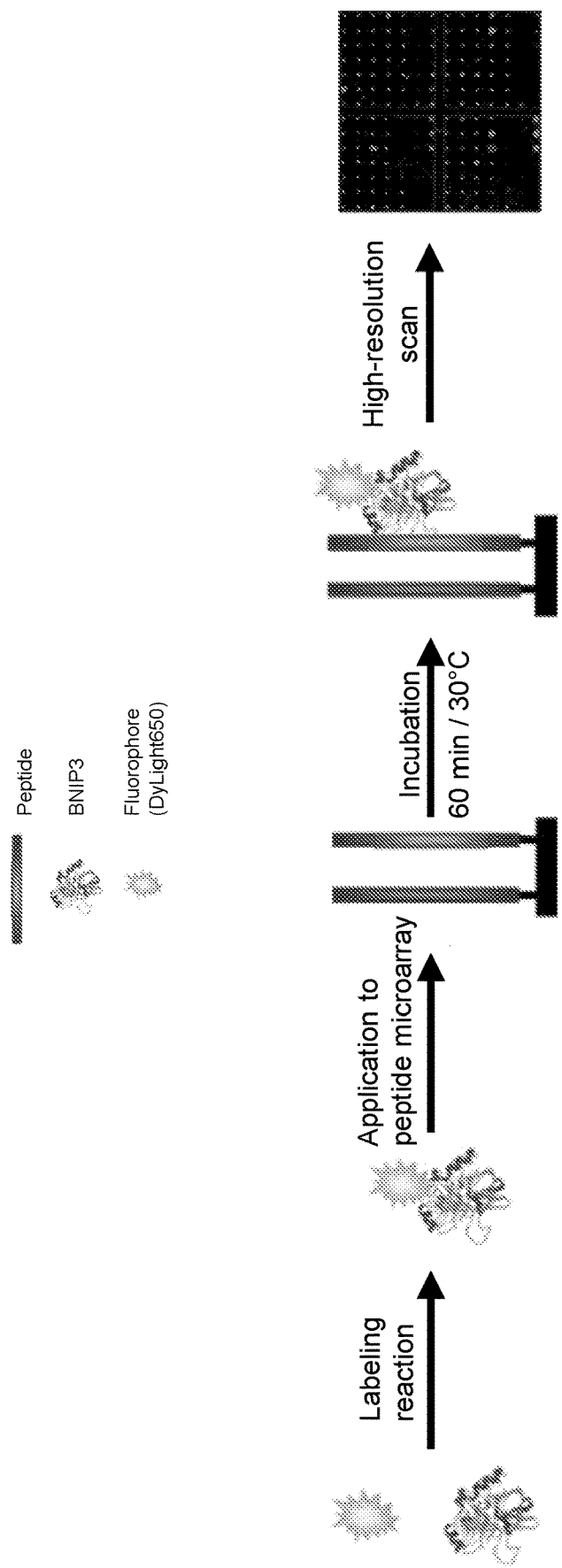
FIG. 2B. Treatment schematic.
Figure 2C:
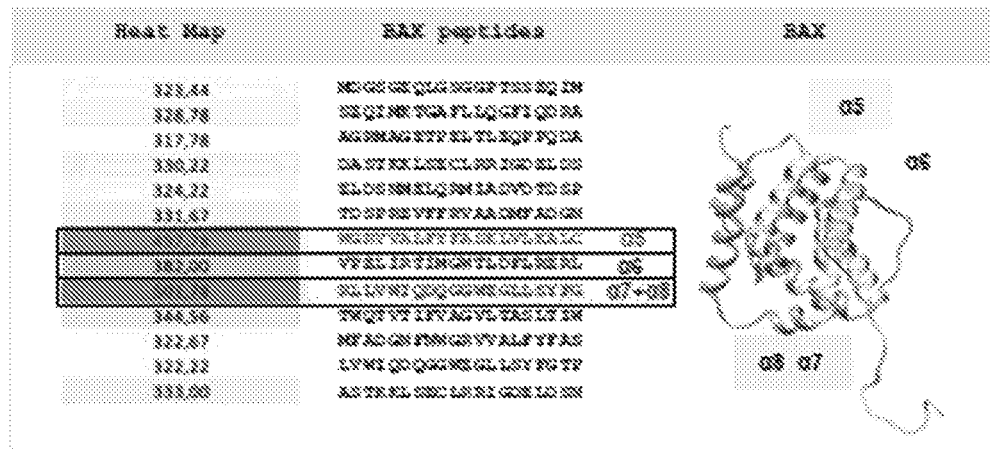
FIG. 2C. BAX peptide binding heat map. Figure discloses SEQ ID NOS 20-32, respectively, in order of appearance.
Figure 2D:
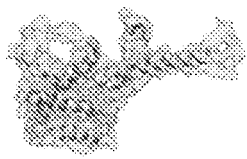
FIG. 2D. BNIP3 folding model.
Figure 2E:
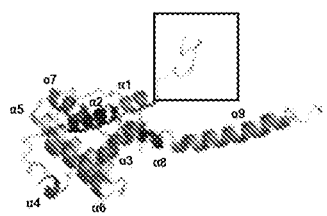
FIG. 2E. BNIP3 N-terminus. Figure discloses SEQ ID NO: 1.
Figure 2F:
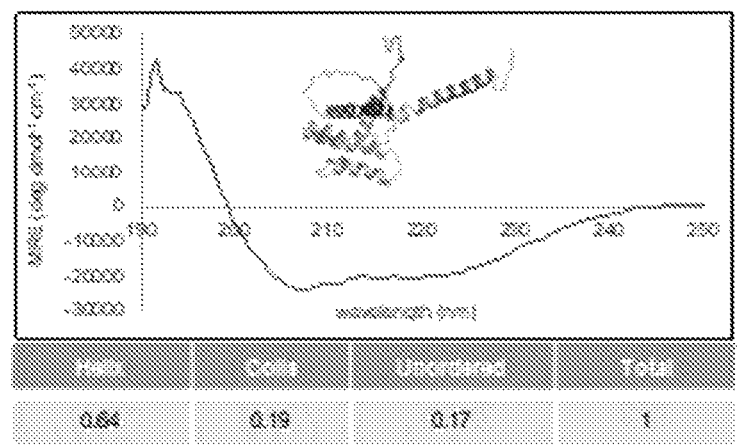
FIG. 2F. BNIP3 Secondary structure prediction.
Figure 2G:
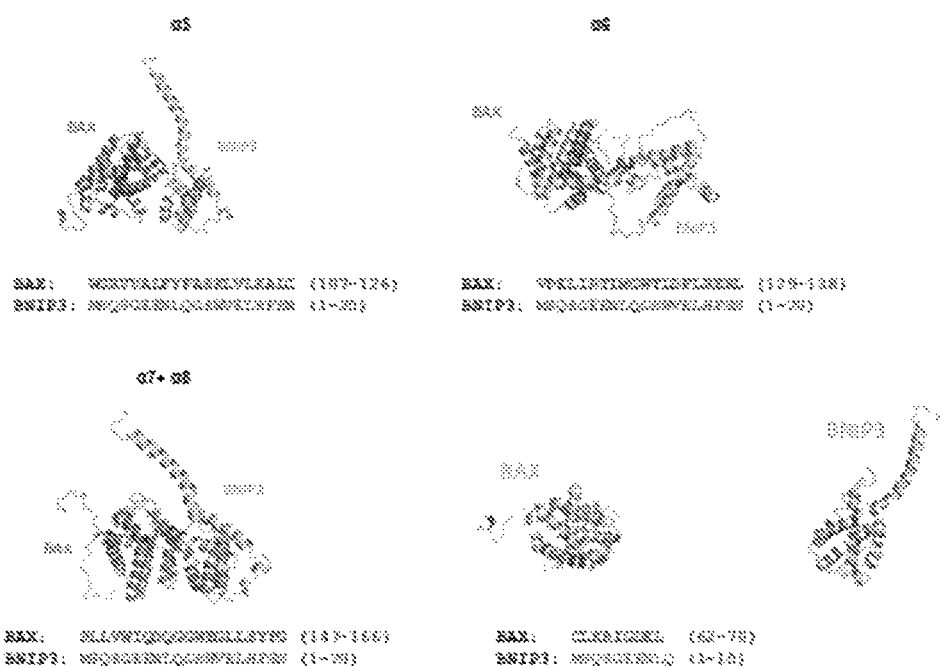
FIG. 2G. BNIP3-BAX binding prediction. Figure discloses SEQ ID NOS 26, 33, 1, 1, and 34-37, respectively, in order of appearance.

To map the interaction domain of BNIP3 and the possible binding sites in BAX, we first confirmed the BNIP3/BAX interaction seen in vivo by an in vitro protein-protein overlay devoid of cellular kinases (FIG. 2A). To identify possible binding sites for BNIP3 in BAX, we employed a protein-peptide interaction study with a library of 13 synthesized BAX peptides immobilized on microarrays (FIG. 2B). Fluorescence-labeled recombinant BNIP3 was incubated on peptide microarrays identifying the helices α5, α6, α7 and α8 of BAX as potential interaction sites with BNIP3 (FIG. 2C). Since the 3D structure of BNIP3 has not been fully solved with the exception of its transmembrane domain located at the C terminus using nuclear magnetic resonance spectroscopy (Bocharov et al., 2007; Sulistijo and Mackenzie, 2009), we predicted in silico the 3D structure of BNIP3 by homology modelling using Modeller 9.15 (Eswar et al., 2006) followed by energy minimization using NAMD 2.9 (Phillips et al., 2005) and the CHARMM36 force field (Vanommeslaeghe and MacKerell, 2015) (FIG. 2D). The template structures corresponded to PDB codes 2K7W (Gavathiotis et al., 2008) and 2KA1 (Sulistijo and Mackenzie, 2009). The 3D model features nine α-helices of variable length representing 64% of the secondary structure, followed by random coils (19%) and unidentified structures (17%) (FIG. 2E). We supported the predicted secondary structure of BNIP3 by circular dichroism (CD) spectroscopy (FIG. 2F). Computational docking simulations performed with Autodock Vina (Trott and Olson, 2010) and HADDOCK (Dominguez et al., 2003) also suggested the BAX helices α5, α6, α7 and α8 and BNIP3 sequence MSQSGEENLQGSWVELHFSN (SEQ ID NO: 1) (amino acids 1-20) as interaction sites while the first 10 amino acids alone failed to bind to BAX (FIG. 2G). Thus, BNIP3 amino acids 1-20 appear to be crucial for BNIP3 binding to BAX.

Example 3. N-Terminus of BNIP3 is a Critical Functional Domain in Human Cardiomyocyte Protection Based on our prediction of amino acids 1-20 of BNIP3 as the BAX interaction site, we hypothesized that this sequence is a functional domain of BNIP3 and may be sufficient to antagonize BNIP3/BAX activity. We initially designed a cell-permeable peptide, TAT-BNIP3-20A, composed of the HIV-1 Tat protein transduction domain48-59 (PTD; GRKKRRQRRRPQ (SEQ ID NO: 13)) (Shoji-Kawata et al., 2013) attached via a covalent bond to 20 amino acids derived from amino acids 1-20 of BNIP3 (FIG. 3A). The BNIP3 amino acids 42-61 were used to generate a control peptide, TAT-BNIP3-20C (FIG. 3B). To test first the efficacy of the peptide, we subjected wild-type mice to I/R with TAT-BNIP3-20A injection. Consistent with our hypothesis, TAT-BNIP3-20A prevented BNIP3 translocation and antagonized BNIP3 activity, demonstrated by a markedly reduced caspase-3 activity (FIGS. 3C and 3D). Notably, TAT-BNIP3-20A resulted in a reduction in infarct size by 41% relative to treatment with vehicle, but no difference was observed between TATBNIP3-20C and vehicle treatments (FIG. 3E). To address the translational aspect, since BNIP3 is expressed in the human myocardium (FIG. 3F) (Chaanine et al., 2013), we assessed mouse/human BNIP3 sequence alignment with focus on the N-terminus region at issue. The comparison revealed amino acids 9-20 as conserved residues (FIG. 3G). To identify the crucial amino acids required for activity, we next performed N-terminal truncation analysis of the first 20 amino acids of BNIP3 and identified the amino acids residues 13-20, WVELHFSN (SEQ ID NO: 2), within the evolutionarily conserved domain (FIG. 3H, FIG. 26). This truncated peptide led to the strongest signal with a 14-fold signal increase compared to the 20 residues of BNIP3-20A peptide in a BNIP3/peptide microarray (FIG. 2A). We next focused on substitution analyses (FIG. 27A-FIG. 27E). No peptides with double or triple alanine scan demonstrated stronger binding of the protein when compared to the wild-type sequence (FIG. 10A). Particular amino acid substitution by natural amino acids (A, C, D, E, F, G, H, I, K, L, M, N, P, Q, R, S, T, V, W, Y) within the truncated sequence identified that the exchanges of W13 and F18 by each of the canonical amino acids severely impaired BNIP3 binding (FIG. 3I). This assigns tryptophan and phenylalanine functional roles in the binding activity. Consistently, a S-to-F substitution at position 19 displayed substantially higher BNIP3 binding, underpinning a critical role for phenylalanine (FIG. 3I). Docking simulations of the discovered sequence with S-to-F substitution, WVELHFFN (SEQ ID NO: 3), and BAX showed that peptide binding to the BAX interface is dominated by conformations of the peptide located over the N terminus of helix α5 (FIGS. 3J and 3K). In addition, the obtained conformations suggest that the better binding of WVELHFFN (SEQ ID NO: 3) to BAX compared to the native sequence WVELHFSN (SEQ ID NO: 2) is related to improved aromatic intrapeptide interactions (Martinez and Iverson, 2012). This was confirmed by a BAX/microarray evidenced by a 4-fold increased signal intensity related the native sequence (FIG. 3K). Our findings indicate that these amino acids are necessary to antagonize BNIP3/BAX activity. We therefore designed a peptide in which the PTD was attached via a covalent bond to eight amino acids derived from amino acids 13-20 of BNIP3, but with the S-to-F-substitution (TAT-WVELHFFN ("WVELHFFN" disclosed as SEQ ID NO: 3); FIG. 3L). The CD spectrum of TAT-WVELHFFN ("WVELHFFN" disclosed as SEQ ID NO: 3) showed that the peptide exhibited a random coil conformation (FIG. 3M). To design a dysfunctional peptide as a control, we substituted potential interfacial residues, including the crucial phenylalanine residues F19 to S19 and F18 to A18 and H17 to A17, thereby generating the TAT-WVELAASN ("WVELAASN" disclosed as SEQ ID NO: 7) peptide (FIG. 10B). BNIP3-TAT-WVELHFFN ("WVELHFFN" disclosed as SEQ ID NO: 3) and BAX-TAT-WVELHFFN ("WVELHFFN" disclosed as SEQ ID NO: 3) fluorescence-based overlay assays then confirmed that TAT-WVELHFFN ("WVELHFFN" disclosed as SEQ ID NO: 3) binds to both BNIP3 and BAX (FIG. 3N). To scrutinize the translational aspect, we conducted hypoxia/reoxygenation experiments on human ventricular cardiomyocytes derived from human induced pluripotent stem cells (human CMs; FIG. 3O), which recapitulated BNIP3/BAX interactions assessed by the proximity ligation assay (FIG. 3P). Upon treatment with TAT-WVELHFFN ("WVELHFFN" disclosed as SEQ ID NO: 3), apoptotic and necrotic cell death and MIM depolarization were diminished relative to control peptide treatment (FIG. 3Q)

Figure 4A:
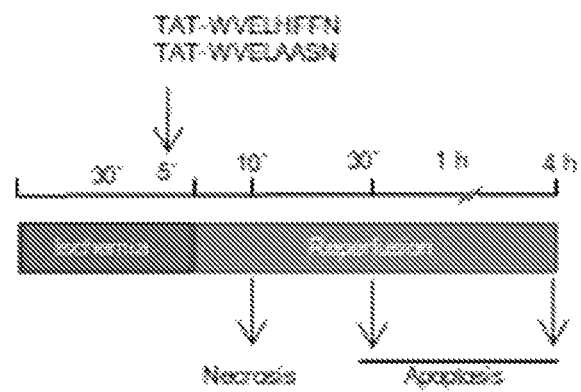
FIG. 4A. Treatment regimen. Figure discloses SEQ ID NOS 3 and 7, respectively, in order of appearance.
Figure 4B:
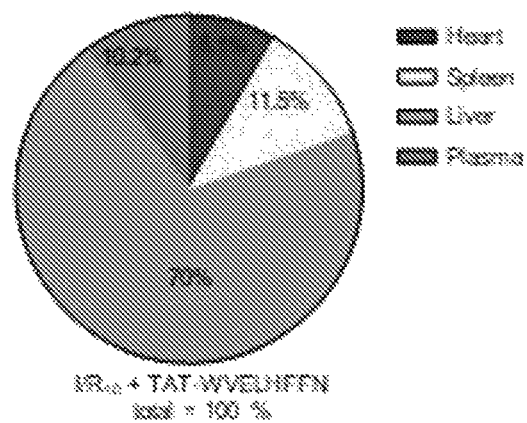
FIG. 4B. Peptide localizations. Figure discloses SEQ ID NO: 3.
Figure 4C:
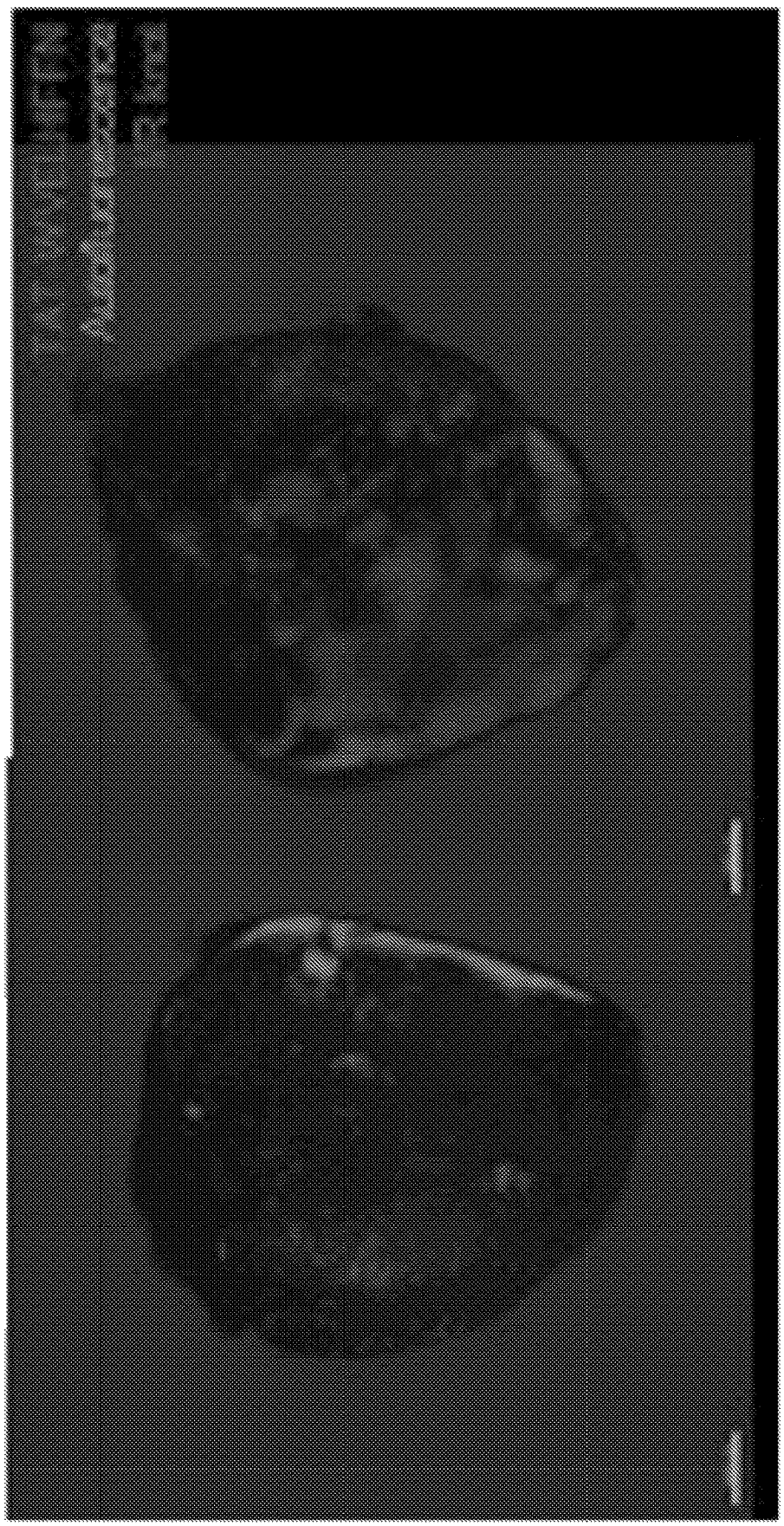
FIG. 4C. Peptide localization image. Figure discloses SEQ ID NO: 3.
Figure 4D:
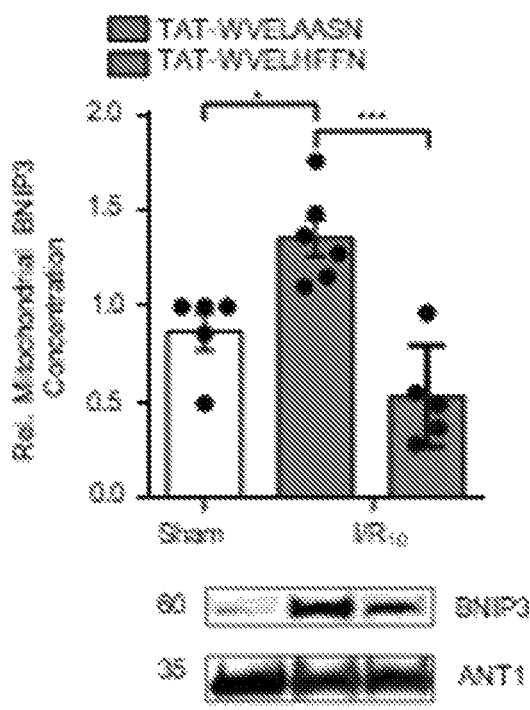
FIG. 4D. TAT-WVELHFFN ("WVELHFFN" disclosed as SEQ ID NO: 3) counteracts TAT-WVELAASN ("WVELAASN" disclosed as SEQ ID NO: 7) increase in relative mitochondrial BNIP3 concentration. Figure discloses SEQ ID NOS 7 and 3, respectively, in order of appearance.
Figure 4E:
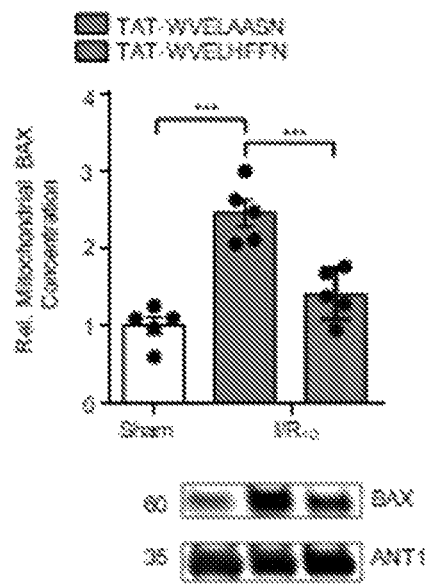
FIG. 4E. TAT-WVELHFFN ("WVELHFFN" disclosed as SEQ ID NO: 3) counteracts TAT-WVELAASN ("WVELAASN" disclosed as SEQ ID NO: 7) increase in relative mitochondrial BAX concentration. Figure discloses SEQ ID NOS 7 and 3, respectively, in order of appearance.
Figure 4F:
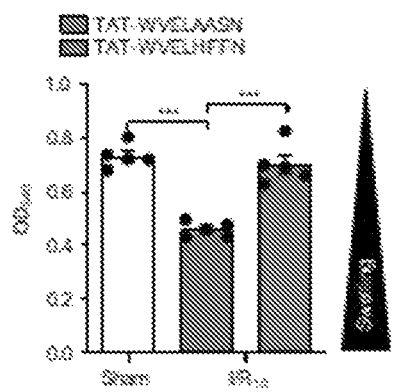
FIG. 4F. TAT-WVELHFFN ("WVELHFFN" disclosed as SEQ ID NO: 3) counteracts TAT-WVELAASN ("WVELAASN" disclosed as SEQ ID NO: 7) increase in relative mitochondrial swelling. Figure discloses SEQ ID NOS 7 and 3, respectively, in order of appearance.
Figure 4G:
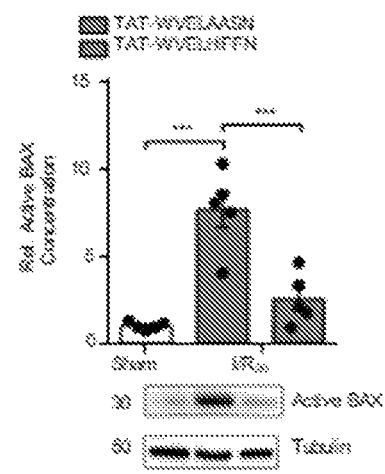
FIG. 4G. TAT-WVELHFFN ("WVELHFFN" disclosed as SEQ ID NO: 3) counteracts TAT-WVELAASN ("WVELAASN" disclosed as SEQ ID NO: 7) increase in relative active BAX concentration. Figure discloses SEQ ID NOS 7 and 3, respectively, in order of appearance.
Figure 4H:
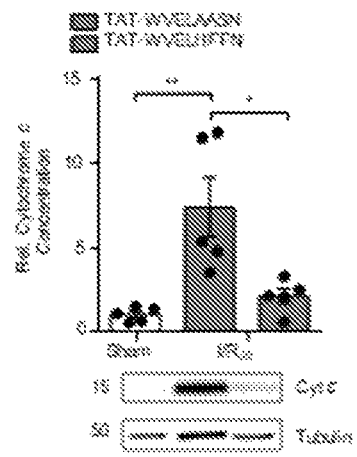
FIG. 4H. TAT-WVELHFFN ("WVELHFFN" disclosed as SEQ ID NO: 3) counteracts TAT-WVELAASN ("WVELAASN" disclosed as SEQ ID NO: 7) increase in relative cytochrome c concentration. Figure discloses SEQ ID NOS 7 and 3, respectively, in order of appearance.
Figure 4I:
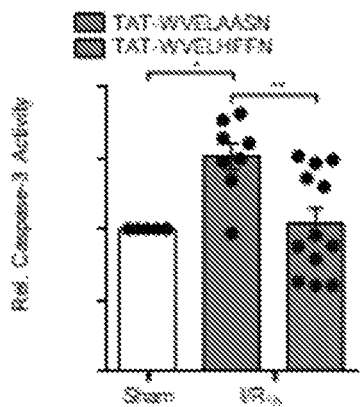
FIG. 4I. TAT-WVELHFFN ("WVELHFFN" disclosed as SEQ ID NO: 3) counteracts TAT-WVELAASN ("WVELAASN" disclosed as SEQ ID NO: 7) increase in relative Caspase 3 activity. Figure discloses SEQ ID NOS 7 and 3, respectively, in order of appearance.

Example 4. WVELHFFN Peptide Functions in Necrotic and Apoptotic Signaling Prevention In Vivo Our results regarding the binding capacity of WVELHFFN (SEQ ID NO: 3) to both BNIP3 and BAX and the protective effect of TAT-WVELHFFN ("WVELHFFN" disclosed as SEQ ID NO: 3) on necrotic and apoptotic death of cardiomyocytes predict an inhibitory effect on the BNIP3/BAX heterodimer induced lethal signaling pathways. To test this, we used the established in vivo myocardial I/R model with focus on the fundamental reperfusion times at 10 and 30 minutes and several complementary methods on the downstream signaling (FIG. 4A). As demonstrated, cell death signaling occurs during the first minutes of reperfusion (FIG. 1). Studies have shown that application of cardioprotective agents after the onset of reperfusion failed to reduce I/R injury (Davidson et al., 2019). Therefore, we decided to administer TAT-WVELHFFN ("WVELHFFN" disclosed as SEQ ID NO: 3) or the control peptide TAT-WVELAASN ("WVELAASN" disclosed as SEQ ID NO: 7) 5 minutes before the end of ischemia, which is a feasible time point for drug application in the clinical setting (FIG. 4A). To ascertain myocardial peptide up-take, distribution and temporal presence following in vivo intracardiac injection, we initially injected ischemic wild-type mice with fluorescence labeled TAT-WVELHFFN ("WVELHFFN" disclosed as SEQ ID NO: 3) 5 minutes before reperfusion. We found that TAT-WVELHFFN ("WVELHFFN" disclosed as SEQ ID NO: 3) was present in the heart at the time of BNIP3/BAX heterodimeric initialization of the cell death cascade (FIG. 4B). As with light sheet microscopic analysis of the whole heart (Merz et al., 2019), the distribution of the peptide occurred also within the area at risk (FIG. 4C). We further evaluated the pharmacokinetic profile of TAT-WVELHFFN ("WVELHFFN" disclosed as SEQ ID NO: 3) in human serum, plasma and whole blood, characterized its toxicity in murine cardiomyocytes and mice and the impact on heart function. The observed stability of TAT-WVELHFFN ("WVELHFFN" disclosed as SEQ ID NO: 3) in human whole blood, plasma and serum over 60 minutes provides in vivo inhibitory capacity (FIG. 11A). Of note, we could not detect signs of overt toxicity in either cardiomyocytes or mice (FIGS. 11B and 11C). Consistent with our hypothesis, upon treatment with TAT-WVELHFFN ("WVELHFFN" disclosed as SEQ ID NO: 3), BNIP3 and BAX translocation to the mitochondria at 10 minutes reperfusion was markedly diminished (FIGS. 4D and 4E). By consequence, necrotic and apoptotic signaling characterized by mitochondrial swelling at 10 minutes of reperfusion as well as BAX activation, cytochrome c release, and caspase-3 activity at 30 minutes reperfusion were strongly reduced (FIGS. 4F-4I).

Figure 5A:
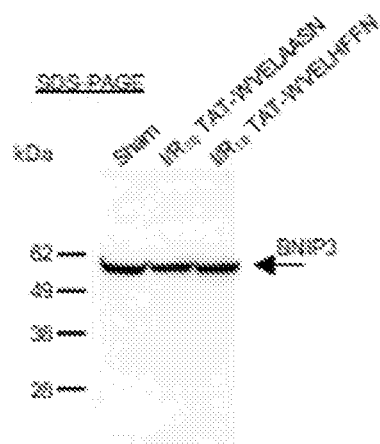
FIG. 5A. BNIP3 accumulation. Figure discloses SEQ ID NOS 7 and 3, respectively, in order of appearance.
Figure 5B:
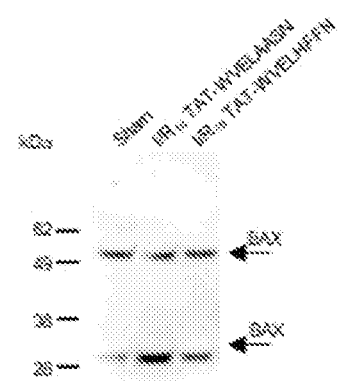
FIG. 5B. BAX accumulation. Figure discloses SEQ ID NOS 7 and 3, respectively, in order of appearance.
Figure 5C:
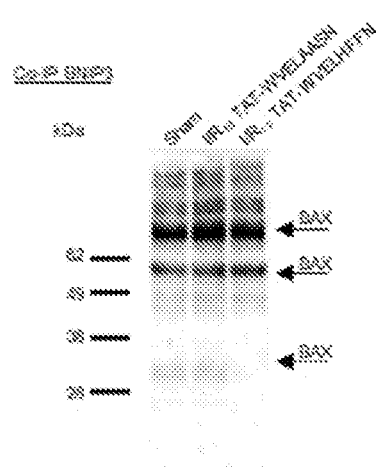
FIG. 5C. BAX accumulation. Figure discloses SEQ ID NOS 7 and 3, respectively, in order of appearance.
Figure 5D:
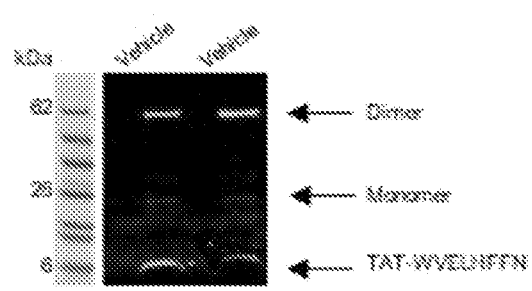
FIG. 5D. BAX accumulation. Figure discloses SEQ ID NO: 3.
Figure 5E:
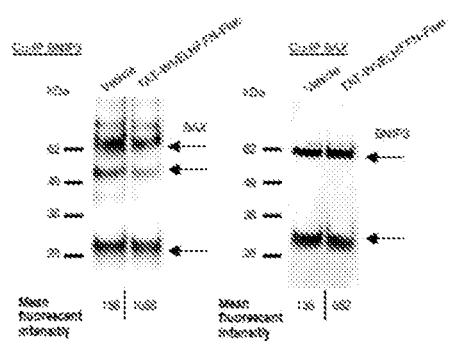
FIG. 5E. BAX and BNIP3 coimmunoprecipitation results. Figure discloses "WVELHFFN-Fluo" as SEQ ID NO: 9.
Figure 5F:
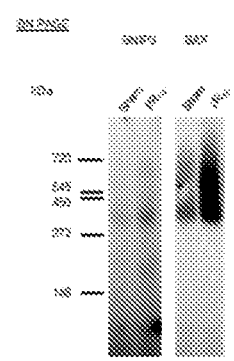
FIG. 5F. BAX and BNIP3 accumulation results.
Figure 5G:
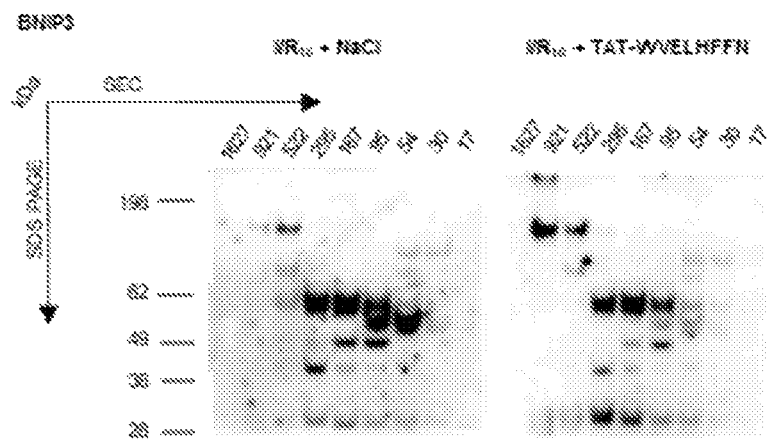
FIG. 5G. BNIP3 accumulation impacted by TAT-WVELHFFN ("WVELHFFN" disclosed as SEQ ID NO: 3). Figure discloses SEQ ID NO: 3.
Figure 5H:
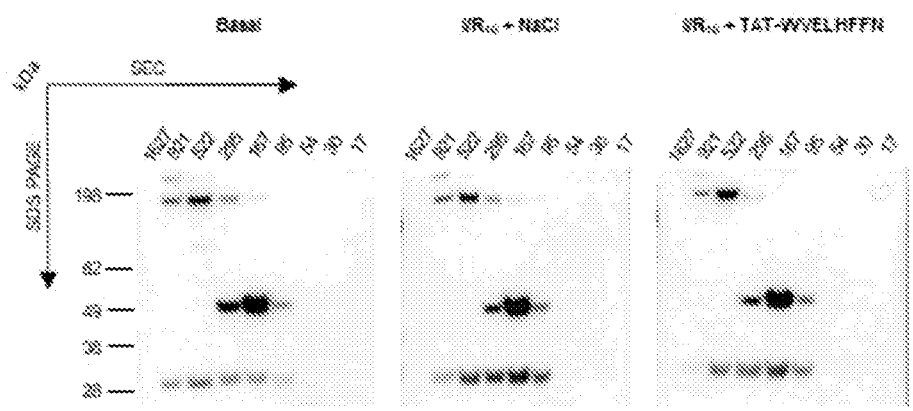
FIG. 5H. Accumulation results. Figure discloses SEQ ID NO: 3.
Figure 5I:
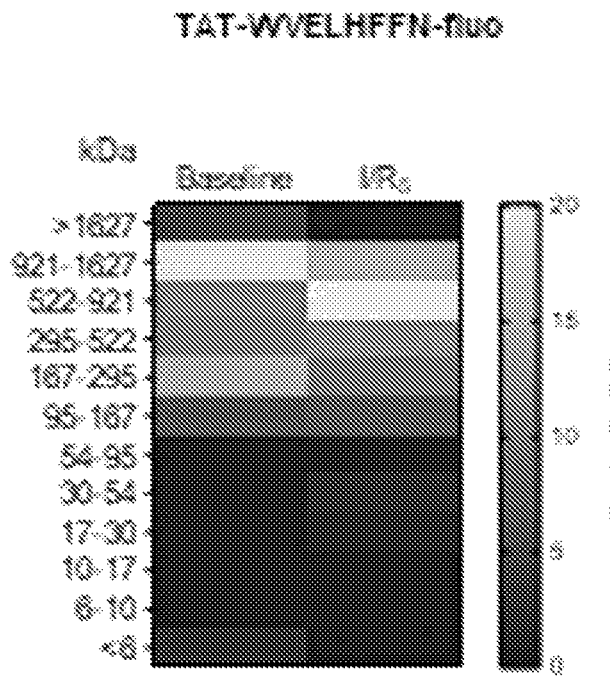
FIG. 5I. TAT-WVELHFFN ("WVELHFFN" disclosed as SEQ ID NO: 3) migration in baseline and I/R tissues. Figure discloses SEQ ID NO: 9.

Example 5. WVELHFFN Functions in Inhibition of BNIP3/BAX Heterodimers as Components of the Mitochondrial Membrane Attack Oligomers Based on the knowledge of cytosolic non-covalent BNIP3/BAX heterodimers at baseline and 10 minutes at reperfusion obtained by co-immunoprecipitation (FIG. 1), we sought to determine the mode of action of WVELHFFN (SEQ ID NO: 3) on BNIP3/BAX heterodimers. Upon peptide treatment, neither BNIP3 nor BAX dimers were influenced at 10 minutes of reperfusion (FIGS. 5A and 5B). In co-immunoprecipitation experiments the unaffected heterodimeric state of BNIP3 and BAX was confirmed (FIG. 5C). To investigate whether TAT-WVELHFFN ("WVELHFFN" disclosed as SEQ ID NO: 3) interacts with the BNIP3/BAX heterodimer, we used fluorescence-labeled TAT-WVELHFFN ("WVELHFFN" disclosed as SEQ ID NO: 3) injected in wild-type mice, which were subjected to I/R. Western Blot analysis revealed the binding of TAT-WVELHFFN-fluo ("WVELHFFN-fluo" disclosed as SEQ ID NO: 9) to dimers (FIG. 5D). We further verified this by coimmunoprecipitation of cytosolic BNIP3 and BAX and photometric fluorescence measurement (FIG. 5E). As expected, 5 minutes post reperfusion, cytosolic BNIP3 and BAX coimmunoprecipitated with TAT-WVELHFFN-fluo ("WVELHFFN-fluo" disclosed as SEQ ID NO: 9) (FIG. 5E). BN-PAGE and size exclusion chromatography followed by SDS-PAGE/Western blotting confirmed the presence of BNIP3 and BAX in apparent oligomers up to a molecular mass between 95 kDa and 1627 kDa, but also showed oligomers with BNIP3 down to a molecular mass of 54 kDa in the cytosol at baseline and in I/R at 10 minutes reperfusion with and without TAT-WVELHFFN ("WVELHFFN" disclosed as SEQ ID NO: 3) treatment (FIG. 1B and FIG. 5F-5H). To discover which oligomeric complex with BNIP3/BAX subunits exerts the harmful activities on mitochondrial membranes, we treated the wild-type mice with the fluorescence-labeled TAT-WVELHFFN ("WVELHFFN" disclosed as SEQ ID NO: 3). Size exclusion chromatography followed by fluorescence measurement revealed that the higher oligomeric complexes led to the strongest signal with up to 250% signal increase compared to the fraction consisting of dimers/oligomers with a molecular mass between 54 and 167 kDa (FIG. 5I). Taken together, these data indicate that BNIP3/BAX heterodimers are components of higher oligomeric structures. As TAT-WVELHFFN ("WVELHFFN" disclosed as SEQ ID NO: 3) prevents BNIP3/BAX induced necrotic and apoptotic signaling, the binding of TAT-WVELHFFN ("WVELHFFN" disclosed as SEQ ID NO: 3) to oligomers outline their status as mitochondrial membrane attack complexes.

Example 6. TAT-WVELHFFN ("WVELHFFN" Disclosed as SEQ ID NO: 3)Improves Clinical Outcomes The infarct size determines prognosis following myocardial infarction and stroke. Hence, we studied whether TAT-WVELHFFN ("WVELHFFN" disclosed as SEQ ID NO: 3) can alter the infarcted area when administered during ischemia, 5 minutes before reperfusion in wild-type mice subjected to myocardial I/R (FIG. 6A), a clinically relevant time-point. Notably, TAT-WVELHFFN ("WVELHFFN" disclosed as SEQ ID NO: 3)reduced myocardial infarct size in a dose-dependent manner by 40% relative to treatment with vehicle, but no difference was observed between TAT-β-Gal, TAT-WVELAASN ("WVELAASN" disclosed as SEQ ID NO: 7) and vehicle treatments (FIGS. 6B-6D). We also observed a lower progression of apoptotic cell death throughout the LV myocardium (FIGS. 6E and 6F). Treating TAT-BNIP3 ΔTM mice (with affected BNIP3 activity) with TAT-WVELHFFN ("WVELHFFN" disclosed as SEQ ID NO: 3) failed to induce further reduction in infarct size to TATBNIP3 ΔTM treatment, indicating a TAT-WVELHFFN ("WVELHFFN" disclosed as SEQ ID NO: 3) effect via BNIP3 (FIG. 6G).

To explore the translational potential, we chose the catheter-based myocardial infarction model in pigs because of similarities of organ size, coronary anatomy, immunology, and physiology to humans (Lindsey et al., 2018; Milani-Nejad and Janssen, 2014). Pigs were exposed to 60 minutes of ischemia by balloon inflation in the left coronary artery followed by 4 hours of reperfusion. TAT-WVELHFFN ("WVELHFFN" disclosed as SEQ ID NO: 3) or sodium chloride was administered 5 minutes prior to reperfusion. Notably, one single intravenous bolus injection of 0.075 mg/kg of the peptide was sufficient to decrease infarct size by 60% in pigs related to controls (FIG. 6H). As BNIP3 might play a critical role in cerebral ischemia (Zhang et al., 2007), we also evaluated the effects of TAT-WVELHFFN ("WVELHFFN" disclosed as SEQ ID NO: 3) on focal cerebral ischemia. We subjected mice to a 30-minute transient middle cerebral artery occlusion and 24 hours of reperfusion. Here, TAT-WVELHFFN ("WVELHFFN" disclosed as SEQ ID NO: 3) treatment immediately before reperfusion markedly reduced the infarct size by 52% compared to controls (FIG. 6I). To explore the effect of a pre-treatment we administered TAT-WVELHFFN ("WVELHFFN" disclosed as SEQ ID NO: 3) on d-7, d-5, d-3, d-1, and 5 minutes before 24 h of reperfusion to wild-type mice subjected to a 30-minute ischemia (FIG. 6J). Here, multiple treatment reduced the infarct size by 40% (FIG. 6K). Treatment with TAT-WVELHFFN ("WVELHFFN" disclosed as SEQ ID NO: 3) on day −7, day −5, day −3, day −1 before the onset of I/R preserves cardiac function (FIG. 6L). To evaluate the effects of TAT-WVELHFN ("WVELHFN" disclosed as SEQ ID NO: 14) administered 5 minutes before reperfusion and on day 1, day 3, day 5, and day 7 after the start of reperfusion to wild-type mice exposed to 50 minutes of ischemia on cardiac function, echocardiographic measurements were performed (FIG. 6M). Notably, treated mice exhibited recovery of LV function at day 3 (FIG. 6N). Taken together, our findings demonstrate that this peptide improves clinical outcome in myocardial infarction and stroke.

Example 7: TAT-WVELHFFN ("WVELHFFN" Disclosed as SEQ ID NO: 3)Ameliorates DOX Induced Human Cardiomyocyte Death and Preserves Mitochondrial Integrity Anthracyclines remain the cornerstone of contemporary chemotherapeutic regimens for a variety of solid cancers and hematologic malignancies. Anthracycline-induced cardiotoxicity (AIC) is a feared side effect limiting their clinical use. The risk of AI heart failure increases with the administered cumulative dose, its incidence reaches nearly 10%. Here we studied whether TAT-WVELHFFN ("WVELHFFN" disclosed as SEQ ID NO: 3) can reduce the chemotherapeutic DOX induced cell death in human cardiomyocytes. Therefore, we administered DOX at 0, 1, and 10 µM to human cardiomyocytes. Cells were incubated for four and 22 hours, and TAT-WVELHFFN ("WVELHFFN" disclosed as SEQ ID NO: 3) was administered at 0 or 1.5 µM. The results show that the attributive damage caused by a 10 µM dose of the chemotherapeutic DOX was ameliorated by the mitochondrial interaction and import inhibitor TAT-WVELHFFN ("WVELHFFN" disclosed as SEQ ID NO: 3) (FIGS. 14A and B). We next explored the effects of TAT-WVELHFFN ("WVELHFFN" disclosed as SEQ ID NO: 3) on DOX-induced mitochondrial damage related to mitochondrial membrane potential destabilization, mPTP opening in the MIM, mitochondrial Ca2+ overload, and generation of mitochondrial ROS. Human cardiomyocytes were incubated with 10 µM DOX for four and 22 hours, respectively. TAT-WVELHFFN ("WVELHFFN" disclosed as SEQ ID NO: 3) was co-administrated. The mitochondrial membrane potential was disrupted and the mPTP opening was activated by administration of 10 µM DOX, while co-administration of TAT-WVELHFFN ("WVELHFFN" disclosed as SEQ ID NO: 3) ameliorated these negative effects of DOX. This indicates that the negative effects of the chemotherapeutic on mitochondrial membrane potential and mPTP opening are ameliorated by co-administration of TAT-WVELHFFN ("WVELHFFN" disclosed as SEQ ID NO: 3) (FIGS. 15 and 16). Furthermore, mitochondrial calcium ion overload was induced by administration of 10 µM DOX for four hours-incubation time and ROS generation was triggered by administration of 10 µM DOX for four- and 22 hours-incubation time. Co-administration of TAT-WVELHFFN ("WVELHFFN" disclosed as SEQ ID NO: 3)prevented the negative effect of DOX on calcium ion overload and ameliorated the negative effect of DOX on ROS generation. This indicates that the negative effects of the chemotherapeutic on mitochondrial Ca2+ overload and mitochondrial ROS generation are ameliorated by co-administration of TAT-WVELHFFN ("WVELHFFN" disclosed as SEQ ID NO: 3).

Example 8 TAT-WVELHFFN ("WVELHFFN" Disclosed as SEQ ID NO: 3)Preserves Cardiac Function by Preventing Cardiomyocyte Death, Protecting Mitochondrial Fitness and Restoring Autophagic Flux In a first attempt, we investigated whether DOX with concomitant administration of TAT-WVELHFFN ("WVELHFFN" disclosed as SEQ ID NO: 3)(PepB) over 42 days has long term detrimental effects on mouse recipients (FIG. 19). Upon Dox treatment with PepB co-administration relative to a sodium chloride carrier control in wild-type mice, we observed no significant differences related to survival, body weight change over time, tibia length, and heart weight (FIG. 20). Cardiac troponin I (cTNI)/body weight was significantly lower for DOX coadministration with PepB relative to DOX administration with an NaCl control. Similarly, creantine kinase (CK)/body weight was significantly lower for DOX coadministration with PepB relative to DOX administration with an NaCl control. LDH/body weight and BNP/body weight were unchanged by administration of PepB (FIG. 21). Next, we explored the effect of DOX treatment on cardiac function assessed with echocardiographic measurements at three time points (TO, T1 16 days, T2 42 days) (FIG. 19).

At both T1 (16 days) and T2 (42 days), DOX negatively impaired ejection fraction (EF %), fractional shortening (FS %), and the isovolumetric relaxation time (IVRT) and this impact was ameliorated by concurrent PepB administration. Heart rate was unaffected by DOX administration, alone or in combination with PepB. Notably, DOX had a dramatic positive effect on cardiomyocyte death, evidenced by high cardiac troponin I (cTnI) levels, and this effect was ameliorated by coadministration of PepB. In a next step, we investigated the impact of PepB on DOX-induced mitochondrial dysfunction. DOX treatment inhibited the respiratory reserve capacity and PepB ameliorated this inhibition. In addition, DOX also affected the maximal respiration and basal respiration, and PepB ameliorated these impairments. The inhibition of Complex II-stimulated respiration was also reduced by PepB co-treatment. To elucidate whether PepB co-administration is able to restore the DOX-induced disturbance of the autophagic flux, we treated the mice with DOX and PepB, and additionally with chloroquine (CQ). As autophagosome marker we measured the expression of LC3-I and LC3-II. DOX abolished the CQ mediated LC3II/I increase, while addition of PepB partially restores this increase. DOX also triggered p62 and BNIP3 accumulation, and addition of PepB counteracted these increases.

Additional methods and materials were drawn from the following sources: REAGENT or RESOURCE SOURCE IDENTIFIER Antibodies Anti-BNIP3 polyclonal antibody, Rabbit Abcam Cat #ab38621, RRID:AB_725737 Anti-BNIP3 monoclonal antibody, Mouse Abcam Cat #ab10433 RRID:AB_2066656 Anti-BAX monoclonal antibody [E63], Rabbit Abcam Cat #ab32503, RRID:AB_725631 Cat #ab7977 RRID:AB_306191 Anti-ANT 1 monoclonal antibody [5F51BB5AG7], Mouse Abcam Cat #ab110322, RRID:AB_10862212 Anti-Troponin I monoclonal Antibody (1H11L19), ABfinity™, Rabbit ThermoFisher Scientific Cat #701585, RRID:AB_2532494 Anti-Phosphoserine monoclonal antibody, clone 4A4, Mouse Merck Millipore Cat #05-1000, RRID:AB_11210897 Anti-TOMM22 Abcam Cat #ab57523 RRID:AB_945897 Anti-BAX (active monomer) monoclonal antibody (6A7) Enzo Life Sciences Cat #ALX-804-224-C100, RRID:AB_2050800 Anti-Tubulin antibody Abcam Cat #ab15246 RRID:AB_302787 Anti-AIF antibody Santa Cruz Cat #Sc9416 RRID:AB_2224665 Anti-Cytochrome C monoclonal antibody, Unconjugated, Clone 7H8.2C12, M Mouse s Abcam Cat #ab13575, RRID: AB_300470 AlexaFluor 488-conjugated goat anti-rabbit secondary antibody Invitrogen Cat #AI 1029 RRID: AB_138404 Goat Anti-rabbit-HRP secondary antibody Invitrogen Cat #32260 RRID:AB_1965959 Goat Anti-mouse-HRP secondary antibody Abcam Cat #AB 6789 RRID:AB_955439 AlexaFluor 594-conjugated goat anti-rabbit secondary antibody Invitrogen Cat #A-11080 RRID: AB_2534124 Bacterial and Virus Strains Tuner DE3pLys Competent Cells Novagen/Merck Millipore 70624 Biological Samples human endomyocardial biopsy Ethics Approval of the Ethics Committee, University Duisburg-Essen, No. 17-7392-BO N/A Chemicals, Peptides, and Recombinant Proteins Bax Mouse Recombinant (Bax Mouse) Novateinbio PT_39984 Recombinant Mouse BCL2/adenovirus E1B 19 kDa protein interacting protein 3(Bnip3) Cusabio CSB-CF002766Mo-50 TAT-BNIP3-20A JPT this paper TAT-BNIP3-20C JPT This paper TAT-WVELAASN ("WVELAASN" disclosed as SEQ ID NO: 7) JPT this paper TAT-WVELHFFN ("WVELHFFN" disclosed as SEQ ID NO: 3) JPT this paper TAT-WVELHFFN ("WVELHFFN" disclosed as SEQ ID NO: 3)-Fam JPT this paper TAT-WVELHFFN-Cy5.5 ("WVELHFFN-Cy5.5" disclosed as SEQ ID NO: 10) JPT this paper TAT-BNIP3 full length this paper TAT-BNIP3 ΔTM this paper Tat-βGal this paper Critical Commercial Assays this paper Duo Link in Situ Starter Kit—Proximity Ligation Assay Sigma DUO92101-1KT Caspase 3 Assay Kit Colorimetric Abcam Ab39401 Apoptag red in Situ Detection Millipore S7165 ATP Detection Kit Abcam Ab83359 Apoptose/Necrose Assay Kit Abcam ab176749 Troponin I Ultra-sensitive Elisa Life Diagnostic CTNI-1-US DyLight Antibody Labeling Kits ThermoFisher Scientific 84535 Ni-NTA Fast Start Kit Qiagen 30600 Peptide microarrays JPT N/A JC-1 Kit ThermoFisher Scientific M34152 RNeasy Mini Kit Qiagen 74104 High Capacity RNA-to-cDNA Kit Life Technologies 4388950 Experimental Models: Cell Lines human IPSC-derived vCMs Axol Bioscience Ax 2505 HL-1 cell line W. C. Claycomb Louisiana State University Medical Center, New Orleans, LA, USA W. C. Claycomb Experimental Models: Organisms/Strains C57BL/6J-TgH (Bnip3–/–) Gerald W. Dorn Gerald Dorn C57BL/6J wild-type Jackson Laboratory 000664 Oligonucleotides 18S rRNA ThermoFisher Scientific Mm03928990_g1 Bnip3 ThermoFisher Scientific Mm00833810 Recombinant DNA TAT-Bnip33/pTriEx-1.1-HT Labor Ruhruniversität Bochum R. Stoll TAT-Bnip3 dTM/pTriEx-1.1-HT Labor Ruhruniversität Bochum, R. Stoll pTAT-HA-β-Gal vector S. F. Dowdy (University of California, San Diego, CA, USA) Science 3 Sep. 1999: Vol. 285, Issue 5433, pp. 1569-1572 DOI: 10.1126/science.285.5 433.1569 Software and Algorithms ImageJ Schneider et al., 2012//imagej.nih.gov/i j/ Inkscape //inkscape.org/ Vevo 2100 Imaging System FUJIFILM, VisualSonics, Netherland Imaris Software (BitPlane) BitPlane www.bitplane.com GraphPad Prism 7 GraphPad Other Superdex 200 Increase 10/300 GL GE Healthcare 28-9909-44

EXPERIMENTAL MODEL AND SUBJECT DETAILS Mice All animal procedures were performed in accordance with institutional guidelines and approval from the local ethics committee in compliance with the European Convention for the Protection of Vertebrate Animals Used for Experimental and other Scientific Purposes (Directive 2010/63/EU). Male mice aged 12±3 weeks with an average body weight of 30 g were used. C57BL/6J wild-type mice were obtained from the Jackson Laboratory (Bar Harbor, ME, USA) and kept for 1 week in the local animal house for acclimatization. C57BL/6J-TgH (Bnip3–/–) mice were bred and maintained in the local animal house of the University Hospital Essen. All mice were housed on a 12-hour light/dark cycle. Cell lines The HL-1 cell line was provided by W. C. Claycomb (Louisiana State University Medical Center, New Orleans, LA, USA) and cultured as previously described (Claycomb et al., 1998). Human CMs were obtained from Axol Bioscience, UK, and cultured according to the manufacturer's instructions. METHOD DETAILS Recombinant protein expression The TAT-BNIP3 and TAT-BNIP3 ΔTM plasmids were provided by R. Stoll (Ruhr-University Bochum, Germany). The pTAT-HA-β-Gal vector was provided by S. F. Dowdy (University of California, San Diego, CA, USA). His-tagged BNIP3 and BNIP3 ΔTM were cloned into the pTriEx-1.1 vector. BNIP3 (full length), BNIP3 ΔTM (amino acids 1-163) and β-galactosidase, all fused to the HIV-1 TAT protein transduction domain (GRKKRRQRRRPQ (SEQ ID NO: 13)), were grown in *Escherichia coli* (BL21) and expressed with 100 mM IPTG for 48 hours at 37° C. The bacteria were resuspended in PBS (pH 8.0), followed by incubation with 1 mg/mL lysozyme for 1 hour at 4° C. and sonication on ice. After centrifugation at 20,000×g for 50 minutes at 4° C., the supernatants were added to columns containing Ni-NTA. The proteins were eluted with 250 mM imidazole in phosphate buffer. Recombinant BAX (rBAX, PT_39984) and recombinant BNIP3 (rBNIP3, CSB-CF002766) were obtained from Hölzel Diagnostika (Cologne, Germany). In vivo I/R models In vivo murine myocardial I/R For in vivo I/R, the open-chest model was used. Briefly, wild-type and Bnip3–/– mice were anesthetized with ketamine (100 mg kg-1 intraperitoneally, i.p.) and xylazine (10 mg kg-1 i.p.), intubated and ventilated. Deep anesthesia was maintained with 1.2-2 Vol % isoflurane in conjunction with a gas mixture of 0.2 l/minutes 02 and 0.21/minutes compressed air. A lateral thoracotomy was performed and left coronary artery (LCA) occlusion was achieved by tightening and tying a 6-0 prolene suture. After 30 minutes, the LCA was re-occluded for the desired reperfusion times. The thoracic cavity was closed using a 4-0 prolene suture. Buprenorphine was injected for analgesia every 8 hours. Infarct size was assessed after 30 minutes of ischemia followed by 24 hours of reperfusion using Evans blue staining for delineation of the ischemic area at risk (AAR) from the non-ischemic zone (remote area) and 1%2, 3,5-triphenyl tetrazolium chloride (TTC) staining for demarcation of the viable and nonviable myocardium within the AAR, as described (Hendgen-Cotta et al., 2007). The infarct area, AAR, and non-ischemic left ventricle were assessed with computer-assisted planimetry by an observer blinded to sample identity. The size of the myocardial infarction is expressed as a percentage of the AAR. Treatment in in vivo marine myocardial I/R To evaluate the (patho)physiological relevance of BNIP3 in vivo, mice were injected with sodium chloride (NaCl) as vehicle, TAT-BNIP3 (67 nmol kg-1, 200 nmol kg-1, or 300 nmol kg-1 in 50 μL 0.9% NaCl) and TAT-BNIP3 ΔTM (33 nmol kg-1, 67 nmol kg-1, or 133 nmol kg-1 in 50 μL 0.9% NaCl). The TAT-fusion proteins were injected into the left ventricular (LV) cavity 5 minutes before ischemia. To assess the in vivo inhibitory effects and efficacy of TAT-BNIP3-20A and TAT-WVELHFFN ("WVELHFFN" disclosed as SEQ ID NO: 3), mice were injected with NaCl, TAT-β-Gal, TAT-BNIP3-20A (67 nmol kg-1 in 50 μL 0.9% NaCl), TAT-BNIP3-20C (67 nmol kg-1 in 50 μL 0.9% NaCl), TAT-WVELHFFN ("WVELHFFN" disclosed as SEQ ID NO: 3), TAT-WVELHFFN-Lys (5(6)Carboxyfluorescein) ("WVELHFFN-Lys(5(6)-Carboxyfluorescein" disclosed as SEQ ID NO: 15), and TAT-WVELHFFN-Cy5.5 ("WVELHFFN-Cy5.5" disclosed as SEQ ID NO: 10) (67 nmol kg-1, 133 nmol kg-1, 267 nmol kg-1, or 667 nmol kg-1 in 50 μL0.9% NaCl) or TAT-WVELAASN ("WVELAASN" disclosed as SEQ ID NO: 7) (267 nmol kg-1 in 50 μL 0.9% NaCl) 5 minutes before reperfusion. In vivo marine brain I/R Focal cerebral ischemia was induced by a 30-minute transient middle cerebral artery occlusion (tMCAO). Briefly, mice were anesthetized with 2% isoflurane in 02. A servo-controlled heating blanket was used to maintain a core body temperature close to 37° C. throughout surgery. After a midline neck incision, a standardized silicon rubber-coated No. 6.0 nylon monofilament (6023910PK10; Doccol, Sharon, MA, USA) was inserted into the right common carotid artery and advanced via the internal carotid artery to occlude the origin of the MCA. After 30 minutes, the mice were re-anesthetized, and the occluding filament was removed to allow reperfusion. Stroke volumes were assessed 24 hours after tMCAO, based on TTC staining. The mice were then randomly assigned to the operation by an independent researcher who was not involved in the data analysis. Investigators involved in the surgery and evaluation of all readout parameters were blinded to the experimental groups. Treatment in in vivo marine brain IR The mice were injected with sodium chloride or TAT-WVELHFFN ("WVELHFFN" disclosed as SEQ ID NO: 3) (267 nmol kg-1 in 50 µL 0.9% NaCl) immediately before reperfusion. In vivo porcine myocardial IR The experiments were performed by Charles River Laboratories, Inc. (Mattawan, MI, USA, Testing facility study No. 2865-001) in accordance with The Animal Welfare Act (9 CFR Parts 1, 2, and 3) of the US Department of Agriculture (USDA), and the Guide for the Care and Use of Laboratory Animals, Institute of Laboratory Animal Resources, National Academy Press, Washington, D C, 2011. For in vivo I/R, the closed-chest model was used. Naïve Domestic Yorkshire crossbred swines (farm pigs, male, body weight ranging from 37.5 to 40.5 kg) were placed in a dorsal recumbency, and the surgical sites were prepared with alternating wipes of chlorhexidine scrub and solution. The animals were connected to a defibrillator and ECG machine and monitored thoroughly throughout the procedure. Following the induction of anesthesia, a small incision was made over the femoral artery and vein; the vessels were isolated. A small opening was made in the artery and a sheath was introduced. In addition, a sheath was placed in the femoral vein to allow for emergency drug administration, if necessary. An appropriate guide catheter was advanced into the ostium of the left anterior descending artery (LAD) using visual guidance followed by fluoroscopy. Non-ionic contrast was used for all procedures. A balloon catheter was introduced by advancing it through the guide catheter to the LAD coronary artery. The balloon was advanced into the coronary arteries through the guide catheter to a suitable place above the first diagonal branch of the LAD. The balloon was then inflated to a pressure sufficient to ensure complete occlusion of the artery, and verified via fluoroscopy. Once verified, the balloon was left inflated in the artery for 60 minutes. At the end of the ischemic period, the balloon was deflated and the ischemic area was allowed to reperfuse for 4 hours. Complete balloon deflation was confirmed via fluoroscopy. At the end of the procedure, all catheters were removed, the artery and vein were ligated, and the incision was closed in a standard fashion. For infarct size assessment, the hearts were removed and flushed with heparinized lactated ringer solution until clear of blood. The LAD was tied off at the location of the balloon occlusion during the myocardial infarction procedure. Once tied off, the LAD, LCX, and RCA were cannulated. Evans blue dye was injected. The hearts were cut from base to apex into approximately 1 cm serial sections. Each section was weighed and photographed. The sections of the heart were stained with TTC for 30 minutes at 37° C. and photographed a second time. The infarct size was calculated as a percent of the AAR. The images (including a ruler) were analyzed and the ratios of infarct/AAR, infarct/LV area, and AAR/LV were calculated. The heart sections were stored frozen in 10% neutral buffered formalin (NBF) at −60° C. to −90° C. for possible future analysis. Treatment in in vivo porcine myocardial I/R Following the 60-minute occlusion, TAT-WVELHFFN ("WVELHFFN" disclosed as SEQ ID NO: 3) (0.075 mg kg-1 BW) or sodium chloride was administered via intravenous bolus injection 5 minutes prior to reperfusion. Transthoracic echocardiography was used to measure LV systolic function in wild-type mice in response to TAT-WVELHFFN ("WVELHFFN" disclosed as SEQ ID NO: 3) treatment. Echocardiography was performed before and 5 hours after injection of TAT-WVELHFFN ("WVELHFFN" disclosed as SEQ ID NO: 3) (267 nmol kg-1) as well as before and after I/R at desired time point using a Vevo 2100 and Vevo 3100 Imaging System (FUJIFILM VisualSonics, The Netherlands). The investigator was blinded with respect to the untreated and treated groups. After sedation with 2 Vol % isoflurane and hair removal, the mice were placed on a heated plate with constant heart rate, respiratory rate and body temperature monitoring via a rectal probe. Fractional shortening was determined via M-mode in the midventricular short parasternal axis. The LV ejection fraction was calculated using Simpson's method. Isolation of cytosol and mitochondria Fractionation The hearts were washed in ice-cold homogenization buffer (250 mM sucrose, 10 mM HEPES, and 1 mM EGTA, pH 7.4), homogenized in 4 ml buffer containing 0.5% bovine serum albumin and centrifuged at 700×g for 10 minutes at 4° C. to remove unbroken tissue and nuclei. For general fractionation, the supernatant was centrifuged at 15,000×g for 10 minutes at 4° C. to obtain the cytosolic fraction in the supernatant and the mitochondria in the pellet. The mitochondrial pellet was further cleared of contaminations by washing twice in isolation buffer. The cytosolic and mitochondrial fractions were further processed for western blotting. Subfractionation of MIM and MOM The hearts were washed in ice-cold homogenization buffer (250 mM sucrose, 10 mM HEPES, and 1 mM EGTA, pH 7.4), homogenized in 4 ml buffer containing 0.5% bovine serum albumin and centrifuged at 700×g for 10 minutes at 4° C. to remove unbroken tissue and nuclei. The supernatant was centrifuged at 15,000×g for 10 minutes at 4° C. to pellet the mitochondria. Then, the supernatant was centrifuged at 105,000×g for 30 minutes at 4° C. to obtain the cytoplasm. The pellet containing the mitochondria was carefully washed two times in homogenization buffer. Mitochondrial protein concentrations were determined by Bradford method. For inner and outer membrane preparation, the isolated mitochondria were suspended in 0.25 M sucrose solution, incubated in 0.3% digitonin for 20 minutes on ice and centrifuged at 9,500×g for 15 minutes. The supernatant was centrifuged at 105,000×g for 1 hour at 4° C. to obtain the MIM in the supernatant. Pellet II was suspended in buffer A (0.25 M sucrose, 10 mM Tris-HCl, pH 7.4) and incubated overnight at 4° C. Pellet I was suspended in 0.1 M Na2CO3 solution, incubated for 20 minutes on ice and centrifuged at 105,000×g for 30 minutes. Pellet III was suspended in buffer A and incubated overnight at 4° C. The next day, pellets II and III were loaded on a discontinuous sucrose gradient (0.5 ml 51.3%, 0.5 ml 44.3%, 1 ml 37.4% and 1 ml 23.2% sucrose in 0.1 M phosphate buffer, pH 7.4) and centrifuged at 105,000×g for 2 hours at 4° C. Fractions (200 L) were collected and analyzed by western blotting with the indicated antibodies. Histopathological analyses Infarct area Mouse hearts were perfused with PBS before collection, fixation and preparation of paraffin embedded sections for histopathological analyses. Standard Gomori Trichrome staining was performed to visualize the infarct area. Slices were incubated in Weigert's iron haematoxylin working solution (Merck, Darmstadt, Germany) for 10 minutes at room temperature and then washed 10 times in $H_2O$. Next, the slices were incubated in Gomori's Trichrome solution (Morphisto, Cologne, Germany) for 15 minutes at RT and washed 10 times in $H_2O$, two times in 0.5% acetic acid and 10 times in $H_2O$. Apoptosis To detect apoptotic nuclei, TUNEL staining was performed using an ApopTag Red In situ Apoptosis Detection Kit (Millipore, S7165, Darmstadt, Germany) according to the manufacturer's instructions. The total numbers of TUNEL-positive nuclei were counted in five plane sections of the heart to calculate the number of TUNEL-positive nuclei per heart and per section for spatial distribution analyses. Images were captured under an inverted epifluorescence microscope (Zeiss Axio Observer Z1, Oberkochen, Germany) and processed in ImageJ software 1.52a (NIH). Necrosis Troponin staining was performed by deparaffinization of mouse heart sections (I/R), washing twice in $H_2O$ and twice in TBS-T (0.1% Tween 20), and blocking with 5% normal goat serum in PBS for 1 hour. Sections were incubated with anti-troponin I antibody (Invitrogen, 1:100 dilution) overnight at 4° C. and stained with the secondary goat anti-rabbit Alexa Fluor 594 antibody (1:200 dilution). After washing with TBS-T and staining with DAPI (Invitrogen, Carlsbad, CA, USA; 1:5, 000 dilution), sections were mounted in ProLong Gold Antifade (ThermoFisher Scientific, Waltham, MA, USA). Images were captured under an inverted epifluorescence microscope (Zeiss Axio Observer Z1, Oberkochen, Germany). Troponin in plasma To examine necrotic cell death, blood was collected from the abdominal aorta after 24 hours of reperfusion following 30 minutes of ischemia; the blood was centrifuged at 3,000×g for 10 minutes at 4° C., and plasma was collected. Troponin I levels were measured using a Troponin I ELISA (Life Diagnostics, CTNI-1-US, Westchester, PA, USA). Real-time quantitative RT-PCR (real-time qRT-PCR). Total RNA was isolated from hearts using an RNeasy Mini Kit (Qiagen, Hilden, Germany, 74104) according to the manufacturer's instructions. Purified RNA was quantified using a NanoDrop instrument (ThermoFisher Scientific, Waltham, MA, USA). cDNA was generated using a High Capacity RNA-to-cDNA Kit (Life Technologies, Carlsbad, CA, USA). Real-time qRT-PCR was performed using TaqMan Gene Expression Assays (ThermoFisher Scientific, Waltham, MA, USA, Mm00833810) in a 7900HT Fast Real-Time PCR System (ABI PRISM® 7900HT, Applied Biosystems, Foster City, CA, USA). Reactions were normalized to 18S rRNA levels, and relative transcript abundance was calculated using the comparative Ct method. Size Exclusion Chromatography One mg of cardiac cytosolic lysate was applied to a Superdex® 200 Increase 10/300 GL (GE Healthcare, Chicago, Illinois, USA) equilibrated in SEC buffer (10 mM Tris (pH 7.5), 1 mM EGTA, 200 mM Sucrose, Protease Phosphatase Inhibitors (Halt, Thermo Fisher Scientific, Waltham, Massachusetts, USA) and run at 4° C. Fractions of 1000 µl were collected of which 500 µl were concentrated to 40 µl using Amicon® Ultra 0.5 ml Centrifugal Filters (Merck Millipore, Burlington, Massachusetts, USA). The recovered sample was directly processed for subsequent SDS-PAGE and Western Blot. To estimate the molecular weight of the BNIP3 oligomer, a gel filtration molecular weight marker (#1511901, BioRad, Hercules, California, USA) was applied to the columns to obtain a standard curve. Fluorescence measurements of Cy5.5 labeled TAT-WVELHFFN ("WVELHFFN" disclosed as SEQ ID NO: 3) were performed in triplicates in an Infinite® 200 PRO microplate reader (Tecan Group Ltd., Switzerland) with a black flat bottom 96-well plate using unprocessed 150 µl SEC-fraction per well. Fluorescence intensity was measured at 630 nm (±9 nm) excitation/680 nm (±20 nm) emission. Western blotting SDS-PAGE Frozen tissues, HL-1 cells and human CMs were lysed in ice-cold RIPA buffer (50 mM Tris-HCl, 150 mM NaCl, 0.5 mM EDTA, 1% NP-40 and protease and phosphatase inhibitor, pH 7.4). Isolated mitochondria were lysed in a Mito-lysis buffer (200 mM sucrose, 10 mM HEPES, 1 mM EGTA, 1% Triton X-100, protease and phosphatase inhibitor, pH 7.4) and lysates were cleared by centrifugation at 20,000×g for 15 minutes at 4° C. Protein concentrations in supernatants were measured using a DC Protein Assay (Bio-Rad Laboratories Inc., Hercules, CA, USA). Then, samples were diluted in 4×LDS sample buffer and 10× reducing agent (Invitrogen, Carlsbad, CA, USA) and boiled at 95° C. for 5 minutes and loaded onto NuPAGE™ 4-12% Bis-Tris Protein Gels (Invitrogen, Carlsbad, CA, USA). Western blot analyses were performed on nitrocellulose membranes after blocking in TBS-T containing 5% milk using the following antibodies incubated over night at 4° C.: anti-ANT1 (Abcam, Cambridge, UK, ab110322, 1:1,000 dilution), anti-AIF (Santa Cruz Biotechnology, Dallas, TX, USA, sc9416, 1:200 dilution), anti-BNIP3 (Abcam, Cambridge, UK, ab38621, 1:1,000 dilution), anti-BAX (Abcam, Cambridge, UK, ab7977, ab32503, 1:500 dilution), anti-cytochrome c (Abcam, Cambridge, UK, ab13575, 1:1,000 dilution), anti-TOMM22 (Abcam, Cambridge, UK, ab57523, 1:500 dilution), anti-tubulin (Abcam, Cambridge, UK, ab15246, 1:5,000 dilution), and anti-active BAX (Enzo Life Sciences, Lörrach, Germany, 6A7, 1:1,000 dilution). The membrane was incubated for 1 hour at room temperature with HRP-conjugated secondary from the appropriate species and exposed to SuperSignal West Pico Plus Substrate (ThermoFisher Scientific, Waltham, MA, USA) as instructed by the manufacturer with subsequent detection. BN-PAGE The protein concentration of the isolated cytosolic fractions was measured using a DC Protein Assay (Bio-Rad Laboratories Inc., Hercules, CA, USA). Then, the samples were diluted in 4× NativePAGE™ Sample Buffer (Invitrogen, Carlsbad, CA, USA) and loaded onto NativePAGE™ 4-16% Bis-Tris Protein Gels (Invitrogen, Carlsbad, CA, USA). The gel-run was performed at 4° C. utilizing the NativePAGE™ Running Buffer Kit (Invitrogen, Carlsbad, CA, USA). Western blot analyses were performed on PVDF membranes using the iBind™ Flex system (Invitrogen, Carlsbad, CA, USA) with anti-BNIP3 (Abcam, Cambridge, UK, ab38621, 1:1,000 dilution) and anti-BAX (Abcam, Cambridge, UK, ab32503, 1:500 dilution). Co-immunoprecipitation experiments Cytosol lysates were cleared by centrifugation at 20,000×g for 15 minutes at 4° C. Protein concentrations in the cytosolic fraction were measured using a DC Protein Assay (Bio-Rad Laboratories Inc., Hercules, CA, USA). Co-immunoprecipitation was performed using protein G-coupled Dynabeads (Invitrogen, Carlsbad, CA, USA) covalently bound to anti-BNIP3 (Abcam, Cambridge, UK, 10 g/sample) or anti-BAX (Abcam, Cambridge, UK, 0.011 g/sample). Unbound antibodies were washed of before subjecting the coupled bead antibodies to 500 µg protein-lysate over night at 4° C. with rotation. The precipitate bound to the bead-antibodies was cleared from unbound lysate and resuspended in 4×LDS sample buffer (Invitrogen, Carlsbad, CA, USA), 10× reducing agent (Invitrogen, Carlsbad, CA, USA) and boiled for 10 minutes at 70° C. to separate the precipitate from the bead-antibodies. The precipitate was then analyzed by western blot on nitrocellulose membranes using anti-BNIP3 (Abcam, Cambridge, UK, ab38621, 1:1,000) and anti-BAX (Abcam, Cambridge, UK, ab32503, 1:500). For fluorescent measurements, the precipitate was resuspended in 10× reducing agent and boiled for 10 minutes at 70° C., excited at 485 nm and emitted light measured at 520 nm. Subsequently 4×LDS was added and western blotting performed as described. Immunostaining of BNIP3 in tissue Wild-type and Bnip3−/− mouse hearts were washed free of blood with NaCl in vivo, and then removed and incubated in 40% sucrose solution overnight at 4° C. After fixation using 4% paraformaldehyde for 15 minutes, 8 m slices were cut and washed three times for 5 minutes with PBS containing 0.5% Triton X-100 for cell permeabilization. Slices were stained with Mito-Tracker orange (Invitrogen, Carlsbad, CA, USA) and incubated with the anti-BNIP3 antibody overnight at 4° C. Staining was performed with an AlexaFluor 488-conjugated goat anti-rabbit secondary antibody and DAPI (Invitrogen, Carlsbad, CA, USA, 1:5,000 dilution). Confocal sections were visualized under a confocal laser scanning microscope using the 63×/1.4 Oil DIC M27 objective (Zeiss Elyra PS; Zeiss, Oberkochen, Germany). Caspase-3 activity Caspase-3 activity was measured in the AAR after 1 hour of reperfusion using a Caspase-3 Assay Kit (Abcam, Cambridge, UK, ab39401), according to the manufacturer's instructions. Bioenergetics For bioenergetics studies, ATP concentrations in the AAR were analyzed after 30 minutes of reperfusion using an ATP Bioluminescent Assay Kit (Sigma-Aldrich, St. Louis, MO, USA, FLAA). Tissue Clearing Hearts were fixed for 4 h in 4% paraformaldehyde (w/v PFA) at 4° C. Samples need to be protected from light in all following steps. Next, hearts were dehydrated using an ascending ethanol series (50%, 70%, 100% (v/v) EtOH in ddH2O) while shaking: overnight in 50% EtOH at 4° C., 30 minutes in 70% EtOH at room temperature, 30 minutes in 70% EtOH at room temperature. In order to enhance sample clarity, samples were bleached for 4 hours at 4° C. while shaking, using freshly prepared bleaching solution (5% (v/v) hydrogen peroxide, 5% (v/v) dimethyl sulfoxide in 100% ethanol). Afterwards samples were washed 3 times in 100% ethanol for 30 minutes at 4° C. while shaking. For the final clearing step, hearts were warmed to room temperature for 5 minutes and subsequently transferred to a glass vial containing pure ethyl cinnamate (ECi, Sigma Aldrich). Samples were cleared for at least 4 hours before imaging and were kept at room temperature and protected from light until and after imaging. Light sheet fluorescence microscopy and image processing Samples were imaged using the Ultramicroscope II and ImSpector software (both LaVision BioTec). Cleared hearts were immersed in pure ECi in a quartz cuvette. Since TAT-WVELHFFN ("WVELHFFN" disclosed as SEQ ID NO: 3) was coupled with Cy 5.5 fluorophores, the excitation wavelengths of the light sheets were set to 639 nm and the corresponding 680/30 band-pass emission filter was used. Additionally, autofluorescence was imaged in the FITC channel (488 nm excitation, 525/50 band-pass emission filter). Samples were clamped in a sample holder, apex and aorta horizontally aligned, between two blocks of ECi-cleared phytagel (1% phytagel in $H_2O$) to prevent deformation. The knot of the ligation, which is used to induce the myocardial I/R, remains in situ and needs to face downwards during imaging to reduce blockage of excitation or emission light. Data sets of whole hearts were obtained with ×1.2 total magnification with 10 m z spacing between optical planes. The sheet width was set to 4200 and numeric aperture to 0.148.The longest wavelength was imaged first, to prevent photobleaching. 16 bit OME.TIF stacks were converted (ImarisFileConverterx64, BitPlane) into Imaris files (.ims). 3D reconstruction and subsequent analysis was done using Imaris software (BitPlane). Mitochondrial experiments MIM permeabilization To analyze the MIM potential, 5',6,6'-tetrachloro-1,1',3,3'-tetraethylbenzimidazolylcarbocyanin iodide (JC-1) was used by performing the MitoProbe™ JC-1 Assay Kit for Flow Cytometry (ThermoFisher Scientific, Waltham, MA, USA, 34152). Each probe contained 250 µg of isolated mitochondria incubated with 1.5 µg JC-1/mg. Changes in mitochondrial MIM potential were analyzed by flow cytometry using FACS Verse (Becton Dickinson, Franklin Lakes, NJ, USA) with an excitation wavelength of 514 nm and emission wavelengths of 529 nm and 590 nm.

To assess MIM permeabilization by mPTP opening, mitochondria were isolated from the AAR after 10 minutes of reperfusion. Mitochondrial swelling was measured by changes in light scattering at 540 nm. The final buffer volume was 200 µl (250 mM sucrose, 10 mM HEPES, and 1 mM EGTA, pH 7.4) containing 0.5 mg/mL mitochondria. To distinguish cytochrome c release induced by mPTP opening or MOMP formation, isolated mitochondria (1 mg/mL) were incubated in buffer (150 mM KCl, 5 mM Tris-HCl, pH 7.4) and energized with 5 mM succinate and 2 µM rotenone. rBNIP3 (1 µg), rBAX (1 g) and 150 mM $Ca^{2+}$ per mg of protein were added. To induce mPTP opening and swelling, 5 mM Pi was used. The optical density at 540 nm was measured over a 40 minutes period. Cytochrome c contents in the supernatants were analyzed by western blotting. MOM permeabilization To demonstrate the need for BNIP3 on BAX pore formation, isolated mitochondria were incubated with cytoplasm. To inhibit VDAC, BAX and BNIP3, the inhibitors DIDS (1 µg), anti-BAX antibody (1 µg) and BNIP3 ΔTM (1 µg) were added. The cytosolic concentrations of cytochrome c, AIF, and active BAX were quantified by western blotting. Cell culture Isolated adult cardiomyocytes To isolate adult cardiomyocytes, wild-type mice were anesthetized with ketamine (100 mg kg-1 i.p.) and xylazine (10 mg kg-1 i.p.), and the hearts were quickly excised. Explanted hearts were perfused in a retrograde manner and digested with HEPES buffer (110 mM NaCl, 2.5 mM KCl, 1.2 mM KH2PO4, 2.5 mM MgSO4, 25 mM HEPES, 10 mM glucose-monohydrate, 4 µM collagenase type II and 28 µM $Ca^{2+}$, pH 7.4) for 25 minutes at 37° C. The cell suspension was filtered through a 250-µm mesh collector and centrifuged at 18×g for 1 minute. The cell pellet was resuspended in 100 µM HEPES buffer with stepwise increases in the $Ca^{2+}$ concentration. The cells were plated on cell culture dishes pre-coated with laminin and washed after 4 hours to remove dead and non-adherent cells. The cells were cultured in modified medium 199 including Earl's salts, 2 mM carnitine, 5 mM creatine and 5 mM taurine supplemented with 100 IU/mL penicillin and 100 g/ml streptomycin. Cytosine-D-arabinofuranoside (10 µM) was added to inhibit the growth of non-myocytes. Hypoxia/reoxygenation (H/R) For hypoxia experiments, cells were incubated in HEPES buffer (113 mM NaCl, 4.7 mM KCl, 12 mM HEPES, 1.2 mM MgSO4, 30 mM taurine, and 1.3 mM CaCl2), pH 7.4) under 1% O2 at 37° C. for 2 h. For reoxygenation, the cells were incubated in HEPES buffer supplemented with 5.5 mM glucose under 21% O2 at 37° C. for 2 hours. Phosphorylation experiments To evaluate BNIP3 serine phosphorylation under AKT inhibition, HL-1 cells were treated with 10 µM AKT1/2 inhibitor (Sigma-Aldrich, St. Louis, MO, USA, A6730). The levels of BNIP3 serine phosphorylation and active BAX were analyzed by western blotting. Peptide effects in human CMs To assess the in vitro effects of TAT-WVELHFFN ("WVELHFFN" disclosed as SEQ ID NO: 3), human CMs were treated with TAT-WVELHFFN ("WVELHFFN" disclosed as SEQ ID NO: 3) (2 nmol in 500 µl HEPES-buffer) and TAT-WVELAASN ("WVELAASN" disclosed as SEQ ID NO: 7) (2 nmol in 500 µl HEPES) during H/R. To visualize apoptotic and necrotic human CMs after H/R, the cells were stained with 7-AAD (red), Apoxin Green (green) and CytoCalcein (blue) using an Apoptosis/Necrosis Detection Kit (Abcam, Cambridge, UK, ab176749), according to the manufacturer's instructions. Images were captured under an EVOS FL microscope (ThermoFisher Scientific, Waltham, MA, USA). To analyze the MIM potential, human CMs were stained with JC-1. The cells were incubated with 6 µM JC-1 in medium at 37° C. for 30 min, washed with PBS buffer at 37° C., and fixed with 4% paraformaldehyde for 15 minutes at RT. DAPI staining was performed, and the cells were analyzed using an EVOS FL microscope (ThermoFisher Scientific, Waltham, MA, USA). Transmission electron microscopy (TEM) Electron microscopic analyses of I/R injury in cardiac tissue specimens and isolated mitochondria were performed as previously described with minor modifications (Hendgen-Cotta et al., 2018). Specifically, cacodylate buffer was used for the fixation and washing steps. The staining procedure was performed by using potassium ferrocyanide (II), thiocarbohydrazide and lead nitrate asparagic acid solution. Samples were infiltrated and embedded in epoxy resin (Durcupan, Sigma-Aldrich, St. Louis, MO, USA). Peptide synthesis L-amino acid peptides were synthesized by JPT Peptide Technologies (Berlin, Germany) using solid-phase resin-based methodology and purified to >90% by HPLC (confirmed by mass spectrometry; Figure S6). The N-terminus of the peptides was capped with an acetyl group, the C-terminus with an amide group. The TAT-BNIP3-20A sequence, GRKKRRQRRRPQMSQSGEENLQGSWVELHFSN (SEQ ID NO: 16), consisted of 12 amino acids from the HIV-1 PTD at the N-terminus and 20 amino acids derived from BNIP3 1-20 at the C-terminus. The TAT-BNIP3-20C sequence, GRKKRRQRRRPQLDAQHES-GRSSSKSSHCDSP (SEQ ID NO: 17), consisted of 12 amino acids from the HIV-1 PTD at the N-terminus and 20 amino acids derived from BNIP3 42-61 at the C-terminus. The TAT-octapeptide sequence, GRKKRRQRRRPQWVELHFFN (SEQ ID NO: 18), consisted of 12 amino acids from the HIV-1 PTD at the Nterminus and eight amino acids derived from BNIP3 13-20 containing the substitution S19F at the C-terminus. The control TAT-octapeptide sequence, GRKKRRQRRRPQWVELAASN (SEQ ID NO: 19), consisted of 12 amino acids from the HIV-1 PTD at the N-terminus and eight amino acids derived from BNIP313-20 containing two substitutions, H17A and F18A, at the C-terminus. For in vivo and cell culture experiments, peptides were dissolved in $H_2O$ and diluted with 0.9% NaCl. For protein-peptide interaction studies, peptide libraries were synthesized and immobilized on microarray slides. Peptides were synthesized and immobilized for: (i) the BNIP3/BAX interaction study (provided in FIG. 25 (FIG. 25 discloses SEQ ID NOS 87, 494, 88-91, 26, 33-34, 29, 92, 31, and 93, respectively in order of appearance.)); (ii) the BNIP3/BNIP3 interaction study, in which C-, N- or C/N-terminal truncations of the wild-type sequence of BNIP3 1-20 were performed (provided in FIG. 26 (FIG. 26 discloses SEQ ID NOS 1, 94-101, 53, 52, 51, 8, 2, 50, 49, 48, 47, 46, 45, 44, 43, 42, 41, 40, and 102-117, respectively, in order of columns.)); and (iii) the BNIP3/BNIP3 interaction study, in which single residues of the wild-type sequence of BNIP3 1-20 were exchanged for 18 neutral amino acids (provided in FIG. 27A-FIG. 27E (FIG. 27A-27E disclose SEQ ID NOS 118-493, respectively, in order of appearance.)). Interaction studies with peptide microarrays Peptide microarrays For protein-peptide binding studies, including the rBNIP3-BAX peptide interaction analysis, rBNIP3-BNIP3 peptide alanine scan, truncation analysis, and substitution analysis, rBNIP3 was used at concentrations of 5 µg/mL and 1 µg/mL. The studies were performed by JPT Peptide Technologies (Berlin, Germany). For fluorescence-labeling, the DyLight Microscale Antibody Labeling Kit (ThermoFisher Scientific, Waltham, MA, USA) with label DyLight 650 was used. The assay was performed using the automated Tecan HS 4800 microarray processing station. Microarrays were incubated with customer-provided samples diluted in blocking buffer for 2 hours at 30° C. Before each step, the microarrays were washed with washing buffer. Microarrays were scanned using a high-resolution fluorescence scanner. The laser settings and applied resolution were identical for all performed measurements. The resulting images were analyzed and quantified using GenePix spot-recognition software (Molecular Devices, Sant José, CA, USA). The mean signal intensity was extracted (between 0 and 65535 arbitrary units) for each spot. For further data evaluation, the so-called MMC2 values were determined. The MMC2 equals the mean value of all three instances on the microarray except for when the coefficient of variation (CV)—the standard deviation divided by the mean value—is >0.5. In this case, the mean of the two closest values (MC2) was assigned to MMC2. Overlay assays For protein-protein/peptide overlay assays, 300 ng rBNIP3 or rBAX were spotted on a nitrocellulose membrane. After 5 minutes of incubation followed by 5 minutes of washing with TBS-T, the membranes were incubated for 1.5 hours with 2.5 µg rBNIP3 or rBAX protein labeled with Dy650 in 200 µl TBS-T or with 50 µg TAT-WVELHFFN ("WVELHFFN" disclosed as SEQ ID NO: 3) labeled with Lys(5(6))-Fam. After washing two times for 5 minutes with TBS-T, fluorescence was detected using the ImageQuant system (Amersham, Little Chalfont, UK). Docking simulation experiments Docking simulation experiments were performed using Autodock Vina and HADDOCK. The structure of BAX (pdb-ID: 4S0O) was taken from the Protein Data Bank, whereas the structure of BNIP3 and the peptide TAT-WVELHFFN ("WVELHFFN" disclosed as SEQ ID NO: 3) was modelled using Modeller 9.15. The template structures corresponded to PDB codes 2K7W and 2KA1. The created model was energy minimized using NAMD2.9 and the CHARMM36 force field. Proximity ligation assay To assess the BNIP3-BAX interaction, proximity ligation assays were performed in human CM after 1 hour hypoxia/1 hour reoxygenation using Duolink In Situ Red Starter Kit Mouse according to the manufacturer's protocol (Sigma-Aldrich, St. Louis, MO, USA, DUO92101-1KT) using antibodies against BNIP3 (ab10433, 1:1,000 dilution) and BAX (ab7977, 1:1,000), followed by visualization by confocal laser microscopy (Zeiss Elyra PS; Zeiss, Oberkochen, Germany). Circular dichroism spectroscopy. The circular dichroism spectra of the BNIP3 protein and the TAT-WVELHFFN ("WVELHFFN" disclosed as SEQ ID NO: 3) peptide were recorded on a Jasco J-715 spectropolarimeter (Jasco, Pfungstadt, Germany) at 37° C. in 1×PBS, pH 7.4. Peptide uptake, distribution and stability For uptake and distribution analyses, mice were injected with TAT-WVELHFFN-Lys(5(6)-FAM ("WVELHFFN-Lys(5(6)-FAM" disclosed as SEQ ID NO: 15)) (267 nmol kg-1 in 50 µL 0.9% NaCl). Sham-operated mice and baseline values served as controls. For the pharmacokinetic studies, TAT-WVELHFFN ("WVELHFFN" disclosed as SEQ ID NO: 3) was incubated in human whole blood, serum and plasma for 0, 10, 20, 30, and 60 minutes at 37° C. Treatment with proteinase K (0.3 mg/ml) served as a control. Human samples Left ventricular tissue samples were obtained from 3 patients with suspected myocarditis who underwent endomyocardial biopsy (Ethics Approval of the Ethics Committee, University Duisburg-Essen, No. 17-7392-Bo). The diagnosis was not confirmed histologically. The three donors had a median age of 47.

Human Cardiomyocytes (HCM)

HCMs were obtained from PromoCell and cultured according to the manufacturer's instructions. The cells were incubated with 0, 1 and 10 µM Doxorubicin and treated simultaneously with 0 and 1.5 pM TAT-WVELHFFN ("WVELHFFN" disclosed as SEQ ID NO: 3) for four and 22 hours, respectively. Mitochondrial membrane potential was measured using TMRM-Kit (Abcam ab228569), calcium overload using Rhod-2AM, cell viability using Cytotoxicity Kit (Molecular Probes L3224), all according to the manufacturer's instructions.

DOX Treatment In Vivo

Wild-type mice aged 12±3 weeks received eight times, every two days, an i.p. injection of 0.9% physiological saline (vehicle control) or DOX (3 mg/kg body weight). TAT-WVELHFFN ("WVELHFFN" disclosed as SEQ ID NO: 3) was administered i.p. simultaneously. Serial echocardiography was performed on all mice at baseline and on day 16 and day 42. Left ventricular ejection fraction, fractional shortening and isovolumetric relaxation time were evaluated. Cardiac troponin I (cTNI-ELISA life Diagnostic CTNI-1-US), BNP (BNP-ELISA EIAM-BNP), and LDH (activity assay Sigma MAK066) were measured according to the manufacturer's instructions. Mitochondrial OCR was assessed with a Seahorse XF24 Analyzer using the mitochondrial stress test (Agilent)

QUANTIFICATION AND STATISTICAL ANALYSIS GraphPad Prism 7 software (GraphPad, San Diego, CA, USA) was used to perform statistical tests and to generate graphs. Data are presented as the means±SEM, and p values were calculated as detailed in the corresponding legends. Sample sizes were determined on the basis of previous experimental experience or based on general practices in the field. All replicates constitute biological replicates. For the in vivo studies, mice were randomly allocated to groups. For all histopathological and immunostaining analyses, the experimenters were blinded to the experimental conditions. Comparisons between characteristics of subject groups were analyzed with two-tailed Student's t-test. For comparisons among more than two groups, one-way or two-way ANOVA with Bonferroni's post hoc test was used. DATA AND SOFTWARE AVAILABILITY The ImageJ software 1.52a and Fiji/ImageJ 1.52e are available at the website//imagej.net/Fiji.

We claim:

1. A method of protecting a subject at risk of infarction damage due to a medical intervention, comprising administering a mitochondrial membrane translocation inhibitor to the subject at least 1 day prior to the medical intervention, wherein the mitochondrial membrane translocation inhibitor comprises a polypeptide comprising a segment differing by no more than 1 residue from a polypeptide of SEQ ID NO:3 and not differing from the polypeptide of SEQ ID NO:3 at SEQ ID NO:3 position 7.

2. The method of claim 1, wherein the mitochondrial membrane translocation inhibitor particularly targets BNIP3/BAX.

3. The method of claim 1, wherein the mitochondrial membrane translocation inhibitor comprises a polypeptide segment identical to SEQ ID NO:3.

4. The method of claim 1, wherein the medical intervention comprises surgery.

5. The method of claim 1, wherein the medical intervention comprises chemotherapy.

6. The method of claim 5, wherein the chemotherapy comprises doxorubicin (DOX) administration.

7. The method of claim 5, wherein the method comprises reducing chemotherapy-associated weight loss.

8. The method of claim 6, wherein the method comprises reducing chemotherapy-associated weight loss.

9. The method of claim 1, wherein the medical intervention comprises bruising.

10. The method of claim 1, wherein the medical intervention comprises a diabetes associated glucose level fluctuation.

11. The method of claim 1, wherein the medical intervention is an intervention that elicits inflammation.

12. The method of claim 1, wherein the administering comprises a single dose.

13. The method of claim 1, wherein the administering comprises a multi-dose treatment regimen.

14. The method of claim 13, wherein the multi-dose regimen comprises administering at least two days prior to the medical intervention.

15. The method of claim 13, wherein the multi-dose regimen comprises administering at least one week prior to the medical intervention.

16. The method of claim 13, wherein the multi-dose regimen comprises administering daily for at least one week prior to the medical intervention.

17. The method of claim 13, wherein the multi-dose regimen comprises administering at least one day prior to the infarction damage risk event and at least one day subsequent to the medical intervention.

18. The method of claim 13, wherein the multi-dose regimen comprises administering at least one day prior to the medical intervention and at least one week subsequent to the medical intervention.

* * * * *

```
                        SEQUENCE LISTING

Sequence total quantity: 494
SEQ ID NO: 1            moltype = AA  length = 20
FEATURE                 Location/Qualifiers
source                  1..20
                        mol_type = protein
                        organism = unidentified
SEQUENCE: 1
MSQSGEENLQ GSWVELHFSN                                                  20

SEQ ID NO: 2            moltype = AA  length = 8
FEATURE                 Location/Qualifiers
source                  1..8
                        mol_type = protein
                        organism = synthetic construct
SEQUENCE: 2
WVELHFSN                                                                8

SEQ ID NO: 3            moltype = AA  length = 8
FEATURE                 Location/Qualifiers
source                  1..8
                        mol_type = protein
                        organism = synthetic construct
SEQUENCE: 3
WVELHFFN                                                                8

SEQ ID NO: 4            moltype = AA  length = 5
FEATURE                 Location/Qualifiers
source                  1..5
                        mol_type = protein
                        organism = unidentified
SEQUENCE: 4
PESTQ                                                                   5

SEQ ID NO: 5            moltype = AA  length = 19
FEATURE                 Location/Qualifiers
source                  1..19
                        mol_type = protein
                        organism = synthetic construct
SEQUENCE: 5
MSQGEENLQG SWVELHFSN                                                   19

SEQ ID NO: 6            moltype = AA  length = 20
FEATURE                 Location/Qualifiers
source                  1..20
                        mol_type = protein
                        organism = synthetic construct
SEQUENCE: 6
LDAQHESGRS SSKSSHCDSP                                                  20

SEQ ID NO: 7            moltype = AA  length = 8
```

-continued

```
FEATURE                 Location/Qualifiers
source                  1..8
                        mol_type = protein
                        organism = synthetic construct
SEQUENCE: 7
WVELAASN                                                                        8

SEQ ID NO: 8            moltype = AA  length = 7
FEATURE                 Location/Qualifiers
source                  1..7
                        mol_type = protein
                        organism = synthetic construct
SEQUENCE: 8
VELHFSN                                                                         7

SEQ ID NO: 9            moltype = AA  length = 8
FEATURE                 Location/Qualifiers
source                  1..8
                        mol_type = protein
                        organism = synthetic construct
SITE                    8
                        note = Residue attached to a fluorophore
SEQUENCE: 9
WVELHFFN                                                                        8

SEQ ID NO: 10           moltype = AA  length = 8
FEATURE                 Location/Qualifiers
source                  1..8
                        mol_type = protein
                        organism = synthetic construct
SITE                    8
                        note = Residue attached to a Cy5.5 fluorophore
SEQUENCE: 10
WVELHFFN                                                                        8

SEQ ID NO: 11           moltype = AA  length = 8
FEATURE                 Location/Qualifiers
source                  1..8
                        mol_type = protein
                        organism = synthetic construct
SEQUENCE: 11
WELVHFFN                                                                        8

SEQ ID NO: 12           moltype = AA  length = 7
FEATURE                 Location/Qualifiers
source                  1..7
                        mol_type = protein
                        organism = synthetic construct
SEQUENCE: 12
WELAASN                                                                         7

SEQ ID NO: 13           moltype = AA  length = 12
FEATURE                 Location/Qualifiers
source                  1..12
                        mol_type = protein
                        organism = Human immunodeficiency virus 1
SEQUENCE: 13
GRKKRRQRRR PQ                                                                  12

SEQ ID NO: 14           moltype = AA  length = 7
FEATURE                 Location/Qualifiers
source                  1..7
                        mol_type = protein
                        organism = synthetic construct
SEQUENCE: 14
WVELHFN                                                                         7

SEQ ID NO: 15           moltype = AA  length = 9
FEATURE                 Location/Qualifiers
source                  1..9
                        mol_type = protein
                        organism = synthetic construct
SITE                    9
                        note = Residue attached to 5(6)-Carboxyfluorescein
SEQUENCE: 15
WVELHFFNK                                                                       9

SEQ ID NO: 16           moltype = AA  length = 32
FEATURE                 Location/Qualifiers
```

```
                        source              1..32
                                            mol_type = protein
                                            organism = synthetic construct
SEQUENCE: 16
GRKKRRQRRR PQMSQSGEEN LQGSWVELHF SN                                     32

SEQ ID NO: 17           moltype = AA   length = 32
FEATURE                 Location/Qualifiers
source                  1..32
                        mol_type = protein
                        organism = synthetic construct
SEQUENCE: 17
GRKKRRQRRR PQLDAQHESG RSSSKSSHCD SP                                     32

SEQ ID NO: 18           moltype = AA   length = 20
FEATURE                 Location/Qualifiers
source                  1..20
                        mol_type = protein
                        organism = synthetic construct
SEQUENCE: 18
GRKKRRQRRR PQWVELHFFN                                                   20

SEQ ID NO: 19           moltype = AA   length = 20
FEATURE                 Location/Qualifiers
source                  1..20
                        mol_type = protein
                        organism = synthetic construct
SEQUENCE: 19
GRKKRRQRRR PQWVELAASN                                                   20

SEQ ID NO: 20           moltype = AA   length = 20
FEATURE                 Location/Qualifiers
source                  1..20
                        mol_type = protein
                        organism = synthetic construct
SEQUENCE: 20
MDGSGKQLGS GGPTSSKQIM                                                   20

SEQ ID NO: 21           moltype = AA   length = 20
FEATURE                 Location/Qualifiers
source                  1..20
                        mol_type = protein
                        organism = synthetic construct
SEQUENCE: 21
SKQIMKTGAF LLQGFIQDRA                                                   20

SEQ ID NO: 22           moltype = AA   length = 20
FEATURE                 Location/Qualifiers
source                  1..20
                        mol_type = protein
                        organism = synthetic construct
SEQUENCE: 22
AGPMAGKTPK LTLKQPPQDA                                                   20

SEQ ID NO: 23           moltype = AA   length = 20
FEATURE                 Location/Qualifiers
source                  1..20
                        mol_type = protein
                        organism = synthetic construct
SEQUENCE: 23
DASTKKLSKC LRRIGDKLDS                                                   20

SEQ ID NO: 24           moltype = AA   length = 20
FEATURE                 Location/Qualifiers
source                  1..20
                        mol_type = protein
                        organism = synthetic construct
SEQUENCE: 24
KLDSNMKLQR MIADVDTDSP                                                   20

SEQ ID NO: 25           moltype = AA   length = 20
FEATURE                 Location/Qualifiers
source                  1..20
                        mol_type = protein
                        organism = synthetic construct
SEQUENCE: 25
TDSPRKVFFR VAADMFADGN                                                   20

SEQ ID NO: 26           moltype = AA   length = 20
```

```
FEATURE                 Location/Qualifiers
source                  1..20
                        mol_type = protein
                        organism = synthetic construct
SEQUENCE: 26
WGRVVALFYF ASKLVLKALC                                                   20

SEQ ID NO: 27           moltype = AA   length = 20
FEATURE                 Location/Qualifiers
source                  1..20
                        mol_type = protein
                        organism = synthetic construct
SEQUENCE: 27
VPKLIRTIMG WTLDFLRKRL                                                   20

SEQ ID NO: 28           moltype = AA   length = 20
FEATURE                 Location/Qualifiers
source                  1..20
                        mol_type = protein
                        organism = synthetic construct
SEQUENCE: 28
RLLVWIQDQG GWEGLLSYFG                                                   20

SEQ ID NO: 29           moltype = AA   length = 20
FEATURE                 Location/Qualifiers
source                  1..20
                        mol_type = protein
                        organism = synthetic construct
SEQUENCE: 29
TWQTVTIFVA GVLTASLTIW                                                   20

SEQ ID NO: 30           moltype = AA   length = 20
FEATURE                 Location/Qualifiers
source                  1..20
                        mol_type = protein
                        organism = synthetic construct
SEQUENCE: 30
MFADGNFNWG RVVALFYFAS                                                   20

SEQ ID NO: 31           moltype = AA   length = 20
FEATURE                 Location/Qualifiers
source                  1..20
                        mol_type = protein
                        organism = synthetic construct
SEQUENCE: 31
LVWIQDQGGW EGLLSYFGTP                                                   20

SEQ ID NO: 32           moltype = AA   length = 20
FEATURE                 Location/Qualifiers
source                  1..20
                        mol_type = protein
                        organism = synthetic construct
SEQUENCE: 32
ASTKKLSECL RRIGDKLDSN                                                   20

SEQ ID NO: 33           moltype = AA   length = 20
FEATURE                 Location/Qualifiers
source                  1..20
                        mol_type = protein
                        organism = synthetic construct
SEQUENCE: 33
VPELIRTIMG WTLDFLRERL                                                   20

SEQ ID NO: 34           moltype = AA   length = 20
FEATURE                 Location/Qualifiers
source                  1..20
                        mol_type = protein
                        organism = synthetic construct
SEQUENCE: 34
RLLVWIQDQG GWEGLLSYFG                                                   20

SEQ ID NO: 35           moltype = AA   length = 9
FEATURE                 Location/Qualifiers
source                  1..9
                        mol_type = protein
                        organism = synthetic construct
SEQUENCE: 35
CLKRIGDEL                                                                9
```

```
SEQ ID NO: 36            moltype = AA   length = 20
FEATURE                  Location/Qualifiers
source                   1..20
                         mol_type = protein
                         organism = synthetic construct
SEQUENCE: 36
MSQSCEENLQ CSWVELHFEN                                                  20

SEQ ID NO: 37            moltype = AA   length = 10
FEATURE                  Location/Qualifiers
source                   1..10
                         mol_type = protein
                         organism = synthetic construct
SEQUENCE: 37
MSQSCEENLQ                                                             10

SEQ ID NO: 38            moltype = AA   length = 187
FEATURE                  Location/Qualifiers
source                   1..187
                         mol_type = protein
                         organism = Mus musculus
SEQUENCE: 38
MSQGEENLQ GSWVELHFSN GNGSSVPASV SIYNGDMEKI LLDAQHESGR SSSKSSHCDS        60
PPRSQTPQDT NRAEIDSHSF GEKNSTLSEE DYIERRREVE SILKKNSDWI WDWSSRPENI       120
PPKEFLFKHP KRTATLSMRN TSVMKKGGIF SADFLKVFLP SLLLSHLLAI GLGIYIGRRL       180
TTSTSTF                                                                187

SEQ ID NO: 39            moltype = AA   length = 194
FEATURE                  Location/Qualifiers
source                   1..194
                         mol_type = protein
                         organism = Homo sapiens
SEQUENCE: 39
MSQNGAPGMQ EESLQGSWVE LHFSNNGNGG SVPASVSIYN GDMEKILLDA QHESGRSSSK       60
SSHCDSPPRS QTPQDTNRAS ETDTHSIGEK NSSQSEEDDI ERRKEVESIL KKNSDWIWDW       120
SSRPENIPPK EFLFKHPKRT ATLSMRNTSV MKKGGIFSAE FLKVFLPSLL LSHLLAIGLG       180
IYIGRRLTTS TSTF                                                        194

SEQ ID NO: 40            moltype = AA   length = 19
FEATURE                  Location/Qualifiers
source                   1..19
                         mol_type = protein
                         organism = synthetic construct
SEQUENCE: 40
SQSGEENLQG SWVELHFSN                                                   19

SEQ ID NO: 41            moltype = AA   length = 18
FEATURE                  Location/Qualifiers
source                   1..18
                         mol_type = protein
                         organism = synthetic construct
SEQUENCE: 41
QSGEENLQGS WVELHFSN                                                    18

SEQ ID NO: 42            moltype = AA   length = 17
FEATURE                  Location/Qualifiers
source                   1..17
                         mol_type = protein
                         organism = synthetic construct
SEQUENCE: 42
SGEENLQGSW VELHFSN                                                     17

SEQ ID NO: 43            moltype = AA   length = 16
FEATURE                  Location/Qualifiers
source                   1..16
                         mol_type = protein
                         organism = synthetic construct
SEQUENCE: 43
GEENLQGSWV ELHFSN                                                      16

SEQ ID NO: 44            moltype = AA   length = 15
FEATURE                  Location/Qualifiers
source                   1..15
                         mol_type = protein
                         organism = synthetic construct
SEQUENCE: 44
EENLQGSWVE LHFSN                                                       15

SEQ ID NO: 45            moltype = AA   length = 14
```

```
FEATURE                 Location/Qualifiers
source                  1..14
                        mol_type = protein
                        organism = synthetic construct
SEQUENCE: 45
ENLQGSWVEL HFSN                                                         14

SEQ ID NO: 46           moltype = AA  length = 13
FEATURE                 Location/Qualifiers
source                  1..13
                        mol_type = protein
                        organism = synthetic construct
SEQUENCE: 46
NLQGSWVELH FSN                                                          13

SEQ ID NO: 47           moltype = AA  length = 12
FEATURE                 Location/Qualifiers
source                  1..12
                        mol_type = protein
                        organism = synthetic construct
SEQUENCE: 47
LQGSWVELHF SN                                                           12

SEQ ID NO: 48           moltype = AA  length = 11
FEATURE                 Location/Qualifiers
source                  1..11
                        mol_type = protein
                        organism = synthetic construct
SEQUENCE: 48
QGSWVELHFS N                                                            11

SEQ ID NO: 49           moltype = AA  length = 10
FEATURE                 Location/Qualifiers
source                  1..10
                        mol_type = protein
                        organism = synthetic construct
SEQUENCE: 49
GSWVELHFSN                                                              10

SEQ ID NO: 50           moltype = AA  length = 9
FEATURE                 Location/Qualifiers
source                  1..9
                        mol_type = protein
                        organism = synthetic construct
SEQUENCE: 50
SWVELHFSN                                                               9

SEQ ID NO: 51           moltype = AA  length = 6
FEATURE                 Location/Qualifiers
source                  1..6
                        mol_type = protein
                        organism = synthetic construct
SEQUENCE: 51
ELHFSN                                                                  6

SEQ ID NO: 52           moltype = AA  length = 5
FEATURE                 Location/Qualifiers
source                  1..5
                        mol_type = protein
                        organism = synthetic construct
SEQUENCE: 52
LHFSN                                                                   5

SEQ ID NO: 53           moltype = AA  length = 4
FEATURE                 Location/Qualifiers
source                  1..4
                        mol_type = protein
                        organism = synthetic construct
SEQUENCE: 53
HFSN                                                                    4

SEQ ID NO: 54           moltype = AA  length = 20
FEATURE                 Location/Qualifiers
source                  1..20
                        mol_type = protein
                        organism = synthetic construct
SEQUENCE: 54
MSQSGEENLQ GSWVELHAAA                                                   20
```

```
SEQ ID NO: 55        moltype = AA  length = 19
FEATURE              Location/Qualifiers
source               1..19
                     mol_type = protein
                     organism = synthetic construct
SEQUENCE: 55
MSQSGEENLQ GSWVEAAAN                                                      19

SEQ ID NO: 56        moltype = AA  length = 20
FEATURE              Location/Qualifiers
source               1..20
                     mol_type = protein
                     organism = synthetic construct
SEQUENCE: 56
MSQSGEENLQ GSWVEAAASN                                                     20

SEQ ID NO: 57        moltype = AA  length = 20
FEATURE              Location/Qualifiers
source               1..20
                     mol_type = protein
                     organism = synthetic construct
SEQUENCE: 57
MSQSGEENLQ GSWVAAAFSN                                                     20

SEQ ID NO: 58        moltype = AA  length = 20
FEATURE              Location/Qualifiers
source               1..20
                     mol_type = protein
                     organism = synthetic construct
SEQUENCE: 58
MSQSGEENLQ GSWAAAHFSN                                                     20

SEQ ID NO: 59        moltype = AA  length = 20
FEATURE              Location/Qualifiers
source               1..20
                     mol_type = protein
                     organism = synthetic construct
SEQUENCE: 59
MSQSGEENLQ AAAVELHFSN                                                     20

SEQ ID NO: 60        moltype = AA  length = 20
FEATURE              Location/Qualifiers
source               1..20
                     mol_type = protein
                     organism = synthetic construct
SEQUENCE: 60
MSQSGEENLA AAWVELHFSN                                                     20

SEQ ID NO: 61        moltype = AA  length = 20
FEATURE              Location/Qualifiers
source               1..20
                     mol_type = protein
                     organism = synthetic construct
SEQUENCE: 61
MSQSGEENAA ASWVELHFSN                                                     20

SEQ ID NO: 62        moltype = AA  length = 20
FEATURE              Location/Qualifiers
source               1..20
                     mol_type = protein
                     organism = synthetic construct
SEQUENCE: 62
MSQSGEEAAA GSWVELHFSN                                                     20

SEQ ID NO: 63        moltype = AA  length = 20
FEATURE              Location/Qualifiers
source               1..20
                     mol_type = protein
                     organism = synthetic construct
SEQUENCE: 63
MSQSGEAAAQ GSWVELHFSN                                                     20

SEQ ID NO: 64        moltype = AA  length = 20
FEATURE              Location/Qualifiers
source               1..20
                     mol_type = protein
                     organism = synthetic construct
SEQUENCE: 64
MSQSGAAALQ GSWVELHFSN                                                     20
```

```
SEQ ID NO: 65            moltype = AA  length = 20
FEATURE                  Location/Qualifiers
source                   1..20
                         mol_type = protein
                         organism = synthetic construct
SEQUENCE: 65
MSQSAAANLQ GSWVELHFSN                                                     20

SEQ ID NO: 66            moltype = AA  length = 20
FEATURE                  Location/Qualifiers
source                   1..20
                         mol_type = protein
                         organism = synthetic construct
SEQUENCE: 66
MSQAAAENLQ GSWVELHFSN                                                     20

SEQ ID NO: 67            moltype = AA  length = 20
FEATURE                  Location/Qualifiers
source                   1..20
                         mol_type = protein
                         organism = synthetic construct
SEQUENCE: 67
MSAAAEENLQ GSWVELHFSN                                                     20

SEQ ID NO: 68            moltype = AA  length = 19
FEATURE                  Location/Qualifiers
source                   1..19
                         mol_type = protein
                         organism = synthetic construct
SEQUENCE: 68
MAAAEENLQG SWVELHFSN                                                      19

SEQ ID NO: 69            moltype = AA  length = 20
FEATURE                  Location/Qualifiers
source                   1..20
                         mol_type = protein
                         organism = synthetic construct
SEQUENCE: 69
AAASGEENLQ GSWVELHFSN                                                     20

SEQ ID NO: 70            moltype = AA  length = 20
FEATURE                  Location/Qualifiers
source                   1..20
                         mol_type = protein
                         organism = synthetic construct
SEQUENCE: 70
MSQSGEENLQ GSWVELHFAA                                                     20

SEQ ID NO: 71            moltype = AA  length = 20
FEATURE                  Location/Qualifiers
source                   1..20
                         mol_type = protein
                         organism = synthetic construct
SEQUENCE: 71
MSQSGEENLQ GSWVELHAAN                                                     20

SEQ ID NO: 72            moltype = AA  length = 20
FEATURE                  Location/Qualifiers
source                   1..20
                         mol_type = protein
                         organism = synthetic construct
SEQUENCE: 72
MSQSGEENLQ GSWVELAASN                                                     20

SEQ ID NO: 73            moltype = AA  length = 20
FEATURE                  Location/Qualifiers
source                   1..20
                         mol_type = protein
                         organism = synthetic construct
SEQUENCE: 73
MSQSGEENLQ GSWVEAAFSN                                                     20

SEQ ID NO: 74            moltype = AA  length = 20
FEATURE                  Location/Qualifiers
source                   1..20
                         mol_type = protein
                         organism = synthetic construct
```

```
SEQUENCE: 74
MSQSGEENLQ GSWVAAHFSN                                              20

SEQ ID NO: 75           moltype = AA  length = 20
FEATURE                 Location/Qualifiers
source                  1..20
                        mol_type = protein
                        organism = synthetic construct
SEQUENCE: 75
MSQSGEENLQ GSWAALHFSN                                              20

SEQ ID NO: 76           moltype = AA  length = 20
FEATURE                 Location/Qualifiers
source                  1..20
                        mol_type = protein
                        organism = synthetic construct
SEQUENCE: 76
MSQSGEENLQ GSAAELHFSN                                              20

SEQ ID NO: 77           moltype = AA  length = 20
FEATURE                 Location/Qualifiers
source                  1..20
                        mol_type = protein
                        organism = synthetic construct
SEQUENCE: 77
MSQSGEENLQ GAAVELHFSN                                              20

SEQ ID NO: 78           moltype = AA  length = 20
FEATURE                 Location/Qualifiers
source                  1..20
                        mol_type = protein
                        organism = synthetic construct
SEQUENCE: 78
MSQSGEENLQ AAWVELHFSN                                              20

SEQ ID NO: 79           moltype = AA  length = 20
FEATURE                 Location/Qualifiers
source                  1..20
                        mol_type = protein
                        organism = synthetic construct
SEQUENCE: 79
MSQSGEENLA ASWVELHFSN                                              20

SEQ ID NO: 80           moltype = AA  length = 20
FEATURE                 Location/Qualifiers
source                  1..20
                        mol_type = protein
                        organism = synthetic construct
SEQUENCE: 80
MSQSGEAALQ GSWVELHFSN                                              20

SEQ ID NO: 81           moltype = AA  length = 20
FEATURE                 Location/Qualifiers
source                  1..20
                        mol_type = protein
                        organism = synthetic construct
SEQUENCE: 81
MSQSGAANLQ GSWVELHFSN                                              20

SEQ ID NO: 82           moltype = AA  length = 20
FEATURE                 Location/Qualifiers
source                  1..20
                        mol_type = protein
                        organism = synthetic construct
SEQUENCE: 82
MSQSAAENLQ GSWVELHFSN                                              20

SEQ ID NO: 83           moltype = AA  length = 20
FEATURE                 Location/Qualifiers
source                  1..20
                        mol_type = protein
                        organism = synthetic construct
SEQUENCE: 83
MSQAAEENLQ GSWVELHFSN                                              20
```

```
SEQ ID NO: 84            moltype = AA  length = 20
FEATURE                  Location/Qualifiers
source                   1..20
                         mol_type = protein
                         organism = synthetic construct
SEQUENCE: 84
MSAAGEENLQ GSWVELHFSN                                                       20

SEQ ID NO: 85            moltype = AA  length = 20
FEATURE                  Location/Qualifiers
source                   1..20
                         mol_type = protein
                         organism = synthetic construct
SEQUENCE: 85
MAASGEENLQ GSWVELHFSN                                                       20

SEQ ID NO: 86            moltype = AA  length = 20
FEATURE                  Location/Qualifiers
source                   1..20
                         mol_type = protein
                         organism = synthetic construct
SEQUENCE: 86
AAQSGEENLQ GSWVELHFSN                                                       20

SEQ ID NO: 87            moltype = AA  length = 20
FEATURE                  Location/Qualifiers
source                   1..20
                         mol_type = protein
                         organism = synthetic construct
SEQUENCE: 87
MDGSGEQLGS GGPTSSEQIM                                                       20

SEQ ID NO: 88            moltype = AA  length = 20
FEATURE                  Location/Qualifiers
source                   1..20
                         mol_type = protein
                         organism = synthetic construct
SEQUENCE: 88
AGRMAGETPE LTLEQPPQDA                                                       20

SEQ ID NO: 89            moltype = AA  length = 20
FEATURE                  Location/Qualifiers
source                   1..20
                         mol_type = protein
                         organism = synthetic construct
SEQUENCE: 89
DASTKKLSEC LRRIGDELDS                                                       20

SEQ ID NO: 90            moltype = AA  length = 20
FEATURE                  Location/Qualifiers
source                   1..20
                         mol_type = protein
                         organism = synthetic construct
SEQUENCE: 90
ELDSNMELQR MIADVDTDSP                                                       20

SEQ ID NO: 91            moltype = AA  length = 20
FEATURE                  Location/Qualifiers
source                   1..20
                         mol_type = protein
                         organism = synthetic construct
SEQUENCE: 91
TDSPREVFFR VAADMFADGN                                                       20

SEQ ID NO: 92            moltype = AA  length = 20
FEATURE                  Location/Qualifiers
source                   1..20
                         mol_type = protein
                         organism = synthetic construct
SEQUENCE: 92
MFADGNFNWG RVVALFYFAS                                                       20

SEQ ID NO: 93            moltype = AA  length = 20
FEATURE                  Location/Qualifiers
source                   1..20
                         mol_type = protein
                         organism = synthetic construct
```

```
SEQUENCE: 93
ASTKKLSECL RRIGDELDSN                                                       20

SEQ ID NO: 94           moltype = AA  length = 4
FEATURE                 Location/Qualifiers
source                  1..4
                        mol_type = protein
                        organism = synthetic construct
SEQUENCE: 94
LQGS                                                                         4

SEQ ID NO: 95           moltype = AA  length = 6
FEATURE                 Location/Qualifiers
source                  1..6
                        mol_type = protein
                        organism = synthetic construct
SEQUENCE: 95
NLQGSW                                                                       6

SEQ ID NO: 96           moltype = AA  length = 8
FEATURE                 Location/Qualifiers
source                  1..8
                        mol_type = protein
                        organism = synthetic construct
SEQUENCE: 96
ENLQGSWV                                                                     8

SEQ ID NO: 97           moltype = AA  length = 10
FEATURE                 Location/Qualifiers
source                  1..10
                        mol_type = protein
                        organism = synthetic construct
SEQUENCE: 97
EENLQGSWVE                                                                  10

SEQ ID NO: 98           moltype = AA  length = 12
FEATURE                 Location/Qualifiers
source                  1..12
                        mol_type = protein
                        organism = synthetic construct
SEQUENCE: 98
GEENLQGSWV EL                                                               12

SEQ ID NO: 99           moltype = AA  length = 14
FEATURE                 Location/Qualifiers
source                  1..14
                        mol_type = protein
                        organism = synthetic construct
SEQUENCE: 99
SGEENLQGSW VELH                                                             14

SEQ ID NO: 100          moltype = AA  length = 16
FEATURE                 Location/Qualifiers
source                  1..16
                        mol_type = protein
                        organism = synthetic construct
SEQUENCE: 100
QSGEENLQGS WVELHF                                                           16

SEQ ID NO: 101          moltype = AA  length = 18
FEATURE                 Location/Qualifiers
source                  1..18
                        mol_type = protein
                        organism = synthetic construct
SEQUENCE: 101
SQSGEENLQG SWVELHFS                                                         18

SEQ ID NO: 102          moltype = AA  length = 4
FEATURE                 Location/Qualifiers
source                  1..4
                        mol_type = protein
                        organism = synthetic construct
SEQUENCE: 102
MSQS                                                                         4

SEQ ID NO: 103          moltype = AA  length = 5
FEATURE                 Location/Qualifiers
```

```
source                    1..5
                          mol_type = protein
                          organism = synthetic construct
SEQUENCE: 103
MSQSG                                                                    5

SEQ ID NO: 104            moltype = AA   length = 6
FEATURE                   Location/Qualifiers
source                    1..6
                          mol_type = protein
                          organism = synthetic construct
SEQUENCE: 104
MSQSGE                                                                   6

SEQ ID NO: 105            moltype = AA   length = 7
FEATURE                   Location/Qualifiers
source                    1..7
                          mol_type = protein
                          organism = synthetic construct
SEQUENCE: 105
MSQSGEE                                                                  7

SEQ ID NO: 106            moltype = AA   length = 8
FEATURE                   Location/Qualifiers
source                    1..8
                          mol_type = protein
                          organism = synthetic construct
SEQUENCE: 106
MSQSGEEN                                                                 8

SEQ ID NO: 107            moltype = AA   length = 9
FEATURE                   Location/Qualifiers
source                    1..9
                          mol_type = protein
                          organism = synthetic construct
SEQUENCE: 107
MSQSGEENL                                                                9

SEQ ID NO: 108            moltype = AA   length = 10
FEATURE                   Location/Qualifiers
source                    1..10
                          mol_type = protein
                          organism = synthetic construct
SEQUENCE: 108
MSQSGEENLQ                                                              10

SEQ ID NO: 109            moltype = AA   length = 11
FEATURE                   Location/Qualifiers
source                    1..11
                          mol_type = protein
                          organism = synthetic construct
SEQUENCE: 109
MSQSGEENLQ G                                                            11

SEQ ID NO: 110            moltype = AA   length = 12
FEATURE                   Location/Qualifiers
source                    1..12
                          mol_type = protein
                          organism = synthetic construct
SEQUENCE: 110
MSQSGEENLQ GS                                                           12

SEQ ID NO: 111            moltype = AA   length = 13
FEATURE                   Location/Qualifiers
source                    1..13
                          mol_type = protein
                          organism = synthetic construct
SEQUENCE: 111
MSQSGEENLQ GSW                                                          13

SEQ ID NO: 112            moltype = AA   length = 14
FEATURE                   Location/Qualifiers
source                    1..14
                          mol_type = protein
                          organism = synthetic construct
SEQUENCE: 112
MSQSGEENLQ GSWV                                                         14

SEQ ID NO: 113            moltype = AA   length = 15
```

```
FEATURE                 Location/Qualifiers
source                  1..15
                        mol_type = protein
                        organism = synthetic construct
SEQUENCE: 113
MSQSGEENLQ GSWVE                                                          15

SEQ ID NO: 114          moltype = AA  length = 16
FEATURE                 Location/Qualifiers
source                  1..16
                        mol_type = protein
                        organism = synthetic construct
SEQUENCE: 114
MSQSGEENLQ GSWVEL                                                         16

SEQ ID NO: 115          moltype = AA  length = 17
FEATURE                 Location/Qualifiers
source                  1..17
                        mol_type = protein
                        organism = synthetic construct
SEQUENCE: 115
MSQSGEENLQ GSWVELH                                                        17

SEQ ID NO: 116          moltype = AA  length = 18
FEATURE                 Location/Qualifiers
source                  1..18
                        mol_type = protein
                        organism = synthetic construct
SEQUENCE: 116
MSQSGEENLQ GSWVELHF                                                       18

SEQ ID NO: 117          moltype = AA  length = 19
FEATURE                 Location/Qualifiers
source                  1..19
                        mol_type = protein
                        organism = synthetic construct
SEQUENCE: 117
MSQSGEENLQ GSWVELHFS                                                      19

SEQ ID NO: 118          moltype = AA  length = 20
FEATURE                 Location/Qualifiers
source                  1..20
                        mol_type = protein
                        organism = synthetic construct
SEQUENCE: 118
MSQSGEENLQ GSWVALHFSN                                                     20

SEQ ID NO: 119          moltype = AA  length = 20
FEATURE                 Location/Qualifiers
source                  1..20
                        mol_type = protein
                        organism = synthetic construct
SEQUENCE: 119
MSQSGERNLQ GSWVELHFSN                                                     20

SEQ ID NO: 120          moltype = AA  length = 20
FEATURE                 Location/Qualifiers
source                  1..20
                        mol_type = protein
                        organism = synthetic construct
SEQUENCE: 120
MSQSKEENLQ GSWVELHFSN                                                     20

SEQ ID NO: 121          moltype = AA  length = 20
FEATURE                 Location/Qualifiers
source                  1..20
                        mol_type = protein
                        organism = synthetic construct
SEQUENCE: 121
MSQSGEENCQ GSWVELHFSN                                                     20

SEQ ID NO: 122          moltype = AA  length = 20
FEATURE                 Location/Qualifiers
source                  1..20
                        mol_type = protein
                        organism = synthetic construct
SEQUENCE: 122
MSQSGEENLQ GSWVELHFSS                                                     20
```

```
SEQ ID NO: 123         moltype = AA   length = 20
FEATURE                Location/Qualifiers
source                 1..20
                       mol_type = protein
                       organism = synthetic construct
SEQUENCE: 123
MSQSGEENLQ GSWVCLHFSN                                                   20

SEQ ID NO: 124         moltype = AA   length = 20
FEATURE                Location/Qualifiers
source                 1..20
                       mol_type = protein
                       organism = synthetic construct
SEQUENCE: 124
MSQSGESNLQ GSWVELHFSN                                                   20

SEQ ID NO: 125         moltype = AA   length = 20
FEATURE                Location/Qualifiers
source                 1..20
                       mol_type = protein
                       organism = synthetic construct
SEQUENCE: 125
MSQSLEENLQ GSWVELHFSN                                                   20

SEQ ID NO: 126         moltype = AA   length = 20
FEATURE                Location/Qualifiers
source                 1..20
                       mol_type = protein
                       organism = synthetic construct
SEQUENCE: 126
MSQSGEENDQ GSWVELHFSN                                                   20

SEQ ID NO: 127         moltype = AA   length = 20
FEATURE                Location/Qualifiers
source                 1..20
                       mol_type = protein
                       organism = synthetic construct
SEQUENCE: 127
MSQSGEENLQ GSWVELHFST                                                   20

SEQ ID NO: 128         moltype = AA   length = 20
FEATURE                Location/Qualifiers
source                 1..20
                       mol_type = protein
                       organism = synthetic construct
SEQUENCE: 128
MSQSGEENLQ GSWVDLHFSN                                                   20

SEQ ID NO: 129         moltype = AA   length = 20
FEATURE                Location/Qualifiers
source                 1..20
                       mol_type = protein
                       organism = synthetic construct
SEQUENCE: 129
MSQSGETNLQ GSWVELHFSN                                                   20

SEQ ID NO: 130         moltype = AA   length = 20
FEATURE                Location/Qualifiers
source                 1..20
                       mol_type = protein
                       organism = synthetic construct
SEQUENCE: 130
MSQSMEENLQ GSWVELHFSN                                                   20

SEQ ID NO: 131         moltype = AA   length = 20
FEATURE                Location/Qualifiers
source                 1..20
                       mol_type = protein
                       organism = synthetic construct
SEQUENCE: 131
MSQSGEENEQ GSWVELHFSN                                                   20

SEQ ID NO: 132         moltype = AA   length = 20
FEATURE                Location/Qualifiers
source                 1..20
                       mol_type = protein
                       organism = synthetic construct
SEQUENCE: 132
MSQSGEENLQ GSWVELHFSV                                                   20
```

```
SEQ ID NO: 133         moltype = AA   length = 20
FEATURE                Location/Qualifiers
source                 1..20
                       mol_type = protein
                       organism = synthetic construct
SEQUENCE: 133
MSQSGEENLQ GSWVFLHFSN                                              20

SEQ ID NO: 134         moltype = AA   length = 20
FEATURE                Location/Qualifiers
source                 1..20
                       mol_type = protein
                       organism = synthetic construct
SEQUENCE: 134
MSQSGEVNLQ GSWVELHFSN                                              20

SEQ ID NO: 135         moltype = AA   length = 20
FEATURE                Location/Qualifiers
source                 1..20
                       mol_type = protein
                       organism = synthetic construct
SEQUENCE: 135
MSQSNEENLQ GSWVELHFSN                                              20

SEQ ID NO: 136         moltype = AA   length = 20
FEATURE                Location/Qualifiers
source                 1..20
                       mol_type = protein
                       organism = synthetic construct
SEQUENCE: 136
MSQSGEENFQ GSWVELHFSN                                              20

SEQ ID NO: 137         moltype = AA   length = 20
FEATURE                Location/Qualifiers
source                 1..20
                       mol_type = protein
                       organism = synthetic construct
SEQUENCE: 137
MSQSGEENLQ GSWVELHFSW                                              20

SEQ ID NO: 138         moltype = AA   length = 20
FEATURE                Location/Qualifiers
source                 1..20
                       mol_type = protein
                       organism = synthetic construct
SEQUENCE: 138
MSQSGEENLQ GSWVGLHFSN                                              20

SEQ ID NO: 139         moltype = AA   length = 20
FEATURE                Location/Qualifiers
source                 1..20
                       mol_type = protein
                       organism = synthetic construct
SEQUENCE: 139
MSQSGEWNLQ GSWVELHFSN                                              20

SEQ ID NO: 140         moltype = AA   length = 20
FEATURE                Location/Qualifiers
source                 1..20
                       mol_type = protein
                       organism = synthetic construct
SEQUENCE: 140
MSQSPEENLQ GSWVELHFSN                                              20

SEQ ID NO: 141         moltype = AA   length = 20
FEATURE                Location/Qualifiers
source                 1..20
                       mol_type = protein
                       organism = synthetic construct
SEQUENCE: 141
MSQSGEENGQ GSWVELHFSN                                              20

SEQ ID NO: 142         moltype = AA   length = 20
FEATURE                Location/Qualifiers
source                 1..20
                       mol_type = protein
                       organism = synthetic construct
```

```
SEQUENCE: 142
MSQSGEENLQ GSWVELHFSY                                               20

SEQ ID NO: 143          moltype = AA  length = 20
FEATURE                 Location/Qualifiers
source                  1..20
                        mol_type = protein
                        organism = synthetic construct
SEQUENCE: 143
MSQSGEENLQ GSWVHLHFSN                                               20

SEQ ID NO: 144          moltype = AA  length = 20
FEATURE                 Location/Qualifiers
source                  1..20
                        mol_type = protein
                        organism = synthetic construct
SEQUENCE: 144
MSQSGEYNLQ GSWVELHFSN                                               20

SEQ ID NO: 145          moltype = AA  length = 20
FEATURE                 Location/Qualifiers
source                  1..20
                        mol_type = protein
                        organism = synthetic construct
SEQUENCE: 145
MSQSGQEENLQ GSWVELHFSN                                              20

SEQ ID NO: 146          moltype = AA  length = 20
FEATURE                 Location/Qualifiers
source                  1..20
                        mol_type = protein
                        organism = synthetic construct
SEQUENCE: 146
MSQSGEENHQ GSWVELHFSN                                               20

SEQ ID NO: 147          moltype = AA  length = 20
FEATURE                 Location/Qualifiers
source                  1..20
                        mol_type = protein
                        organism = synthetic construct
SEQUENCE: 147
MSQSGEEALQ GSWVELHFSN                                               20

SEQ ID NO: 148          moltype = AA  length = 20
FEATURE                 Location/Qualifiers
source                  1..20
                        mol_type = protein
                        organism = synthetic construct
SEQUENCE: 148
MSQSGEENLQ GSWVILHFSN                                               20

SEQ ID NO: 149          moltype = AA  length = 20
FEATURE                 Location/Qualifiers
source                  1..20
                        mol_type = protein
                        organism = synthetic construct
SEQUENCE: 149
MSQSGEENLQ GSWVELHASN                                               20

SEQ ID NO: 150          moltype = AA  length = 20
FEATURE                 Location/Qualifiers
source                  1..20
                        mol_type = protein
                        organism = synthetic construct
SEQUENCE: 150
MSQSREENLQ GSWVELHFSN                                               20

SEQ ID NO: 151          moltype = AA  length = 20
FEATURE                 Location/Qualifiers
source                  1..20
                        mol_type = protein
                        organism = synthetic construct
SEQUENCE: 151
MSQSGEENIQ GSWVELHFSN                                               20

SEQ ID NO: 152          moltype = AA  length = 20
FEATURE                 Location/Qualifiers
```

```
source                      1..20
                            mol_type = protein
                            organism = synthetic construct
SEQUENCE: 152
MSQSGEECLQ GSWVELHFSN                                                    20

SEQ ID NO: 153              moltype = AA  length = 20
FEATURE                     Location/Qualifiers
source                      1..20
                            mol_type = protein
                            organism = synthetic construct
SEQUENCE: 153
MSQSGEENLQ GSWVKLHFSN                                                    20

SEQ ID NO: 154              moltype = AA  length = 20
FEATURE                     Location/Qualifiers
source                      1..20
                            mol_type = protein
                            organism = synthetic construct
SEQUENCE: 154
MSQSGEENLQ GSWVELHCSN                                                    20

SEQ ID NO: 155              moltype = AA  length = 20
FEATURE                     Location/Qualifiers
source                      1..20
                            mol_type = protein
                            organism = synthetic construct
SEQUENCE: 155
MSQSSEENLQ GSWVELHFSN                                                    20

SEQ ID NO: 156              moltype = AA  length = 20
FEATURE                     Location/Qualifiers
source                      1..20
                            mol_type = protein
                            organism = synthetic construct
SEQUENCE: 156
MSQSGEENKQ GSWVELHFSN                                                    20

SEQ ID NO: 157              moltype = AA  length = 20
FEATURE                     Location/Qualifiers
source                      1..20
                            mol_type = protein
                            organism = synthetic construct
SEQUENCE: 157
MSQSGEEDLQ GSWVELHFSN                                                    20

SEQ ID NO: 158              moltype = AA  length = 20
FEATURE                     Location/Qualifiers
source                      1..20
                            mol_type = protein
                            organism = synthetic construct
SEQUENCE: 158
MSQSGEENLQ GSWVLLHFSN                                                    20

SEQ ID NO: 159              moltype = AA  length = 20
FEATURE                     Location/Qualifiers
source                      1..20
                            mol_type = protein
                            organism = synthetic construct
SEQUENCE: 159
MSQSGEENLQ GSWVELHDSN                                                    20

SEQ ID NO: 160              moltype = AA  length = 20
FEATURE                     Location/Qualifiers
source                      1..20
                            mol_type = protein
                            organism = synthetic construct
SEQUENCE: 160
MSQSTEENLQ GSWVELHFSN                                                    20

SEQ ID NO: 161              moltype = AA  length = 20
FEATURE                     Location/Qualifiers
source                      1..20
                            mol_type = protein
                            organism = synthetic construct
SEQUENCE: 161
MSQSGEENMQ GSWVELHFSN                                                    20

SEQ ID NO: 162              moltype = AA  length = 20
```

```
FEATURE              Location/Qualifiers
source               1..20
                     mol_type = protein
                     organism = synthetic construct
SEQUENCE: 162
MSQSGEEELQ GSWVELHFSN                                              20

SEQ ID NO: 163       moltype = AA  length = 20
FEATURE              Location/Qualifiers
source               1..20
                     mol_type = protein
                     organism = synthetic construct
SEQUENCE: 163
MSQSGEENLQ GSWVMLHFSN                                              20

SEQ ID NO: 164       moltype = AA  length = 20
FEATURE              Location/Qualifiers
source               1..20
                     mol_type = protein
                     organism = synthetic construct
SEQUENCE: 164
MSQSGEENLQ GSWVELHESN                                              20

SEQ ID NO: 165       moltype = AA  length = 20
FEATURE              Location/Qualifiers
source               1..20
                     mol_type = protein
                     organism = synthetic construct
SEQUENCE: 165
MSQSVEENLQ GSWVELHFSN                                              20

SEQ ID NO: 166       moltype = AA  length = 20
FEATURE              Location/Qualifiers
source               1..20
                     mol_type = protein
                     organism = synthetic construct
SEQUENCE: 166
MSQSGEENNQ GSWVELHFSN                                              20

SEQ ID NO: 167       moltype = AA  length = 20
FEATURE              Location/Qualifiers
source               1..20
                     mol_type = protein
                     organism = synthetic construct
SEQUENCE: 167
MSQSGEEFLQ GSWVELHFSN                                              20

SEQ ID NO: 168       moltype = AA  length = 20
FEATURE              Location/Qualifiers
source               1..20
                     mol_type = protein
                     organism = synthetic construct
SEQUENCE: 168
MSQSGEENLQ GSWVNLHFSN                                              20

SEQ ID NO: 169       moltype = AA  length = 20
FEATURE              Location/Qualifiers
source               1..20
                     mol_type = protein
                     organism = synthetic construct
SEQUENCE: 169
MSQSGEENLQ GSWVELHGSN                                              20

SEQ ID NO: 170       moltype = AA  length = 20
FEATURE              Location/Qualifiers
source               1..20
                     mol_type = protein
                     organism = synthetic construct
SEQUENCE: 170
MSQSWEENLQ GSWVELHFSN                                              20

SEQ ID NO: 171       moltype = AA  length = 20
FEATURE              Location/Qualifiers
source               1..20
                     mol_type = protein
                     organism = synthetic construct
SEQUENCE: 171
MSQSGEENPQ GSWVELHFSN                                              20
```

```
SEQ ID NO: 172        moltype = AA   length = 20
FEATURE               Location/Qualifiers
source                1..20
                      mol_type = protein
                      organism = synthetic construct
SEQUENCE: 172
MSQSGEEGLQ GSWVELHFSN                                                    20

SEQ ID NO: 173        moltype = AA   length = 20
FEATURE               Location/Qualifiers
source                1..20
                      mol_type = protein
                      organism = synthetic construct
SEQUENCE: 173
MSQSGEENLQ GSWVPLHFSN                                                    20

SEQ ID NO: 174        moltype = AA   length = 20
FEATURE               Location/Qualifiers
source                1..20
                      mol_type = protein
                      organism = synthetic construct
SEQUENCE: 174
MSQSGEENLQ GSWVELHHSN                                                    20

SEQ ID NO: 175        moltype = AA   length = 20
FEATURE               Location/Qualifiers
source                1..20
                      mol_type = protein
                      organism = synthetic construct
SEQUENCE: 175
MSQSYEENLQ GSWVELHFSN                                                    20

SEQ ID NO: 176        moltype = AA   length = 20
FEATURE               Location/Qualifiers
source                1..20
                      mol_type = protein
                      organism = synthetic construct
SEQUENCE: 176
MSQSGEENQQ GSWVELHFSN                                                    20

SEQ ID NO: 177        moltype = AA   length = 20
FEATURE               Location/Qualifiers
source                1..20
                      mol_type = protein
                      organism = synthetic construct
SEQUENCE: 177
MSQSGEEHLQ GSWVELHFSN                                                    20

SEQ ID NO: 178        moltype = AA   length = 20
FEATURE               Location/Qualifiers
source                1..20
                      mol_type = protein
                      organism = synthetic construct
SEQUENCE: 178
MSQSGEENLQ GSWVQLHFSN                                                    20

SEQ ID NO: 179        moltype = AA   length = 20
FEATURE               Location/Qualifiers
source                1..20
                      mol_type = protein
                      organism = synthetic construct
SEQUENCE: 179
MSQSGEENLQ GSWVELHISN                                                    20

SEQ ID NO: 180        moltype = AA   length = 20
FEATURE               Location/Qualifiers
source                1..20
                      mol_type = protein
                      organism = synthetic construct
SEQUENCE: 180
MSQSGEENLQ GSWVELAFSN                                                    20

SEQ ID NO: 181        moltype = AA   length = 20
FEATURE               Location/Qualifiers
source                1..20
                      mol_type = protein
                      organism = synthetic construct
SEQUENCE: 181
MSQSGEENRQ GSWVELHFSN                                                    20
```

```
SEQ ID NO: 182            moltype = AA   length = 20
FEATURE                   Location/Qualifiers
source                    1..20
                          mol_type = protein
                          organism = synthetic construct
SEQUENCE: 182
MSQSGEEILQ GSWVELHFSN                                                    20

SEQ ID NO: 183            moltype = AA   length = 20
FEATURE                   Location/Qualifiers
source                    1..20
                          mol_type = protein
                          organism = synthetic construct
SEQUENCE: 183
MSQSGEENLQ GSWVRLHFSN                                                    20

SEQ ID NO: 184            moltype = AA   length = 20
FEATURE                   Location/Qualifiers
source                    1..20
                          mol_type = protein
                          organism = synthetic construct
SEQUENCE: 184
MSQSGEENLQ GSWVELHKSN                                                    20

SEQ ID NO: 185            moltype = AA   length = 20
FEATURE                   Location/Qualifiers
source                    1..20
                          mol_type = protein
                          organism = synthetic construct
SEQUENCE: 185
MSQSGEENLQ GSWVELCFSN                                                    20

SEQ ID NO: 186            moltype = AA   length = 20
FEATURE                   Location/Qualifiers
source                    1..20
                          mol_type = protein
                          organism = synthetic construct
SEQUENCE: 186
MSQSGEENSQ GSWVELHFSN                                                    20

SEQ ID NO: 187            moltype = AA   length = 20
FEATURE                   Location/Qualifiers
source                    1..20
                          mol_type = protein
                          organism = synthetic construct
SEQUENCE: 187
MSQSGEEKLQ GSWVELHFSN                                                    20

SEQ ID NO: 188            moltype = AA   length = 20
FEATURE                   Location/Qualifiers
source                    1..20
                          mol_type = protein
                          organism = synthetic construct
SEQUENCE: 188
MSQSGEENLQ GSWVSLHFSN                                                    20

SEQ ID NO: 189            moltype = AA   length = 20
FEATURE                   Location/Qualifiers
source                    1..20
                          mol_type = protein
                          organism = synthetic construct
SEQUENCE: 189
MSQSGEENLQ GSWVELHLSN                                                    20

SEQ ID NO: 190            moltype = AA   length = 20
FEATURE                   Location/Qualifiers
source                    1..20
                          mol_type = protein
                          organism = synthetic construct
SEQUENCE: 190
MSQSGEENLQ GSWVELDFSN                                                    20

SEQ ID NO: 191            moltype = AA   length = 20
FEATURE                   Location/Qualifiers
source                    1..20
                          mol_type = protein
                          organism = synthetic construct
```

```
SEQUENCE: 191
MSQSGEENTQ GSWVELHFSN                                               20

SEQ ID NO: 192          moltype = AA  length = 20
FEATURE                 Location/Qualifiers
source                  1..20
                        mol_type = protein
                        organism = synthetic construct
SEQUENCE: 192
MSQSGEELLQ GSWVELHFSN                                               20

SEQ ID NO: 193          moltype = AA  length = 20
FEATURE                 Location/Qualifiers
source                  1..20
                        mol_type = protein
                        organism = synthetic construct
SEQUENCE: 193
MSQSGEENLQ GSWVTLHFSN                                               20

SEQ ID NO: 194          moltype = AA  length = 20
FEATURE                 Location/Qualifiers
source                  1..20
                        mol_type = protein
                        organism = synthetic construct
SEQUENCE: 194
MSQSGEENLQ GSWVELHMSN                                               20

SEQ ID NO: 195          moltype = AA  length = 20
FEATURE                 Location/Qualifiers
source                  1..20
                        mol_type = protein
                        organism = synthetic construct
SEQUENCE: 195
MSQSGEENLQ GSWVELEFSN                                               20

SEQ ID NO: 196          moltype = AA  length = 20
FEATURE                 Location/Qualifiers
source                  1..20
                        mol_type = protein
                        organism = synthetic construct
SEQUENCE: 196
MSQSGEENVQ GSWVELHFSN                                               20

SEQ ID NO: 197          moltype = AA  length = 20
FEATURE                 Location/Qualifiers
source                  1..20
                        mol_type = protein
                        organism = synthetic construct
SEQUENCE: 197
MSQSGEEMLQ GSWVELHFSN                                               20

SEQ ID NO: 198          moltype = AA  length = 20
FEATURE                 Location/Qualifiers
source                  1..20
                        mol_type = protein
                        organism = synthetic construct
SEQUENCE: 198
MSQSGEENLQ GSWVVLHFSN                                               20

SEQ ID NO: 199          moltype = AA  length = 20
FEATURE                 Location/Qualifiers
source                  1..20
                        mol_type = protein
                        organism = synthetic construct
SEQUENCE: 199
MSQSGEENLQ GSWVELHNSN                                               20

SEQ ID NO: 200          moltype = AA  length = 20
FEATURE                 Location/Qualifiers
source                  1..20
                        mol_type = protein
                        organism = synthetic construct
SEQUENCE: 200
MSQSGEENLQ GSWVELFFSN                                               20

SEQ ID NO: 201          moltype = AA  length = 20
FEATURE                 Location/Qualifiers
```

```
source                  1..20
                        mol_type = protein
                        organism = synthetic construct
SEQUENCE: 201
MSQSGEENWQ GSWVELHFSN                                            20

SEQ ID NO: 202          moltype = AA  length = 20
FEATURE                 Location/Qualifiers
source                  1..20
                        mol_type = protein
                        organism = synthetic construct
SEQUENCE: 202
MSQSGEEPLQ GSWVELHFSN                                            20

SEQ ID NO: 203          moltype = AA  length = 20
FEATURE                 Location/Qualifiers
source                  1..20
                        mol_type = protein
                        organism = synthetic construct
SEQUENCE: 203
MSQSGEENLQ GSWVWLHFSN                                            20

SEQ ID NO: 204          moltype = AA  length = 20
FEATURE                 Location/Qualifiers
source                  1..20
                        mol_type = protein
                        organism = synthetic construct
SEQUENCE: 204
MSQSGEENLQ GSWVELHPSN                                            20

SEQ ID NO: 205          moltype = AA  length = 20
FEATURE                 Location/Qualifiers
source                  1..20
                        mol_type = protein
                        organism = synthetic construct
SEQUENCE: 205
MSQSGEENLQ GSWVELGFSN                                            20

SEQ ID NO: 206          moltype = AA  length = 20
FEATURE                 Location/Qualifiers
source                  1..20
                        mol_type = protein
                        organism = synthetic construct
SEQUENCE: 206
MSQSGEENYQ GSWVELHFSN                                            20

SEQ ID NO: 207          moltype = AA  length = 20
FEATURE                 Location/Qualifiers
source                  1..20
                        mol_type = protein
                        organism = synthetic construct
SEQUENCE: 207
MSQSGEEQLQ GSWVELHFSN                                            20

SEQ ID NO: 208          moltype = AA  length = 20
FEATURE                 Location/Qualifiers
source                  1..20
                        mol_type = protein
                        organism = synthetic construct
SEQUENCE: 208
MSQSGEENLQ GSWVYLHFSN                                            20

SEQ ID NO: 209          moltype = AA  length = 20
FEATURE                 Location/Qualifiers
source                  1..20
                        mol_type = protein
                        organism = synthetic construct
SEQUENCE: 209
MSQSGEENLQ GSWVELHQSN                                            20

SEQ ID NO: 210          moltype = AA  length = 20
FEATURE                 Location/Qualifiers
source                  1..20
                        mol_type = protein
                        organism = synthetic construct
SEQUENCE: 210
MSQSGEENLQ GSWVELIFSN                                            20

SEQ ID NO: 211          moltype = AA  length = 20
```

```
FEATURE              Location/Qualifiers
source               1..20
                     mol_type = protein
                     organism = synthetic construct
SEQUENCE: 211
ASQSGEENLQ GSWVELHFSN                                              20

SEQ ID NO: 212       moltype = AA  length = 20
FEATURE              Location/Qualifiers
source               1..20
                     mol_type = protein
                     organism = synthetic construct
SEQUENCE: 212
MSQSGEERLQ GSWVELHFSN                                              20

SEQ ID NO: 213       moltype = AA  length = 20
FEATURE              Location/Qualifiers
source               1..20
                     mol_type = protein
                     organism = synthetic construct
SEQUENCE: 213
MSQSGAENLQ GSWVELHFSN                                              20

SEQ ID NO: 214       moltype = AA  length = 20
FEATURE              Location/Qualifiers
source               1..20
                     mol_type = protein
                     organism = synthetic construct
SEQUENCE: 214
MSQSGEENLQ GSWVELHRSN                                              20

SEQ ID NO: 215       moltype = AA  length = 20
FEATURE              Location/Qualifiers
source               1..20
                     mol_type = protein
                     organism = synthetic construct
SEQUENCE: 215
MSQSGEENLQ GSWVELKFSN                                              20

SEQ ID NO: 216       moltype = AA  length = 20
FEATURE              Location/Qualifiers
source               1..20
                     mol_type = protein
                     organism = synthetic construct
SEQUENCE: 216
CSQSGEENLQ GSWVELHFSN                                              20

SEQ ID NO: 217       moltype = AA  length = 20
FEATURE              Location/Qualifiers
source               1..20
                     mol_type = protein
                     organism = synthetic construct
SEQUENCE: 217
MSQSGEESLQ GSWVELHFSN                                              20

SEQ ID NO: 218       moltype = AA  length = 20
FEATURE              Location/Qualifiers
source               1..20
                     mol_type = protein
                     organism = synthetic construct
SEQUENCE: 218
MSQSGCENLQ GSWVELHFSN                                              20

SEQ ID NO: 219       moltype = AA  length = 20
FEATURE              Location/Qualifiers
source               1..20
                     mol_type = protein
                     organism = synthetic construct
SEQUENCE: 219
MSQSGEENLQ GSWVELHSSN                                              20

SEQ ID NO: 220       moltype = AA  length = 20
FEATURE              Location/Qualifiers
source               1..20
                     mol_type = protein
                     organism = synthetic construct
SEQUENCE: 220
MSQSGEENLQ GSWVELLFSN                                              20
```

```
SEQ ID NO: 221         moltype = AA  length = 20
FEATURE                Location/Qualifiers
source                 1..20
                       mol_type = protein
                       organism = synthetic construct
SEQUENCE: 221
DSQSGEENLQ GSWVELHFSN                                                  20

SEQ ID NO: 222         moltype = AA  length = 20
FEATURE                Location/Qualifiers
source                 1..20
                       mol_type = protein
                       organism = synthetic construct
SEQUENCE: 222
MSQSGEETLQ GSWVELHFSN                                                  20

SEQ ID NO: 223         moltype = AA  length = 20
FEATURE                Location/Qualifiers
source                 1..20
                       mol_type = protein
                       organism = synthetic construct
SEQUENCE: 223
MSQSGDENLQ GSWVELHFSN                                                  20

SEQ ID NO: 224         moltype = AA  length = 20
FEATURE                Location/Qualifiers
source                 1..20
                       mol_type = protein
                       organism = synthetic construct
SEQUENCE: 224
MSQSGEENLQ GSWVELHTSN                                                  20

SEQ ID NO: 225         moltype = AA  length = 20
FEATURE                Location/Qualifiers
source                 1..20
                       mol_type = protein
                       organism = synthetic construct
SEQUENCE: 225
MSQSGEENLQ GSWVELMFSN                                                  20

SEQ ID NO: 226         moltype = AA  length = 20
FEATURE                Location/Qualifiers
source                 1..20
                       mol_type = protein
                       organism = synthetic construct
SEQUENCE: 226
ESQSGEENLQ GSWVELHFSN                                                  20

SEQ ID NO: 227         moltype = AA  length = 20
FEATURE                Location/Qualifiers
source                 1..20
                       mol_type = protein
                       organism = synthetic construct
SEQUENCE: 227
MSQSGEEVLQ GSWVELHFSN                                                  20

SEQ ID NO: 228         moltype = AA  length = 20
FEATURE                Location/Qualifiers
source                 1..20
                       mol_type = protein
                       organism = synthetic construct
SEQUENCE: 228
MSQSGFENLQ GSWVELHFSN                                                  20

SEQ ID NO: 229         moltype = AA  length = 20
FEATURE                Location/Qualifiers
source                 1..20
                       mol_type = protein
                       organism = synthetic construct
SEQUENCE: 229
MSQSGEENLQ GSWVELHVSN                                                  20

SEQ ID NO: 230         moltype = AA  length = 20
FEATURE                Location/Qualifiers
source                 1..20
                       mol_type = protein
                       organism = synthetic construct
SEQUENCE: 230
MSQSGEENLQ GSWVELNFSN                                                  20
```

```
SEQ ID NO: 231         moltype = AA  length = 20
FEATURE                Location/Qualifiers
source                 1..20
                       mol_type = protein
                       organism = synthetic construct
SEQUENCE: 231
FSQSGEENLQ GSWVELHFSN                                                  20

SEQ ID NO: 232         moltype = AA  length = 20
FEATURE                Location/Qualifiers
source                 1..20
                       mol_type = protein
                       organism = synthetic construct
SEQUENCE: 232
MSQSGEEWLQ GSWVELHFSN                                                  20

SEQ ID NO: 233         moltype = AA  length = 20
FEATURE                Location/Qualifiers
source                 1..20
                       mol_type = protein
                       organism = synthetic construct
SEQUENCE: 233
MSQSGGENLQ GSWVELHFSN                                                  20

SEQ ID NO: 234         moltype = AA  length = 20
FEATURE                Location/Qualifiers
source                 1..20
                       mol_type = protein
                       organism = synthetic construct
SEQUENCE: 234
MSQSGEENLQ GSWVELHWSN                                                  20

SEQ ID NO: 235         moltype = AA  length = 20
FEATURE                Location/Qualifiers
source                 1..20
                       mol_type = protein
                       organism = synthetic construct
SEQUENCE: 235
MSQSGEENLQ GSWVELPFSN                                                  20

SEQ ID NO: 236         moltype = AA  length = 20
FEATURE                Location/Qualifiers
source                 1..20
                       mol_type = protein
                       organism = synthetic construct
SEQUENCE: 236
GSQSGEENLQ GSWVELHFSN                                                  20

SEQ ID NO: 237         moltype = AA  length = 20
FEATURE                Location/Qualifiers
source                 1..20
                       mol_type = protein
                       organism = synthetic construct
SEQUENCE: 237
MSQSGEEYLQ GSWVELHFSN                                                  20

SEQ ID NO: 238         moltype = AA  length = 20
FEATURE                Location/Qualifiers
source                 1..20
                       mol_type = protein
                       organism = synthetic construct
SEQUENCE: 238
MSQSGHENLQ GSWVELHFSN                                                  20

SEQ ID NO: 239         moltype = AA  length = 20
FEATURE                Location/Qualifiers
source                 1..20
                       mol_type = protein
                       organism = synthetic construct
SEQUENCE: 239
MSQSGEENLQ GSWVELHYSN                                                  20

SEQ ID NO: 240         moltype = AA  length = 20
FEATURE                Location/Qualifiers
source                 1..20
                       mol_type = protein
                       organism = synthetic construct
```

```
SEQUENCE: 240
MSQSGEENLQ GSWVELQFSN                                                            20

SEQ ID NO: 241         moltype = AA  length = 20
FEATURE                Location/Qualifiers
source                 1..20
                       mol_type = protein
                       organism = synthetic construct
SEQUENCE: 241
HSQSGEENLQ GSWVELHFSN                                                            20

SEQ ID NO: 242         moltype = AA  length = 20
FEATURE                Location/Qualifiers
source                 1..20
                       mol_type = protein
                       organism = synthetic construct
SEQUENCE: 242
MSQSGEENLA GSWVELHFSN                                                            20

SEQ ID NO: 243         moltype = AA  length = 20
FEATURE                Location/Qualifiers
source                 1..20
                       mol_type = protein
                       organism = synthetic construct
SEQUENCE: 243
MSQSGIENLQ GSWVELHFSN                                                            20

SEQ ID NO: 244         moltype = AA  length = 20
FEATURE                Location/Qualifiers
source                 1..20
                       mol_type = protein
                       organism = synthetic construct
SEQUENCE: 244
MSQSGEENLQ ASWVELHFSN                                                            20

SEQ ID NO: 245         moltype = AA  length = 20
FEATURE                Location/Qualifiers
source                 1..20
                       mol_type = protein
                       organism = synthetic construct
SEQUENCE: 245
MSQSGEENLQ GSWVELRFSN                                                            20

SEQ ID NO: 246         moltype = AA  length = 20
FEATURE                Location/Qualifiers
source                 1..20
                       mol_type = protein
                       organism = synthetic construct
SEQUENCE: 246
ISQSGEENLQ GSWVELHFSN                                                            20

SEQ ID NO: 247         moltype = AA  length = 20
FEATURE                Location/Qualifiers
source                 1..20
                       mol_type = protein
                       organism = synthetic construct
SEQUENCE: 247
MSQSGEENLC GSWVELHFSN                                                            20

SEQ ID NO: 248         moltype = AA  length = 20
FEATURE                Location/Qualifiers
source                 1..20
                       mol_type = protein
                       organism = synthetic construct
SEQUENCE: 248
MSQSGKENLQ GSWVELHFSN                                                            20

SEQ ID NO: 249         moltype = AA  length = 20
FEATURE                Location/Qualifiers
source                 1..20
                       mol_type = protein
                       organism = synthetic construct
SEQUENCE: 249
MSQSGEENLQ CSWVELHFSN                                                            20

SEQ ID NO: 250         moltype = AA  length = 20
FEATURE                Location/Qualifiers
```

```
                                -continued source                  1..20
                        mol_type = protein
                        organism = synthetic construct
SEQUENCE: 250
MSQSGEENLQ GSWVELSFSN                                            20

SEQ ID NO: 251          moltype = AA  length = 20
FEATURE                 Location/Qualifiers
source                  1..20
                        mol_type = protein
                        organism = synthetic construct
SEQUENCE: 251
KSQSGEENLQ GSWVELHFSN                                            20

SEQ ID NO: 252          moltype = AA  length = 20
FEATURE                 Location/Qualifiers
source                  1..20
                        mol_type = protein
                        organism = synthetic construct
SEQUENCE: 252
MSQSGEENLD GSWVELHFSN                                            20

SEQ ID NO: 253          moltype = AA  length = 20
FEATURE                 Location/Qualifiers
source                  1..20
                        mol_type = protein
                        organism = synthetic construct
SEQUENCE: 253
MSQSGLENLQ GSWVELHFSN                                            20

SEQ ID NO: 254          moltype = AA  length = 20
FEATURE                 Location/Qualifiers
source                  1..20
                        mol_type = protein
                        organism = synthetic construct
SEQUENCE: 254
MSQSGEENLQ DSWVELHFSN                                            20

SEQ ID NO: 255          moltype = AA  length = 20
FEATURE                 Location/Qualifiers
source                  1..20
                        mol_type = protein
                        organism = synthetic construct
SEQUENCE: 255
MSQSGEENLQ GSWVELTFSN                                            20

SEQ ID NO: 256          moltype = AA  length = 20
FEATURE                 Location/Qualifiers
source                  1..20
                        mol_type = protein
                        organism = synthetic construct
SEQUENCE: 256
LSQSGEENLQ GSWVELHFSN                                            20

SEQ ID NO: 257          moltype = AA  length = 20
FEATURE                 Location/Qualifiers
source                  1..20
                        mol_type = protein
                        organism = synthetic construct
SEQUENCE: 257
MSQSGEENLE GSWVELHFSN                                            20

SEQ ID NO: 258          moltype = AA  length = 20
FEATURE                 Location/Qualifiers
source                  1..20
                        mol_type = protein
                        organism = synthetic construct
SEQUENCE: 258
MSQSGMENLQ GSWVELHFSN                                            20

SEQ ID NO: 259          moltype = AA  length = 20
FEATURE                 Location/Qualifiers
source                  1..20
                        mol_type = protein
                        organism = synthetic construct
SEQUENCE: 259
MSQSGEENLQ ESWVELHFSN                                            20

SEQ ID NO: 260          moltype = AA  length = 20
```

```
                        FEATURE                Location/Qualifiers
                        source                 1..20
                                               mol_type = protein
                                               organism = synthetic construct
SEQUENCE: 260
MSQSGEENLQ GSWVELVFSN                                                            20

SEQ ID NO: 261          moltype = AA   length = 20
FEATURE                 Location/Qualifiers
source                  1..20
                        mol_type = protein
                        organism = synthetic construct
SEQUENCE: 261
NSQSGEENLQ GSWVELHFSN                                                            20

SEQ ID NO: 262          moltype = AA   length = 20
FEATURE                 Location/Qualifiers
source                  1..20
                        mol_type = protein
                        organism = synthetic construct
SEQUENCE: 262
MSQSGEENLF GSWVELHFSN                                                            20

SEQ ID NO: 263          moltype = AA   length = 20
FEATURE                 Location/Qualifiers
source                  1..20
                        mol_type = protein
                        organism = synthetic construct
SEQUENCE: 263
MSQSGNENLQ GSWVELHFSN                                                            20

SEQ ID NO: 264          moltype = AA   length = 20
FEATURE                 Location/Qualifiers
source                  1..20
                        mol_type = protein
                        organism = synthetic construct
SEQUENCE: 264
MSQSGEENLQ FSWVELHFSN                                                            20

SEQ ID NO: 265          moltype = AA   length = 20
FEATURE                 Location/Qualifiers
source                  1..20
                        mol_type = protein
                        organism = synthetic construct
SEQUENCE: 265
MSQSGEENLQ GSWVELWFSN                                                            20

SEQ ID NO: 266          moltype = AA   length = 20
FEATURE                 Location/Qualifiers
source                  1..20
                        mol_type = protein
                        organism = synthetic construct
SEQUENCE: 266
PSQSGEENLQ GSWVELHFSN                                                            20

SEQ ID NO: 267          moltype = AA   length = 20
FEATURE                 Location/Qualifiers
source                  1..20
                        mol_type = protein
                        organism = synthetic construct
SEQUENCE: 267
MSQSGEENLG GSWVELHFSN                                                            20

SEQ ID NO: 268          moltype = AA   length = 20
FEATURE                 Location/Qualifiers
source                  1..20
                        mol_type = protein
                        organism = synthetic construct
SEQUENCE: 268
MSQSGPENLQ GSWVELHFSN                                                            20

SEQ ID NO: 269          moltype = AA   length = 20
FEATURE                 Location/Qualifiers
source                  1..20
                        mol_type = protein
                        organism = synthetic construct
SEQUENCE: 269
MSQSGEENLQ HSWVELHFSN                                                            20
```

```
SEQ ID NO: 270         moltype = AA  length = 20
FEATURE                Location/Qualifiers
source                 1..20
                       mol_type = protein
                       organism = synthetic construct
SEQUENCE: 270
MSQSGEENLQ GSWVELYFSN                                                     20

SEQ ID NO: 271         moltype = AA  length = 20
FEATURE                Location/Qualifiers
source                 1..20
                       mol_type = protein
                       organism = synthetic construct
SEQUENCE: 271
QSQSGEENLQ GSWVELHFSN                                                     20

SEQ ID NO: 272         moltype = AA  length = 20
FEATURE                Location/Qualifiers
source                 1..20
                       mol_type = protein
                       organism = synthetic construct
SEQUENCE: 272
MSQSGEENLH GSWVELHFSN                                                     20

SEQ ID NO: 273         moltype = AA  length = 20
FEATURE                Location/Qualifiers
source                 1..20
                       mol_type = protein
                       organism = synthetic construct
SEQUENCE: 273
MSQSGQENLQ GSWVELHFSN                                                     20

SEQ ID NO: 274         moltype = AA  length = 20
FEATURE                Location/Qualifiers
source                 1..20
                       mol_type = protein
                       organism = synthetic construct
SEQUENCE: 274
MSQSGEENLQ ISWVELHFSN                                                     20

SEQ ID NO: 275         moltype = AA  length = 20
FEATURE                Location/Qualifiers
source                 1..20
                       mol_type = protein
                       organism = synthetic construct
SEQUENCE: 275
MSQSGEENLQ GSWVEAHFSN                                                     20

SEQ ID NO: 276         moltype = AA  length = 20
FEATURE                Location/Qualifiers
source                 1..20
                       mol_type = protein
                       organism = synthetic construct
SEQUENCE: 276
RSQSGEENLQ GSWVELHFSN                                                     20

SEQ ID NO: 277         moltype = AA  length = 20
FEATURE                Location/Qualifiers
source                 1..20
                       mol_type = protein
                       organism = synthetic construct
SEQUENCE: 277
MSQSGEENLI GSWVELHFSN                                                     20

SEQ ID NO: 278         moltype = AA  length = 20
FEATURE                Location/Qualifiers
source                 1..20
                       mol_type = protein
                       organism = synthetic construct
SEQUENCE: 278
MSQSGRENLQ GSWVELHFSN                                                     20

SEQ ID NO: 279         moltype = AA  length = 20
FEATURE                Location/Qualifiers
source                 1..20
                       mol_type = protein
                       organism = synthetic construct
SEQUENCE: 279
MSQSGEENLQ KSWVELHFSN                                                     20
```

| | | |
|---|---|---|
| SEQ ID NO: 280<br>FEATURE<br>source | moltype = AA length = 20<br>Location/Qualifiers<br>1..20<br>mol_type = protein<br>organism = synthetic construct | |
| SEQUENCE: 280<br>MSQSGEENLQ GSWVECHFSN | | 20 |
| SEQ ID NO: 281<br>FEATURE<br>source | moltype = AA length = 20<br>Location/Qualifiers<br>1..20<br>mol_type = protein<br>organism = synthetic construct | |
| SEQUENCE: 281<br>SSQSGEENLQ GSWVELHFSN | | 20 |
| SEQ ID NO: 282<br>FEATURE<br>source | moltype = AA length = 20<br>Location/Qualifiers<br>1..20<br>mol_type = protein<br>organism = synthetic construct | |
| SEQUENCE: 282<br>MSQSGEENLK GSWVELHFSN | | 20 |
| SEQ ID NO: 283<br>FEATURE<br>source | moltype = AA length = 20<br>Location/Qualifiers<br>1..20<br>mol_type = protein<br>organism = synthetic construct | |
| SEQUENCE: 283<br>MSQSGSENLQ GSWVELHFSN | | 20 |
| SEQ ID NO: 284<br>FEATURE<br>source | moltype = AA length = 20<br>Location/Qualifiers<br>1..20<br>mol_type = protein<br>organism = synthetic construct | |
| SEQUENCE: 284<br>MSQSGEENLQ LSWVELHFSN | | 20 |
| SEQ ID NO: 285<br>FEATURE<br>source | moltype = AA length = 20<br>Location/Qualifiers<br>1..20<br>mol_type = protein<br>organism = synthetic construct | |
| SEQUENCE: 285<br>MSQSGEENLQ GSWVEDHFSN | | 20 |
| SEQ ID NO: 286<br>FEATURE<br>source | moltype = AA length = 20<br>Location/Qualifiers<br>1..20<br>mol_type = protein<br>organism = synthetic construct | |
| SEQUENCE: 286<br>TSQSGEENLQ GSWVELHFSN | | 20 |
| SEQ ID NO: 287<br>FEATURE<br>source | moltype = AA length = 20<br>Location/Qualifiers<br>1..20<br>mol_type = protein<br>organism = synthetic construct | |
| SEQUENCE: 287<br>MSQSGEENLL GSWVELHFSN | | 20 |
| SEQ ID NO: 288<br>FEATURE<br>source | moltype = AA length = 20<br>Location/Qualifiers<br>1..20<br>mol_type = protein<br>organism = synthetic construct | |
| SEQUENCE: 288<br>MSQSGTENLQ GSWVELHFSN | | 20 |
| SEQ ID NO: 289<br>FEATURE<br>source | moltype = AA length = 20<br>Location/Qualifiers<br>1..20<br>mol_type = protein<br>organism = synthetic construct | |

```
SEQUENCE: 289
MSQSGEENLQ MSWVELHFSN                                                  20

SEQ ID NO: 290          moltype = AA  length = 20
FEATURE                 Location/Qualifiers
source                  1..20
                        mol_type = protein
                        organism = synthetic construct
SEQUENCE: 290
MSQSGEENLQ GSWVEEHFSN                                                  20

SEQ ID NO: 291          moltype = AA  length = 20
FEATURE                 Location/Qualifiers
source                  1..20
                        mol_type = protein
                        organism = synthetic construct
SEQUENCE: 291
VSQSGEENLQ GSWVELHFSN                                                  20

SEQ ID NO: 292          moltype = AA  length = 20
FEATURE                 Location/Qualifiers
source                  1..20
                        mol_type = protein
                        organism = synthetic construct
SEQUENCE: 292
MSQSGEENLM GSWVELHFSN                                                  20

SEQ ID NO: 293          moltype = AA  length = 20
FEATURE                 Location/Qualifiers
source                  1..20
                        mol_type = protein
                        organism = synthetic construct
SEQUENCE: 293
MSQSGVENLQ GSWVELHFSN                                                  20

SEQ ID NO: 294          moltype = AA  length = 20
FEATURE                 Location/Qualifiers
source                  1..20
                        mol_type = protein
                        organism = synthetic construct
SEQUENCE: 294
MSQSGEENLQ NSWVELHFSN                                                  20

SEQ ID NO: 295          moltype = AA  length = 20
FEATURE                 Location/Qualifiers
source                  1..20
                        mol_type = protein
                        organism = synthetic construct
SEQUENCE: 295
MSQSGEENLQ GSWVEFHFSN                                                  20

SEQ ID NO: 296          moltype = AA  length = 20
FEATURE                 Location/Qualifiers
source                  1..20
                        mol_type = protein
                        organism = synthetic construct
SEQUENCE: 296
WSQSGEENLQ GSWVELHFSN                                                  20

SEQ ID NO: 297          moltype = AA  length = 20
FEATURE                 Location/Qualifiers
source                  1..20
                        mol_type = protein
                        organism = synthetic construct
SEQUENCE: 297
MSQSGEENLN GSWVELHFSN                                                  20

SEQ ID NO: 298          moltype = AA  length = 20
FEATURE                 Location/Qualifiers
source                  1..20
                        mol_type = protein
                        organism = synthetic construct
SEQUENCE: 298
MSQSGWENLQ GSWVELHFSN                                                  20

SEQ ID NO: 299          moltype = AA  length = 20
FEATURE                 Location/Qualifiers
```

```
source                      1..20
                            mol_type = protein
                            organism = synthetic construct
SEQUENCE: 299
MSQSGEENLQ PSWVELHFSN                                                        20

SEQ ID NO: 300              moltype = AA  length = 20
FEATURE                     Location/Qualifiers
source                      1..20
                            mol_type = protein
                            organism = synthetic construct
SEQUENCE: 300
MSQSGEENLQ GSWVEGHFSN                                                        20

SEQ ID NO: 301              moltype = AA  length = 20
FEATURE                     Location/Qualifiers
source                      1..20
                            mol_type = protein
                            organism = synthetic construct
SEQUENCE: 301
YSQSGEENLQ GSWVELHFSN                                                        20

SEQ ID NO: 302              moltype = AA  length = 20
FEATURE                     Location/Qualifiers
source                      1..20
                            mol_type = protein
                            organism = synthetic construct
SEQUENCE: 302
MSQSGEENLP GSWVELHFSN                                                        20

SEQ ID NO: 303              moltype = AA  length = 20
FEATURE                     Location/Qualifiers
source                      1..20
                            mol_type = protein
                            organism = synthetic construct
SEQUENCE: 303
MSQSGYENLQ GSWVELHFSN                                                        20

SEQ ID NO: 304              moltype = AA  length = 20
FEATURE                     Location/Qualifiers
source                      1..20
                            mol_type = protein
                            organism = synthetic construct
SEQUENCE: 304
MSQSGEENLQ QSWVELHFSN                                                        20

SEQ ID NO: 305              moltype = AA  length = 20
FEATURE                     Location/Qualifiers
source                      1..20
                            mol_type = protein
                            organism = synthetic construct
SEQUENCE: 305
MSQSGEENLQ GSWVEHHFSN                                                        20

SEQ ID NO: 306              moltype = AA  length = 20
FEATURE                     Location/Qualifiers
source                      1..20
                            mol_type = protein
                            organism = synthetic construct
SEQUENCE: 306
MSQSGEENLQ GSWVELHFSA                                                        20

SEQ ID NO: 307              moltype = AA  length = 20
FEATURE                     Location/Qualifiers
source                      1..20
                            mol_type = protein
                            organism = synthetic construct
SEQUENCE: 307
MSQSGEENLR GSWVELHFSN                                                        20

SEQ ID NO: 308              moltype = AA  length = 20
FEATURE                     Location/Qualifiers
source                      1..20
                            mol_type = protein
                            organism = synthetic construct
SEQUENCE: 308
MSQSGEANLQ GSWVELHFSN                                                        20

SEQ ID NO: 309              moltype = AA  length = 20
```

```
                         -continued

FEATURE                  Location/Qualifiers
source                   1..20
                         mol_type = protein
                         organism = synthetic construct
SEQUENCE: 309
MSQSGEENLQ RSWVELHFSN                                              20

SEQ ID NO: 310           moltype = AA   length = 20
FEATURE                  Location/Qualifiers
source                   1..20
                         mol_type = protein
                         organism = synthetic construct
SEQUENCE: 310
MSQSGEENLQ GSWVEIHFSN                                              20

SEQ ID NO: 311           moltype = AA   length = 20
FEATURE                  Location/Qualifiers
source                   1..20
                         mol_type = protein
                         organism = synthetic construct
SEQUENCE: 311
MSQSGEENLQ GSWVELHFSC                                              20

SEQ ID NO: 312           moltype = AA   length = 20
FEATURE                  Location/Qualifiers
source                   1..20
                         mol_type = protein
                         organism = synthetic construct
SEQUENCE: 312
MSQSGEENLS GSWVELHFSN                                              20

SEQ ID NO: 313           moltype = AA   length = 20
FEATURE                  Location/Qualifiers
source                   1..20
                         mol_type = protein
                         organism = synthetic construct
SEQUENCE: 313
MSQSGECNLQ GSWVELHFSN                                              20

SEQ ID NO: 314           moltype = AA   length = 20
FEATURE                  Location/Qualifiers
source                   1..20
                         mol_type = protein
                         organism = synthetic construct
SEQUENCE: 314
MSQSGEENLQ SSWVELHFSN                                              20

SEQ ID NO: 315           moltype = AA   length = 20
FEATURE                  Location/Qualifiers
source                   1..20
                         mol_type = protein
                         organism = synthetic construct
SEQUENCE: 315
MSQSGEENLQ GSWVEKHFSN                                              20

SEQ ID NO: 316           moltype = AA   length = 20
FEATURE                  Location/Qualifiers
source                   1..20
                         mol_type = protein
                         organism = synthetic construct
SEQUENCE: 316
MSQSGEENLQ GSWVELHFSD                                              20

SEQ ID NO: 317           moltype = AA   length = 20
FEATURE                  Location/Qualifiers
source                   1..20
                         mol_type = protein
                         organism = synthetic construct
SEQUENCE: 317
MSQSGEENLT GSWVELHFSN                                              20

SEQ ID NO: 318           moltype = AA   length = 20
FEATURE                  Location/Qualifiers
source                   1..20
                         mol_type = protein
                         organism = synthetic construct
SEQUENCE: 318
MSQSGEDNLQ GSWVELHFSN                                              20
```

-continued

```
SEQ ID NO: 319            moltype = AA  length = 20
FEATURE                   Location/Qualifiers
source                    1..20
                          mol_type = protein
                          organism = synthetic construct
SEQUENCE: 319
MSQSGEENLQ TSWVELHFSN                                                   20

SEQ ID NO: 320            moltype = AA  length = 20
FEATURE                   Location/Qualifiers
source                    1..20
                          mol_type = protein
                          organism = synthetic construct
SEQUENCE: 320
MSQSGEENLQ GSWVEMHFSN                                                   20

SEQ ID NO: 321            moltype = AA  length = 20
FEATURE                   Location/Qualifiers
source                    1..20
                          mol_type = protein
                          organism = synthetic construct
SEQUENCE: 321
MSQSGEENLQ GSWVELHFSE                                                   20

SEQ ID NO: 322            moltype = AA  length = 20
FEATURE                   Location/Qualifiers
source                    1..20
                          mol_type = protein
                          organism = synthetic construct
SEQUENCE: 322
MSQSGEENLV GSWVELHFSN                                                   20

SEQ ID NO: 323            moltype = AA  length = 20
FEATURE                   Location/Qualifiers
source                    1..20
                          mol_type = protein
                          organism = synthetic construct
SEQUENCE: 323
MSQSGEFNLQ GSWVELHFSN                                                   20

SEQ ID NO: 324            moltype = AA  length = 20
FEATURE                   Location/Qualifiers
source                    1..20
                          mol_type = protein
                          organism = synthetic construct
SEQUENCE: 324
MSQSGEENLQ VSWVELHFSN                                                   20

SEQ ID NO: 325            moltype = AA  length = 20
FEATURE                   Location/Qualifiers
source                    1..20
                          mol_type = protein
                          organism = synthetic construct
SEQUENCE: 325
MSQSGEENLQ GSWVENHFSN                                                   20

SEQ ID NO: 326            moltype = AA  length = 20
FEATURE                   Location/Qualifiers
source                    1..20
                          mol_type = protein
                          organism = synthetic construct
SEQUENCE: 326
MSQSGEENLQ GSWVELHFSF                                                   20

SEQ ID NO: 327            moltype = AA  length = 20
FEATURE                   Location/Qualifiers
source                    1..20
                          mol_type = protein
                          organism = synthetic construct
SEQUENCE: 327
MSQSGEENLW GSWVELHFSN                                                   20

SEQ ID NO: 328            moltype = AA  length = 20
FEATURE                   Location/Qualifiers
source                    1..20
                          mol_type = protein
                          organism = synthetic construct
SEQUENCE: 328
MSQSGEGNLQ GSWVELHFSN                                                   20
```

```
SEQ ID NO: 329         moltype = AA  length = 20
FEATURE                Location/Qualifiers
source                 1..20
                       mol_type = protein
                       organism = synthetic construct
SEQUENCE: 329
MSQSGEENLQ WSWVELHFSN                                              20

SEQ ID NO: 330         moltype = AA  length = 20
FEATURE                Location/Qualifiers
source                 1..20
                       mol_type = protein
                       organism = synthetic construct
SEQUENCE: 330
MSQSGEENLQ GSWVEPHFSN                                              20

SEQ ID NO: 331         moltype = AA  length = 20
FEATURE                Location/Qualifiers
source                 1..20
                       mol_type = protein
                       organism = synthetic construct
SEQUENCE: 331
MSQSGEENLQ GSWVELHFSG                                              20

SEQ ID NO: 332         moltype = AA  length = 20
FEATURE                Location/Qualifiers
source                 1..20
                       mol_type = protein
                       organism = synthetic construct
SEQUENCE: 332
MSQSGEENLY GSWVELHFSN                                              20

SEQ ID NO: 333         moltype = AA  length = 20
FEATURE                Location/Qualifiers
source                 1..20
                       mol_type = protein
                       organism = synthetic construct
SEQUENCE: 333
MSQSGEHNLQ GSWVELHFSN                                              20

SEQ ID NO: 334         moltype = AA  length = 20
FEATURE                Location/Qualifiers
source                 1..20
                       mol_type = protein
                       organism = synthetic construct
SEQUENCE: 334
MSQSGEENLQ YSWVELHFSN                                              20

SEQ ID NO: 335         moltype = AA  length = 20
FEATURE                Location/Qualifiers
source                 1..20
                       mol_type = protein
                       organism = synthetic construct
SEQUENCE: 335
MSQSGEENLQ GSWVEQHFSN                                              20

SEQ ID NO: 336         moltype = AA  length = 20
FEATURE                Location/Qualifiers
source                 1..20
                       mol_type = protein
                       organism = synthetic construct
SEQUENCE: 336
MSQSGEENLQ GSWVELHFSH                                              20

SEQ ID NO: 337         moltype = AA  length = 20
FEATURE                Location/Qualifiers
source                 1..20
                       mol_type = protein
                       organism = synthetic construct
SEQUENCE: 337
MSASGEENLQ GSWVELHFSN                                              20

SEQ ID NO: 338         moltype = AA  length = 20
FEATURE                Location/Qualifiers
source                 1..20
                       mol_type = protein
                       organism = synthetic construct
```

```
SEQUENCE: 338
MSQSGEINLQ GSWVELHFSN                                                          20

SEQ ID NO: 339          moltype = AA  length = 20
FEATURE                 Location/Qualifiers
source                  1..20
                        mol_type = protein
                        organism = synthetic construct
SEQUENCE: 339
MSQSAEENLQ GSWVELHFSN                                                          20

SEQ ID NO: 340          moltype = AA  length = 20
FEATURE                 Location/Qualifiers
source                  1..20
                        mol_type = protein
                        organism = synthetic construct
SEQUENCE: 340
MSQSGEENLQ GSWVERHFSN                                                          20

SEQ ID NO: 341          moltype = AA  length = 20
FEATURE                 Location/Qualifiers
source                  1..20
                        mol_type = protein
                        organism = synthetic construct
SEQUENCE: 341
MSQSGEENLQ GSWVELHFSI                                                          20

SEQ ID NO: 342          moltype = AA  length = 20
FEATURE                 Location/Qualifiers
source                  1..20
                        mol_type = protein
                        organism = synthetic construct
SEQUENCE: 342
MSCSGEENLQ GSWVELHFSN                                                          20

SEQ ID NO: 343          moltype = AA  length = 20
FEATURE                 Location/Qualifiers
source                  1..20
                        mol_type = protein
                        organism = synthetic construct
SEQUENCE: 343
MSQSGEKNLQ GSWVELHFSN                                                          20

SEQ ID NO: 344          moltype = AA  length = 20
FEATURE                 Location/Qualifiers
source                  1..20
                        mol_type = protein
                        organism = synthetic construct
SEQUENCE: 344
MSQSCEENLQ GSWVELHFSN                                                          20

SEQ ID NO: 345          moltype = AA  length = 20
FEATURE                 Location/Qualifiers
source                  1..20
                        mol_type = protein
                        organism = synthetic construct
SEQUENCE: 345
MSQSGEENLQ GSWVESHFSN                                                          20

SEQ ID NO: 346          moltype = AA  length = 20
FEATURE                 Location/Qualifiers
source                  1..20
                        mol_type = protein
                        organism = synthetic construct
SEQUENCE: 346
MSQSGEENLQ GSWVELHFSK                                                          20

SEQ ID NO: 347          moltype = AA  length = 20
FEATURE                 Location/Qualifiers
source                  1..20
                        mol_type = protein
                        organism = synthetic construct
SEQUENCE: 347
MSDSGEENLQ GSWVELHFSN                                                          20

SEQ ID NO: 348          moltype = AA  length = 20
FEATURE                 Location/Qualifiers
```

-continued

```
source                    1..20
                          mol_type = protein
                          organism = synthetic construct
SEQUENCE: 348
MSQSGELNLQ GSWVELHFSN                                                       20

SEQ ID NO: 349            moltype = AA  length = 20
FEATURE                   Location/Qualifiers
source                    1..20
                          mol_type = protein
                          organism = synthetic construct
SEQUENCE: 349
MSQSDEENLQ GSWVELHFSN                                                       20

SEQ ID NO: 350            moltype = AA  length = 20
FEATURE                   Location/Qualifiers
source                    1..20
                          mol_type = protein
                          organism = synthetic construct
SEQUENCE: 350
MSQSGEENLQ GSWVETHFSN                                                       20

SEQ ID NO: 351            moltype = AA  length = 20
FEATURE                   Location/Qualifiers
source                    1..20
                          mol_type = protein
                          organism = synthetic construct
SEQUENCE: 351
MSQSGEENLQ GSWVELHFSL                                                       20

SEQ ID NO: 352            moltype = AA  length = 20
FEATURE                   Location/Qualifiers
source                    1..20
                          mol_type = protein
                          organism = synthetic construct
SEQUENCE: 352
MSESGEENLQ GSWVELHFSN                                                       20

SEQ ID NO: 353            moltype = AA  length = 20
FEATURE                   Location/Qualifiers
source                    1..20
                          mol_type = protein
                          organism = synthetic construct
SEQUENCE: 353
MSQSGEMNLQ GSWVELHFSN                                                       20

SEQ ID NO: 354            moltype = AA  length = 20
FEATURE                   Location/Qualifiers
source                    1..20
                          mol_type = protein
                          organism = synthetic construct
SEQUENCE: 354
MSQSEEENLQ GSWVELHFSN                                                       20

SEQ ID NO: 355            moltype = AA  length = 20
FEATURE                   Location/Qualifiers
source                    1..20
                          mol_type = protein
                          organism = synthetic construct
SEQUENCE: 355
MSQSGEENLQ GSWVEVHFSN                                                       20

SEQ ID NO: 356            moltype = AA  length = 20
FEATURE                   Location/Qualifiers
source                    1..20
                          mol_type = protein
                          organism = synthetic construct
SEQUENCE: 356
MSQSGEENLQ GSWVELHFSM                                                       20

SEQ ID NO: 357            moltype = AA  length = 20
FEATURE                   Location/Qualifiers
source                    1..20
                          mol_type = protein
                          organism = synthetic construct
SEQUENCE: 357
MSFSGEENLQ GSWVELHFSN                                                       20

SEQ ID NO: 358            moltype = AA  length = 20
```

```
FEATURE                  Location/Qualifiers
source                   1..20
                         mol_type = protein
                         organism = synthetic construct
SEQUENCE: 358
MSQSGENNLQ GSWVELHFSN                                              20

SEQ ID NO: 359           moltype = AA  length = 20
FEATURE                  Location/Qualifiers
source                   1..20
                         mol_type = protein
                         organism = synthetic construct
SEQUENCE: 359
MSLSGEENLQ GSWVELHFSN                                              20

SEQ ID NO: 360           moltype = AA  length = 20
FEATURE                  Location/Qualifiers
source                   1..20
                         mol_type = protein
                         organism = synthetic construct
SEQUENCE: 360
MSQSGEENLQ GSWVELHFCN                                              20

SEQ ID NO: 361           moltype = AA  length = 20
FEATURE                  Location/Qualifiers
source                   1..20
                         mol_type = protein
                         organism = synthetic construct
SEQUENCE: 361
MLQSGEENLQ GSWVELHFSN                                              20

SEQ ID NO: 362           moltype = AA  length = 20
FEATURE                  Location/Qualifiers
source                   1..20
                         mol_type = protein
                         organism = synthetic construct
SEQUENCE: 362
MSQYGEENLQ GSWVELHFSN                                              20

SEQ ID NO: 363           moltype = AA  length = 20
FEATURE                  Location/Qualifiers
source                   1..20
                         mol_type = protein
                         organism = synthetic construct
SEQUENCE: 363
MSQSGEPNLQ GSWVELHFSN                                              20

SEQ ID NO: 364           moltype = AA  length = 20
FEATURE                  Location/Qualifiers
source                   1..20
                         mol_type = protein
                         organism = synthetic construct
SEQUENCE: 364
MSMSGEENLQ GSWVELHFSN                                              20

SEQ ID NO: 365           moltype = AA  length = 20
FEATURE                  Location/Qualifiers
source                   1..20
                         mol_type = protein
                         organism = synthetic construct
SEQUENCE: 365
MSQSGEENLQ GSWVELHFDN                                              20

SEQ ID NO: 366           moltype = AA  length = 20
FEATURE                  Location/Qualifiers
source                   1..20
                         mol_type = protein
                         organism = synthetic construct
SEQUENCE: 366
MMQSGEENLQ GSWVELHFSN                                              20

SEQ ID NO: 367           moltype = AA  length = 20
FEATURE                  Location/Qualifiers
source                   1..20
                         mol_type = protein
                         organism = synthetic construct
SEQUENCE: 367
MSQSGEENLQ GSWAELHFSN                                              20
```

```
SEQ ID NO: 368           moltype = AA   length = 20
FEATURE                  Location/Qualifiers
source                   1..20
                         mol_type = protein
                         organism = synthetic construct
SEQUENCE: 368
MSQSGEQNLQ GSWVELHFSN                                                    20

SEQ ID NO: 369           moltype = AA   length = 20
FEATURE                  Location/Qualifiers
source                   1..20
                         mol_type = protein
                         organism = synthetic construct
SEQUENCE: 369
MSNSGEENLQ GSWVELHFSN                                                    20

SEQ ID NO: 370           moltype = AA   length = 20
FEATURE                  Location/Qualifiers
source                   1..20
                         mol_type = protein
                         organism = synthetic construct
SEQUENCE: 370
MSQSGEENLQ GSWVELHFEN                                                    20

SEQ ID NO: 371           moltype = AA   length = 20
FEATURE                  Location/Qualifiers
source                   1..20
                         mol_type = protein
                         organism = synthetic construct
SEQUENCE: 371
MNQSGEENLQ GSWVELHFSN                                                    20

SEQ ID NO: 372           moltype = AA   length = 20
FEATURE                  Location/Qualifiers
source                   1..20
                         mol_type = protein
                         organism = synthetic construct
SEQUENCE: 372
MSQSGEENLQ GSWCELHFSN                                                    20

SEQ ID NO: 373           moltype = AA   length = 20
FEATURE                  Location/Qualifiers
source                   1..20
                         mol_type = protein
                         organism = synthetic construct
SEQUENCE: 373
MSQSFEENLQ GSWVELHFSN                                                    20

SEQ ID NO: 374           moltype = AA   length = 20
FEATURE                  Location/Qualifiers
source                   1..20
                         mol_type = protein
                         organism = synthetic construct
SEQUENCE: 374
MSPSGEENLQ GSWVELHFSN                                                    20

SEQ ID NO: 375           moltype = AA   length = 20
FEATURE                  Location/Qualifiers
source                   1..20
                         mol_type = protein
                         organism = synthetic construct
SEQUENCE: 375
MSQSGEENLQ GSWVELHFFN                                                    20

SEQ ID NO: 376           moltype = AA   length = 20
FEATURE                  Location/Qualifiers
source                   1..20
                         mol_type = protein
                         organism = synthetic construct
SEQUENCE: 376
MPQSGEENLQ GSWVELHFSN                                                    20

SEQ ID NO: 377           moltype = AA   length = 20
FEATURE                  Location/Qualifiers
source                   1..20
                         mol_type = protein
                         organism = synthetic construct
SEQUENCE: 377
MSQSGEENLQ GSWRELHFSN                                                    20
```

| | | |
|---|---|---|
| SEQ ID NO: 378<br>FEATURE<br>source | moltype = AA  length = 20<br>Location/Qualifiers<br>1..20<br>mol_type = protein<br>organism = synthetic construct | |
| SEQUENCE: 378<br>MSQSHEENLQ GSWVELHFSN | | 20 |
| SEQ ID NO: 379<br>FEATURE<br>source | moltype = AA  length = 20<br>Location/Qualifiers<br>1..20<br>mol_type = protein<br>organism = synthetic construct | |
| SEQUENCE: 379<br>MSRSGEENLQ GSWVELHFSN | | 20 |
| SEQ ID NO: 380<br>FEATURE<br>source | moltype = AA  length = 20<br>Location/Qualifiers<br>1..20<br>mol_type = protein<br>organism = synthetic construct | |
| SEQUENCE: 380<br>MSQSGEENLQ GSWVELHFGN | | 20 |
| SEQ ID NO: 381<br>FEATURE<br>source | moltype = AA  length = 20<br>Location/Qualifiers<br>1..20<br>mol_type = protein<br>organism = synthetic construct | |
| SEQUENCE: 381<br>MQQSGEENLQ GSWVELHFSN | | 20 |
| SEQ ID NO: 382<br>FEATURE<br>source | moltype = AA  length = 20<br>Location/Qualifiers<br>1..20<br>mol_type = protein<br>organism = synthetic construct | |
| SEQUENCE: 382<br>MSQSGEENLQ GSWSELHFSN | | 20 |
| SEQ ID NO: 383<br>FEATURE<br>source | moltype = AA  length = 20<br>Location/Qualifiers<br>1..20<br>mol_type = protein<br>organism = synthetic construct | |
| SEQUENCE: 383<br>MSQSIEENLQ GSWVELHFSN | | 20 |
| SEQ ID NO: 384<br>FEATURE<br>source | moltype = AA  length = 20<br>Location/Qualifiers<br>1..20<br>mol_type = protein<br>organism = synthetic construct | |
| SEQUENCE: 384<br>MSSSGEENLQ GSWVELHFSN | | 20 |
| SEQ ID NO: 385<br>FEATURE<br>source | moltype = AA  length = 20<br>Location/Qualifiers<br>1..20<br>mol_type = protein<br>organism = synthetic construct | |
| SEQUENCE: 385<br>MSQSGEENLQ GSWVELHFHN | | 20 |
| SEQ ID NO: 386<br>FEATURE<br>source | moltype = AA  length = 20<br>Location/Qualifiers<br>1..20<br>mol_type = protein<br>organism = synthetic construct | |
| SEQUENCE: 386<br>MRQSGEENLQ GSWVELHFSN | | 20 |
| SEQ ID NO: 387<br>FEATURE<br>source | moltype = AA  length = 20<br>Location/Qualifiers<br>1..20<br>mol_type = protein<br>organism = synthetic construct | |

```
SEQUENCE: 387
MSQSGEENLQ GSWTELHFSN                                                    20

SEQ ID NO: 388          moltype = AA  length = 20
FEATURE                 Location/Qualifiers
source                  1..20
                        mol_type = protein
                        organism = synthetic construct
SEQUENCE: 388
MSQSGEENLQ GSWVEWHFSN                                                    20

SEQ ID NO: 389          moltype = AA  length = 20
FEATURE                 Location/Qualifiers
source                  1..20
                        mol_type = protein
                        organism = synthetic construct
SEQUENCE: 389
MSVSGEENLQ GSWVELHFSN                                                    20

SEQ ID NO: 390          moltype = AA  length = 20
FEATURE                 Location/Qualifiers
source                  1..20
                        mol_type = protein
                        organism = synthetic construct
SEQUENCE: 390
MSQSGEENLQ GSWVELHFIN                                                    20

SEQ ID NO: 391          moltype = AA  length = 20
FEATURE                 Location/Qualifiers
source                  1..20
                        mol_type = protein
                        organism = synthetic construct
SEQUENCE: 391
MSQKGEENLQ GSWVELHFSN                                                    20

SEQ ID NO: 392          moltype = AA  length = 20
FEATURE                 Location/Qualifiers
source                  1..20
                        mol_type = protein
                        organism = synthetic construct
SEQUENCE: 392
MSQSGEENLQ GSWWELHFSN                                                    20

SEQ ID NO: 393          moltype = AA  length = 20
FEATURE                 Location/Qualifiers
source                  1..20
                        mol_type = protein
                        organism = synthetic construct
SEQUENCE: 393
MSQSGEENLQ GSWVEYHFSN                                                    20

SEQ ID NO: 394          moltype = AA  length = 20
FEATURE                 Location/Qualifiers
source                  1..20
                        mol_type = protein
                        organism = synthetic construct
SEQUENCE: 394
MSWSGEENLQ GSWVELHFSN                                                    20

SEQ ID NO: 395          moltype = AA  length = 20
FEATURE                 Location/Qualifiers
source                  1..20
                        mol_type = protein
                        organism = synthetic construct
SEQUENCE: 395
MSQSGEENLQ GSWVELHFKN                                                    20

SEQ ID NO: 396          moltype = AA  length = 20
FEATURE                 Location/Qualifiers
source                  1..20
                        mol_type = protein
                        organism = synthetic construct
SEQUENCE: 396
MSQLGEENLQ GSWVELHFSN                                                    20

SEQ ID NO: 397          moltype = AA  length = 20
FEATURE                 Location/Qualifiers
```

```
                           -continued source                  1..20
                        mol_type = protein
                        organism = synthetic construct
SEQUENCE: 397
MSQSGEENLQ GSWYELHFSN                                         20

SEQ ID NO: 398          moltype = AA   length = 20
FEATURE                 Location/Qualifiers
source                  1..20
                        mol_type = protein
                        organism = synthetic construct
SEQUENCE: 398
MSQSGEENAQ GSWVELHFSN                                         20

SEQ ID NO: 399          moltype = AA   length = 20
FEATURE                 Location/Qualifiers
source                  1..20
                        mol_type = protein
                        organism = synthetic construct
SEQUENCE: 399
MSYSGEENLQ GSWVELHFSN                                         20

SEQ ID NO: 400          moltype = AA   length = 20
FEATURE                 Location/Qualifiers
source                  1..20
                        mol_type = protein
                        organism = synthetic construct
SEQUENCE: 400
MSQSGEENLQ GSWVELHFLN                                         20

SEQ ID NO: 401          moltype = AA   length = 20
FEATURE                 Location/Qualifiers
source                  1..20
                        mol_type = protein
                        organism = synthetic construct
SEQUENCE: 401
MSQMGEENLQ GSWVELHFSN                                         20

SEQ ID NO: 402          moltype = AA   length = 20
FEATURE                 Location/Qualifiers
source                  1..20
                        mol_type = protein
                        organism = synthetic construct
SEQUENCE: 402
MSQSGEENLQ GSAVELHFSN                                         20

SEQ ID NO: 403          moltype = AA   length = 20
FEATURE                 Location/Qualifiers
source                  1..20
                        mol_type = protein
                        organism = synthetic construct
SEQUENCE: 403
MSQSGEENLQ GSWVELHFSP                                         20

SEQ ID NO: 404          moltype = AA   length = 20
FEATURE                 Location/Qualifiers
source                  1..20
                        mol_type = protein
                        organism = synthetic construct
SEQUENCE: 404
MSQSGEENLQ GAWVELHFSN                                         20

SEQ ID NO: 405          moltype = AA   length = 20
FEATURE                 Location/Qualifiers
source                  1..20
                        mol_type = protein
                        organism = synthetic construct
SEQUENCE: 405
MDQSGEENLQ GSWVELHFSN                                         20

SEQ ID NO: 406          moltype = AA   length = 20
FEATURE                 Location/Qualifiers
source                  1..20
                        mol_type = protein
                        organism = synthetic construct
SEQUENCE: 406
MSQNGEENLQ GSWVELHFSN                                         20

SEQ ID NO: 407          moltype = AA   length = 20
```

```
FEATURE              Location/Qualifiers
source               1..20
                     mol_type = protein
                     organism = synthetic construct
SEQUENCE: 407
MSQSGEENLQ GSCVELHFSN                                                    20

SEQ ID NO: 408       moltype = AA  length = 20
FEATURE              Location/Qualifiers
source               1..20
                     mol_type = protein
                     organism = synthetic construct
SEQUENCE: 408
MSQSGEENLQ GSWVELHFSQ                                                    20

SEQ ID NO: 409       moltype = AA  length = 20
FEATURE              Location/Qualifiers
source               1..20
                     mol_type = protein
                     organism = synthetic construct
SEQUENCE: 409
MSQSGEENLQ GCWVELHFSN                                                    20

SEQ ID NO: 410       moltype = AA  length = 20
FEATURE              Location/Qualifiers
source               1..20
                     mol_type = protein
                     organism = synthetic construct
SEQUENCE: 410
MEQSGEENLQ GSWVELHFSN                                                    20

SEQ ID NO: 411       moltype = AA  length = 20
FEATURE              Location/Qualifiers
source               1..20
                     mol_type = protein
                     organism = synthetic construct
SEQUENCE: 411
MSQPGEENLQ GSWVELHFSN                                                    20

SEQ ID NO: 412       moltype = AA  length = 20
FEATURE              Location/Qualifiers
source               1..20
                     mol_type = protein
                     organism = synthetic construct
SEQUENCE: 412
MSQSGEENLQ GSDVELHFSN                                                    20

SEQ ID NO: 413       moltype = AA  length = 20
FEATURE              Location/Qualifiers
source               1..20
                     mol_type = protein
                     organism = synthetic construct
SEQUENCE: 413
MSQSGEENLQ GSWVELHFSR                                                    20

SEQ ID NO: 414       moltype = AA  length = 20
FEATURE              Location/Qualifiers
source               1..20
                     mol_type = protein
                     organism = synthetic construct
SEQUENCE: 414
MSQSGEENLQ GDWVELHFSN                                                    20

SEQ ID NO: 415       moltype = AA  length = 20
FEATURE              Location/Qualifiers
source               1..20
                     mol_type = protein
                     organism = synthetic construct
SEQUENCE: 415
MFQSGEENLQ GSWVELHFSN                                                    20

SEQ ID NO: 416       moltype = AA  length = 20
FEATURE              Location/Qualifiers
source               1..20
                     mol_type = protein
                     organism = synthetic construct
SEQUENCE: 416
MSQQGEENLQ GSWVELHFSN                                                    20
```

```
SEQ ID NO: 417         moltype = AA  length = 20
FEATURE                Location/Qualifiers
source                 1..20
                       mol_type = protein
                       organism = synthetic construct
SEQUENCE: 417
MSQSGEENLQ GSEVELHFSN                                                      20

SEQ ID NO: 418         moltype = AA  length = 20
FEATURE                Location/Qualifiers
source                 1..20
                       mol_type = protein
                       organism = synthetic construct
SEQUENCE: 418
MSGSGEENLQ GSWVELHFSN                                                      20

SEQ ID NO: 419         moltype = AA  length = 20
FEATURE                Location/Qualifiers
source                 1..20
                       mol_type = protein
                       organism = synthetic construct
SEQUENCE: 419
MSQSGEENLQ GTWVELHFSN                                                      20

SEQ ID NO: 420         moltype = AA  length = 20
FEATURE                Location/Qualifiers
source                 1..20
                       mol_type = protein
                       organism = synthetic construct
SEQUENCE: 420
MGQSGEENLQ GSWVELHFSN                                                      20

SEQ ID NO: 421         moltype = AA  length = 20
FEATURE                Location/Qualifiers
source                 1..20
                       mol_type = protein
                       organism = synthetic construct
SEQUENCE: 421
MSQRGEENLQ GSWVELHFSN                                                      20

SEQ ID NO: 422         moltype = AA  length = 20
FEATURE                Location/Qualifiers
source                 1..20
                       mol_type = protein
                       organism = synthetic construct
SEQUENCE: 422
MSQSGEENLQ GSFVELHFSN                                                      20

SEQ ID NO: 423         moltype = AA  length = 20
FEATURE                Location/Qualifiers
source                 1..20
                       mol_type = protein
                       organism = synthetic construct
SEQUENCE: 423
MSHSGEENLQ GSWVELHFSN                                                      20

SEQ ID NO: 424         moltype = AA  length = 20
FEATURE                Location/Qualifiers
source                 1..20
                       mol_type = protein
                       organism = synthetic construct
SEQUENCE: 424
MSQSGEENLQ GVWVELHFSN                                                      20

SEQ ID NO: 425         moltype = AA  length = 20
FEATURE                Location/Qualifiers
source                 1..20
                       mol_type = protein
                       organism = synthetic construct
SEQUENCE: 425
MHQSGEENLQ GSWVELHFSN                                                      20

SEQ ID NO: 426         moltype = AA  length = 20
FEATURE                Location/Qualifiers
source                 1..20
                       mol_type = protein
                       organism = synthetic construct
SEQUENCE: 426
MSQTGEENLQ GSWVELHFSN                                                      20
```

```
SEQ ID NO: 427          moltype = AA  length = 20
FEATURE                 Location/Qualifiers
source                  1..20
                        mol_type = protein
                        organism = synthetic construct
SEQUENCE: 427
MSQSGEENLQ GSGVELHFSN                                                    20

SEQ ID NO: 428          moltype = AA  length = 20
FEATURE                 Location/Qualifiers
source                  1..20
                        mol_type = protein
                        organism = synthetic construct
SEQUENCE: 428
MSISGEENLQ GSWVELHFSN                                                    20

SEQ ID NO: 429          moltype = AA  length = 20
FEATURE                 Location/Qualifiers
source                  1..20
                        mol_type = protein
                        organism = synthetic construct
SEQUENCE: 429
MSQSGEENLQ GWWVELHFSN                                                    20

SEQ ID NO: 430          moltype = AA  length = 20
FEATURE                 Location/Qualifiers
source                  1..20
                        mol_type = protein
                        organism = synthetic construct
SEQUENCE: 430
MIQSGEENLQ GSWVELHFSN                                                    20

SEQ ID NO: 431          moltype = AA  length = 20
FEATURE                 Location/Qualifiers
source                  1..20
                        mol_type = protein
                        organism = synthetic construct
SEQUENCE: 431
MSQVGEENLQ GSWVELHFSN                                                    20

SEQ ID NO: 432          moltype = AA  length = 20
FEATURE                 Location/Qualifiers
source                  1..20
                        mol_type = protein
                        organism = synthetic construct
SEQUENCE: 432
MSQSGEENLQ GSHVELHFSN                                                    20

SEQ ID NO: 433          moltype = AA  length = 20
FEATURE                 Location/Qualifiers
source                  1..20
                        mol_type = protein
                        organism = synthetic construct
SEQUENCE: 433
MSKSGEENLQ GSWVELHFSN                                                    20

SEQ ID NO: 434          moltype = AA  length = 20
FEATURE                 Location/Qualifiers
source                  1..20
                        mol_type = protein
                        organism = synthetic construct
SEQUENCE: 434
MSQSGEENLQ GYWVELHFSN                                                    20

SEQ ID NO: 435          moltype = AA  length = 20
FEATURE                 Location/Qualifiers
source                  1..20
                        mol_type = protein
                        organism = synthetic construct
SEQUENCE: 435
MKQSGEENLQ GSWVELHFSN                                                    20

SEQ ID NO: 436          moltype = AA  length = 20
FEATURE                 Location/Qualifiers
source                  1..20
                        mol_type = protein
                        organism = synthetic construct
```

```
SEQUENCE: 436
MSQWGEENLQ GSWVELHFSN                                                    20

SEQ ID NO: 437           moltype = AA  length = 20
FEATURE                  Location/Qualifiers
source                   1..20
                         mol_type = protein
                         organism = synthetic construct
SEQUENCE: 437
MSQSGEENLQ GSIVELHFSN                                                    20

SEQ ID NO: 438           moltype = AA  length = 20
FEATURE                  Location/Qualifiers
source                   1..20
                         mol_type = protein
                         organism = synthetic construct
SEQUENCE: 438
MSQSGEENLQ GEWVELHFSN                                                    20

SEQ ID NO: 439           moltype = AA  length = 20
FEATURE                  Location/Qualifiers
source                   1..20
                         mol_type = protein
                         organism = synthetic construct
SEQUENCE: 439
MSQSGEENLQ GSWVELHFMN                                                    20

SEQ ID NO: 440           moltype = AA  length = 20
FEATURE                  Location/Qualifiers
source                   1..20
                         mol_type = protein
                         organism = synthetic construct
SEQUENCE: 440
MTQSGEENLQ GSWVELHFSN                                                    20

SEQ ID NO: 441           moltype = AA  length = 20
FEATURE                  Location/Qualifiers
source                   1..20
                         mol_type = protein
                         organism = synthetic construct
SEQUENCE: 441
MSQSGEENLQ GSWDELHFSN                                                    20

SEQ ID NO: 442           moltype = AA  length = 20
FEATURE                  Location/Qualifiers
source                   1..20
                         mol_type = protein
                         organism = synthetic construct
SEQUENCE: 442
MSQSGEENLQ GSKVELHFSN                                                    20

SEQ ID NO: 443           moltype = AA  length = 20
FEATURE                  Location/Qualifiers
source                   1..20
                         mol_type = protein
                         organism = synthetic construct
SEQUENCE: 443
MSQSGEENLQ GFWVELHFSN                                                    20

SEQ ID NO: 444           moltype = AA  length = 20
FEATURE                  Location/Qualifiers
source                   1..20
                         mol_type = protein
                         organism = synthetic construct
SEQUENCE: 444
MSQSGEENLQ GSWVELHFNN                                                    20

SEQ ID NO: 445           moltype = AA  length = 20
FEATURE                  Location/Qualifiers
source                   1..20
                         mol_type = protein
                         organism = synthetic construct
SEQUENCE: 445
MVQSGEENLQ GSWVELHFSN                                                    20

SEQ ID NO: 446           moltype = AA  length = 20
FEATURE                  Location/Qualifiers
```

```
source                      1..20
                            mol_type = protein
                            organism = synthetic construct
SEQUENCE: 446
MSQSGEENLQ GSWEELHFSN                                                    20

SEQ ID NO: 447              moltype = AA   length = 20
FEATURE                     Location/Qualifiers
source                      1..20
                            mol_type = protein
                            organism = synthetic construct
SEQUENCE: 447
MSQSGEENLQ GSLVELHFSN                                                    20

SEQ ID NO: 448              moltype = AA   length = 20
FEATURE                     Location/Qualifiers
source                      1..20
                            mol_type = protein
                            organism = synthetic construct
SEQUENCE: 448
MSQSGEENLQ GGWVELHFSN                                                    20

SEQ ID NO: 449              moltype = AA   length = 20
FEATURE                     Location/Qualifiers
source                      1..20
                            mol_type = protein
                            organism = synthetic construct
SEQUENCE: 449
MSQSGEENLQ GSWVELHFPN                                                    20

SEQ ID NO: 450              moltype = AA   length = 20
FEATURE                     Location/Qualifiers
source                      1..20
                            mol_type = protein
                            organism = synthetic construct
SEQUENCE: 450
MWQSGEENLQ GSWVELHFSN                                                    20

SEQ ID NO: 451              moltype = AA   length = 20
FEATURE                     Location/Qualifiers
source                      1..20
                            mol_type = protein
                            organism = synthetic construct
SEQUENCE: 451
MSQSGEENLQ GSWFELHFSN                                                    20

SEQ ID NO: 452              moltype = AA   length = 20
FEATURE                     Location/Qualifiers
source                      1..20
                            mol_type = protein
                            organism = synthetic construct
SEQUENCE: 452
MSQSGEENLQ GSMVELHFSN                                                    20

SEQ ID NO: 453              moltype = AA   length = 20
FEATURE                     Location/Qualifiers
source                      1..20
                            mol_type = protein
                            organism = synthetic construct
SEQUENCE: 453
MSQSGEENLQ GHWVELHFSN                                                    20

SEQ ID NO: 454              moltype = AA   length = 20
FEATURE                     Location/Qualifiers
source                      1..20
                            mol_type = protein
                            organism = synthetic construct
SEQUENCE: 454
MSQSGEENLQ GSWVELHFQN                                                    20

SEQ ID NO: 455              moltype = AA   length = 20
FEATURE                     Location/Qualifiers
source                      1..20
                            mol_type = protein
                            organism = synthetic construct
SEQUENCE: 455
MYQSGEENLQ GSWVELHFSN                                                    20

SEQ ID NO: 456              moltype = AA   length = 20
```

```
FEATURE                 Location/Qualifiers
source                  1..20
                        mol_type = protein
                        organism = synthetic construct
SEQUENCE: 456
MSQSGEENLQ GSWGELHFSN                                                    20

SEQ ID NO: 457          moltype = AA  length = 20
FEATURE                 Location/Qualifiers
source                  1..20
                        mol_type = protein
                        organism = synthetic construct
SEQUENCE: 457
MSQSGEENLQ GSNVELHFSN                                                    20

SEQ ID NO: 458          moltype = AA  length = 20
FEATURE                 Location/Qualifiers
source                  1..20
                        mol_type = protein
                        organism = synthetic construct
SEQUENCE: 458
MSQSGEENLQ GIWVELHFSN                                                    20

SEQ ID NO: 459          moltype = AA  length = 20
FEATURE                 Location/Qualifiers
source                  1..20
                        mol_type = protein
                        organism = synthetic construct
SEQUENCE: 459
MSQSGEENLQ GSWVELHFRN                                                    20

SEQ ID NO: 460          moltype = AA  length = 20
FEATURE                 Location/Qualifiers
source                  1..20
                        mol_type = protein
                        organism = synthetic construct
SEQUENCE: 460
MSQAGEENLQ GSWVELHFSN                                                    20

SEQ ID NO: 461          moltype = AA  length = 20
FEATURE                 Location/Qualifiers
source                  1..20
                        mol_type = protein
                        organism = synthetic construct
SEQUENCE: 461
MSQSGEENLQ GSWHELHFSN                                                    20

SEQ ID NO: 462          moltype = AA  length = 20
FEATURE                 Location/Qualifiers
source                  1..20
                        mol_type = protein
                        organism = synthetic construct
SEQUENCE: 462
MSQSGEENLQ GSPVELHFSN                                                    20

SEQ ID NO: 463          moltype = AA  length = 20
FEATURE                 Location/Qualifiers
source                  1..20
                        mol_type = protein
                        organism = synthetic construct
SEQUENCE: 463
MSQSGEENLQ GKWVELHFSN                                                    20

SEQ ID NO: 464          moltype = AA  length = 20
FEATURE                 Location/Qualifiers
source                  1..20
                        mol_type = protein
                        organism = synthetic construct
SEQUENCE: 464
MSQSGEENLQ GSWVELHFTN                                                    20

SEQ ID NO: 465          moltype = AA  length = 20
FEATURE                 Location/Qualifiers
source                  1..20
                        mol_type = protein
                        organism = synthetic construct
SEQUENCE: 465
MSQCGEENLQ GSWVELHFSN                                                    20
```

```
SEQ ID NO: 466          moltype = AA   length = 20
FEATURE                 Location/Qualifiers
source                  1..20
                        mol_type = protein
                        organism = synthetic construct
SEQUENCE: 466
MSQSGEENLQ GSWIELHFSN                                                    20

SEQ ID NO: 467          moltype = AA   length = 20
FEATURE                 Location/Qualifiers
source                  1..20
                        mol_type = protein
                        organism = synthetic construct
SEQUENCE: 467
MSQSGEENLQ GSQVELHFSN                                                    20

SEQ ID NO: 468          moltype = AA   length = 20
FEATURE                 Location/Qualifiers
source                  1..20
                        mol_type = protein
                        organism = synthetic construct
SEQUENCE: 468
MSQSGEENLQ GLWVELHFSN                                                    20

SEQ ID NO: 469          moltype = AA   length = 20
FEATURE                 Location/Qualifiers
source                  1..20
                        mol_type = protein
                        organism = synthetic construct
SEQUENCE: 469
MSQSGEENLQ GSWVELHFVN                                                    20

SEQ ID NO: 470          moltype = AA   length = 20
FEATURE                 Location/Qualifiers
source                  1..20
                        mol_type = protein
                        organism = synthetic construct
SEQUENCE: 470
MSQDGEENLQ GSWVELHFSN                                                    20

SEQ ID NO: 471          moltype = AA   length = 20
FEATURE                 Location/Qualifiers
source                  1..20
                        mol_type = protein
                        organism = synthetic construct
SEQUENCE: 471
MSQSGEENLQ GSWKELHFSN                                                    20

SEQ ID NO: 472          moltype = AA   length = 20
FEATURE                 Location/Qualifiers
source                  1..20
                        mol_type = protein
                        organism = synthetic construct
SEQUENCE: 472
MSQSGEENLQ GSRVELHFSN                                                    20

SEQ ID NO: 473          moltype = AA   length = 20
FEATURE                 Location/Qualifiers
source                  1..20
                        mol_type = protein
                        organism = synthetic construct
SEQUENCE: 473
MSQSGEENLQ GMWVELHFSN                                                    20

SEQ ID NO: 474          moltype = AA   length = 20
FEATURE                 Location/Qualifiers
source                  1..20
                        mol_type = protein
                        organism = synthetic construct
SEQUENCE: 474
MSQSGEENLQ GSWVELHFWN                                                    20

SEQ ID NO: 475          moltype = AA   length = 20
FEATURE                 Location/Qualifiers
source                  1..20
                        mol_type = protein
                        organism = synthetic construct
SEQUENCE: 475
MSQEGEENLQ GSWVELHFSN                                                    20
```

| | | |
|---|---|---|
| SEQ ID NO: 476<br>FEATURE<br>source | moltype = AA  length = 20<br>Location/Qualifiers<br>1..20<br>mol_type = protein<br>organism = synthetic construct | |
| SEQUENCE: 476<br>MSQSGEENLQ GSWLELHFSN | | 20 |
| SEQ ID NO: 477<br>FEATURE<br>source | moltype = AA  length = 20<br>Location/Qualifiers<br>1..20<br>mol_type = protein<br>organism = synthetic construct | |
| SEQUENCE: 477<br>MSQSGEENLQ GSSVELHFSN | | 20 |
| SEQ ID NO: 478<br>FEATURE<br>source | moltype = AA  length = 20<br>Location/Qualifiers<br>1..20<br>mol_type = protein<br>organism = synthetic construct | |
| SEQUENCE: 478<br>MSQSGEENLQ GNWVELHFSN | | 20 |
| SEQ ID NO: 479<br>FEATURE<br>source | moltype = AA  length = 20<br>Location/Qualifiers<br>1..20<br>mol_type = protein<br>organism = synthetic construct | |
| SEQUENCE: 479<br>MSQSGEENLQ GSWVELHFYN | | 20 |
| SEQ ID NO: 480<br>FEATURE<br>source | moltype = AA  length = 20<br>Location/Qualifiers<br>1..20<br>mol_type = protein<br>organism = synthetic construct | |
| SEQUENCE: 480<br>MSQFGEENLQ GSWVELHFSN | | 20 |
| SEQ ID NO: 481<br>FEATURE<br>source | moltype = AA  length = 20<br>Location/Qualifiers<br>1..20<br>mol_type = protein<br>organism = synthetic construct | |
| SEQUENCE: 481<br>MSQSGEENLQ GSWMELHFSN | | 20 |
| SEQ ID NO: 482<br>FEATURE<br>source | moltype = AA  length = 20<br>Location/Qualifiers<br>1..20<br>mol_type = protein<br>organism = synthetic construct | |
| SEQUENCE: 482<br>MSQSGEENLQ GPWVELHFSN | | 20 |
| SEQ ID NO: 483<br>FEATURE<br>source | moltype = AA  length = 20<br>Location/Qualifiers<br>1..20<br>mol_type = protein<br>organism = synthetic construct | |
| SEQUENCE: 483<br>MSQSGEENLQ GSWVELHFAN | | 20 |
| SEQ ID NO: 484<br>FEATURE<br>source | moltype = AA  length = 20<br>Location/Qualifiers<br>1..20<br>mol_type = protein<br>organism = synthetic construct | |
| SEQUENCE: 484<br>MSQGGEENLQ GSWVELHFSN | | 20 |
| SEQ ID NO: 485<br>FEATURE<br>source | moltype = AA  length = 20<br>Location/Qualifiers<br>1..20<br>mol_type = protein<br>organism = synthetic construct | |

```
SEQUENCE: 485
MSQSGEENLQ GSWNELHFSN                                                    20

SEQ ID NO: 486          moltype = AA  length = 20
FEATURE                 Location/Qualifiers
source                  1..20
                        mol_type = protein
                        organism = synthetic construct
SEQUENCE: 486
MSQSGEENLQ GQWVELHFSN                                                    20

SEQ ID NO: 487          moltype = AA  length = 20
FEATURE                 Location/Qualifiers
source                  1..20
                        mol_type = protein
                        organism = synthetic construct
SEQUENCE: 487
MAQSGEENLQ GSWVELHFSN                                                    20

SEQ ID NO: 488          moltype = AA  length = 20
FEATURE                 Location/Qualifiers
source                  1..20
                        mol_type = protein
                        organism = synthetic construct
SEQUENCE: 488
MSQHGEENLQ GSWVELHFSN                                                    20

SEQ ID NO: 489          moltype = AA  length = 20
FEATURE                 Location/Qualifiers
source                  1..20
                        mol_type = protein
                        organism = synthetic construct
SEQUENCE: 489
MSQSGEENLQ GSWPELHFSN                                                    20

SEQ ID NO: 490          moltype = AA  length = 20
FEATURE                 Location/Qualifiers
source                  1..20
                        mol_type = protein
                        organism = synthetic construct
SEQUENCE: 490
MSQSGEENLQ GRWVELHFSN                                                    20

SEQ ID NO: 491          moltype = AA  length = 20
FEATURE                 Location/Qualifiers
source                  1..20
                        mol_type = protein
                        organism = synthetic construct
SEQUENCE: 491
MCQSGEENLQ GSWVELHFSN                                                    20

SEQ ID NO: 492          moltype = AA  length = 20
FEATURE                 Location/Qualifiers
source                  1..20
                        mol_type = protein
                        organism = synthetic construct
SEQUENCE: 492
MSQIGEENLQ GSWVELHFSN                                                    20

SEQ ID NO: 493          moltype = AA  length = 20
FEATURE                 Location/Qualifiers
source                  1..20
                        mol_type = protein
                        organism = synthetic construct
SEQUENCE: 493
MSQSGEENLQ GSWQELHFSN                                                    20

SEQ ID NO: 494          moltype = AA  length = 20
FEATURE                 Location/Qualifiers
source                  1..20
                        mol_type = protein
                        organism = synthetic construct
SEQUENCE: 494
SEQIMKTGAF LLQGFIQDRA                                                    20
```